(12) United States Patent
Bauman et al.

(10) Patent No.: US 6,977,258 B2
(45) Date of Patent: Dec. 20, 2005

(54) PIPERAZINE DERIVATIVES AND THEIR USE AS ANTI-INFLAMMATORY AGENTS

(75) Inventors: John G. Bauman, El Sobrante, CA (US); Brad O. Buckman, Oakland, CA (US); Ameen F. Ghannam, Briarcliff Manor, NY (US); Joseph E. Hesselgesser, San Francisco, CA (US); Richard Horuk, Lafayette, CA (US); Imadul Islam, Hercules, CA (US); Meina Liang, Danville, CA (US); Karen B. May, Napa, CA (US); Sean D. Monahan, Madison, WI (US); Michael M. Morrissey, Danville, CA (US); Howard P. Ng, El Sobrante, CA (US); Kenneth J. Shaw, Brookside, NJ (US); Guo Ping Wei, San Ramon, CA (US); Wei Xu, Danville, CA (US); Zuchun Zhao, Richmond, CA (US); Wei Zheng, Blue Bell, PA (US)

(73) Assignee: Schering Aktiengesellschaft, Berlin (DE)

( * ) Notice: Subject to any disclaimer, the term of this patent is extended or adjusted under 35 U.S.C. 154(b) by 24 days.

(21) Appl. No.: 10/347,530

(22) Filed: Jan. 17, 2003

(65) Prior Publication Data

US 2003/0139425 A1 Jul. 24, 2003

Related U.S. Application Data

(60) Division of application No. 09/714,937, filed on Nov. 16, 2000, now Pat. No. 6,573,266, which is a division of application No. 09/094,397, filed on Jun. 9, 1998, now Pat. No. 6,207,665, which is a continuation-in-part of application No. 08/873,599, filed on Jun. 12, 1997, now abandoned.

(51) Int. Cl.[7] .................... A61K 31/495; C07D 241/04
(52) U.S. Cl. ............................. 514/255.01; 514/235.8; 544/121; 544/391
(58) Field of Search ............................. 544/391, 121; 514/235.8, 255.01

(56) References Cited

U.S. PATENT DOCUMENTS

| | | |
|---|---|---|
| 3,324,117 A | 6/1967 | Schorr et al. |
| 4,294,851 A | 10/1981 | Metz et al. |
| 4,439,606 A | 3/1984 | Du et al. |
| 4,645,525 A | 2/1987 | Forster et al. |
| 4,859,700 A | 8/1989 | Lavielle et al. |
| 4,885,299 A | 12/1989 | Lavielle et al. |
| 4,970,301 A | 11/1990 | Rolland et al. |
| 4,987,132 A | 1/1991 | Mase et al. |
| 5,232,923 A * | 8/1993 | Fukazawa et al. ....... 514/237.5 |
| 5,272,175 A | 12/1993 | Hansen, Jr. et al. |
| 5,280,024 A | 1/1994 | Bolland et al. |
| 5,389,645 A | 2/1995 | Hansen, Jr. et al. |
| 5,596,000 A | 1/1997 | Esser et al. |
| 5,668,138 A | 9/1997 | Baziard-Mouysset et al. |
| 5,691,340 A | 11/1997 | Baziard-Mouysset et al. |
| 6,518,276 B2 | 2/2003 | Arzeno et al. |
| 6,521,619 B2 | 2/2003 | Link et al. |
| 6,528,509 B1 | 3/2003 | Hale et al. |

FOREIGN PATENT DOCUMENTS

| | | |
|---|---|---|
| AT | 389 112 | 10/1987 |
| CZ | 260089 | 5/1987 |
| EP | 0090202 | 3/1983 |
| EP | 0090203 | 3/1983 |
| EP | 0 190 685 | 1/1986 |
| EP | 0 284 632 | 3/1987 |
| EP | 0 252 422 | 7/1987 |
| EP | 0 319 412 | 12/1988 |
| EP | 0 333 522 | 3/1989 |
| EP | 0 372 410 | 12/1989 |
| EP | 0 655 442 | 11/1994 |
| FR | 7524 M | 3/1968 |
| GB | 1 434 323 | 5/1976 |
| WO | WO 92/21361 | 12/1992 |
| WO | WO 95/01343 | 1/1995 |
| WO | WO 95/09159 | 4/1995 |
| WO | WO 96/34864 | 11/1996 |
| WO | WO 98/02151 | 1/1998 |
| ZA | 87/2972 | 4/1987 |

OTHER PUBLICATIONS

Trivedi et al. in Annual Reports in Medicinal Chemistry, vol. 35, p. 191–200 (2000).*
Vadodaria et al., "Synthesis and Central Nervous System Depressant Activity of New Piperazine Derivatives and Related Compounds II", *J. Med Chem* (1969) 12(5):860–865.
Hertz and Deghengi, "Effect of rat and beta–human interferons on hyperacute experimental allergic encephhaomyelitis in rats", *Agents Actions* (1985) 16(5):397–403.
Rudick et al., "In vivo effects on interferon beta–1a on immunosuppressive cytokines in multiple sclerosis", *Neurology* (1998) 50:1294–1300.
Ruuls et al., "The length of treatment determines whether IFN–beta prevents or aggravates experimental autoimmune encephalomyelitis in Lewis rats", *J. Immunol.* (1996) 157: 5721–5731.

(Continued)

Primary Examiner—Richard L. Raymond
(74) Attorney, Agent, or Firm—Berlex, Inc.

(57) ABSTRACT

This invention is directed to acyl piperazine derivatives of formula (Ia):

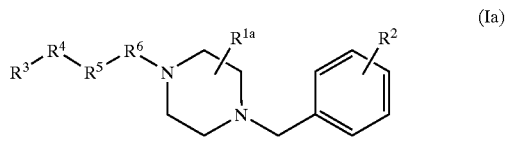

wherein $R^{1a}$, $R^2$, $R^3$, $R^4$, $R^5$ and $R^6$ are defined herein, which are useful as anti-inflammatory agents. This invention is also directed to other acyl piperazine derivatives, pharmaceutical compositions containing the compounds of the invention, and methods of using the compounds to treat inflammatory disorders in humans.

19 Claims, No Drawings

OTHER PUBLICATIONS

Yu et al., "Interferon beta inhibits progression of relapsing–remitting experimental autoimmune encephalomyelitis", *J. Neuroimmunol.* (1996) 64:91–100.

Rottman et al., Central Role of CCR1+ Cells in the Immunopathogenesis of Experimental Allergic Encephalomyelitis (EAE), *FASEB* (1999) 13(5):A666 Abstract 492–16.

Protiva et al., *Chemical Abstracts* (1990), vol. 112, pp. 722–723, No. 158270d.

Eng et al., "Inflammation in EAE: Role of Chemokine/Cytokine Expression by Resident and Infiltrating Cells", *Neurochem. Res.* (1996) 21:511–525.

Wells et al., "The Molecular Basis of the Chemokine/Chemokine Receptor Interaction—Scope for Design of Chemokine Antagonists", *Methods* (1996) 10:126–134.

Leuschner, "N–Acyl substituted piperazines", *Chemical Abstracts* (1974) 81:429–430, No. 136185u.

Okada and Shimabayashi, "Synthesis of N–(1–Methyl–2–piperazinoethyl)proprionanilides and 2–Alkoxy–6–[N–[1–methyl–2–2(4–phenylethylpiperazino)ethyl]–proprionamide]benzothiazoles", *Chem. Pharm. Bull.* (1980). 28:3315–3322.

Ransohoff et al., "Chemokines in Immune–mediated Inflammation of the Central Nervous System", *Cytokine & Growth Factor Rev.* (1996) 7:35–46.

Karpus and Ransohoff, "Cutting Edge Commentary: Chemokine Regulation of Experimental Autoimmune Encephalomyelitis: Temporal and Spatial Expression Patterns Govern Disease Pathogenesis", *J. Immunol.* (1998) 161:2667–2671.

Karpus et al., "An Important Role for the Chemokine Macrophage Inflammatory Protein–1a in the Pathogenesis of the T Cell–Mediated Autoimmune Disease, Experimental Autoimmune Encephalomyelitis", *J. Immunol.* (1995) 155:5003–5010.

Trebst et al., "CCR1+/CCR5+ Mononuclear Phagocytes Accumulate in the Central Nervous System of Patients with Multiple Sclerosis", *Am. J. Pathol.* (2001) 159:1701–1710.

Rottman et al., "Leukocyte recruitment during onset of experimental allergic encephalomyelitis is CCR1 dependent", *Eur. J. Immunol.* (2000) 30:2372–2377.

Liang et al., "Identification and Characterization of a Potent, Selective, and Orally Active Antagonist of the CC Chemokine Receptor–1", *J. Biol. Chem.* (2000) 275:19000–19008.

Zikolova et al., "Analogs of N1–benzhydryl–N4–cinnamylpiperazine (oinnarizine) II N1–Substituted –N4–benzhydrylpiprazines", *Tr. Nauchnoizsled. Khim.–Farm. Inst.* (1972), 8:59–6.

Ivanova et al., "Synthesis and pharmacological studies of a group of N–acylpiperazines", *Farmatsiya (Sofia)* (1976), 26(4): 10–14.

Nikolova et al., "Preliminary pharmacological investigation of some piperazine derivatives", *Farmatsiya (Sofia)* (1969), 19(2):31–37.

Zikolova et al., "Synthesis of piperazine derivatives VI Symmetric and asymmetric N–acylpiperazines with possible biological activity", *Tr. Nauchnoizsled. Khim.–Farm. Inst.* (1972), 7:109–115.

Azize et al., "Thermal behavior and elastic properties of phospholipid bilayers under the effect of a synthetic flavonoid derivative, LEW–10", *Chemistry and Physics of Lipids* (1992), 63:169–177.

Carceller et al., "(Pyridylcyanomethyl) piperazines as Orally Active PAF Antagonists", *J. Med. Chem*(1992), 35:4118–4134.

Valenta et al., "Synthesis of 4–Methoxyphenoxyacetic and 3,4,5–Trimethoxyphenoxyacetic Acid Amides and Hydrazides as Potential Neurotropic and Cardiovascular Agents", *Collection Czechoslovak Chem. Commun.* (1987), 52:3013–3023.

Valenta et al., "Basic Amides of 2,4,5–Trichlorophenoxyacetic, 2,4,6–Trimethylphenoxyacetic and 4–Bromo–3,5–Dimethylphenoxyacetic Acid and Some Related Compounds, Synthesis and Pharmacological Screening", *Collection Czechoslovak Chem. Commun.* (1983), 48:1089–1096.

Protiva et al., "Basic Amides of 3,4,5–Trimethoxyphenoxy Acedic Acid: Synthesis and Pharmacology of Trimethophenoxamide and Analogues", *Collection Czechoslovak Chem. Commun.* (1977), 42:3628–3642.

Petigara et al., Synthesis and Central Nervous System Depressant Activity of New Piperazine and Related Derivatives III, *J. Med Chem* (1969) 12(5):865–870.

Vadodaria et al., "Synthesis and Central Nervous System Depressant Activity of New Piperazine Derivatives and Related Compounds II", *J. Med Chem* (1969) 12(5):860–865.

Hertz and Deghengi, "Effect of rat and beta–human interferons on hyperacute experimental allergic encephhaomyelitis in rats", *Agents Actions* (1985) 16(5):397–403.

Rudick et al., "In vivo effects on interferon beta–1a on immunosuppressive cytokines in multiple sclerosis", *Neurology* (1998) 50:1294–1300.

Ruuls et al., "The length of treatment determines whether IFN–beta prevents or aggravates experimental autoimmune encephalomyelitis in Lewis rats", *J. Immunol.* (1996) 157: 5721–5731.

* cited by examiner

PIPERAZINE DERIVATIVES AND THEIR USE AS ANTI-INFLAMMATORY AGENTS

This application is a division of U.S. Ser. No. 09/714,937, filed Nov. 16, 2000, now U.S. Pat. No. 6,573,266 which is a division of U.S. Ser. No. 09/094,397, filed Jun. 9, 1998, now U.S. Pat. No. 6,207,665, which issued on Mar. 27, 2001, and which is a continuation-in-part of U.S. Ser. No. 08/873,599, filed Jun. 12, 1997, now abandoned, the disclosures of which are incorporated herein in full by reference.

FIELD OF THE INVENTION

The present invention is directed to piperazine derivatives and their pharmaceutically acceptable salts, which inhibit the activity of the chemokines, MIP-1α and RANTES, thereby being useful as anti-inflammatory agents. It also relates to pharmaceutical compositions containing the derivatives or their pharmaceutically acceptable salts, and methods of their use.

BACKGROUND OF THE INVENTION

An important component of the inflammatory process involves the migration and activation of select populations of leukocytes from the circulation and their accumulation in the affected tissue. While the idea of leukocyte trafficking is not new, it has enjoyed a renaissance recently following the discovery and characterization of the selectin and integrin families of adhesion molecules and the large family of selective chemotactic cytokines known as chemokines. Chemokine receptors are expressed on leukocytes and process the signals following the binding of the chemokine whereby such signals are eventually transduced into migration or activation of the leukocytes towards the source of the chemokine. Therefore, by regulating the migration and activation of leukocytes from the peripheral blood to extravascular sites in organs, skin, articulations or connective, tissue, chemokines play a critical role in the maintenance of host defense as well as in the development of the immune response.

Originally, the chemokine family of molecules was divided into two groups: the "C—X—C" subfamily and the "C—C" subfamily. The characteristic feature of both of these subfamilies is the presence of four cysteine residues in highly conserved positions in the molecules. In the "C—C" chemokine subfamily, the first two residues are adjacent to each other, white in the "C—X—C" subfamily, the cysteine residues are separated by a single amino acid residue. A recent description of a "—C—" chemokine appears to represent a new family of chemokines in that the "—C" chemokine lacks two of the four cysteine residues present in the "C—C" subfamily or the "C—X—C" subfamily.

One member of the "C—C" subfamily of chemokines is macrophage inflammatory protein-1α ("MIP-1α"). It is expressed by cells such as macrophages, T and B lymphocytes, neutrophils and fibroblasts. A recent study (see Karpus, W. J. et al., *J. Immunol.* (1995), Vol. 155, pp. 5003–5010) provides strong in vivo concept validation for a role of MIP-1α in a mouse experimental autoimmune encephalomyelitis (EAE) model of multiple sclerosis. Multiple sclerosis is an autoimmune disease mediated by T and B lymphocytes and macrophages, resulting in extensive inflammation and demyelination of white matter in the central nervous system. The study showed that antibodies to MIP-1α prevented the development of both initial and relapsing disease as well as preventing the infiltration of mononuclear cells into the central nervous system. Treatment with the antibodies was also able to ameliorate the severity of ongoing clinical disease. These results led the investigators to conclude that MIP-1α plays an important role in the etiology of multiple sclerosis. In addition, another study (see Godiska, R. et al., *J. Neuroimmunology* (1995), Vol. 58, pp. 167–176) demonstrated an upregulation of mRNA for a number of chemokines, including MIP-1α, in the lesions and spinal cord of SJL mice (a strain of mice susceptible to $Th_1$ diseases such as EAE) during the course of acute EAE.

RANTES is another member of the C—C chemokine subfamily (the name RANTES is an acronym derived from some of the original observed and predicted characteristics of the protein and its gene: Regulated upon Activation Normal T cell Expressed presumed Secreted). A wide variety of tissues have been found to express RANTES in a similar pattern to MIP-1α. Strong evidence exists linking RANTES to organ transplant rejection, particularly of the kidney. The infiltration of mononuclear cells into the interstitium of organ transplants is the hallmark of acute cellar rejection. This cellular infiltrate primarily consists of T cells, macrophages and eosinophils. In a study of RANTES expression during acute renal allograft rejection, RANTES mRNA expression was found in infiltrating mononuclear cells and renal tubular epithelial cells and RANTES itself was found to be bound to the endothelial surface of the microvasculature within the rejecting graft (see Pattison, J. et al, *Lancet* (1994), Vol. 343, pp. 209–211 and Wiedermann, C. J. et al., *Curr. Biol.* (1993), Vol. 3, pp. 735–739).

There is also evidence from a number of studies to implicate the abnormal production of RANTES in the progression of rheumatoid arthritis (see Rathanaswami, P. et a., *J. Biol. Chem.* (1993), Vol. 268, pp. 5834–5839 and Snowden, N. et al., *Lancet* (1994), Vol. 343, pp. 547–548). Rheumatoid arthritis is a chronic inflammatory disease characterized in part by a memory T lymphocyte and monocyte infiltration, which is believed to be mediated by chemotactic factors released by inflamed tissues.

In addition, there is strong evidence from other studies implicating RANTES in the pathophysiology of rheumatoid arthritis (see Barnes, D. A. et al., *J. Clin. Invest.* (1998, in press) and Plater-Zyberk, C. A. et al, *Immunol. Lett.* (1997), Vol. 57, pp. 117–120). For example, in an adjuvant-induced arthritis (AIA) model in the rat, antibodies to RANTES greatly reduced the development of disease in rats induced for AIA.

These studies and others provide strong evidence that MIP-1α levels are increased in EAE models of multiple sclerosis and that RANTES levels are increased in rheumatoid arthritis and kidney transplant rejection (see, e.g., Glabinski, A. R. et al., *Am. J. Pathol.* (1997), Vol. 150, pp. 617–630; Glabinski, A. R. et al., *Methods. Enzymol.* (1997), Vol. 288, 182–190; and Miyagishi, R. S. et al., *J. Neuroimmunol.* (1997), Vol. 77, pp. 17–26). In addition, as described above, these chemokines are chemoattractants for T cells and monocytes which are the major cell types that are involved in the pathophysiology of these diseases. Therefore, any molecule that inhibits the activity of either of these chemokines would be beneficial in treating these diseases and would therefore be useful as an anti-inflammatory agent.

Related Disclosures

Piperazine derivatives of the type similar to the compounds of the invention are known in the literature as being useful for a variety of pharmaceutical indications, particularly as cardiotonic, neurotropic or anti-inflammatory agents. For example, published European Patent Application 0 702 010 (Adir) describes certain piperazine derivatives as being useful as central nervous system depressants and in the treatment of Alzheimer's and other diseases of immunological origin, such as arthritis and intestinal peristaltism. Published European Patent Application 0 655 442 (Fujisawa) describes similar piperazine derivatives as tachykinin antagonists useful in treating inflammatory diseases such as rheumatoid arthritis and osteoarthritis. A Czech published patent application, 260089, and related article, Valenta, V. et al., *Collection Czechoslovak Chem. Commun.* (1987), Vol.52, pp. 3013–3023, disclose piperazine derivatives as potential neurotropic and cardiovascular agents. European Published Patent Application 0 252 422 (Mitsubishi) and German Published Patent Application 3614363 (Hoechst) describe piperazine derivatives as being useful as cardiotonic agents. European Published Patent Application 0 190 685 (G. D. Searle) describes piperazine derivatives which block the 5-lipoxygenase pathway of the arachidonic acid cascade, thereby being useful in the treatment of allergic and hypersensitivity reactions and inflammation. PCT Published Patent Application, WO 96/34864 (Schering Plough) discloses piperazine derivatives useful as neurokinin antagonists.

All of the above references are incorporated herein in full by reference.

None of the above references describe the piperazine derivatives described herein or their usefulness in treating inflammatory disorders in humans by inhibition of the activity of the chemokines, MIP-1α and RANTES.

SUMMARY OF THE INVENTION

This invention is directed to compounds or their pharmaceutically acceptable salts which inhibit the activity of the chemokines, MIP-1α and RANTES and are therefore useful as pharmacological agents for the treatment of inflammatory disorders in humans.

Accordingly, in one aspect, this invention provides compounds of the following formula (Ia):

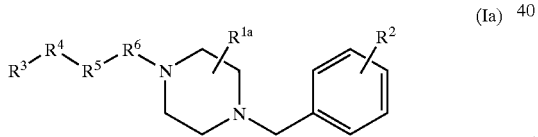

wherein:

$R^{1a}$ is one or more substituents independently selected from the group consisting of oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;

$R^2$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy) carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl) aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

or $R^3$ is a heterocyclic ring system substituted by one or more substituents independently selected from the group consisting of hydrogen, hydroxy, halo, alkyl, alkylsufonyl, arylsulfonyl, alkoxy, hydroxyalkoxy, haloalkyl, formyl, nitro, cyano, haloalkoxy, alkenyl, alkynyl, aryl, aralkyl, amino, monoalkylamino, dialkylamino, monoarylamino, monoaralkylamino, alkylcarbonylamino, alkoxycarbonylamino, alkenylcarbonylamino, cycloalkylcarbonylamino, arylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, alkylcarbonylaminoalkyl, arylcarbonylaminoalkyl, (alkylcarbonyl)(alkyl)aminoalkyl, alkoxycarbonylaminoalkyl, carboxy, alkoxycarbonyl, aralkoxycarbonyl, alkylcarbonyl, arylcarbonyl, aralkylcarbonyl, aminocarbonyl, monoalkylaminocarbonyl, dialkylaminocarbonyl, monoarylaminocarbonyl, aminocarbonylalkyl, monoalkylaminocarbonylalkyl, dialkylaminocarbonylalkyl, monoarylaminocarbonylalkyl, guanidino, ureido, monoalkylureido, ureidoalkyl, monoalkylureidoalkyl, and glycinamido;

$R^4$ is —O—, —N($R^7$)—, —C($R^8$)$_2$— or a bond;

$R^5$ is an alkylene chain or an alkylidene chain, or, if $R^4$ is a bond, $R^5$ is an alkylidene chain optionally substituted by aryl or —N($R^7$)$_2$;

$R^6$ is —C(O)—, —C(S)—, —CH$_2$— or a bond;

each $R^7$ is independently selected from the group consisting of hydrogen, alkyl, aryl, aralkyl, alkylcarbonyl, alkylcarbonylalkyl, aralkylcarbonyl, aralkylcarbonylalkyl, aminocarbonyl, monoalkylaminocarbonyl, dialkylaminocarbonyl, and alkoxycarbonyl; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, arylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl;

provided that when $R^4$ is —N($R^7$)—, $R^3$ can not be a heterocyclic ring system containing 4–8 members consisting of carbon atoms and only one nitrogen atom, and as a single stereoisomer or a mixture thereof; or a pharmaceutically acceptable salt thereof.

In another aspect, this invention provides pharmaceutical compositions useful in treating an inflammatory disorder in a human in need of such treatment, which composition comprises a therapeutically effective amount of a compound of formula (Ia) as described above, and a pharmaceutically acceptable excipient.

In another aspect, this invention provides a method of treating an inflammatory disorder in a human, which method comprises administering to a human in need of such treatment a therapeutically effective amount of a compound of formula (Ia) as described above.

In another aspect, this invention provides pharmaceutical compositions useful in treating an inflammatory disorder in a human in need of such treatment, which composition comprises a therapeutically effective amount of a compound of formula (Ib):

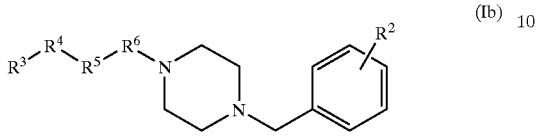
(Ib)

wherein $R^2$, $R^3$, $R^4$, $R^5$ and $R^6$ are the same as described above for compounds of formula (Ia);
and a pharmaceutically acceptable excipient.

In another aspect, this invention provides a method of treating an inflammatory disorder in a human, which method comprises administering to a human in need of such treatment a therapeutically effective amount of a compound of formula (Ib) as described above.

In another aspect, this invention provides compounds of the following formula (Ic):

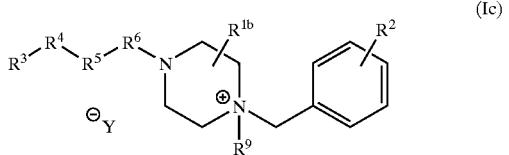
(Ic)

wherein:
$R^2$, $R^3$, $R^4$, $R^5$ and $R^6$ are the same as described above for the compounds of formula (Ia);
Y is a pharmaceutically acceptable counterion:
$R^{1b}$ is one or more substituents independently selected from the group consisting of hydrogen, oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxyalkylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl; and $R^9$ is alkyl, aralkyl, haloalkyl, hydroxyalkyl, alkoxyalkyl, carboxyalkyl, alkoxycarbonylalkyl, alkylcarbonylalkyl, alkylcarbonylaminoalkyl, aminocarbonylalkyl, monoalkylaminocarbonylalkyl, dialkylaminocarbonylalkyl, hetereocyclylalkyl, or cycloalkylalkyl;

as a single stereoisomer or a mixture thereof; or a pharmaceutically acceptable salt thereof.

In another aspect, this invention provides a pharmaceutical composition useful in treating an inflammatory disorder, which composition comprises a therapeutically effective amount of a compound of formula (Ic) as described above, and a pharmaceutically acceptable excipient.

In another aspect, this invention provides a method of treating an inflammatory disorder in a human, which method comprises administration to a human in need thereof of such treatment of a therapeutically effective amount of a compound of formula (Ic) as described above.

In another aspect, this invention provides compounds of the following formula (Id):

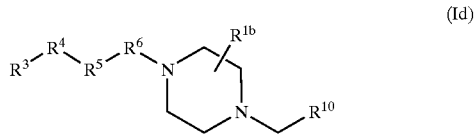
(Id)

wherein:
$R^3$, $R^4$, $R^5$ and $R^6$ are the same as described above for the compounds of formula (Ia);
$R^{1b}$ is one or more substituents independently selected from the group consisting of oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl; and $R^{10}$ is a heterocyclyl optionally substituted by one or more substituents selected from the group consisting of hydroxy, mercapto, halo, alkyl, alkenyl, alkynyl, phenyl, phenylalkyl, phenylalkenyl, alkoxy, phenoxy, phenylalkoxy, haloalkyl, haloalkoxy, formyl, nitro, cyano, amidino, cycloalkyl, hydroxyalkyl, alkoxyalkyl, phenoxyalkyl, phenylalkoxyalkyl, amino, monoalkylamino, dialkylamino, monophenylamino, monophenylalkylamino, aminoalkyl, monoalkylaminoalkyl, dialkylaminoalkyl, monophenylaminoalkyl, monophenylalkylaminoalkyl, carboxy, alkoxycarbonyl, phenylcarbonyl, benzylcarbonyl, alkylcarbonyl, carboxyalkyl, alkoxycarbonylalkyl, aminocarbonyl, monoalkylaminocarbonyl, dialkylaminocarbonyl, phenylaminocarbonyl, aminocarbonylalkyl, monoalkylaminocarbonylalkyl, dialkylaminocarbonylalkyl, ureido, monoalkylureido, monophenylureido, and monobenzylureido;

as a single stereoisomer or a mixture thereof; or a pharmaceutically acceptable salt thereof.

In another aspect, this invention provides a pharmaceutical composition useful in treating an inflammatory disorder in a human in need of such treatment, which composition comprises a therapeutically effective amount of a compound of formula (Id), as described above, and a pharmaceutically acceptable excipient.

In another aspect, this invention provides a method of treating an inflammatory disorder in a human, which method comprises administering to a human in need of such treatment a therapeutically effective amount of a compound of formula (Id) as described above.

DETAILED DESCRIPTION OF THE INVENTION

Definitions

As used in the specification and appended claims, unless specified to the contrary, the following terms have the meaning indicated:

"Alkyl" refers to a straight or branched chain monovalent or divalent radical consisting solely of carbon and hydrogen, containing no unsaturation and having from one to eight carbon atoms, e.g., methyl, ethyl, n-propyl, 1-methylethyl (iso-propyl), n-butyl, n-pentyl, 1,1-dimethylethyl (t-butyl), n-heptyl, and the like.

"Alkylcarbonyl" refer to a radical of the formula —C(O)—$R_a$ where $R_a$ is an alkyl radical as defined above, e.g., acetyl, ethylcarbonyl, n-propylcarbonyl, and the like.

"Alkylcarbonylalkyl" refers to a radical of the formula —$R_a$—C(O)—$R_a$ where each $R_a$ is independently an alkyl radical as defined above, e.g., (acetyl)methyl, 2-(acetyl)ethyl, 4-(ethylcarbonyl)butyl, and the like.

"Alkylcarbonylamino" refers to a radical of the formula —N(H)—C(O)—$R_a$ where $R_a$ is an alkyl radical as defined above, e.g., acetylamino, ethylcarbonylamino, n-propylcarbonylamino, and the like.

"(Alkylcarbonyl)(alkyl)amino" refers to a radical of the formula —N($R_a$)—C(O)—$R_a$ where each $R_a$ is independently an alkyl radical as defined above, e.g., N-methyl-N-acetylamino, N-ethyl-N-(ethylcarbonyl)amino, and the like.

"Alkylcarbonylaminoalkyl" refers to a radical of the formula —$R_a$—N(H)C(O)—$R_a$ where each $R_a$ is independently an alkyl radical as defined above, e.g., acetylaminomethyl, 2-(acetylamino)ethyl, 4-(ethylcarbonylamino)butyl, and the like.

"(Alkylcarbonyl)(alkyl)aminoalkyl" refers to a radical of the formula —$R_a$—N($R_a$)—C(O)—$R_a$ where each $R_a$ is independently an alkyl radical as defined above, e.g., (N-methyl-N-acetylamino)methyl, 2-(N-ethyl-N-(ethylcarbonyl)amino)propyl, and the like.

"Alkylthio" refers to a radical of the formula —S—$R_a$ where $R_a$ is an alkyl radical as defined above, e.g., methylthio, ethylthio, n-propylthio, and the like.

"Alkylsulfinyl" refers to a radical of the formula —S(O)$R_a$ where $R_a$ is an alkyl radical as defined above, e.g., methylsulfinyl, ethylsulfinyl, n-propylsulfinyl, and the like.

"Alkylsulfonyl" refers to a radical of the formula —S(O)$_2R_a$ where $R_a$ is an alkyl radical as defined above, e.g., methylsulfonyl, ethylsulfonyl, n-propylsulfonyl, and the like.

"Alkylthioalkyl" refers to a radical of the formula —$R_a$—S—$R_a$ where each $R_a$ is independently an alkyl radical as defined above, e.g., methylthiomethyl, 2-methylthioethyl, 2-ethylthiopropyl, and the like.

"Alkylsulfinylalkyl" refers to a radical of the formula —$R_a$—S(O)—$R_a$ where each $R_a$ is independently an alkyl radical as defined above, e.g., methylsulfinylmethyl, 2-methylsulfinylethyl, 2-ethylsulfinylpropyl, and the like.

"Alkylsulfonylalkyl" refers to a radical of the formula —$R_a$—S(O)$_2$—$R_a$ where each $R_a$ is independently an alkyl radical as defined above, e.g., methylsulfonylmethyl, 2-methylsulfonylethyl, 2-ethylsulfonylpropyl, and the like.

"Alkylsulfonylamino" refers to a radical of the formula —N(H)—S(O)$_2$—$R_a$ where $R_a$ is an alkyl radical as defined above, e.g., methylsulfonylamino, ethylsulfonylamino, iso-propylsulfonylamino, and the like.

"Alkylsulfonylaminoalkyl" refers to a radical of the formula —$R_a$—N(H)—S(O)$_2$—$R_a$ where each $R_a$ is independently an alkyl radical as defined above, e.g., methylsulfonylaminomethyl, 2-(ethylsulfonylamino)ethyl, 3-(iso-propylsulfonylamino)propyl, and the like.

"(Alkylsulfonyl)(alkyl)aminoalkyl" refers to a radical of the formula —$R_a$—N($R_a$)—S(O)$_2$—$R_a$ where each $R_a$ is independently an alkyl radical as defined above, e.g., (methylsulfonyl)(methyl)aminomethyl, 2-((ethylsulfonyl)(methyl)amino)ethyl, 3-((iso-propylsulfonyl)(ethyl)amino)propyl, and the like.

"Alkenyl" refers to a straight or branched chain monovalent or divalent radical consisting solely of carbon and hydrogen, containing at least one double bond and having from two to eight carbon atoms, e.g., ethenyl, prop-1-enyl, but-1-enyl, pent-1-enyl, penta-1,4-dienyl, and the like.

"Alkenylcarbonylamino" refers to a radical of the formula —N(H)—C(O)—$R_c$ where $R_c$ is an alkenyl radical as defined above, e.g., ethenylcarbonylamino, prop-2-enylcarbonylamino, but-2-enylcarbonylamino, and the like.

"Alkynyl" refers to a straight or branched chain monovalent or divalent radical consisting solely of carbon and hydrogen, containing at least one triple bond and having from two to eight carbon atoms, e.g., ethynyl, prop-1-ynyl, but-1-ynyl, pent-1-ynyl, pent-3-ynyl, and the like.

"Alkoxy" refers to a radical of the formula —O$R_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkoxycarbonyl" refers to a radical of the formula —C(O)O$R_a$ where $R_a$ is an alkyl radical as defined above, e.g., methoxycarbonyl, ethoxycarbonyl, n-propoxycarbonyl, and the like.

"Alkoxycarbonylalkyl" refers to a radical of the formula —$R_a$—C(O)O$R_a$ where each $R_a$ is independently an alkyl radical as defined above, e.g., methoxycarbonylmethyl, 2-(ethoxycarbonyl)ethyl, 2-(methoxycarbonyl)propyl, and the like.

"Alkoxyalkylcarbonyloxyalkyl" refers to a radical of the formula —$R_a$—OC(O)—$R_a$—O$R_a$ where each $R_a$ is independently an alkyl radical as defined above, e.g., methoxymethylcarbonyloxymethyl, 2-(2-(2-(ethoxy)ethylcarbonyloxy)ethyl)ethyl, 2-(3-(2-(ethoxy)ethylcarbonyloxy)propyl)ethyl, and the like.

"Alkoxycarbonylamino" refers to a radical of the formula —N(H)—C(O)—O$R_a$ where $R_a$ is an alkyl radical as defined above, e.g., methoxycarbonylamino, ethoxycarbonylamino, isopropoxycarbonylamino, and the like.

"(Alkoxycarbonyl)(alkyl)amino" refers to a radical of the formula —N($R_a$)(C(O)O$R_a$) where each $R_a$ is independently an alkyl radical as defined above, e.g., N-methyl-N-methoxycarbonylamino, N-ethyl-N-ethoxycarbonylamino, and the like.

"Alkoxycarbonylaminoalkyl" refers to a radical of the formula —$R_a$—N(H)—C(O)—O$R_a$ where each $R_a$ is independently an alkyl radical as defined above, e.g., methoxycarbonylaminomethyl, 2-(ethoxycarbonylamino)ethyl, isopropoxycarbonylaminomethyl, and the like.

"(Alkoxycarbonyl)(alkyl)aminoalkyl" refers to a radical of the formula —$R_a$—N($R_a$)(C(O)O$R_a$) where each $R_a$ is independently an alkyl radical as defined above, e.g., N-methyl-N-methoxycarbonylaminomethyl, 2-(N-ethyl-N-ethoxycarbonylamino)ethyl, and the like.

"(Alkoxy)aralkyl" refers to an aralkyl radical wherein the alkyl group therein is substituted by an alkoxy radical as defined above, e.g., 2-phenyl-1-methoxyethyl, phenyl(methoxy)methyl, and the like.

"Alkoxyalkylcarbonylamino" refers to a radical of the formula —N(H)—C(O)—$R_a$—O—$R_a$ where each $R_a$ is an alkyl radical as defined above, e.g., methoxymethylcarbonylamino, ethoxyethylcarbonylamino, methoxyethylcarbonylamino, and the like.

"Alkoxycarbonylalkylcarbonylamino" refers to a radical of the formula —N(H)—C(O)—$R_a$—C(O)O$R_a$ where each $R_a$ is independently an alkyl radical as defined above, e.g., ethoxycarbonylmethylcarbonylamino, methoxycarbonylmethylcarbonylamino, (2-ethoxycarbonylethyl)carbonylamino, (2-methoxycarbonylethyl)carbonylamino, and the like.

"Alkoxycarbonylalkylcarbonylaminoalkyl" refers to a radical of the formula —$R_a$—N(H)—C(O)—$R_a$—C(O)O$R_a$ where each $R_a$ is independently an alkyl radical as defined above, e.g., ethoxycarbonylmethylcarbonylaminomethyl, 2-(methoxycarbonylmethylcarbonylamino)ethyl, 1-((2-ethoxycarbonylethyl)carbonylamino)ethyl, (2-methoxycarbonylethyl)carbonylaminomethyl, and the like.

"(Alkoxycarbonylalkyl)aminocarbonyl" refers to a radical of the formula —C(O)—N(H)—$R_a$—C(O)—O$R_a$ where each $R_a$ is independently an alkyl radical as defined above, e.g., (methoxycarbonylmethyl)aminocarbonyl, (2-(ethoxycarbonyl)ethyl)aminocarbonyl, (1-(methoxycarbonyl)ethyl)aminocarbonyl, and the like.

"(Alkoxycarbonylalkyl)ureidoalkyl" refers to a radical of the formula —$R_a$—N(H)—C(O)—N(H)—$R_a$—C(O)—O$R_a$ where each $R_a$ is independently an alkyl radical as defined above and where the nitrogen to which —$R_a$—C(O)—O$R_a$ is attached is indicated as "N'", e.g., (ethoxycarbonylmethyl)ureidomethyl, (2-(ethoxycarbonyl)ethyl)ureidomethyl, 2-((2-(ethoxycarbonyl)ethyl)ureido)ethyl, and the like.

"(Alkoxycarbonylalkylcarbonyl)(alkyl)glycinamido" refers to a radical of the formula —N(H)—C(O)—CH$_2$—N($R_a$—C(O)—$R_a$—C(O)—O$R_a$ where each $R_a$ is independently an alkyl radical as defined above, e.g., (methoxycarbonylmethylcarbonyl)(methyl)glycinamido, ((2-ethoxycarbonylethyl)carbonyl)(ethyl)glycinamido, and the like.

"(Alkoxyalkylcarbonyl)glycinamido" refers to a radical of the formula —N(H)—C(O)—CH$_2$—N(H)—C(O)—$R_a$—O—$R_a$ where each $R_a$ is independently an alkyl radical as defined above, e.g., (methoxyacetyl)glycinamido, (ethoxyacetyl)glycinamido, and the like.

"Alkylene chain" refers to straight or branched chain divalent radical consisting solely of carbonyl and hydrogen, containing no unsaturation and having from one to eight carbon atoms, e.g., methylene, ethylene, propylene, n-butylene, and the like.

"Alkylidene chain" refers to a straight or branched chain unsaturated divalent radical consisting solely of carbon and hydrogen atoms, having from one to eight carbon atoms, wherein the unsaturation is present only as double bonds and wherein a double bond can exist between the first carbon of the chain and the rest of the molecule, e.g., ethylidene, propylidene, n-butylidene, and the like.

"Amino" refers to the radical —NH$_2$.

"Aminoalkyl" refers to a radical of the formula —$R_a$NH$_2$ where $R_a$ is an alkyl radical as defined above, e.g., aminomethyl, 2-aminoethyl, 3-aminopropyl, 2-aminopropyl, and the like.

"Aminoalkylamino" refers to a radical of the formula —N(H)—$R_a$—NH$_2$ where $R_a$ is an alkyl radical as defined above, e.g., aminomethylamino, (2-aminoethyl)amino, (2-aminopropyl)amino, and the like.

"Aminoalkoxy" refers to a radical of a formula —O$R_a$—NH$_2$ where $R_a$ is an alkyl radical as defined above, e.g., aminomethoxy, 2-aminoethoxy, 3-aminopropoxy, 2-aminopropoxy, 4-aminobutoxy, and the like.

"Aminocarbonyl" refers to the radical —C(O)NH$_2$.

"Aminocarbonylglycinamido" refers to a radical of the formula —N(H)—C(O)—CH$_2$—N(H)—C(O)—NH$_2$.

"(Aminocarbonyl)(alkyl)glycinamido" refers to a radical of the formula —N(H)—C(O)—CH$_2$—N($R_a$)—C(O)—NH$_2$ where $R_a$ is an alkyl radical as defined above and where the nitrogen with the $R_a$ substituent is designated as "N'", e.g., (aminocarbonyl)(N'-methyl)glycinamido, (aminocarbonyl)(N'-ethyl)glycinamido, and the like.

"Aminocarbonylalkyl" refers to a radical of the formula —$R_a$—C(O)NH$_2$ where $R_a$ is an alkyl radical as defined above, e.g., aminocarbonylmethyl, 2-(aminocarbonyl)ethyl, 2-(aminocarbonyl)propyl, and the like.

"(Aminocarbonylalkyl)aminocarbonyl" refers to a radical of the formula —C(O)—N(H)—$R_a$—C(O)—NH$_2$ where $R_a$ is an alkyl radical as defined above, e.g., (aminocarbonylmethyl)aminocarbonyl, (2-aminocarbonylethyl)aminocarbonyl, (1-aminocarbonylethyl)aminocarbonyl, and the like.

"(Aminoalkyl)aminocarbonyl" refers to a radical of the formula —C(O)—N(H)—$R_a$—NH$_2$ where $R_a$ is an alkyl radical as defined above, e.g., (aminomethyl)aminocarbonyl, (2-aminoethyl)aminocarbonyl, (1-aminoethyl)aminocarbonyl, and the like.

"Amidino" refers to the radical —C(NH)NH$_2$.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of hydroxy, mercapto, halo, alkyl, alkenyl, alkynyl, phenyl, phenylalkyl, phenylalkenyl, alkoxy, phenoxy, phenylalkoxy, haloalkyl, haloalkoxy, formyl, nitro, cyano, amidino, cycloalkyl, hydroxyalkyl, alkoxyalkyl, phenoxyalkyl, phenylalkoxyalkyl, amino, monoalkylamino, dialkylamino, monophenylamino, monophenylalkylamino, aminoalkyl, monoalkylaminoalkyl, dialkylaminoalkyl, monophenylaminoalkyl, monophenylalkylaminoalkyl, alkylcarbonyl, carboxy, alkoxycarbonyl, carboxyalkyl, alkoxycarbonylalkyl, aminocarbonyl, monoalkylaminocarbonyl, dialkylaminocarbonyl, aminocarbonylalkyl, monoalkylaminocarbonylalkyl, dialkylaminocarbonylalkyl, as defined herein.

"Arylcarbonyl" refers to a radical of the formula —C(O)$R_b$ where $R_b$ is an aryl radical as defined above, e.g., phenylcarbonyl and naphthalen-2-ylcarbonyl, and the like.

"Arylcarbonylalkyl" refers to a radical of the formula —$R_aC(O)R_b$ where $R_a$ is an alkyl radical as defined above and $R_b$ is an aryl radical as defined above, e.g., phenylcarbonylmethyl, 2-(phenylcarbonyl)ethyl, 3-(naphthalen-2-ylcarbonyl)propyl, and the like.

"Arylcarbonylaminoalkyl" refers to a radical of the formula —$R_a$—N(H)—C(O)—$R_b$ where $R_a$ is an alkyl radical as defined above and $R_b$ is an aryl radical as defined above, e.g., (4-methoxyphenyl)carbonylaminomethyl, 2-((4-fluorophenyl)carbonylamino)ethyl, 1-((4-chlorophenyl)carbonylamino)ethyl, and the like.

"Arylsulfonyl" refers to a radical of the formula —S(O)$_2$—$R_b$ where $R_b$ is an aryl radical as defined above, e.g., phenylsulfonyl, (4-chlorophenyl)sulfonyl, (3-nitrophenyl)sulfonyl, and the like.

"Arylsulfonylamino" refers to a radical of the formula —N(H)—S(O)$_2$—$R_b$ where $R_b$ is an aryl radical as defined above, e.g., phenylsulfonylamino, (4-chlorophenyl)sulfonylamino, (4-fluorophenyl)sulfonylamino, (3-nitrophenyl)sulfonylamino), and the like.

"Arylsulfonylaminoalkyl" refers to a radical of the formula —$R_a$—N(H)—S(O)$_2$—$R_b$ where $R_a$ is an alkyl radical as defined above and $R_b$ is an aryl radical as defined above, e.g., phenylsulfonylaminomethyl, (4-chlorophenyl)sulfonylaminomethyl, 2-((4-fluorophenyl)sulfonylamino)ethyl, 1-((3-nitrophenyl)sulfonylamino)ethyl, and the like.

"(Arylsulfonyl)(alkyl)aminoalkyl" refers to a radical of the formula —$R_a$—N($R_a$)—S(O)$_2$—$R_b$ where each $R_a$ is independently an alkyl radical as defined above and $R_b$ is an aryl radical as defined above, e.g., (phenylsulfonyl)(methyl)aminomethyl, ((4-chlorophenyl)sulfonyl)(ethyl)aminomethyl, 2-(((4-fluorophenyl)sulfonyl)(methyl)amino)ethyl, 1-(((3-nitrophenyl)sulfonyl)(ethyl)amino)ethyl, and the like.

"(Alkoxycarbonylaminoalkylcarbonyl)glycinamido" refers to a radical of the formula —N(H)—C(O)—CH$_2$—N(H)—C(O)—N(H)—C(O)—O$R_a$ where $R_a$ is an alkyl radical as defined above, e.g., (ethoxycarbonylaminocarbonyl)glycinamido, (methoxycarbonylaminocarbonyl)glycinamido, and the like.

"Arylcarbonylglycinamido" refers to a radical of the formula —N(H)—C(O)—CH$_2$—N(H)—C(O)—$R_b$ where $R_b$ is an aryl radical as defined above, e.g., phenylcarbonylglycinamido, (4-fluoro-3-trifluoromethylphenyl)carbonylglycinamido, (4-fluorophenyl)carbonylglycinamido, and the like.

"(Arylcarbonyl)(alkyl)glycinamido" refers to a radical of the formula —N(H)—C(O)—CH$_2$—N($R_a$)—C(O)—$R_b$ where $R_a$ is an alkyl radical as defined above and $R_b$ is an aryl radical as defined above and the nitrogen to which the $R_a$ radical is attached is designated as "N", e.g., (phenylcarbonyl)(N'-methyl)glycinamido, ((4-fluoro-3-trifluoromethylphenyl)carbonyl)(N'-ethyl)glycinamido, ((4-fluorophenyl)carbonyl)(N'-methyl)glycinamido, and the like.

"Aralkyl" refers to a radical of the formula —$R_aR_b$ where $R_a$ is an alkyl radical as defined above and $R_b$ is an aryl radical as defined above, e.g., benzyl, and the like.

"Aralkylcarbonyl" refers to a radical of the formula —C(O)—$R_d$ where $R_d$ is an aralkyl radical as defined above, e.g., benzylcarbonyl, 1-(phenyl)ethylcarbonyl, and the like.

"Aralkylcarbonylalkyl" refers to a radical of the formula —$R_aC(O)R_d$ where $R_a$ is an alkyl radical as defined above and $R_d$ is an aralkyl radical as defined above, e.g., benzylcarbonylmethyl, 2-(1-(phenyl)ethylcarbonyl)ethyl, and the like.

"Aralkenyl" refers to a radical of the formula —$R_cR_b$ where $R_b$ is an aryl radical as defined above and $R_c$ is an alkenyl radical as defined above, e.g., 3-phenylpropylid-1-enyl, and the like.

"Aryloxy" refers to a radical of the formula —O$R_b$ where $R_b$ is an aryl radical as defined above, e.g., phenoxy and naphthoxy, and the like.

"Aralkoxycarbonyl" refers to a radical of the formula —C(O)O$R_d$ where $R_d$ is an aralkyl radical as defined above, e.g., benzyloxycarbonyl, and the like.

"Aralkoxycarbonylalkyl" refers to a radical of the formula —$R_aC(O)OR_d$ where $R_a$ is an alkyl radical as defined above and $R_d$ is an aralkyl radical as defined above, e.g., benzyloxycarbonylmethyl, 2-(benzyloxycarbonyl)ethyl, 3-((naphthalen-2-yl)oxy)carbonyl)propyl, and the like.

"Aryloxyalkyl" refers to a radical of the formula —$R_a$—O$R_b$ where $R_a$ is an alkyl radical as defined above and $R_b$ is an aryl radical as defined above, e.g., phenoxymethyl, 2-(phenoxy)ethyl, 3-(phenoxy)propyl, and the like.

"Aryloxyalkylcarbonyloxyalkyl" refers to a radical of the formula —$R_a$—OC(O)—$R_a$—O$R_b$ where each $R_a$ is independently an alkyl radical as defined above and $R_b$ is an aryl radical as defined above, e.g., phenoxymethylcarbonyloxymethyl, (2-phenoxyethyl)carbonyloxymethyl, 3-((2-phenoxyethyl)carbonyloxy)propyl, and the like.

"Aralkoxy" refers to a radical of the formula —O$R_d$ where $R_d$ is an aralkyl radical as defined above, e.g., benzyloxy, and the like.

"Aralkoxyalkyl" refers to a radical of the formula —$R_a$—O$R_d$ where $R_a$ is an alkyl radical as defined above and $R_d$ is an aralkyl radical as defined above, e.g., benzyloxymethyl, 2-phenylethoxymethyl, and the like.

"Aralkoxyalkylcarbonyloxyalkyl" refers to a radical of the formula —$R_a$—OC(O)—$R_a$—O$R_d$ where each $R_a$ is independently an alkyl radical as defined above and $R_d$ is an aralkyl radical as defined above, e.g., benzyloxymethylcarbonyloxymethyl, (2-(phenyl)ethoxymethyl)-carbonyloxymethyl, 2-((2-(phenyl)ethoxymethyl)carbonyloxy)ethyl, and the like.

"Alkoxyalkyl" refers to a radical of the formula —$R_aOR_a$ where each $R_a$ is independently an alkyl radical as defined above, e.g., methoxyethyl, ethoxymethyl, propoxymethyl, propoxyethyl, and the like.

"Alaninamido" refers to a radical of the formula —N(H)—C(O)—C(CH$_3$)H—NH$_2$.

"Alanimamidoalkyl" refers to a radical of the formula —$R_a$—N(H)—C(O)—C(CH$_3$)H—NH$_2$ where $R_a$ is an alkyl radical as defined above, e.g., alaninamidomethyl, 2-(alaninamido)ethyl, 1-(alaninamido)ethyl, 3-(alaninamido)propyl, and the like.

"Azidoalkyl" refers to radical of the formula —$R_a$—N$_3$ where $R_a$ is an alkyl radical as defined above, e.g., 2-azidoethyl, 3-azidopropyl, 2-azidopropyl, 4-azidobutyl, and the like.

"Benzyl" refers to a radical of the formula —CH$_2$—$R_h$ where $R_h$ is a phenyl radical optionally substituted by one or more substituents selected from the group consisting of hydroxy, halo, alkyl, haloalkyl, alkoxy, alkenyl, nitro, cyano, amino, monoalkylamino, dialkylamino, alkylcarbonyl, carboxy, alkoxycarbonyl, and aminocarbonyl.

"Benzylcarbonyl" refers to a radical of the formula —C(O)—CH$_2$—R$_h$ where R$_h$ is a phenyl radical as defined above, e.g., (4-methoxybenzyl)carbonyl, (3-fluorobenzyl) carbonyl, and the like.

"Carboxy" refers to the radical —C(O)OH.

"Carboxyalkyl" refers to the radical of the formula —R$_a$—C(O)OH where R$_a$ is an alkyl radical as defined above, e.g., carboxymethyl, 2-carboxyethyl, 3-carboxypropyl, and the like.

"(Carboxyalkyl)aminocarbonyl" refers to a radical of the formula —C(O)—N(H)—R$_a$—C(O)OH where R$_a$ is an alkyl radical as defined above, e.g., (carboxymethyl) aminocarbonyl, (2-carboxyethyl)aminocarbonyl, (1-carboxyethyl)aminocarbonyl, and the like.

"Carbocyclic ring system" refers to a stable 3- to 15-membered ring radical consisting solely of carbon and hydrogen atoms. For purposes of this invention, the carbocyclic ring system radical may be a monocyclic, bicyclic or tricyclic ring system, and may include fused or bridged ring systems, and the ring system may be partially or fully saturated or aromatic, and the carbon atoms in the ring system may be optionally oxidized. Examples of such carbocyclic ring system radicals include, but are not limited to, cyclopropyl, cyclobutyl, cyclohexyl, norbornane, norbornene, adamantyl, bicyclo[2.2.2]octane, phenyl, naphthyl, indenyl, azulenyl, fluorenyl, anthracenyl, and the like.

"Cycloalkyl" refers to a stable 3- to 10-membered monocyclic or bicyclic radical which is saturated, and which consist solely of carbon and hydrogen atoms, e.g., cyclopropyl, cyclobutyl, cyclobutyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, halo, hydroxy, amino, nitro, alkoxy, carboxy, phenyl and alkoxycarbonyl.

"Cycloalkylalkyl" refers to a radical of the formula —R$_a$—R$_e$ where R$_a$ is an alkyl radical as defined above and R$_e$ is a cycloalkyl radical as defined above, e.g., cyclopropylmethyl, 2-cyclobutylethyl, 3-cyclohexylpropyl, and the like.

"Cycloalkylamino" refers to a radical of the formula —N(H)—R$_e$ where R$_e$ is a cycloalkyl radical as defined above, e.g., cyclopropylamino, cyclobutylamino, cyclohexylamino, and the like.

"Cycloalkylaminoalkyl" refers to a radical of the formula —R$_a$—N(H)—R$_e$ where R$_a$ is an alkyl radical as defined above and R$_e$ is a cycloalkyl radical as defined above, e.g., cyclopropylaminomethyl, 2-(cyclobutylamino)ethyl, cyclohexylaminomethyl, and the like.

"(Cycloalkylalkyl)amino" refers to a radical of the formula —N(H)—R$_a$—R$_e$ where R$_a$ is an alkyl radical as defined above and R$_e$ is a cycloalkyl radical as defined above, e.g., (cyclopropylmethyl)amino, (2-cyclobutylethyl) amino, (3-cyclohexylpropyl)amino, and the like.

"(Cycloalkylalkyl)aminoalkyl" refers to a radical of the formula —R$_a$—N(H)—R$_a$—R$_e$ where each R$_a$ is independently an alkyl radical as defined above and R$_e$ is a cycloalkyl radical as defined above, e.g., (cyclopropylmethyl)aminomethyl, 2-((2-cyclobutylethyl) amino)ethyl, (3-cyclohexylpropyl)aminomethyl, and the like.

"Cycloalkylcarbonylamino" refers to a radical of the formula —C(O)—N(H)—R$_e$ where R$_e$ is a cycloalkyl radical as defined above, e.g., cyclopropylcarbonylamino, (2-phenylcyclopropyl)carbonylamino, cyclohexylcarbonylamino, 4-cyanodecalinylcarbonylamino, cyclopentylcarbonylamino, and the like.

"Cycloalkylcarbonylaminoalkyl" refers to a radical of the formula —R$_a$—C(O)—N(H)—R$_e$ where R$_a$ is an alkyl radical as defined above and R$_e$ is a cycloalkyl radical as defined above, e.g., cyclopropylcarbonylaminomethyl, 2-((2-phenylcyclopropyl)carbonylamino)ethyl, 1-(cyclohexylcarbonylamino)ethyl, (3-phenylcyclopentyl) carbonylaminomethyl, and the like.

"Cycloalkylalkylcarbonylamino" refers to a radical of the formula —C(O)—N(H)—R$_a$—R$_e$ where R$_a$ is an alkyl radical as defined above and R$_e$ is a cycloalkyl radical as defined above, e.g., (cyclopropylmethyl)carbonylamino, ((2-phenylcyclopropyl)methyl)carbonylamino, (2-cyclohexylethyl)carbonylamino, (1-cyclohexylethyl) carbonylamino, and the like.

"Cyano" refers to the radical —CN.

"Cyanoalkyl" refers to a radical of the formula —R$_a$CN where R$_a$ is an alkyl radical as defined above, cyanomethyl, 2-(cyano)ethyl, 3-(cyano)propyl, and the like.

"DMF" refers to N,N-dimethylformamide.

"DMSO" refers to dimethylsulfoxide.

"Dialkylamino" refers to a radical of the formula —N(R$_a$)R$_a$ where each R$_a$ is independently an alkyl radical as defined above, e.g., dimethylamino, methylethylamino, diethylamino, dipropylamino, ethylpropylamino, and the like.

"Dialkylaminoalkyl" refers to a radical of the formula —R$_a$—N(R$_a$)R$_a$ where each R$_a$ is independently an alkyl radical as defined above, e.g., dimethylaminomethyl, methyethylaminomethyl, 2-diethylaminoethyl, 3-dipropylaminopropyl, and the like.

"Dialkylaminocarbonyl" refers to a radical of the formula —C(O)N(R$_a$)R$_a$ where each R$_a$ is independently an alkyl radical as defined above, e.g., dimethylaminocarbonyl, methylethylaminocarbonyl, diethylaminocarbonyl, dipropylaminocarbonyl, ethylpropylaminocarbonyl, and the like.

"Dialkylaminocarbonylalkyl" refers to a radical of the formula —R$_a$—C(O)N(R$_a$)R$_a$ where each R$_a$ is independently an alkyl radical as defined above, e.g., dimethylaminocarbonylmethyl, 2-(methylethylaminocarbonyl)ethyl, 3-(diethylaminocarbonyl)propyl, 2-(dipropylaminocarbonyl)propyl, and the like.

"Dialkylaminocarbonyloxyalkyl" refers to a radical of the formula —R$_a$—O—C(O)—N(R$_a$)R$_a$ where each R$_a$ is independently an alkyl radical as defined above, e.g, dimethylaminocarbonyloxymethyl, 2-(methylethylaminocarbonyloxy)ethyl, 3-(diethylaminocarbonyloxy)propyl, 2-(dipropylaminocarbonyloxy)propyl, and the like.

"Dialkylureido" refers to a radical of the formula —N(H)—C(O)—N(R$_a$)(R$_a$) or a radical of the formula —N(R$_a$)—C(O)—N(R$_a$)H where each R$_a$ is independently an alkyl radical as defined above and the attaching nitrogen is designated as "N" and the other nitrogen is designated as "N'", e.g., N',N'-di(methyl)ureido, N'-methyl-N'-ethylureido, N',N'-di(ethyl)ureido, N',N'-di(propyl)ureido, N-methyl-N'-ethylureido, and the like.

"Diarylureido" refers to a radical of the formula —N(H)—C(O)—N(R$_b$)(R$_b$) or a radical of the formula —N(R$_b$)—C(O)—N(R$_b$)H where each R$_b$ is independently an aryl radical as defined above and the attaching nitrogen is designated as "N" and the other nitrogen is designated as "N'", e.g., N',N'-di(phenyl)ureido, N'-phenyl-N'-(3-nitro)phenylureido, N',N'-di(4-methoxyphenyl)ureido, N',N'-di(4-chlorophenyl)ureido, N-4-chlorophenyl-N'-(3-chlorophenyl)ureido and the like.

"Dialkylureidoalkyl" refers to a radical of the formula —R$_a$—N(H)—C(O)—N(R$_a$)(R$_a$) or a radical of the formula —R$_a$—N(R$_a$)—C(O)—N(R$_a$)H where each R$_a$ is independently an alkyl radical as defined above and the attached nitrogen is designated as "N" and the other nitrogen is designated as "N'", e.g., N',N'-di(methyl)ureidomethyl, 2-(N'-methyl-N'-ethylureido)ethyl, 1-(N',N'-di(ethyl)ureido)ethyl, 3-(N',N'-di(propyl)ureido)propyl, 2-(N-methyl-N'-ethylureido)ethyl, and the like.

"Formyl" refers to the radical —C(O)H.

"Formylalkyl" refers to a radical —R$_a$—C(O)H where R$_a$ is an alkyl radical as defined above, e.g., formylmethyl, 2-(formyl)ethyl, 3-(formyl)propyl, and the like.

"Glycinamido" refers to a radical of the formula —N(H)—C(O)—CH$_2$—NH$_2$.

"Glycinamidoalkyl" refers to a radical of the formula —R$_a$—N(H)—C(O)—CH$_2$—NH$_2$ where R$_a$ is an alkyl radical as defined above, e.g., glycinamidomethyl, 2-(glycinamido)ethyl, 1-(glycinamido)ethyl, 3-(glycinamido)propyl, and the like.

"Guanidino" refers to the radical —N(H)—C(NH)—NH$_2$.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —OR$_f$ where R$_f$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Haloalkylcarbonylamino" refers to a radical of the formula —N(H)—C(O)—R$_f$ where R$_f$ is an haloalkyl radical as defined above, e.g., trifluoromethylcarbonylamino, trifluoromethylcarbonylamino, 2-bromoethylcarbonylamino, and the like.

"(Haloalkylcarbonyl)ureido" refers to a radical of the formula —N(H)—C(O)—N(H)—C(O)—R$_f$ where R$_f$ is a haloalkyl radical as defined above, e.g., (trichloromethylcarbonyl)ureido, (3-fluoropropylcarbonyl)ureido, and the like.

"(Haloalkyl)(alkyl)ureidoalkyl" refers to a radical of the formula —R$_a$—N(R$_a$)—C(O)—N(H)—R$_f$ or a a radical of the formula —R$_a$—N(R$_f$)—C(O)—N(H)—R$_a$ or a radical of the formula —R$_a$—N(H)—C(O)—N(R$_a$)R$_f$ where each R$_a$ is independently an alkyl radical as defined above and R$_f$ is an haloalkyl radical as defined above and terminal nitrogen is designated as "N" and the other nitrogen is designated as "N'", e.g., N'-(2-chloroethyl)-N-(methyl)ureidomethyl, and 2-(N'-(2-chloroethyl)-N-(methyl)ureido)ethyl, and the like.

"Haloalkylcarbonylaminoalkyl" refers to a radical of the formula —R$_a$—N(H)—C(O)—R$_f$ where R$_a$ is an alkyl radical as defined above and R$_f$ is an haloalkyl radical as defined above, e.g., trifluoromethylcarbonylaminomethyl, 2-(trifluoromethylcarbonylamino)ethyl, and the like.

"Hydroxy" refers to the radical —OH.

"Hydroxyalkyl" refers to a alkyl radical as defined above that is substituted by a hydroxy radical, e.g., hydroxymethyl, 2-hydroxyethyl, 2-hydroxypropyl, 3-hydroxypropyl, 4-hydroxybutyl, 3-hydroxybutyl, and the like.

"(Hydroxyalkyl)aminocarbonyl" refers to a radical of the formula —C(O)—N(H)—R$_a$—OH where R$_a$ is an alkyl radical as defined above, e.g., hydroxymethylaminocarbonyl, (2-hydroxyethyl)aminocarbonyl, (1-hydroxyethyl)aminocarbonyl, and the like.

"Hydroxyalkoxy" refers to a radical of the formula —OR$_a$—OH where R$_a$ is an alkyl radical as defined above, e.g., 2-hydroxyethoxy, 2-hydroxypropoxy, 4-hydroxybutoxy, 3-hydroxybutoxy, and the like.

"(Hydroxyalkoxy)carbonyl" refers to a radical of the formula —C(O)—OR$_a$—OH where R$_a$ is an alkyl radical as defined above, e.g., (2-hydroxyethoxy)carbonyl, (2-hydroxypropoxy)carbonyl, (4-hydroxybutoxy)carbonyl, (3-hydroxybutoxy)carbonyl, and the like.

"(Hydroxy)aralkyl" refers to an aralkyl radical as defined above wherein the alkyl radical therein is substituted by a hydroxy radical, e.g., (phenyl)(hydroxy)methyl, 2-phenyl-1-hydroxyethyl, 2-phenyl-3-hydroxypropyl, and the like.

"(Hydroxyalkylthio)alkyl" refers to an alkylthioalkyl radical as defined above that is substituted by an hydroxy radical, e.g., 2-hydroxyethylthiomethyl, 2-(hydroxymethylthio)ethyl, and the like.

"Hydroxyalkenyl" refers to an alkenyl radical as defined above that is substituted by a hydroxy radical, e.g., 3-hydroxyprop-1-enyl, 4-hydroxybut-1-enyl, 4-hydroxypent-1-enyl, 5-hydroxypenta-1,3-dienyl, and the like.

"Hydroxyalkynyl" refers to an alkynyl radical as defined above that is substituted by a hydroxy radical, e.g., 3-hydroxyprop-ynyl, 4-hydroxypent-2-ynyl, 1-hydroxybut-3-ynyl, and the like.

"(Hydroxy)cycloalkylalkyl" refers to a radical of the formula —R$_a$(OH)—R$_e$ where R$_a$ is an alkyl radical as defined above and R$_e$ is a cycloalkyl radical as defined above and where the OH radical is a substituent on any carbon of the R$_a$ radical, e.g., 2-cyclopropyl-1-hydroxyethyl, (4-hydroxycyclohexyl)methyl, and the like.

"Hydroxyalkylaminoalkyl" refers to a monoalkylaminoalkyl radical as defined below that is substituted by a hydroxy radical, e.g., 2-hydroxyethylaminomethyl, 2-(3-hydroxypropylamino)ethyl, and the like.

"Hydroxyamidino" refers to a radical of the formula —C(NH$_2$)=NOH.

"Heterocyclic ring system" refers to a stable 3- to 15-membered ring radical which consists of carbon atoms and from one to five heteroatoms selected from the group consisting of nitrogen, oxygen and sulfur. For purposes of this invention, the heterocyclic ring system radical may be a monocyclic, bicyclic or tricyclic ring system, which may include fused or bridged ring systems; and the nitrogen, carbon or sulfur atoms in the heterocyclic ring system radical may be optionally oxidized; the nitrogen atom may be optionally quaternized; and the heterocyclic ring system may be partially or fully saturated or aromatic. The heterocyclic ring system may be attached to the main structure at any heteroatom or carbon atom which results in the creation of a stable compound. Examples of such heterocyclic radicals include, but are not limited to, azepinyl, acridinyl, benzimidazolyl, benzothiazolyl, benzoxazolyl, benzopyranyl, benzopyranonyl, benzofuranyl, benzofuranonyl, benzothienyl, carbazolyl, cinnolinyl, decahydroisoquinolyl, dioxolanyl, furanyl, isothiazolyl, quinuclidinyl, imidazolyl, imidazolinyl, imidazolidinyl, isothiazolidinyl, indolyl, isoindolyl, indolinyl, isoindolinyl, indanyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone.

"Heterocyclyl" refers to a heterocyclic ring system as defined above. Unless stated otherwise specifically in the specification, the term "heterocyclyl" is meant to include a heterocyclic ring system as defined above which is optionally substituted by one or more substituents selected from the group consisting of hydroxy, mercapto, halo, alkyl, alkenyl, alkynyl, phenyl, phenylalkyl, phenylalkenyl, alkoxy, phenoxy, phenylalkoxy, haloalkyl, haloalkoxy, formyl, nitro, cyano, amidino, cycloalkyl, hydroxyalkyl, alkoxyalkyl, phenoxyalkyl, phenylalkoxyalkyl, amino, monoalkylamino, dialkylamino, monophenylamino, monophenylalkylamino, aminoalkyl, monoalkylaminoalkyl, dialkylaminoalkyl, monophenylaminoalkyl, monophenylalkylaminoalkyl, carboxy, alkoxycarbonyl, phenylcarbonyl, benzylcarbonyl, alkylcarbonyl, carboxyalkyl, alkoxycarbonylalkyl, aminocarbonyl, monoalkylaminocarbonyl, dialkylaminocarbonyl, phenylaminocarbonyl, aminocarbonylalkyl, monoalkylaminocarbonylalkyl, dialkylaminocarbonylalkyl, ureido, monoalkylureido, monophenylureido, monobenzylureido, as defined herein.

"Heterocyclylalkyl" refers to a radical of the formula —$R_a R_g$ where $R_a$ is an alkyl radical as defined above and $R_g$ is a heterocyclyl radical as defined above, e.g., indolinylmethyl or imidazolylmethyl, and the like.

"Heterocyclylamino" refers to a radical of the formula —N(H)—$R_g$ where $R_g$ is a heterocyclyl radical as defined above, e.g., oxazol-2-ylamino; piperidin-4-ylamino, and the like.

"Heterocyclylaminoalkyl" refers to a radical of the formula —$R_a$—N(H)—$R_g$ where $R_a$ is an alkyl radical as defined above and $R_g$ is a heterocyclyl radical as defined above, e.g., oxazol-2-ylaminomethyl, 2-(oxazol-2-ylamino)ethyl, piperidin-4-ylaminomethyl, 2-(piperidin-4-ylamino)ethyl, and the like.

"Heterocyclylcarbonylamino" refers to a radical of the formula —N(H)—C(O)—$R_g$ where $R_g$ is a heterocyclyl radical as defined above, e.g., piperidin-4-ylcarbonylamino, furan-2-ylcarbonylamino, morpholin-4-ylcarbonylamino, and the like.

"Heterocyclylcarbonylaminoalkyl" refers to a radical of the formula —$R_a$—N(H)—C(O)—$R_g$ where $R_a$ is an alkyl radical as defined above and $R_g$ is a heterocyclyl radical as defined above, e.g., piperidin-4-ylcarbonylaminomethyl, 2-(furan-2-ylcarbonylamino)ethyl, 1-(morpholin-4-ylcarbonylamino)ethyl, and the like.

"Mercapto" refers to the radical —SH.

"Mercaptoalkyl" refers to a radical of the formula —$R_a$—SH where $R_a$ is an alkyl radical as defined above, e.g., mercaptomethyl, 2-mercaptoethyl, 3-mercaptopropyl, 2-mercaptobutyl and the like.

"Monoalkylamino" refers to a radical of the formula —N(H)$R_a$ where $R_a$ is an alkyl radical as defined above, e.g., methylamino, ethylamino, propylamino, and the like.

"Monoalkylaminoalkyl" refers to a radical of the formula —$R_a$—N(H)$R_a$ where each $R_a$ is independently an alkyl radical as defined above, e.g., methylaminomethyl, ethylaminomethyl, 2-(propylamino)ethyl, and the like.

"(Monoalkylamino)aralkyl" refers to a radical of the formula —$R_d$—N(H)$R_a$ where $R_a$ is an alkyl radical a defined above and $R_d$ is an aralkyl radical as defined above, e.g., (methylamino)(phenyl)methyl, 1-(ethylamino)-1-(4-methoxyphenyl)ethyl, 2-(isopropylamino)-3-(3-chlorophenyl)propyl, and the like.

"Monoarylamino" refers to a radical of the formula —N(H)$R_b$ where $R_b$ is an aryl radical as defined above, e.g., phenylamino, (4-methoxyphenyl)amino, (3,4,5-trimethoxyphenyl)amino and the like.

"Monoarylaminoalkyl" refers to a radical of the formula —$R_a$—N(H)$R_b$ where $R_a$ is an alkyl radical as defined above and $R_b$ is an aryl radical as defined above, e.g., phenylaminomethyl, 2-((4-methoxyphenyl)amino)ethyl, 3-((3,4,5-trimethoxyphenyl)amino)propyl, and the like.

"Monoaralkylamino" refers to a radical of the formula —N(H)$R_d$ where $R_d$ is an aralkyl radical as defined above, e.g., benzylamino, (3,4,5-trimethoxybenzyl)amino, (4-chlorobenzyl)amino, and the like.

"Monoaralkylaminoalkyl" refers to a radical of the formula —$R_a$—N(H)$R_d$ where $R_a$ is an. alkyl radical as defined above and $R_d$ is an aralkyl radical as defined above, e.g., benzylaminomethyl, (3-phenylpropyl)aminomethyl, 2-(benzylamino)ethyl, and the like.

"Monoalkylaminocarbonyl" refers to a radical of the formula —C(O)N(H)$R_a$ where $R_a$ is an alkyl radical as defined above, e.g., methylaminocarbonyl, ethylaminocarbonyl, propylaminocarbonyl, and the like.

"Monoalkylaminocarbonylalkyl" refers to a radical of the formula —$R_a$—C(O)N(H)$R_a$ where each $R_a$ is independently an alkyl radical as defined above, e.g., methylaminocarbonylmethyl, 2-(ethylaminocarbonyl)ethyl, 3-(propylaminocarbonyl)propyl, and the like.

"Monoarylaminocarbonyl" refers to a radical of the formula —C(O)N(H)$R_b$ where $R_b$ is an aryl radical as defined above, e.g., phenylaminocarbonyl, (3,4,5-tris(trifluoromethoxy)phenyl)-aminocarbonyl, (4-chlorophenyl)aminocarbonyl, and the like.

"Monoarylaminocarbonylalkyl" refers to a radical of the formula —$R_a$—C(O)N(H)$R_b$ where $R_a$ is an alkyl radical as defined above and $R_b$ is an aryl radical as defined above, e.g., phenylaminocarbonylmethyl, 2-((4-chlorophenyl)aminocarbonyl)ethyl, 3-((3,4,5-trimethoxyphenyl)aminocarbonyl)propyl, and the like.

"Monoaralkylaminocarbonyl" refers to a radical of the formula —C(O)N(H)$R_d$ where $R_d$ is an aralkyl radical as defined above, e.g., benzylaminocarbonyl, (3,4,5-tris(trifluoromethoxy)benzyl)-aminocarbonyl, (4-chlorobenzyl)aminocarbonyl, and the like.

"Monoaralkylaminocarbonylalkyl" refers to a radical of the formula —$R_a$—C(O)N(H)$R_d$ where $R_a$ is an alkyl radical as defined above and $R_d$ is an aralkyl radical as defined above, e.g., benzylaminocarbonylmethyl, 2-((4-chlorobenzyl)aminocarbonyl)ethyl, 3-((3,4,5-trimethoxybenzyl)aminocarbonyl)propyl, and the like.

"(Monoalkylaminocarbonylalkyl)aminocarbonyl" refers to a radical of the formula —C(O)—N(H)—$R_a$—C(O)—N(H)$R_a$ where each $R_a$ is independently an alkyl radical as defined above, e.g., (methylaminocarbonylmethyl)aminocarbonyl, (2-(methylaminocarbonyl)ethyl)aminocarbonyl, (1-(ethylaminocarbonyl)ethyl)aminocarbonyl, and the like.

"Monoalkylalaninamido" refers to radical of the formula —N(H)—C(O)—C(CH$_3$)H—N(H)$R_a$ where $R_a$ is an alkyl radical as defined above and the attached nitrogen is designated as "N" and the other nitrogen (having the $R_a$ substituent) is designated as "N'", e.g., N'-methylalanimido, N'-ethylalanimido, and the like.

"Monoalkylglycinamido" refers to a radical of the formula —N(H)—C(O)—CH$_2$—N(H)R$_a$ where R$_a$ is an alkyl radical as defined above and the attaching nitrogen is designated as "N" and the other nitrogen (having the R$_a$ substituent) is designated as "N'", e.g., N'-methylglycinamido, N'-ethylglycinamido, and the like.

"(Monoarylaminocarbonyl)glycinamido" refers to a radical of the formula —N(H)—C(O)—CH$_2$—N(H)—C(O)—N(H)R$_b$ where R$_b$ is an aryl radical as defined above, e.g., ((4-phenoxyphenyl)aminocarbonyl)glycinamido, ((4-chlorophenyl)aminocarbonyl)glycinamido, (phenylaminocarbonyl)glycinamido, and the like.

"(Monoarylaminocarbonyl)(alkyl)glycinamido" refers to a radical of the formula —N(H)—C(O)—CH$_2$—N(R$_a$)—C(O)—N(H)R$_b$ where R$_a$ is an alkyl radical as defined above and R$_b$ is an aryl radical as defined above and the nitrogen to which R$_a$ is attached is designated as "N", e.g., ((4-phenoxyphenyl)aminocarbonyl)(N'-methyl)glycinamido, ((4-chlorophenyl)aminocarbonyl)(N'-ethyl)glycinamido, (phenylaminocarbonyl)(N'-methyl)glycinamido, and the like.

"(Monoaralkylaminocarbonyl)glycinamido" refers to a radical of the formula —N(H)—C(O)—CH$_2$—N(H)—C(O)—N(H)R$_d$ where R$_d$ is an aralkyl radical as defined above, e.g., ((4-phenoxybenzyl)aminocarbonyl)glycinamido, ((4-chlorobenzyl)aminocarbonyl)glycinamido, (benzylaminocarbonyl)glycinamido, and the like.

"(Monoaralkylaminocarbonyl)(alkyl)glycinamido" refers to a radical of the formula —N(H)—C(O)—CH$_2$—N(R$_a$)—C(O)—N(H)R$_d$ where R$_a$ is an alkyl radical as defined above and R$_d$ is an aralkyl radical as defined above and the nitrogen to which the R$_a$ is attached is designated as "N", e.g., ((4-phenoxybenzyl)aminocarbonyl)(N'-methyl)glycinamido, ((4-chlorobenzyl)aminocarbonyl)(N'-ethyl)glycinamido, (benzylaminocarbonyl)(N'-methyl)glycinamido, and the like.

"Monoalkylureido" refers to a radical of the formula —N(H)—C(O)—N(H)R$_a$ or a radical of the formula —N(R$_a$)—C(O)—NH$_2$ where R$_a$ is an alkyl radical as defined above and the attaching nitrogen is designated as "N" and the other nitrogen is designated as "N'", e.g., N'-methylureido, N'-ethylureido, N'-propylureido, N-methylureido, N-ethylureido, N-propylureido, and the like.

"Monophenylureido" refers to a radical of the formula —N(H)—C(O)—N(H)R$_h$ where R$_h$ is a phenyl radical as defined above, and the attaching nitrogen is designated as "N" and the other nitrogen is designated as "N'", e.g., N'-phenylureido, N'-(4-nitrophenyl)ureido, N'-(3-chlorophenyl)ureido, and the like.

"Monobenzylureido" refers to a radical of the formula —N(H)—C(O)—N(H)—CH$_2$—R$_h$ where R$_h$ is a phenyl radical as defined above, and the attaching nitrogen is designated as "N" and the other nitrogen is designated as "N'", e.g., N'-benzylureido, N'-(4-nitrobenzyl)ureido, N'-(3-chlorobenzyl)ureido, and the like.

"Monohaloalkylureido" refers to a radical of the formula —N(H)—C(O)—N(H)R$_f$ or a radical of the formula —N(R$_f$)—C(O)—NH$_2$ where R$_f$ is a haloalkyl radical as defined above and the attaching nitrogen is designated as "N" and the other nitrogen is designated as "N'", e.g., N'-chloromethylureido, N'-(2,2-difluoroethyl)ureido, N'-(3-chloropropyl)ureido, N-(trifluoromethyl)ureido, N-(pentafluoroethyl)ureido, N-(3-iodopropyl)ureido, and the like.

"Monoarylureido" refers to a radical of the formula —N(H)—C(O)—N(H)R$_b$ or a radical of the formula —N(R$_b$)—C(O)—NH$_2$ where R$_b$ is an aryl radical as defined above and the attaching nitrogen is designated as "N" and the other nitrogen is designated as "N'", e.g., N'-phenylureido, N'-(4-methoxyphenyl)ureido, N'-(3-chlorophenyl)ureido, N-phenylureido, N-(2-trifluoromethylphenyl)ureido, N-(4-chlorophenyl)ureido, and the like.

"Monoaralkylureido" refers to a radical of the formula —N(H)—C(O)—N(H)R$_d$ or a radical of the formula —N(R$_d$)—C(O)—NH$_2$ where R$_d$ is an aralkyl radical as defined above and the attaching nitrogen is designated as "N" and the other nitrogen is designated as "N'", e.g., N'-benzylureido, N'-(4-methoxybenzyl)ureido, N'-(3-chlorobenzyl)ureido, N-benzylureido, N-(2-trifluoromethylbenzyl)ureido, N-(4-chlorobenzyl)ureido, and the like.

"(Monoalkyl)(monoaryl)ureido" refers to a radical of the formula —N(R$_a$)—C(O)—N(R$_b$)H, or a radical of the formula —N(R$_b$)—C(O)—N(R$_a$)H, or a radical of the formula —N(H)—C(O)—N(R$_a$)(R$_b$) where R$_a$ is an alkyl radical as defined above and R$_b$ is an aryl radical as defined above, and where the attaching nitrogen is designated as "N" and the other nitrogen is designated as "N'", e.g., N-methyl-N'-phenylureido, N-phenyl-N'-ethylureido, N-methyl-N'-(4-fluorophenyl)ureido, N'-ethyl-N'-(3-cyanophenyl)ureido, and the like.

"Monoalkylureidoalkyl" refers to a radical of the formula —R$_a$—N(H)—C(O)—N(H)R$_a$ or a radical of the formula —R$_a$—N(R$_a$)—C(O)—NH$_2$ where R$_a$ is an alkyl radical as defined above and the attaching nitrogen is designated as "N" and the other nitrogen is designated as "N'", e.g., N'-methylureidomethyl, 2-(N'-ethylureido)ethyl, 1-(N'-propylureido)ethyl, N-methylureidomethyl, 2-(N-ethylureido)ethyl, 1-(N-propylureido)ethyl, and the like.

"Monohaloalkylureidoalkyl" refers to a radical of the formula —R$_a$—N(H)—C(O)—N(H)R$_f$ or a radical of the formula —R$_a$—N(R$_f$)—C(O)—NH$_2$ where R$_a$ is an alkyl radical as defined above and R$_f$ is a haloalkyl radical as defined above and the attaching nitrogen is designated as "N" and the other nitrogen is designated as "N'", e.g., N'-chloromethylureidomethyl, 2-(N'-(2,2-difluoroethyl)ureido)ethyl, 1-(N'-(3-chloropropyl)ureido)ethyl, N-(trifluoromethyl)ureidomethyl, 2-(N-(pentafluoroethyl)ureido)ethyl, 1-(N-(3-iodopropyl)ureido)ethyl, and the like.

"Monoarylureidoalkyl" refers to a radical of the formula —R$_a$—N(H)—C(O)—N(H)R$_b$ or a radical of the formula —R$_a$—N(R$_b$)—C(O)—NH$_2$ where R$_a$ is an alkyl radical as defined above and R$_b$ is an aryl radical as defined above and the attaching nitrogen is designated as "N" and the other nitrogen is designated as "N'", e.g., N'-phenylureidomethyl, 2-(N'-(4-methoxyphenyl)ureido)ethyl, 1-(N'-(3-chlorophenyl)ureido)ethyl, N-phenylureidomethyl, 2-(N-(2-trifluoromethylphenyl)ureido)ethyl, 1-(N-(4-chlorophenyl)ureido)ethyl, and the like.

"Monoaralkylureidoalkyl" refers to a radical of the formula —R$_a$—N(H)—C(O)—N(H)R$_d$ or a radical of the formula —R$_a$—N(R$_d$)—C(O)—NH$_2$ where R$_a$ is an alkyl radical as defined above and R$_b$ is an aralkyl radical as defined above and the attaching nitrogen is designated as "N" and the other nitrogen is designated as "N'", e.g., N'-benzylureidomethyl, 2-(N'-(4-methoxybenzyl)ureido)ethyl, 1-(N'-(3-chlorobenzyl)ureido)ethyl, N'-benzylureidomethyl, 2-(N-(2-trifluoromethylbenzyl) ureido)ethyl, 1-(N-(4-chlorobenzyl)ureido)ethyl, and the like.

"Monophenylamino" refers to an amino radical substituted by a phenyl radical as defined herein.

"Monophenylalkylamino" refers to an amino radical substituted by a phenylalkyl group as defined below, e.g., benzylamino, 2-(benzyl)butylamino, and the like.

"Monophenylaminoalkyl" refers to an alkyl radical as defined above substituted by a monophenylamino group as defined above, e.g., (phenylamino)methyl, 2-(1-(phenyl)ethylamino)ethyl, and the like.

"Monophenylalkylaminoalkyl" refers to an alkyl radical as defined above substituted by a monophenylalkylamino group as defined above, e.g., (benzylamino)methyl, 2-(2-benzyl)butylamino)ethyl, and the like.

"Nitro" refers to the radical —$NO_2$.

"Oxo" refers to the subsituent =O.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Phenyl" refers to the benzene radical optionally substituted by one or more substituents selected from the group consisting of hydroxy, halo, alkyl, haloalkyl, alkoxy, alkenyl, nitro, cyano, amino, monoalkylamino, dialkylamino, alkylcarbonyl, carboxy, alkoxycarbonyl, and aminocarbonyl.

"Phenoxy" refers to the radical of the formula —$R_h$ where $R_h$ is phenyl as defined above.

"Phenylalkyl" refers to an alkyl radical as defined above substituted by a phenyl radical, e.g., benzyl, and the like.

"Phenylalkenyl" refers to an alkenyl radical as defined above substituted by a phenyl radical, e.g., 3-phenylprop-2-enyl, and the like.

"Phenylalkoxy" refers to a radical of the formula —$OR_i$ where $R_i$ is a phenylalkyl radical as defined above, e.g., benzyloxy, and the like.

"Phenylalkoxyalkyl" refers to an alkyl radical as defined above substituted by a phenylalkoxy radical as defined above, e.g., benzyloxymethyl, and the like.

"Phenylcarbonyl" refers to a radical of the formula —C(O)—$R_h$ where $R_h$ is a phenyl radical as defined above, e.g., (4-chlorophenyl)carbonyl, (4-fluorophenyl)carbonyl, and the like.

"Phenylaminocarbonyl" refers to a radical of the formula —C(O)—N(H)—$R_h$ where $R_h$ is a phenyl radical as defined above, e.g., (4-chlorophenyl)aminocarbonyl, (4-methoxyphenyl)aminocarbonyl, and the like.

"Pharmaceutically acceptable counterion" "refers to those anions which retain the biological effectiveness and properties of the parent compound, which are not biologically or otherwise undesirable. Examples of such anions may be found in Berge, S. M. et al., *Journal of Pharmaceutical Sciences* (1977), Vol. 66, No. 1, pp. 1–19.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"THF" refers to tetrahydrofuran.

"Therapeutically effective amount" refers to that amount of a compound of formula (I) which, when administered to a human in need of such administration, is sufficient to effect treatment, as defined below, for inflammatory disorders which are alleviated by the inhibition of the activity of the chemokines, MIP-1α and RANTES, in particular, for inflammatory disorders characterized by migration, accumulation and activation of leukocytes to the affected tissue. The amount of a compound of formula (I) which constitutes a "therapeutically effective amount" will vary depending on the compound, the disorder and its severity, and the age of the human to be treated, but can be determined routinely by one of ordinary skill in the art having regard to his own knowledge and to this disclosure.

"Treating" or "treatment" as used herein cover the treatment of an inflammatory disorder in a human; and include:

(i) preventing the disorder from occurring in a human, in particular, when such human is predisposed to the disorder but has not yet been diagnosed as having it;

(ii) inhibiting the disorder, i.e., arresting its development; or (iii) relieving the disorder, i.e., causing regression of the disorder.

"Ureido" refers to a radical of the formula —N(H)—C(O)—$NH_2$.

"Ureidoalkyl" refers to a radical of the formula —$R_a$—N(H)C(O)$NH_2$ where $R_a$ is an alkyl radical as defined above, e.g., ureidomethyl, 2-(ureido)ethyl, 3-(ureido)propyl, and the like.

It is understood from the above definitions and examples that for radicals containing a substituted alkyl group any substitution thereon can occur on any carbon of the alkyl group.

The compounds of the invention, or their pharmaceutically acceptable salts, may have asymmetric carbon atoms in their structure. The compounds of the invention and their pharmaceutically acceptable salts may therefore exist as single stereoisomers, racemates, and as mixtures of enantiomers and diastereomers. All such single stereoisomers, racemates and mixtures thereof are intended to be within the scope of this invention. Absolute configuration of certain carbon atoms within the compounds, if known, are indicated by the appropriate absolute descriptor R or S. The descriptor "trans" is used to indicate that the $R^{1b}$ or the $R^{1b}$ substituents are on opposite sides of the piperazine plane. The descriptor "cis" is used to indicate that the $R^{1a}$ or the $R^{1b}$ substituents are on the same side of the piperazine plane.

The nomenclature used herein is a modified form of the I.U.P.A.C. system wherein the compounds of the invention are named as piperazine derivatives. For example, a compound of formula (Ia) wherein $R^6$ is —C(O)—, $R^5$ is ethylene, $R^4$ is —O—, $R^{1a}$ is in the 2-position of the piperazine ring and is ethoxycarbonyl, $R^2$ is 2-(ethylamino)ethyl in the 4-position of the phenyl ring and $R^3$ is naphthalen-1-yl substituted at the 4-position by methoxy, i.e., the compound of the following formula:

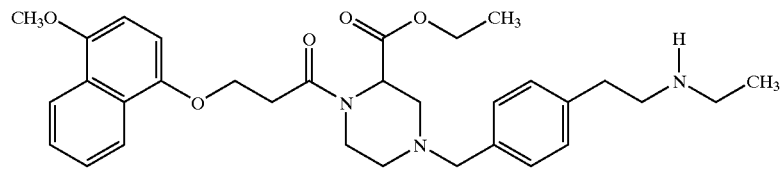

is named herein as 1-(2-((4-methoxynaphthalen-1-yl)oxy)ethyl)carbonyl-2-ethoxycarbonyl4-(4-(2-(ethylamino)ethyl)benzyl)piperazine.

Utility and Administration

A. Utility

The compounds of the invention inhibit the activity of the chemokines MIP-1α and RANTES and are therefore useful as anti-inflammatory agents. In particular, the compounds are useful in treating inflammatory disorders such as multiple sclerosis, leukoencephalopathy, encephalomyelitis, Alzheimer's disease, Guillian-Barre syndrome, acute cell-mediated renal transplant rejection, allograft rejection, rheumatoid arthritis, atherosclerosis, uricaria, angioderma, allergic conjunctivitis, atopic dermatitis, allergic contact dermatitis, drug or insect sting allergy or systemic anaphylaxis. Of particular interest to the invention is the use of the compounds to treat multiple sclerosis.

B. Testing

To demonstrate that the compounds inhibit the activity of MIP-1α or RANTES several assays may be employed. One assay utilizes a microphysiometer, which uses a patented silicon-based light addressable potentiometric sensor to continuously monitor subtle changes in extracellular pH levels. These changes result from the generation of acidic metabolites excreted by living cells into their immediate microenvironment during basal and stimulated conditions. It has been previously demonstrated by microphysiometry that THP-1 cells, which have been shown to express the chemokine receptors, CCR1 and CCR2, respond dose-responsively to their respective chemokines, including MIP-1α, RANTES and MCP-1 (a ligand for CCR2). See, e.g., Hirst, M. et al, "Chemokine receptors," *Journal of NIH Research* (1995), Vol. 80.

Another assay which may be used to demonstrate the ability of the compounds to inhibit the activity of MIP-1α and RANTES is based on the measurement of intracellular $Ca^{2+}$ concentrations and/or increases in intracellular [$^3$H] inositol phosphate release from MIP-1a and RANTES stimulated cells. Ligand binding to the CCR1 receptor results in G-protein induced activation of phospholipase C, which leads to the conversion of phosphatidyl inositol phosphate to inositol phosphate and diacyglycerol. Inositol phosphate in turn binds to a receptor located at intracellular sites to release $Ca^{2+}$ into the cytoplasm. In addition to $Ca^{2+}$ concentration increases due to release from intracellular stores, binding of inositol phosphate to its receptor leads to an increased flux of extracellular calcium across the membrane and into the cell. Thus the activation of the CCR1 receptor by MIP-1α and RANTES and, subsequently, inhibition of the activation by the compounds of the invention can be determined by assaying for an increase in free intracellular $Ca^{2+}$ levels. Typically this can be achieved by the use of calcium-sensitive fluorescent probes such as quin-2, fura-2 and indo-1. Alternatively, functional activation or inhibition of the activation of the CCR1 receptor can be measured by quantitation of [$^3$H] inositol phosphate release from the cell pre-labeled with [$^3$H] inositol.

Standard in vitro binding assays may be employed to demonstrate the affinity of the compounds for the CCR1 receptor (thereby inhibiting the activity of MIP-1α and RANTES by competitive binding to the receptor). See, e.g., Neote, K. et al., *Cell* (1993), Vol. 72, pp. 415–425. One particular assay employs the use of HEK293 cells which have been stably transfected to express human CCR1 receptor.

Standard in vivo assays which may be employed to demonstrate the compounds usefulness as anti-inflammatory agents are the animal model for experimental autoimmune encephalomyelitis (EAE) model for multiple sclerosis and the adjuvant-induced arthritis (AIA) model for rheumatoid arthritis.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, sublingually, intramuscular, subcutaneously, or intravenously in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of one or more suitable pharmaceutical excipient(s). Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients. Such excipients include non-toxic and chemically compatible fillers, binders, disintegrants, buffers, preservatives, anti-oxidants, lubricants, flavorings, thickeners, coloring agents, emulsifiers, and the like, for example, pharmaceutical grades of mannitol, lactose, starch, pregelatinized starch, magnesium stearate, sodium saccharine, talcum, cellulose ether derivatives, glucose, gelatin, sucrose, citrate, cyclodextrin, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%), and propylene glycol.

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, aqueous cyclodextrin, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of an inflammatory disorder alleviated by the inhibition of the activity of the chemokines, MIP-1α and RANTES.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Generally, a therapeutically effective daily dose is from about 0.014 mg to about 14.0 mg/kg of body weight per day of a compound of the invention, or a pharmaceutically acceptable salt thereof; preferably, from about 0.14 mg to about 10.0 mg/kg of body weight per day; and most preferably, from about 1.4 mg to about 7.0 mg/kg of body weight per day. For example, for administration to a 70 kg person, the dosage range would be from about 1.0 mg to about 1.0 gram per day of a compound of the invention, or a pharmaceutically acceptable salt thereof, preferably from about 10 mg to about 700 mg per day, and most preferably from about 100 mg to about 500 mg per day.

Preferred Embodiments

One aspect of the invention are the compounds of formula (Ia) as defined above in the Summary of the Invention. Of these compounds, a preferred group of compounds of formula (Ia) is that group of compounds wherein:

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl)

aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl.

Of this group of compounds, a preferred subgroup of compounds is that group of compounds wherein:

$R^4$ is —O—, —N($R^7$)— or —C($R^8$)—;

$R^5$ is an alkylene chain;

$R^7$ is selected from the group consisting of hydrogen, alkyl, aryl, aralkyl, alkylcarbonyl, alkylcarbonylalkyl, aralkylcarbonyl, aralkylcarbonylalkyl, aminocarbonyl, monoalkylaminocarbonyl, dialkylaminocarbonyl, and alkoxycarbonyl; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl) aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl.

Of this subgroup of compounds, a preferred class of compounds is that group of compounds wherein:

$R^4$ is —O—;

$R^5$ is methylene; and $R^6$ is —C(O)—.

Of this class of compounds, a preferred subclass of compounds is that group of compounds wherein:

$R^{1a}$ is one or more substituents independently selected from the group consisting of halo, alkyl, cycloalkyl, cycloalkylaminoalkyl, haloalkyl, hydroxyalkyl, hydroxyalkenyl, hydroxyalkynyl, (hydroxy)aralkyl, cyanoalkyl, haloalkylcarbonylaminoalkyl, alkoxyalkyl, aralkoxyalkyl, alkylthioalkyl, hydroxyalkylthioalkyl, aminoalkyl, monoalkylaminoalkyl, dialkylaminoalkyl, monoarylaminoalkyl, monoaralkylaminoalkyl, azidoalkyl, monoalkylureidoalkyl, (alkoxycarbonylalkyl)ureidoalkyl, hydroxyalkylaminoalkyl, aryloxyalkylcarbonyloxyalkyl, aralkoxyalkylcarbonyloxyalkyl, alkylcarbonylalkyl, alkoxycarbonyl, alkoxycarbonylalkyl, and heterocyclylalkyl;

$R^2$ is one or more substituents independently selected from the group consisting of hydrogen and halo;

$R^3$ is phenyl optionally substituted by one or more substituents independently selected from the group consisting of hydrogen, hydroxy, halo, alkyl, alkoxy, hydroxyalkoxy, haloalkyl, formyl, nitro, cyano, aminoalkoxy, cycloalkyl, cycloalkylaminoalkyl, aralkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, alkylsulfonylamino, aminoalkyl, monoalkylaminoalkyl, dialkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl) aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl) aminoalkyl, arylsulfonylaminoalkyl, (arylsulfonyl) (alkyl)aminoalkyl, heterocyclylaminoalkyl, carboxy, alkoxycarbonyl, alkylcarbonyl, (hydroxyalkoxy) carbonyl, aminocarbonyl, monoalkylaminocarbonyl, monoarylaminocarbonyl, (aminocarbonylalkyl) aminocarbonyl, (aminoalkyl)aminocarbonyl, (hydroxyalkyl)aminocarbonyl, dialkylaminocarbonylalkyl, hydroxyamidino, ureido, monoalkylureido, monoarylureido, monoaralkylureido, (monoalkyl)(monoaryl)ureido, (haloalkylcarbonyl) ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl) ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, alaninamido, heterocyclyl and heterocyclylalkyl.

Preferred compounds within this subclass of compounds are selected from the group consisting of the following compounds:

(2S)-1-((4-chlorophenoxy)methyl)carbonyl-2-methyl-4-(4-fluorobenzyl)piperazine;
1-((phenoxy)methyl)carbonyl-2-ethyl-4-(4-fluorobenzyl)piperazine;
4-(4-fluorobenzyl)-1-((4-chlorophenoxy)methyl)carbonyl-2-ethylpiperazine;
4-(4-fluorobenzyl)-1-((4-chlorophenoxy)methyl)carbonyl-2-(methoxymethyl)piperazine;
4-(4-fluorobenzyl)-1-((4-chlorophenoxy)methyl)carbonyl-2-((acetylamino)methyl)piperazine;
1-((4-chlorophenoxy)methyl)carbonyl-2-(2-((4-fluorobenzyl)amino)ethyl)-4-(4-fluorobenzyl)piperazine;
1-((4-chlorophenoxy)methyl)carbonyl-2-(2-((methyl)amino)ethyl)-4-(4-fluorobenzyl)piperazine;
1-((4-chlorophenoxy)methyl)carbonyl-2-(2-((2-hydroxyethyl)amino)ethyl)-4-(4-fluorobenzyl)piperazine;
4-(4-fluorobenzyl)-1-((4-chlorophenoxy)methyl)carbonyl-3-((((4-chlorophenoxy)methyl)carbonyl)oxy)methyl-5-methylpiperazine;
4-(4-fluorobenzyl)-1-((4-chlorophenoxy)methyl)carbonyl-3-(ethoxycarbonyl)piperazine;
4-(4-fluorobenzyl)-1-((4-chlorophenoxy)methyl)carbonyl-3-(methoxycarbonyl)methylpiperazine;
4-(4-fluorobenzyl)-1-((4-chlorophenoxy)methyl)carbonyl-3-((methoxy)methyl)piperazine;
4-(4-fluorobenzyl)-1-((4-chlorophenoxy)methyl)carbonyl-3-(2-(methoxy)ethyl)piperazine;
4-(4-fluorobenzyl)-1-((4-chlorophenoxy)methyl)carbonyl-3-(2-hydroxy-2-(4-methylphenyl)-ethyl)piperazine;
4-(4-fluorobenzyl)-1-((4-chlorophenoxy)methyl)carbonyl-3-(2-hydroxypropyl)piperazine;
4-(4-fluorobenzyl)-1-((4-chlorophenoxy)methyl)carbonyl-3-(2-hydroxybut-4-ynyl)piperazine;
4-(4-fluorobenzyl)-1-((4-chlorophenoxy)methyl)carbonyl-5-(2-hydroxy-2-methylpropyl)piperazine;
4-(4-fluorobenzyl)-1-((4-chlorophenoxy)methyl)carbonyl-3-(2-hydroxyethyl)piperazine;
1-((4-chlorophenoxy)methyl)carbonyl-3-(2-((2-hydroxyethyl)amino)ethyl)-4-(4-fluorobenzyl)piperazine;
(cis)-4-(4-fluorobenzyl)-1-((4-chlorophenoxy)methyl)carbonyl-2,3-dimethylpiperazine;
(2S,5R)-1-((4-chloro-3,5-dimethoxyphenoxy)methyl)carbonyl-2,5-dimethyl-4-(4-fluorobenzyl)piperazine;
(2S,5S)-4-(4-fluorobenzyl)-1-((4-chlorophenoxy)methyl)carbonyl-2,5-dimethylpiperazine;
(2R,5S)-4-(4-fluorobenzyl)-1-((4-chlorophenoxy)methyl)carbonyl-2-methyl-5-(2-methylthio)ethylpiperazine;
(2R,5R)-4-(4-fluorobenzyl)-1-((4-chlorophenoxy)methyl)carbonyl-2-methyl-5-(benzyloxy)methylpiperazine;
(2R,5R)-1-((4-chlorophenoxy)methyl)carbonyl-2-methyl-4-(4-fluorobenzyl)-5-(((2-hydroxyethyl)thio)methyl)piperazine;
4-(4-fluorobenzyl)-1-((4-chlorophenoxy)methyl)carbonyl-2-(N'-(ethoxycarbonylmethyl) ureido)methyl)piperazine;
(2R,5S)-1-((4-chlorophenoxy)methyl)carbonyl-2-methyl-5-((amino)carbonyloxy)methyl-4-(4-fluorobenzyl)piperazine;
4-(4-fluorobenzyl)-1-((4-chlorophenoxy)methyl)carbonyl-3-((acetyl)methyl)piperazine;
(2R,5R)4-(4-fluorobenzyl)-1-((4-chlorophenoxy)methyl)carbonyl-2-methyl-5-(1-hydroxy-1-(phenyl)methyl)piperazine;
(2R,5R)-4-(4-fluorobenzyl)-1-((4-chlorophenoxy)methyl)carbonyl-2-methyl-5-(1-hydroxybutyl)piperazine;
(2R,5S)-1-((4-chlorophenoxy)methyl)carbonyl-2-methyl-4-(4-fluorobenzyl)-5-((diethylamino)methyl)piperazine;
(2R,5S)-1-((4-chlorophenoxy)methyl)carbonyl-2-methyl-4-(4-fluorobenzyl)-5-((dimethylamino)methyl)piperazine;
(2R,5S)-1-((4-chlorophenoxy)methyl)carbonyl-2-methyl-4-(4-fluorobenzyl)-5-(((cyclopropyl)amino)methyl)piperazine;
(2R,5S)-1-((4-chlorophenoxy)methyl)carbonyl-2-methyl-4-(4-fluorobenzyl)-5-((morpholin-4-yl)methyl)piperazine;
(2R,5R)-1-((4-chlorophenoxy)methyl)carbonyl-2-methyl-4-(4-fluorobenzyl)-5-((piperazin-1-yl)methyl)piperazine;
(cis)-1-((3,4,5-trimethoxyphenoxy)methyl)carbonyl-2,6-dimethyl-4-(4-fluorobenzyl)piperazine;
(cis)-4-(4-fluorobenzyl)-1-((4-chlorophenoxy)methyl)carbonyl-2,6-dimethylpiperazine;
1-((phenoxy)methyl)carbonyl-2-methyl-4-(4-fluorobenzyl)piperazine;
1-((2-(acetylamino)phenoxy)methyl)carbonyl-2-methyl-4-(4-fluorobenzyl)piperazine;
1-((4-chlorophenoxy)methyl)carbonyl-2-(2-hydroxypropyl)-4-(4-fluorobenzyl)piperazine;
1-((4-chlorophenoxy)methyl)carbonyl-2-(2-hydroxybut-3-enyl)-4-(4-fluorobenzyl)piperazine;
1-((4-chlorophenoxy)methyl)carbonyl-3-trifluoromethyl-4-(4-fluorobenzyl)piperazine; and
(trans)-1-((4-chloro-2-((4-(2,5-di(trifluoromethyl)phenylcarbonyl)piperazin-1-yl)methyl)phenoxy)methyl)carbonyl-2,5-dimethyl-4-(4-fluorobenzyl)piperazine.

Of this subclass of compounds, a preferred group of compounds is that group of compounds wherein:

$R^{1a}$ is one or more substituents independently selected from the group consisting of alkyl, cycloalkyl, hydroxyalkyl, hydroxyalkenyl, cyanoalkyl, alkoxyalkyl, monoalkylaminoalkyl, azidoalkyl, monoalkylureidoalkyl, aryloxyalkylcarbonyloxyalkyl, and heterocyclylalkyl;

$R^2$ is one or more substituents independently selected from the group consisting of hydrogen, chloro or fluoro;

$R^3$ is phenyl substituted by one or more substituents independently selected from the group consisting of hydroxy, halo, alkyl, alkoxy, formyl, nitro, cyano, aminoalkoxy, cycloalkylaminoalkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, monoaralkylaminoalkyl, alkylcarbonylaminoalkyl, arylcarbonylaminoalkyl, (alkylcarbonyl)(alkyl) aminoalkyl, (cycloalkyalkyl)aminoalkyl, alkoxycarbonylalkylcarbonylaminoalkyl, alkylsulfonylaminoalkyl, (alkylsulfonyl)(alkyl) aminoalkyl, arylsulfonylaminoalkyl, (arylsulfonyl) (alkyl)aminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl) aminocarbonyl, (aminoalkyl)aminocarbonyl, (hydroxyalkyl)aminocarbonyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl)(alkyl) glycinamido, (monoarylaminocarbonyl)glycinamido, (monoarylaminocarbonyl)(alkyl)glycinamido, alaninamido, heterocyclyl and heterocyclylalkyl.

Preferred compounds within this group of compounds in this subclass group of compounds are selected from the group consisting of the following compounds:

1-((3,4,5-trimethoxyphenoxy)methyl)carbonyl-2-methyl-4-(4-fluorobenzyl)piperazine;

1-((4-chlorophenoxy)methyl)carbonyl-2-methyl-4-(4-fluorobenzyl)piperazine;

4-(4-fluorobenzyl)-1-((4-chlorophenoxy)methyl) carbonyl-2-ethylpiperazine;

(2R)-4-(4-fluorobenzyl)-1-((4-chlorophenoxy)methyl) carbonyl-2-propylpiperazine;

(2S)-4-(4-fluorobenzyl)-1-((4-chlorophenoxy)methyl) carbonyl-2-propylpiperazine;

4-(4-fluorobenzyl)-1-(((4-chlorophenoxy)methyl) carbonyl)spiro[cyclopropane-1,2'-piperazine];

1-((4-chlorophenoxy)methyl)carbonyl-2-hydroxymethyl-4-(4-fluorobenzyl)piperazine;

4-(4-fluorobenzyl)-1-((4-chlorophenoxy)methyl) carbonyl-2-(2-(methoxy)ethyl)piperazine;

1-((4-chlorophenoxy)methyl)carbonyl-2-(2-((2-methylpropyl)amino)ethyl)-4-(4-fluorobenzyl) piperazine;

1-((4-chlorophenoxy)methyl)carbonyl-3-methyl-4-(4-fluorobenzyl)piperazine;

1-((4-chlorophenoxy)methyl)carbonyl4-(4-fluorobenzyl)-5-methylpiperazine;

(2R)-1-((4-chlorophenoxy)methyl)carbonyl-3-methyl-4-(4-fluorobenzyl)piperazine;

(2S)-1-((4-chlorophenoxy)methyl)carbonyl-3-methyl-4-(4-fluorobenzyl)piperazine;

4-(4-fluorobenzyl)-1-((4-chlorophenoxy)methyl) carbonyl-3-(hydroxymethyl)piperazine;

4-(4-fluorobenzyl)-1-((4-chlorophenoxy)methyl) carbonyl-3-(2-hydroxyethyl)piperazine;

4-(4-fluorobenzyl)-1-((4-chlorophenoxy)methyl) carbonyl-2-(((methyl)ureido)methyl)piperazine;

(2R,3R)-4-(4-fluorobenzyl)-1-((4-chlorophenoxy) methyl)carbonyl-2,3-dimethylpiperazine;

(cis)-1-((4-chlorophenoxy)methyl)carbonyl-3,5-dimethyl-4-(4-fluorobenzyl)piperazine;

4-(4-fluorobenzyl)-1-((4-chlorophenoxy)methyl) carbonyl-2-(2-(((4-chlorophenoxy)methyl)carbonyl) oxy)ethyl-5-methylpiperazine;

(2R,5R)-1-((4-chlorophenoxy)methyl)carbonyl-2-methyl-4-(4-fluorobenzyl)-5-((hydroxy)methyl) piperazine;

(2R,5R)-4-(4-fluorobenzyl)-1-((4-chlorophenoxy) methyl)carbonyl-2-methyl-5-((methoxy)-methyl) piperazine;

(2R,5S)-4-(4-fluorobenzyl)-1-((4-chlorophenoxy) methyl)carbonyl-2-methyl-5-(1-methylethyl) piperazine;

(2R,5R)-4-(4-fluorobenzyl)-1-((4-chlorophenoxy) methyl)carbonyl-2-methyl-5-(1-hydroxyethyl) piperazine;

(2R,5R)-4-(4-fluorobenzyl)-1-((4-chlorophenoxy) methyl)carbonyl-2-methyl-5-(1-hydroxyprop-3-enyl) piperazine;

(2R,5S)-1-((4-chlorophenoxy)methyl)carbonyl-2-methyl-4-(4-fluorobenzyl)-5-((cyano)methyl) piperazine;

(2R,5R)-1-((4-chlorophenoxy)methyl)carbonyl-2-methyl-4-(4-fluorobenzyl)-5-((1,2,4-triazol-2-yl) methyl)piperazine;

(2R,5R)-1-((4-chlorophenoxy)methyl)carbonyl-2-methyl-4-(4-fluorobenzyl)-5-((tetrazolyl)methyl) piperazine;

(3S,5S)-4-(4-fluorobenzyl)-1-((4-chlorophenoxy)methyl) carbonyl-3,5-dimethylpiperazine;

1-((4-chloro-3-nitrophenoxy)methyl)carbonyl-2-methyl-4-(4-fluorobenzyl)piperazine;

(trans)-1-((4-chloro-2-methylphenoxy)methyl)carbonyl-2,5-dimethyl-4-(4-fluorobenzyl)piperazine;

(trans)-1-((4-chloro-2-(diethylamino)phenoxy)methyl) carbonyl-2,5-dimethyl-4-(4-fluorobenzyl)piperazine;

(trans)-1-((4-chloro-2-hydroxyphenoxy)methyl) carbonyl-2,5-dimethyl-4-(4-fluorobenzyl)piperazine;

(trans)-1-((5-chloro-2-methoxyphenoxy)methyl) carbonyl-2,5-dimethyl-4-(4-fluorobenzyl)piperazine;

(trans)-1-((4-chloro-2-((ethyl)(1-methylbutyl) aminomethyl)phenoxy)methyl)carbonyl-2,5-dimethyl-4-(4-fluorobenzyl)piperazine;

1-((4-chloro-2-aminophenoxy)methyl)carbonyl-2-methyl-4-(4-fluorobenzyl)piperazine;

1-((4-chloro-3-nitrophenoxy)methyl)carbonyl-2-methyl-4-(4-fluorobenzyl)piperazine;

(trans)-1-((4-chloro-2-(benzylamino)phenoxy)methyl) carbonyl-2,5-dimethyl-4-(4-fluorobenzyl)piperazine;

(trans)-1-((4-chloro-2-((1-methylbutyl)amino)phenoxy) methyl)carbonyl-2,5-dimethyl-4-(4-fluorobenzyl) piperazine;

(trans)-1-((4-chloro-2-(iso-propylcarbonylamino) phenoxy)methyl)carbonyl-2,5-dimethyl-4-(4-fluorobenzyl)piperazine;

(trans)-1-((4-chloro-2-(N'-(2,4-dichlorophenyl)ureido) phenoxy)methyl)carbonyl-2,5-dimethyl-4-(4-fluorobenzyl)piperazine;

(trans)-1-((4-chloro-2-(N'-(4-nitrophenyl)ureido)
   phenoxy)methyl)carbonyl-2,5-dimethyl-4-(4-
   fluorobenzyl)piperazine;
(trans)-1-((4-chloro-2-(N'-(4-methylphenyl)ureido)
   phenoxy)methyl)carbonyl-2,5-dimethyl-4-(4-
   fluorobenzyl)piperazine;
(trans)-1-((4-chloro-2-(N'-benzylureido)phenoxy)methyl)
   carbonyl-2,5-dimethyl-4-(4-fluorobenzyl)piperazine;
(trans)-1-((4-chloro-2-((cyclopropylmethyl)
   aminomethyl)phenoxy)methyl)carbonyl-2,5-dimethyl-
   4-(4-fluorobenzyl)piperazine;
(trans)-1-((4-chloro-2-(phenylaminomethyl)phenoxy)
   methyl)carbonyl-2,5-dimethyl-4-(4-fluorobenzyl)
   piperazine;
(trans)-1-((4-chloro-2-(acetylaminomethyl)phenoxy)
   methyl)carbonyl-2,5-dimethyl-4-(4-fluorobenzyl)
   piperazine;
(trans)-1-((4-chloro-2-((methylamino)(phenyl)methyl)
   phenoxy)methyl)carbonyl-2,5-dimethyl-4-(4-
   fluorobenzyl)piperazine;
(trans)-1-((4-chloro-2-(1-(phenylsulfonyl)(methyl)
   aminoethyl)phenoxy)methyl)carbonyl-2,5-dimethyl-4-
   (4-fluorobenzyl)piperazine;
(trans)-1-((4-chloro-2-(1-(acetyl)(methyl)aminoethyl)
   phenoxy)methyl)carbonyl-2,5-dimethyl-4-(4-
   fluorobenzyl)piperazine;
(trans)-1-((4-chloro-2-(1-(N-methyl-N'-ethylureido)
   ethyl)phenoxy)methyl)carbonyl-2,5-dimethyl-4-(4-
   fluorobenzyl)piperazine;
(trans)-1-((4-chloro-2-(1-((methyl)(ethyl)amino)ethyl)
   phenoxy)methyl)carbonyl-2,5-dimethyl-4-(4-
   fluorobenzyl)piperazine;
(trans)-1-((4-chloro-2-(1-(dimethylamino)ethyl)phenoxy)
   methyl)carbonyl-2,5-dimethyl-4-(4-fluorobenzyl)
   piperazine;
(2R)-1-((4-chloro-2-((4-t-butoxycarbonylpiperazin-1-yl)
   methyl)phenoxy)methyl)carbonyl-2-methyl-4-(4-
   fluorobenzyl)piperazine;
(trans)-1-((4-chloro-2-((piperazin-1-yl)methyl)phenoxy)
   methyl)carbonyl-2,5-dimethyl-4-(4-fluorobenzyl)
   piperazine;
(trans)-1-((4-chloro-2-(oxazol-2-ylaminomethyl)
   phenoxy)methyl)carbonyl-2,5-dimethyl-4-(4-
   fluorobenzyl)piperazine;
1-((4-chloro-2-(morpholin-4-ylmethyl)phenoxy)methyl)
   carbonyl-2-methyl-4-(4-fluorobenzyl)piperazine;
(trans)-1-((4-bromo-2-formylphenoxy)methyl)carbonyl-
   2,5-dimethyl-4-(4-fluorobenzyl)piperazine;
(trans)-1-((4-fluoro-3-chlorophenoxy)methyl)carbonyl-2,
   5-dimethyl-4-(4-fluorobenzyl)piperazine;
1-((4-chloro-2-methoxycarbonylphenoxy)methyl)
   carbonyl-2-methyl-4-(4-fluorobenzyl)piperazine;
(trans)-1-((4-chloro-2-methoxycarbonylphenoxy)methyl)
   carbonyl-2,5-dimethyl-4-(4-fluorobenzyl)piperazine;
1-((4-chloro-2-aminocarbonylphenoxy)methyl)carbonyl-
   2-methyl-4-(4-fluorobenzyl)piperazine;
(trans)-1-((4-chloro-2-carboxyphenoxy)methyl)carbonyl-
   2,5-dimethyl-4-(4-fluorobenzyl)piperazine;
(trans)-1-((4-chloro-2-formylphenoxy)methyl)carbonyl-
   2,5-dimethyl-4-(4-fluorobenzyl)piperazine;
(trans)-1-((4-chloro-2-cyanophenoxy)methyl)carbonyl-2,
   5-dimethyl-4-(4-fluorobenzyl)piperazine;
(trans)-1-((3-cyanophenoxy)methyl)carbonyl-2,5-
   dimethyl-4-(4-fluorobenzyl)piperazine;
(trans)-1-((4-methyl-2-aminophenoxy)methyl)carbonyl-
   2,5-dimethyl-4-(4-fluorobenzyl)piperazine;
(trans)-1-((3-formylphenoxy)methyl)carbonyl-2,5-
   dimethyl-4-(4-fluorobenzyl)piperazine;
(trans)-1-((4-methyl-2-acetylphenoxy)methyl)carbonyl-
   2,5-dimethyl-4-(4-fluorobenzyl)piperazine;
(trans)-1-((2-methoxycarbonylphenoxy)methyl)carbonyl-
   2,5-dimethyl-4-(4-fluorobenzyl)piperazine;
(trans)-1-((3-nitrophenoxy)methyl)carbonyl-2,5-
   dimethyl-4-(4-fluorobenzyl)piperazine;
(trans)-1-((4-acetyl-2-(aminocarbonyl)phenoxy)methyl)
   carbonyl-2,5-dimethyl-4-(4-fluorobenzyl)piperazine;
(trans)-1-((4-nitro-3-methylphenoxy)methyl)carbonyl-2,
   5-dimethyl-4-(4-fluorobenzyl)piperazine;
(trans)-1-((5-nitro-2-methylphenoxy)methyl)carbonyl-2,
   5-dimethyl-4-(4-fluorobenzyl)piperazine;
(trans)-1-((4-amino-3-nitrophenoxy)methyl)carbonyl-2,
   5-dimethyl-4-(4-fluorobenzyl)piperazine;
(trans)-1-((5-nitro-2-aminophenoxy)methyl)carbonyl-2,
   5-dimethyl-4-(4-fluorobenzyl)piperazine;
(trans)-1-((2-aminophenoxy)methyl)carbonyl-2,5-
   dimethyl-4-(4-fluorobenzyl)piperazine;
(trans)-1-((3-methoxyphenoxy)methyl)carbonyl-2,5-
   dimethyl-4-(4-fluorobenzyl)piperazine;
(trans)-1-((4-methoxy-2-acetylphenoxy)methyl)
   carbonyl-2,5-dimethyl-4-(4-fluorobenzyl)piperazine;
(trans)-1-((5-methoxy-2-acetylphenoxy)methyl)
   carbonyl-2,5-dimethyl-4-(4-fluorobenzyl)piperazine;
(trans)-1-((2-((2-hydroxyethyl)aminocarbonyl)phenoxy)
   methyl)carbonyl-2,5-dimethyl-4-(4-fluorobenzyl)
   piperazine;
(trans)-1-((2-((2-hydroxyethoxy)carbonyl)phenoxy)
   methyl)carbonyl-2,5-dimethyl-4-(4-fluorobenzyl)
   piperazine;
(trans)-1-((2-(2-hydroxyethoxy)phenoxy)methyl)
   carbonyl-2,5-dimethyl-4-(4-fluorobenzyl)piperazine;
(trans)-1-((2-acetyl-4,5-dimethylphenoxy)methyl)
   carbonyl-2,5-dimethyl-4-(4-fluorobenzyl)piperazine;
(trans)-1-((5-methoxy-2-(methoxycarbonyl)phenoxy)
   methyl)carbonyl-2,5-dimethyl-4-(4-fluorobenzyl)
   piperazine;
4-(4-fluorobenzyl)-1-((4-chlorophenoxy)methyl)
   carbonyl-2-(N'-methylureido)-amino)methyl)
   piperazine;
(trans)-1-((4-methyl-2-formylphenoxy)methyl)carbonyl-
   2,5-dimethyl-4-(4-fluorobenzyl)piperazine;
(trans)-1-((3-chloro-5-methoxyphenoxy)methyl)
   carbonyl-2,5-dimethyl-4-(4-fluorobenzyl)piperazine;
(trans)-1-((2-methoxy-5-nitrophenoxy)methyl)carbonyl-
   2,5-dimethyl-4-(4-fluorobenzyl)piperazine;
(trans)-1-((2-(hydroxymethyl)phenoxy)methyl)carbonyl-
   2,5-dimethyl-4-(4-fluorobenzyl)piperazine;
(trans)-1-((2-methylphenoxy)methyl)carbonyl-2,5-
   dimethyl-4-(4-fluorobenzyl)piperazine;
1-((4-chlorophenoxy)methyl)carbonyl-2-(2-azidoethyl)-
   4-(4-fluorobenzyl)piperazine;
(trans)-1-((4-chloro-2-(phthalimido)phenoxy)methyl)
   carbonyl-2,5-dimethyl-4-(4-fluorobenzyl)piperazine;
(trans)-1-((4-chloro-2-(maleimido)phenoxy)methyl)
   carbonyl-2,5-dimethyl-4-(4-fluorobenzyl)piperazine;
(trans)-1-((4-chloro-2-((4-(benzylcarbonyl)piperazin-1-
   yl)methyl)phenoxy)methyl)-carbonyl-2,5-dimethyl-4-
   (4-fluorobenzyl)piperazine;

(trans)-1-((4-chloro-2-((4-((2,3,4-trifluorophenyl)aminocarbonyl)piperazin-1-yl)methyl)phenoxy)methyl)carbonyl-2,5-dimethyl-4-(4-fluorobenzyl)piperazine;

(trans)-1-((4-chloro-2-((4-((2-fluorophenyl)aminocarbonyl)piperazin-1-yl)methyl)phenoxy)methyl)carbonyl-2,5-dimethyl-4-(4-fluorobenzyl)piperazine;

(trans)-1-((4-chloro-2-((N'-(2,6-difluorophenyl)ureido)phenoxy)methyl)carbonyl-2,5-dimethyl-4-(4-fluorobenzyl)piperazine;

(trans)-1-((4-chloro-2-(ethenylcarbonylamino)phenoxy)methyl)carbonyl-2,5-dimethyl-4-(4-fluorobenzyl)piperazine;

(trans)-1-((4-chloro-2-(cyclopropylcarbonylamino)phenoxy)methyl)carbonyl-2,5-dimethyl-4-(4-fluorobenzyl)piperazine;

(trans)-1-((4-chloro-2-(cyclopentylcarbonylamino)phenoxy)methyl)carbonyl-2,5-dimethyl-4-(4-fluorobenzyl)piperazine;

(trans)-1-((4-chloro-2-((furan-2-yl)carbonylamino)phenoxy)methyl)carbonyl-2,5-dimethyl-4-(4-fluorobenzyl)piperazine;

(trans)-1-((4-chloro-2-(phenylcarbonylamino)phenoxy)methyl)carbonyl-2,5-dimethyl-4-(4-fluorobenzyl)piperazine;

(trans)-1-((4-chloro-2-((N'(3-methoxyphenyl)ureido)phenoxy)methyl)carbonyl-2,5-dimethyl-4-(4-fluorobenzyl)piperazine;

(trans)-1-((4-chloro-2-((N'-(methoxycarbonylmethylcarbonyl)-N'-(methyl)glycinamido)phenoxy)methyl)carbonyl-2,5-dimethyl-4-(4-fluorobenzyl)piperazine;

(trans)-1-((4-chloro-2-((N'-(2-methoxycarbonylethyl)carbonyl-N'-(methyl)glycinamido)phenoxy)methyl)carbonyl-2,5-dimethyl-4-(4-fluorobenzyl)piperazine;

(trans)-1-((4-chloro-2-((N'-(3-methylbenzyl)aminocarbonyl-N'-(methyl)glycinamido)phenoxy)methyl)carbonyl-2,5-dimethyl-4-(4-fluorobenzyl)piperazine;

(trans)-1-((4-chloro-2-((N'-(3-trifluoromethyl-4-fluorophenyl)carbonyl-N'-(methyl)glycinamido)phenoxy)methyl)carbonyl-2,5-dimethyl-4-(4-fluorobenzyl)piperazine;

(trans)-1-((4-chloro-2-((N'-(4-methylbenzyl)aminocarbonyl-N'-(methyl)glycinamido)phenoxy)methyl)carbonyl-2,5-dimethyl-4-(4-fluorobenzyl)piperazine;

(trans)-1-((4-chloro-2-((N'(3-chlorophenyl)carbonyl-N'-(methyl)glycinamido)phenoxy)methyl)carbonyl-2,5-dimethyl-4-(4-fluorobenzyl)piperazine;

(trans)-1-((4-chloro-2-((N'-(4-fluorobenzyl)aminocarbonyl-N'-(methyl)glycinamido)phenoxy)methyl)carbonyl-2,5-dimethyl-4-(4-fluorobenzyl)piperazine;

(trans)-1-((4-chloro-2-(N'-(2-iodophenylcarbonyl)glycinamido)phenoxy)methyl)carbonyl-2,5-dimethyl-4-(4-fluorobenzyl)piperazine;

(trans)-1-((4-chloro-2-(N'(2,3-difluorophenylcarbonyl)glycinamido)phenoxy)-methyl)carbonyl-2,5-dimethyl-4-(4-fluorobenzyl)piperazine;

(trans)-1-((4-chloro-2-(N'-((4-phenoxyphenyl)aminocarbonyl)glycinamido)phenoxy)-methyl)carbonyl-2,5-dimethyl-4-(4-fluorobenzyl)piperazine;

(trans)-1-((4-chloro-2-(N'-(2,4-difluorophenylcarbonyl)glycinamido)phenoxy)methyl)-carbonyl-2,5-dimethyl-4-(4-fluorobenzyl)piperazine;

(trans)-1-((4-chloro-2-((2-iodophenylcarbonyl)aminomethyl)phenoxy)methyl)carbonyl-2,5-dimethyl-4-(4-fluorobenzyl)piperazine;

(trans)-1-((4-chloro-2-((ethoxycarbonylmethylcarbonyl)aminomethyl)phenoxy)-methyl)carbonyl-2,5-dimethyl-4-(4-fluorobenzyl)piperazine;

(trans)-1-((4-chloro-2-(N'-(3-chloropropyl)ureidomethyl)phenoxy)methyl)carbonyl-2,5-dimethyl-4-(4-fluorobenzyl)piperazine;

(trans)-1-((4-chloro-2-(N'-(2-fluoro-6-trifluoromethylphenyl)ureidomethyl)phenoxy)-methyl)carbonyl-2,5-dimethyl-4-(4-fluorobenzyl)piperazine;

(trans)-1-((4-chloro-2-((3-fluorophenyl)carbonylaminomethyl)phenoxy)methyl)carbonyl-2,5-dimethyl-4-(4-fluorobenzyl)piperazine;

(trans)-1-((4-chloro-2-(N'-(2-(ethoxycarbonyl)ethyl)ureidomethyl)phenoxy)-methyl)carbonyl-2,5-dimethyl-4-(4-fluorobenzyl)piperazine;

(2S)-1-((4-chloro-2-(ureido)phenoxy)methyl)carbonyl-2-methyl-4-(4-fluorobenzyl)piperazine;

(trans)-1-((4-chloro-2-((2,5-di(trifluoromethyl)phenyl)carbonylaminomethyl)-phenoxy)methyl)carbonyl-2,5-dimethyl-4-(4-fluorobenzyl)piperazine; and (trans)-1-((4-chloro-2-(N'-(2-(phenyl)cyclopropyl)ureidomethyl)phenoxy)methyl)carbonyl-2,5-dimethyl-4-(4-fluorobenzyl)piperazine.

A more preferred group of compounds in this subclass group of compounds are those compounds wherein:

$R^{1a}$ is one or more substituents independently selected from the group consisting of alkyl and hydroxyalkyl;

$R^2$ is one or more substituents independently selected from the group consisting of hydrogen, chloro or fluoro;

$R^3$ is phenyl substituted by one or more substituents independently selected from the group consisting of halo, alkyl, alkoxy, formyl, nitro, cycloalkylaminoalkyl, hydroxyalkyl, amino, alkylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, (alkylsulfonyl)(alkyl)aminoalkyl, alkylcarbonyl, aminocarbonyl, monoalkylaminocarbonyl, monoarylaminocarbonyl, (aminocarbonylalkyl)aminocarbonyl, (aminoalkyl)aminocarbonyl, hydroxyamidino, ureido, (haloalkylcarbonyl)ureido, ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylaminoalkylcarbonyl)glycinamido, alaninamido, and heterocyclylalkyl.

Preferred compounds within this more preferred group of compounds in this subclass group of compounds are selected from the group consisting of the following compounds:

(trans)-1-((4-chloro-3-nitrophenoxy)methyl)carbonyl-2,5-dimethyl-4-(4-fluorobenzyl)piperazine;

(trans)-1-((4-chloro-2-(hydroxymethyl)phenoxy)methyl)carbonyl-2,5-dimethyl-4-(4-fluorobenzyl)piperazine;

(trans)-1-((4-chloro-2-(aminocarbonyl)phenoxy)methyl)carbonyl-2,5-dimethyl-4-(4-fluorobenzyl)piperazine;

(2R,5S)-1-((4-chloro-2-(aminocarbonyl)phenoxy)methyl)carbonyl-2,5-dimethyl-4-(4-fluorobenzyl)piperazine;

(2S,5R)-1-((4-bromo-3,5-dimethoxyphenoxy)methyl)carbonyl-2,5-dimethyl-4-(4-fluorobenzyl)piperazine;

(2R,5S)-1-((3-hydroxy-5-methylphenoxy)methyl)carbonyl-2,5-dimethyl-4-(4-fluorobenzyl)piperazine;

(2S,5R)-1-((4-nitro-3-formylphenoxy)methyl)carbonyl-2,5-dimethyl-4-(4-fluorobenzyl)piperazine;

(2R)-1-((4-chlorophenoxy)methyl)carbonyl-2-methyl-4-(4-fluorobenzyl)piperazine;

4-(4-fluorobenzyl)-1-((4-chlorophenoxy)methyl)carbonyl-2-(2-hydroxyethyl)piperazine;

(trans)-4-(4-fluorobenzyl)-1-((4-chlorophenoxy)methyl)carbonyl-2,5-dimethylpiperazine;

(2R,5S)-4-(4-fluorobenzyl)-1-((4-chlorophenoxy)methyl)carbonyl-2,5-dimethylpiperazine;

(trans)-1-((4-chloro-3,5-dimethoxyphenoxy)methyl)carbonyl-2,5-dimethyl-4-(4-fluorobenzyl)piperazine;

(2R,5S)-1-((4-chloro-3,5-dimethoxyphenoxy)methyl)carbonyl-2,5-dimethyl-4-(4-fluorobenzyl)piperazine;

(2R,5S)-4-(4-fluorobenzyl)-1-((4-chlorophenoxy)methyl)carbonyl-2-(2-hydroxyethyl)-5-methylpiperazine;

(2R,6R)-4-(4-fluorobenzyl)-1-((4-chlorophenoxy)methyl)carbonyl-2,6-dimethylpiperazine;

(trans)-1-((4-chloro-2-methoxyphenoxy)methyl)carbonyl-2,5-dimethyl-4-(4-fluorobenzyl)piperazine;

1-((4-chloro-2-(hydroxymethyl)phenoxy)methyl)carbonyl-2-methyl-4-(4-fluorobenzyl)piperazine;

(2R,5S)-1-((4-chloro-3-(hydroxymethyl)phenoxy)methyl)carbonyl-2,5-dimethyl-4-(4-fluorobenzyl)piperazine;

(trans)-1-((4-chloro-2-(1-hydroxyethyl)phenoxy)methyl)carbonyl-2,5-dimethyl-4-(4-fluorobenzyl)piperazine;

(trans)-1-((4-chloro-2-(aminomethyl)phenoxy)methyl)carbonyl-2,5-dimethyl-4-(4-fluorobenzyl)piperazine;

(trans)-1-((4-chloro-2-(ureidomethyl)phenoxy)methyl)carbonyl-2,5-dimethyl-4-(4-fluorobenzyl)piperazine;

(trans)-1-((4-chloro-2-aminophenoxy)methyl)carbonyl-2,5-dimethyl-4-(4-fluorobenzyl)piperazine;

1-((4-chloro-2-(acetylamino)phenoxy)methyl)carbonyl-2-methyl-4-(4-fluorobenzyl)piperazine;

(trans)-4-(4-fluorobenzyl)-1-((2-acetylamino-4-chlorophenoxy)methyl)carbonyl-2,5-dimethylpiperazine;

(trans)-1-((4-chloro-2-(propylcarbonylamino)phenoxy)methyl)carbonyl-2,5-dimethyl-4-(4-fluorobenzyl)piperazine;

(trans)-1-((4-chloro-2-(methoxymethylcarbonylamino)phenoxy)methyl)carbonyl-2,5-dimethyl-4-(4-fluorobenzyl)piperazine;

(trans)-1-((4-chloro-2-(2-(methoxycarbonyl)ethylcarbonylamino)phenoxy)-methyl)carbonyl-2,5-dimethyl-4-(4-fluorobenzyl)piperazine;

(trans)-1-((4-chloro-2-(2-(ethoxycarbonyl)ethylcarbonylamino)phenoxy)methyl)carbonyl-2,5-dimethyl-4-(4-fluorobenzyl)piperazine;

(trans)-1-((4-chloro-2-(methylsulfonylamino)phenoxy)methyl)carbonyl-2,5-dimethyl-4-(4-fluorobenzyl)piperazine;

(trans)-1-((4-chloro-2-(bromomethylcarbonylamino)phenoxy)methyl)carbonyl-2,5-dimethyl-4-(4-fluorobenzyl)piperazine;

(2R)-1-((4-chloro-2-(glycinamido)phenoxy)methyl)carbonyl-2-methyl-4-(4-fluorobenzyl)piperazine;

(trans)-1-((4-chloro-2-((N'-methylglycinamido)phenoxy)methyl)carbonyl-2,5-dimethyl-4-(4-fluorobenzyl)piperazine;

(trans)-1-((4-chloro-2-(alaninamido)phenoxy)methyl)carbonyl-2,5-dimethyl-4-(4-fluorobenzyl)piperazine;

(trans)-1-((4-chloro-2-((aminocarbonyl)glycinamido)phenoxy)methyl)carbonyl-2,5-dimethyl-4-(4-fluorobenzyl)piperazine;

(trans)-1-((4-chloro-2-((aminocarbonyl)(methyl)glycinamido)phenoxy)methyl)carbonyl-2,5-dimethyl-4-(4-fluorobenzyl)piperazine;

(trans)-1-((4-chloro-2-(N'-ethyluredio)phenoxy)methyl)carbonyl-2,5-dimethyl-4-(4-fluorobenzyl)piperazine;

(trans)-1-((4-chloro-2-(ethylcarbonylamino)phenoxy)methyl)carbonyl-2,5-dimethyl-4-(4-fluorobenzyl)piperazine;

(trans)-1-((4-chloro-2-amino-5-nitrophenoxy)methyl)carbonyl-2,5-dimethyl-4-(4-fluorobenzyl)piperazine, dihydrochloride salt;

(trans)-1-((4-chloro-2-(((ethyl)amino)methyl)phenoxy)methyl)carbonyl-2,5-dimethyl-4-(4-fluorobenzyl)piperazine;

(trans)-1-((4-chloro-2-(((diethyl)amino)methyl)phenoxy)methyl)carbonyl-2,5-dimethyl-4-(4-fluorobenzyl)piperazine;

(trans)-1-((4-chloro-2-(((cyclopropyl)amino)methyl)phenoxy)methyl)carbonyl-2,5-dimethyl-4-(4-fluorobenzyl)piperazine;

(trans)-1-((4-chloro-2-(((dimethyl)amino)methyl)phenoxy)methyl)carbonyl-2,5-dimethyl-4-(4-fluorobenzyl)piperazine;

(trans)-1-((4-chloro-2-(((methyl)amino)methyl)phenoxy)methyl)carbonyl-2,5-dimethyl-4-(4-fluorobenzyl)piperazine;

(trans)-1-((4-chloro-2-((amino)methyl)phenoxy)methyl)carbonyl-2,5-dimethyl-4-(4-fluorobenzyl)piperazine;

(trans)-1-((4-chloro-2-((4-methylpiperazin-1-yl)methyl)phenoxy)methyl)carbonyl-2,5-dimethyl-4-(4-fluorobenzyl)piperazine;

(trans)-1-((4-chloro-2-((piperazin-1-yl)methyl)phenoxy)methyl)carbonyl-2,5-dimethyl-4-(4-fluorobenzyl)piperazine;

(trans)-1-((4-chloro-2-(ethylaminomethyl)phenoxy)methyl)carbonyl-2,5-dimethyl-4-(4-fluorobenzyl)piperazine;

(trans)-1-((4-chloro-2-(1-(methylamino)ethyl)phenoxy)methyl)carbonyl-2,5-dimethyl-4-(4-fluorobenzyl)piperazine;

(trans)-1-((4-chloro-2-(1-(methylsulfonyl)(methyl)aminoethyl)phenoxy)methyl)carbonyl-2,5-dimethyl-4-(4-fluorobenzyl)piperazine;

(2R)-1-((4-chloro-2-((piperazin-1-yl)methyl)phenoxy)methyl)carbonyl-2-methyl-4-(4-fluorobenzyl)piperazine;

(2R,5S)-1-((4-chloro-2-((piperazin-1-yl)methyl)phenoxy)methyl)carbonyl-2,5-dimethyl-4-(4-fluorobenzyl)piperazine;

(trans)-1-((4-chloro-2-((4-t-butoxycarbonylpiperazin-1-yl)methyl)phenoxy)methyl)carbonyl-2,5-dimethyl-4-(4-fluorobenzyl)piperazine;

(trans)-1-((4-chloro-2-(imidazol-1-ylmethyl)phenoxy)methyl)carbonyl-2,5-dimethyl-4-(4-fluorobenzyl)piperazine;

(trans)-1-((4-chloro-2-(1-(imidazol-1-yl)ethyl)phenoxy)methyl)carbonyl-2,5-dimethyl-4-(4-fluorobenzyl)piperazine;

(trans)-1-((4-chloro-2-(triazol-1-ylmethyl)phenoxy)methyl)carbonyl-2,5-dimethyl-4-(4-fluorobenzyl)piperazine;

(trans)-1-((4-chloro-2-(tetrazol-1-ylmethyl)phenoxy)methyl)carbonyl-2,5-dimethyl-4-(4-fluorobenzyl)piperazine;

(trans)-1-((4-chloro-2-((morpholin-4-yl)methyl)phenoxy)methyl)carbonyl-2,5-dimethyl-4-(4-fluorobenzyl)piperazine;

(2R)-1-((4-chloro-2-aminocarbonylphenoxy)methyl)carbonyl-2-methyl-4-(4-fluorobenzyl)piperazine;

1-((4-chloro-2-formylphenoxy)methyl)carbonyl-2-methyl-4-(4-fluorobenzyl)piperazine;

(2R,5S)-1-((4-chloro-2-formylphenoxy)methyl)carbonyl-2,5-dimethyl-4-(4-fluorobenzyl)piperazine;

(2R)-1-((4-chloro-2-formylphenoxy)methyl)carbonyl-2-methyl-4-(4-fluorobenzyl)piperazine;

(trans)-1-((4-chloro-2-(methylaminocarbonyl)phenoxy)methyl)carbony-2,5-dimethyl-4-(4-fluorobenzyl)piperazine;

(trans)-1-((4-chloro-2-((aminocarbonylmethyl)aminocarbonyl)phenoxy)methyl)carbonyl-2,5-dimethyl-4-(4-fluorobenzyl)piperazine;

(trans)-1-((4-chloro-2-((2-aminoethyl)aminocarbonyl)phenoxy)methyl)carbonyl-2,5-dimethyl-4-(4-fluorobenzyl)piperazine;

(trans)-1-((4-chloro-2-((4-aminocarbonylphenyl)aminocarbonyl)phenoxy)methyl)carbonyl-2,5-dimethyl-4-(4-fluorobenzyl)piperazine;

(trans)-1-((4-chloro-2-(hydroxyamidino)phenoxy)methyl)carbonyl-2,5-dimethyl-4-(4-fluorobenzyl)piperazine;

(trans)-1-((4-chloro-2-acetylphenoxy)methyl)carbonyl-2,5-dimethyl-4-(4-fluorobenzyl)piperazine;

(trans)-1-((2-(aminocarbonyl)phenoxy)methyl)carbonyl-2,5-dimethyl-4-(4-fluorobenzyl)piperazine;

(trans)-1-((4-chloro-2-((N'-(trichloromethylcarbonyl)ureido)phenoxy)methyl)carbonyl-2,5-dimethyl-4-(4-fluorobenzyl)piperazine;

(trans)-1-((4-chloro-2-(N'-(methoxymethylcarbonyl)glycinamido)phenoxy)methyl)-carbonyl-2,5-dimethyl-4-(4-fluorobenzyl)piperazine; and (trans)-1-((4-chloro-2-(N'-(ethoxycarbonylaminocarbonyl)-glycinamido)phenoxy)methyl)carbonyl-2,5-dimethyl-4-(4-fluorobenzyl)piperazine.

The most preferred group of compounds within this subclass group of compounds are those compounds wherein R² is 4-fluoro and R³ is phenyl substituted at the 4-position with chloro and at the 2-position by aminocarbonyl, ureido, or glycinamido.; namely, the compounds selected from the group consisting of the following compounds:

(2R,5S)-1-((4-chloro-2-(aminocarbonyl)phenoxy)methyl)carbonyl-2,5-dimethyl-4-(4-fluorobenzyl)piperazine;

(trans)-1-((4-chloro-2-(glycinamido)phenoxy)methyl)carbonyl-2,5-dimethyl-4-(4-fluorobenzyl)piperazine;

(2R)-1-((4-chloro-2-(ureido)phenoxy)methyl)carbonyl-2-methyl-4-(4-fluorobenzyl)piperazine;

(trans)-1-((4-chloro-2-(ureido)phenoxy)methyl)carbonyl-2,5-dimethyl-4-(4-fluorobenzyl)piperazine;

(2R,5S)-1-((4-chloro-2-(ureido)phenoxy)methyl)carbonyl-2,5-dimethyl-4-(4-fluorobenzyl)piperazine; and (2R,5S)-1-((4-chloro-2-(glycinamido)phenoxy)methyl)carbonyl-2,5-dimethyl-4-(4-fluorobenzyl)piperazine.

Of the subgroup of compounds as set forth above, another preferred class of compounds are those compounds wherein:

$R^4$ is —N($R^7$)—;

$R^5$ is methylene;

$R^6$ is —C(O)—; and $R^7$ is selected from the group consisting of hydrogen, alkyl, aryl, aralkyl, alkylcarbonyl, alkylcarbonylalkyl, aralkylcarbonyl, aralkylcarbonylalkyl, aminocarbonyl, monoalkylaminocarbonyl, dialkylaminocarbonyl, and alkoxycarbonyl.

Of this class of compounds, a preferred subclass of compounds are those compounds wherein:

$R^{1a}$ is one or more substituents independently selected from the group consisting of halo, alkyl, cycloalkyl, cycloalkylaminoalkyl, haloalkyl, hydroxyalkyl, hydroxyalkenyl, hydroxyalkynyl, (hydroxy)aralkyl, cyanoalkyl, haloalkylcarbonylaminoalkyl, alkoxyalkyl, aralkoxyalkyl, alkylthioalkyl, hydroxyalkylthioalkyl, aminoalkyl, monoalkylaminoalkyl, dialkylaminoalkyl, monoarylaminoalkyl, monoaralkylaminoalkyl, azidoalkyl, monoalkylureidoalkyl, (alkoxycarbonylalkyl)ureidoalkyl, hydroxyalkylaminoalkyl, aryloxyalkylcarbonyloxyalkyl, aralkoxyalkylcarbonyloxyalkyl, alkylcarbonylalkyl, alkoxycarbonyl, alkoxycarbonylalkyl, and heterocyclylalkyl;

$R^2$ is one or more substituents independently selected from the group consisting of hydrogen and halo;

$R^3$ is phenyl optionally substituted by one or more substituents independently selected from the group consisting of hydrogen, hydroxy, halo, alkyl, alkoxy, hydroxyalkoxy, haloalkyl, formyl, nitro, cyano, aminoalkoxy, cycloalkyl, cycloalkylaminoalkyl, aralkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, alkylsulfonylamino, aminoalkyl, monoalkylaminoalkyl, dialkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, dialkylaminocarbonylalkyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl) ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, alaninamido, heterocyclyl and heterocyclylalkyl.

A preferred group of compounds in this subclass group of compounds is that group wherein:

$R^{1a}$ is one or more substituents independently selected from the group consisting of alkyl, cycloalkyl, hydroxyalkyl, hydroxyalkenyl, cyanoalkyl, alkoxyalkyl, monoalkylaminoalkyl, azidoalkyl, monoalkylureidoalkyl, aryloxyalkylcarbonyloxyalkyl, and heterocyclylalkyl;

$R^2$ is one or more substituents independently selected from the group consisting of hydrogen, chloro or fluoro;

$R^3$ is phenyl substituted by one or more substituents independently selected from the group consisting of hydroxy, halo, alkyl, alkoxy, formyl, nitro, cyano, aminoalkoxy, cycloalkylaminoalkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, monoaralkylaminoalkyl, alkylcarbonylaminoalkyl, arylcarbonylaminoalkyl, (alkylcarbonyl)(alkyl) aminoalkyl, (cycloalkyalkyl)aminoalkyl, alkoxycarbonylalkylcarbonylaminoalkyl, alkylsulfonylaminoalkyl, (alkylsulfonyl)(alkyl) aminoalkyl, arylsulfonylaminoalkyl, (arylsulfonyl) (alkyl)aminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl) aminocarbonyl, (aminoalkyl)aminocarbonyl, (hydroxyalkyl)aminocarbonyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl)(alkyl) glycinamido, (monoarylaminocarbonyl)glycinamido, (monoarylaminocarbonyl)(alkyl)glycinamido, alaninamido, heterocyclyl and heterocyclylalkyl.

A more preferred group in this subclass group of compounds are those compounds wherein:

$R^{1a}$ is one or more substituents independently selected from the group consisting of alkyl and hydroxyalkyl;

$R^2$ is one or more substituents independently selected from the group consisting of hydrogen, chloro or fluoro;

$R^3$ is phenyl substituted by one or more substituents independently selected from the group consisting of halo, alkyl, alkoxy, formyl, nitro, cycloalkylaminoalkyl, hydroxyalkyl, amino, alkylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, (alkylsulfonyl)(alkyl)aminoalkyl, alkylcarbonyl, aminocarbonyl, monoalkylaminocarbonyl, monoarylaminocarbonyl, (aminocarbonylalkyl) aminocarbonyl, (aminoalkyl)aminocarbonyl, hydroxyamidino, ureido, (haloalkylcarbonyl)ureido, ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylaminoalkylcarbonyl)glycinamido, alaninamido, and heterocyclylalkyl.

An even more preferred group of compounds in this subclass group of compounds are those compounds wherein $R^2$ is 4-fluoro and $R^3$ is phenyl substituted at the 4-position with chloro and optionally substituted at the 2-position by aminocarbonyl, ureido, or glycinamido. Preferred compounds in this group selected from the group consisting of the following compounds:

(trans)-1-((4-chlorophenylamino)methyl)carbonyl-2,5-dimethyl-4-(4-fluorobenzyl)piperazine 1-((4-chloro-2-(aminocarbonyl)phenylamino)methyl) carbonyl-2-methyl-4-(4-fluorobenzyl)piperazine; and 1-((4-chlorophenylamino)methyl)carbonyl-2-methyl-4-(4-fluorobenzyl)piperazine;.

Of the subgroup of compounds as set forth above, another preferred class of compounds are those compounds wherein:

$R^4$ is —C($R^8$)$_2$—;

$R^5$ is methylene;

$R^6$ is —C(O)—; and each $R^8$ is independently selected from the group consisting of hydrogen, alkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, alkylcarbonylaminoalkyl, cycloalkylcarbonylaminoalkyl, alkoxycarbonylaminoalkyl, heterocyclylcarbonylaminoalkyl, arylsulfonylamino, alkylsulfonylaminoalkyl, ureido, monoalkylureido, monohaloalkylureido, ureidoalkyl, monoalkylureidoalkyl, monohaloalkylureidoalkyl, aminoalkyl, monoalkylaminoalkyl, and dialkylaminoalkyl.

A preferred subclass of compounds of this class of compounds are those compounds wherein:

$R^{1a}$ is one or more substituents independently selected from the group consisting of halo, alkyl, cycloalkyl, cycloalkylaminoalkyl, haloalkyl, hydroxyalkyl, hydroxyalkenyl, hydroxyalkynyl, (hydroxy)aralkyl, cyanoalkyl, haloalkylcarbonylaminoalkyl, alkoxyalkyl, aralkoxyalkyl, alkylthioalkyl, hydroxyalkylthioalkyl, aminoalkyl, monoalkylaminoalkyl, dialkylaminoalkyl, monoarylaminoalkyl, monoaralkylaminoalkyl, azidoalkyl, monoalkylureidoalkyl, (alkoxycarbonylalkyl)ureidoalkyl, hydroxyalkylaminoalkyl, aryloxyalkylcarbonyloxyalkyl, aralkoxyalkylcarbonyloxyalkyl, alkylcarbonylalkyl, alkoxycarbonyl, alkoxycarbonylalkyl, and heterocyclylalkyl;

$R^2$ is one or more substituents independently selected from the group consisting of hydrogen and halo;

$R^3$ is phenyl optionally substituted by one or more substituents independently selected from the group consisting of hydrogen, hydroxy, halo, alkyl, alkoxy, hydroxyalkoxy, haloalkyl, formyl, nitro, cyano, aminoalkoxy, cycloalkyl, cycloalkylaminoalkyl, aralkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, alkylsulfonylamino, aminoalkyl, monoalkylaminoalkyl, dialkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, dialkylaminocarbonylalkyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoarylaminocarbonyl)(alkyl)glycinamido, (monoarylaminocarbonyl)glycinamido, (monoarylaminocarbonyl)(alkyl)glycinamido, alaninamido, heterocyclyl and heterocyclylalkyl.

A preferred group of compounds within this preferred subclass of compounds are those compounds wherein:

$R^{1a}$ is one or more substituents independently selected from the group consisting of alkyl, cycloalkyl, hydroxyalkyl, hydroxyalkenyl, cyanoalkyl, alkoxyalkyl, monoalkylaminoalkyl, azidoalkyl, monoalkylureidoalkyl, aryloxyalkylcarbonyloxyalkyl, and heterocyclylalkyl;

$R^2$ is one or more substituents independently selected from the group consisting of hydrogen, chloro or fluoro;

$R^3$ is phenyl substituted by one or more substituents independently selected from the group consisting of hydroxy, halo, alkyl, alkoxy, formyl, nitro, cyano, aminoalkoxy, cycloalkylaminoalkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylalkylcarbonylaminoalkyl, alkylsulfonylaminoalkyl, (alkylsulfonyl)(alkyl)aminoalkyl, arylsulfonylaminoalkyl, (arylsulfonyl)(alkyl)aminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)(alkyl)glycinamido, (monoarylaminocarbonyl)glycinamido, (monoarylaminocarbonyl)(alkyl)glycinamido, alaninamido, heterocyclyl and heterocyclylalkyl.

A more preferred group of compounds within this subclass of compounds are those compounds wherein:

$R^{1a}$ is one or more substituents independently selected from the group consisting of alkyl and hydroxyalkyl;

$R^2$ is one or more substituents independently selected from the group consisting of hydrogen, chloro or fluoro;

$R^3$ is phenyl substituted by one or more substituents independently selected from the group consisting of halo, alkyl, alkoxy, formyl, nitro, cycloalkylaminoalkyl, hydroxyalkyl, amino, alkylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, (alkylsulfonyl)(alkyl)aminoalkyl, alkylcarbonyl, aminocarbonyl, monoalkylaminocarbonyl, monoarylaminocarbonyl, (aminocarbonylalkyl)aminocarbonyl, (aminoalkyl)aminocarbonyl, hydroxyamidino, ureido, (haloalkylcarbonyl)ureido, ureidoalkyl, glycinamido, monoalkylglycinamido, aminocarbonylglycinamido, (alkoxyalkylcarbonyl)
glycinamido, (aminocarbonyl)(alkyl)glycinamido,
(alkoxycarbonylaminoalkylcarbonyl)glycinamido,
alaninamido, and heterocyclylalkyl.

An even more preferred group of compounds of this subclass group of compounds are those compounds wherein:

$R^2$ is 4-fluoro;

$R^3$ is phenyl substituted at the 4-position with chloro and optionally substituted at the 2-position by aminocarbonyl, ureido, or glycinamido; and one $R^8$ is hydrogen and the other $R^8$ is selected from the group consisting of amino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, alkylcarbonylaminoalkyl, cycloalkylcarbonylaminoalkyl, alkoxycarbonylaminoalkyl, heterocyclylcarbonylaminoalkyl, arylsulfonylamino, alkylsulfonylaminoalkyl, ureido, monoalkylureido, monohaloalkylureido, ureidoalkyl, monoalkylureidoalkyl, monohaloalkylureidoalkyl, and aminoalkyl.

Preferred compounds in this even more preferred group are those compounds selected from the group consisting of the following compounds:

(trans)-1-(2-(4-chlorophenyl)-3-(methylsulfonylamino)propyl)carbonyl-2,5-dimethyl-4-(4-fluorobenzyl)piperazine;

(trans)-1-(2-(4-chlorophenyl)-3-(acetylamino)propyl)carbonyl-2,5-dimethyl-4-(4-fluorobenzyl)piperazine;

(trans)-1-(2-(4-chlorophenyl)-2-(methylsulfonylamino)ethyl)carbonyl-2,5-dimethyl-4-(4-fluorobenzyl)piperazine;

(trans)-1-(2-(4-chlorophenyl)-2-(acetylamino)ethyl)carbonyl-2,5-dimethyl-4-(4-fluorobenzyl)piperazine;

(trans)-1-(2(4-chlorophenyl)-2-(amino)ethyl)carbonyl-2,5-dimethyl-4-(4-fluorobenzyl)piperazine;

(trans)-1-(2-(4-chlorophenyl)-2-(ureido)ethyl)carbonyl-2,5-dimethyl-4-(4-fluorobenzyl)piperazine;

(trans)-1-(2-(4-chlorophenyl)-3-(ureido)propyl)carbonyl-2,5-dimethyl-4-(4-fluorobenzyl)piperazine;

(trans)-1-(2-(4-chlorophenyl)-3-(amino)propyl)carbonyl-2,5-dimethyl-4-(4-fluorobenzyl)piperazine;

(trans)-1-(2-(4-chlorophenyl)-3-(t-butoxycarbonylamino)propyl)carbonyl-2,5-dimethyl-4-(4-fluorobenzyl)piperazine;

(trans)-1-(2-(4-chlorophenyl)-2-((ethoxycarbonylmethylcarbonylamino)ethyl)carbonyl-2,5-dimethyl-4-(4-fluorobenzyl)piperazine;

(trans)-1-(2-(4-chlorophenyl)-2-(N'-iso-propylureido)ethyl)carbonyl-2,5-dimethyl-4-(4-fluorobenzyl)piperazine;

(trans)-1-(2-(4-chlorophenyl)-2-(N'-(2-chloroethyl)ureido)ethyl)carbonyl-2,5-dimethyl-4-(4-fluorobenzyl)piperazine;

(trans)-1-(2-(4-chlorophenyl)-2-((2-nitrophenyl)carbonylamino)ethyl)carbonyl-2,5-dimethyl-4-(4-fluorobenzyl)piperazine;

(trans)-1-(2-(4-chlorophenyl)-2-((4-methoxyphenylmethyl)carbonylamino)ethyl)carbonyl-2,5-dimethyl-4-(4-fluorobenzyl)piperazine;

(trans)-1-(2-(4-chlorophenyl)-2-((2,4-dinitrophenyl)sulfonylamino)ethyl)carbonyl-2,5-dimethyl-4-(4-fluorobenzyl)piperazine;

(trans)-1-(2-(4-chlorophenyl)-2-(cyclopropylcarbonylamino)ethyl)carbonyl-2,5-dimethyl-4-(4-fluorobenzyl)piperazine;

(trans)-1-(2-(4-chlorophenyl)-2-((2-cyclopropylethyl)carbonylamino)ethyl)carbonyl-2,5-dimethyl-4-(4-fluorobenzyl)piperazine;

(trans)-1-(2-(4-chlorophenyl)-3-((2-methylpropyl)carbonylamino)propyl)carbonyl-2,5-dimethyl-4-(4-fluorobenzyl)piperazine;

(trans)-1-(2-(4-chlorophenyl)-3-(cyclopentylcarbonylamino)propyl)carbonyl-2,5-dimethyl-4-(4-fluorobenzyl)piperazine;

(trans)-1-(2-(4-chlorophenyl)-3-(N'(t-butyl)ureido)propyl)carbonyl-2,5-dimethyl-4-(4-fluorobenzyl)piperazine;

(trans)-1-(2-(4-chlorophenyl)-3-(N'(ethyl)ureido)propyl)carbonyl-2,5-dimethyl-4-(4-fluorobenzyl)piperazine;

(trans)-1-(2-(4-chlorophenyl)-3-(N'-(3-choropropyl)ureido)propyl)carbonyl-2,5-dimethyl-4-(4-fluorobenzyl)piperazine; and (trans)-1-(2-(4-chlorophenyl)-3-((morpholin-4-yl)carbonylamino)propyl)carbonyl-2,5-dimethyl-4-(4-fluorobenzyl)piperazine.

Of the compounds of formula (Ia), another preferred group of compounds are those compounds wherein:

$R^3$ is a heterocyclic ring system substituted by one or more substituents independently selected from the group consisting of hydrogen, hydroxy, halo, alkyl, alkylsufonyl, arylsulfonyl, alkoxy, hydroxyalkoxy, haloalkyl, formyl, nitro, cyano, haloalkoxy, alkenyl, alkynyl, aryl, aralkyl, amino, monoalkylamino, dialkylamino, monoarylamino, monoaralkylamino, alkylcarbonylamino, alkoxycarbonylamino, alkenylcarbonylamino, cycloalkylcarbonylamino, arylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, alkylcarbonylaminoalkyl, arylcarbonylaminoalkyl, (alkylcarbonyl)(alkyl)aminoalkyl, alkoxycarbonylaminoalkyl, carboxy, alkoxycarbonyl, aralkoxycarbonyl, alkylcarbonyl, arylcarbonyl, aralkylcarbonyl, aminocarbonyl, monoalkylaminocarbonyl, dialkylaminocarbonyl, monoarylaminocarbonyl, aminocarbonylalkyl, monoalkylaminocarbonylalkyl, dialkylaminocarbonylalkyl, monoarylaminocarbonylalkyl, guanidino, ureido, monoalkylureido, ureidoalkyl, monoalkylureidoalkyl, and glycinamido.

Of this group of compounds, a preferred subgroup of compounds is that group of compounds wherein:

$R^4$ is —O—, —N($R^7$)— or —C($R^8$)—;

$R^5$ is an alkylene chain;

$R^7$ is selected from the group consisting of hydrogen, alkyl, aryl, aralkyl, alkylcarbonyl, alkylcarbonylalkyl, aralkylcarbonyl, aralkylcarbonylalkyl, aminocarbonyl, monoalkylaminocarbonyl, dialkylaminocarbonyl, and alkoxycarbonyl; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino,
cycloalkylalkylcarbonylamino, alkoxycarbonylamino,
alkylsulfonylamino, arylcarbonylamino,
alkoxycarbonylalkylcarbonylamino, (alkylcarbonyl)
(alkyl)amino, aralkylcarbonylamino, (aralkylcarbonyl)
(alkyl)amino, alkylcarbonylaminoalkyl,
cycloalkylcarbonylaminoalkyl,
alkoxycarbonylaminoalkyl, (alkylcarbonyl)(alkyl)
aminoalkyl, aralkylcarbonylaminoalkyl,
heterocyclylcarbonylaminoalkyl, (aralkylcarbonyl)
(alkyl)aminoalkyl, arylsulfonylamino,
alkylsulfonylaminoalkyl, ureido, monoalkylureido,
monohaloalkylureido, dialkylureido, ureidoalkyl,
monoalkylureidoalkyl, dialkylureidoalkyl,
monohaloalkylureidoalkyl, aminoalkyl,
monoalkylaminoalkyl, dialkylaminoalkyl,
carboxyalkyl, alkoxycarbonylalkyl,
aminocarbonylalkyl, monoalkylaminocarbonylalkyl,
and dialkylaminocarbonylalkyl.

Of this subgroup of compounds, a preferred class of compounds are those compounds wherein:

$R^4$ is —O—;
$R^5$ is methylene; and
$R^6$ is —C(O)—.

Of this class of compounds, a preferred subclass group of compounds are those compounds wherein:

$R^{1a}$ is one or more substituents independently selected from the group consisting of halo, alkyl, cycloalkyl, cycloalkylaminoalkyl, haloalkyl, hydroxyalkyl, hydroxyalkenyl, hydroxyalkynyl, (hydroxy)aralkyl, cyanoalkyl, haloalkylcarbonylaminoalkyl, alkoxyalkyl, aralkoxyalkyl, alkylthioalkyl, hydroxyalkylthioalkyl, aminoalkyl, monoalkylaminoalkyl, dialkylaminoalkyl, monoarylaminoalkyl, monoaralkylaminoalkyl, azidoalkyl, monoalkylureidoalkyl, (alkoxycarbonylalkyl)ureidoalkyl, hydroxyalkylaminoalkyl, aryloxyalkylcarbonyloxyalkyl, aralkoxyalkylcarbonyloxyalkyl, alkylcarbonylalkyl, alkoxycarbonyl, alkoxycarbonylalkyl, and heterocyclylalkyl; and $R^2$ is one or more substituents independently selected from the group consisting of hydrogen and halo.

A preferred group of compounds in this preferred subclass group of compounds are those compounds wherein $R^3$ is selected from the group consisting of azepinyl, acridinyl, benzimidazolyl, benzothiazolyl, benzoxazolyl, benzopyranyl, benzopyranonyl, benzofuranyl, benzofuranonyl, benzothienyl, carbazolyl, cinnolinyl, decahydroisoquinolyl, dioxolanyl, furyl, isothiazolyl, quinuclidinyl, imidazolyl, imidazolinyl, imidazolidinyl, isothiazolidinyl, indolyl, isoindolyl, indolinyl, isoindolinyl, indanyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, tetrahydropyranyl, thienyl, thiamorpholinyl, thiamorpholinyl sulfoxide, and thiamorpholinyl sulfone.

A more preferred group of compounds in this preferred subclass of compounds are those compounds wherein $R^3$ is benzopyranyl, benzopyranonyl, benzfuranyl, benzofuranonyl, quinolinyl, indolyl, indolinyl, oxazolyl, imidazolyl, or benzothienyl.

A preferred compound in this more preferred group is (trans)-1-((benzo[b]pyran-2-on-7-yloxy)methyl)carbonyl-2,5-dimethyl-4-(4-fluorobenzyl)piperazine.

Another aspect of the invention is a method of treating an inflammatory disorder in a human, which method comprises administering to a human in need of such treatment a therapeutically effective amount of a compound of formula (Ia) as described above. A preferred method is the method of treating inflammatory disorders selected from the group consisting of multiple sclerosis, leukoencephalopathy, encephalomyelitis, Alzheimer's disease, Guillian-Barre syndrome, acute cell-mediated renal transplant rejection, allograft rejection, rheumatoid arthritis, atherosclerosis, uricaria, angioderma, allergic conjunctivitis, atopic dermatitis, allergic contact dermatitis, drug or insect sting allergy and systemic anaphylaxis.

Another aspect of the invention is a method of treating an inflammatory disorder in a human, which method comprises administering to a human in need of such treatment a therapeutically effective amount of a compound of formula (Ib) as described in the Summary of the Invention.

A preferred method is that method which comprises administering to a human in need of such treatment a therapeutically effective amount of a compound of formula (Ib) wherein:

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)

carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl) aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl.

An even more preferred method is that method which comprises administering to a human in need of such treatment a therapeutically effective amount of a compound of formula (Ib) wherein:

$R^4$ is —O—, —N($R^7$)— or —C($R^8$)—;

$R^5$ is an alkylene chain;

$R^7$ is selected from the group consisting of hydrogen, alkyl, aryl, aralkyl, alkylcarbonyl, alkylcarbonylalkyl, aralkylcarbonyl, aralkylcarbonylalkyl, aminocarbonyl, monoalkylaminocarbonyl, dialkylaminocarbonyl, and alkoxycarbonyl; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl) (alkyl)amino, aralkylcarbonylamino, (aralkylcarbonyl) (alkyl)amino, alkylcarbonylaminoalkyl, cycloalkylcarbonylaminoalkyl, alkoxycarbonylaminoalkyl, (alkylcarbonyl)(alkyl) aminoalkyl, aralkylcarbonylaminoalkyl, heterocyclylcarbonylaminoalkyl, (aralkylcarbonyl) (alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl.

An even more preferred method is that method which comprises administering to a human in need of such treatment a therapeutically effective amount of a compound of formula (Ib) wherein:

$R^4$ is —O—;

$R^5$ is methylene; and $R^6$ is —C(O)—.

The most preferred method is that method which comprises administering to a human in need of such treatment a therapeutically effective amount of a compound of formula (Ib) wherein:

$R^2$ is one or more substituents independently selected from the group consisting of hydrogen and halo;

$R^3$ is phenyl optionally substituted by one or more substituents independently selected from the group consisting of hydrogen, hydroxy, halo, alkyl, alkoxy, hydroxyalkoxy, haloalkyl, formyl, nitro, cyano, aminoalkoxy, cycloalkyl, cycloalkylaminoalkyl, aralkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl) (alkyl)amino, alkylsulfonylamino, aminoalkyl, monoalkylaminoalkyl, dialkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkylalkyl) aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl) aminoalkyl, arylsulfonylaminoalkyl, (arylsulfonyl) (alkyl)aminoalkyl, heterocyclylaminoalkyl, carboxy, alkoxycarbonyl, alkylcarbonyl, (hydroxyalkoxy) carbonyl, aminocarbonyl, monoalkylaminocarbonyl, monoarylaminocarbonyl, (aminocarbonylalkyl) aminocarbonyl, (aminoalkyl)aminocarbonyl, (hydroxyalkyl)aminocarbonyl, dialkylaminocarbonylalkyl, hydroxyamidino, ureido, monoalkylureido, monoarylureido, monoaralkylureido, (monoalkyl)(monoaryl)ureido, (haloalkylcarbonyl) ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl) ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, alaninamido, heterocyclyl and heterocyclylalkyl.

Particularly preferred is that method which comprises administering to a human in need of such treatment a therapeutically effective amount of a compound of formula (Ib) selected from the group consisting of the following compounds:

1-((3,4,5-trimethoxyphenoxy)methyl)carbonyl-4-(benzyl)piperazine;

1-((3,5-dimethoxyphenoxy)methyl)carbonyl-4-(4-chlorobenzyl)piperazine;

1-((2-(hydroxymethyl)phenoxy)methyl)carbonyl-4-(4-chlorobenzyl)piperazine;

1-((4-iodophenoxy)methyl)carbonyl-4-(4-chlorobenzyl)piperazine;

1-((2-methylphenoxy)methyl)carbonyl-4-(4-chlorobenzyl)piperazine;

1-((4-methylphenoxy)methyl)carbonyl-4-(4-chlorobenzyl)piperazine;

1-((2,4-dichlorophenoxy)methyl)carbonyl-4-(4-chlorobenzyl)piperazine;

1-((4-bromo-2-chlorophenoxy)methyl)carbonyl-4-(4-chlorobenzyl)piperazine;

1-((4-chloro-3-nitrophenoxy)methyl)carbonyl-4-(4-chlorobenzyl)piperazine;

1-((2-bromophenoxy)methyl)carbonyl-4-(4-chlorobenzyl)piperazine;

1-((4-bromophenoxy)methyl)carbonyl-4-(benzyl)piperazine;

1-((2,4-dibromophenoxy)methyl)carbonyl-4-(4-chlorobenzyl)piperazine;

1-((2-formylphenoxy)methyl)carbonyl-4-(4-chlorobenzyl)piperazine;

1-((2-methoxy-5-nitrophenoxy)methyl)carbonyl-4-(4-chlorobenzyl)piperazine;

1-((3,4,5-trimethoxyphenoxy)methyl)carbonyl-4-(4-fluorobenzyl)piperazine;

1-((4-chlorophenoxy)methyl)carbonyl-4-(4-chlorobenzyl)piperazine;

1-((4-chlorophenoxy)methyl)carbonyl-4-(4-fluorobenzyl)piperazine;

1-((3-fluoro-4-chlorophenoxy)methyl)carbonyl-4-(4-chlorobenzyl)piperazine;

1-((3,5-dimethoxy-4-chlorophenoxy)methyl)carbonyl-4-(4-chlorobenzyl)piperazine;

1-((4-bromo-2-formylphenoxy)methyl)carbonyl-4-(4-chlorobenzyl)piperazine;

1-((3-formyl-4-nitrophenoxy)methyl)carbonyl-4-(4-fluorobenzyl)piperazine;

1-((2-aminocarbonyl-4-chlorophenoxy)methyl)carbonyl-4-(4-fluorobenzyl)piperazine;

1-((3,5-dimethoxy-4-bromophenoxy)methyl)carbonyl-4-(4-fluorobenzyl)piperazine; and 1-((2-acetylaminophenoxy)methyl)carbonyl-4-(4-fluorobenzyl)piperazine.

Preparation of Compounds of The Invention

The following Reaction Schemes are directed to the preparation of compounds of formula (Ia), formula (Ib) and formula (Ic). It is understood that those compounds of the invention which are not specifically prepared in the following Reaction Schemes may be prepared by similar synthetic processes with the appropriately substituted starting materials and reagents. It is also understood that in the following descriptions, combinations of the various substituents (e.g., $R^{1a}$, $R^2$ and $R^3$ substituents) on the depicted formulae are permissible only if such combinations result in stable compounds.

For the purposes of convenience only, preparation of compounds of the invention where $R^3$ is only phenyl are illustrated below. It is understood that other $R^3$ groups (including other carbocyclic and heterocyclic ring systems) may be prepared in a similar manner.

It is also understood that during the preparation of the compounds of the invention, as described below, additional reactive groups (for example, hydroxy, amino or carboxy groups) on the intermediate compounds utilized in the preparation may be protected as needed by the appropriate protecting group by treating the intermediate compound prior to the desired reaction with the appropriate protecting group precursor by methods known to those of ordinary skill in the art. The protecting groups may then be removed as desired by methods known to those of ordinary skill in the art, for example, by acidic or basic hydrolysis. Such protecting groups and methods are described in detail in Greene, T. W. and Wuts, P. G. M., "Protective Groups in Organic Synthesis", 2nd Edition, 1991, John Wiley & Sons. Also, dimethylpiperazines can be prepared in an asymmetric synthesis according to the method outlined in Mickelson, J. W., Belonga, K. L., Jacobsen, E. J., *Journal of Organic Chemistry* (1995), Vol. 60, pp. 4177–4123.

It should be noted that the only difference in the two groups of compounds covered by formula (Ia) and formula (Ib) as described above in the Summary of the Invention is the required substitution of the piperazine ring in the compounds of formula (Ia). Accordingly, it is understood that, unless otherwise indicated, the following Reaction Schemes directed to the preparation of the compounds of formula (Ia) may be used to prepare compounds of formula (Ib), and the following Reaction Schemes directed to the preparation of the compounds of formula (Ib) may be used to prepare compounds of formula (Ia).

In addition, compounds of formula (Id) may be prepared in a similar manner as those described herein for compounds of formula (Ia) and (Ib).

A. Preparation of Compounds of Formula (C)

Compounds of formula (C) are intermediates in the preparation of the compounds of the invention. They are prepared according to the following Reaction Scheme 1 wherein $R^{1a1}$ is one or more independently selected $R^{1a}$ substituents as described above in the Summary of the Invention for compounds of formula (Ia) (except that $R^{1a1}$ can not be aminoalkyl or monoalkylaminoalkyl unless appropriately protected); X is chloro, bromo or iodo; and R is as described above for compounds of formula (Ia):

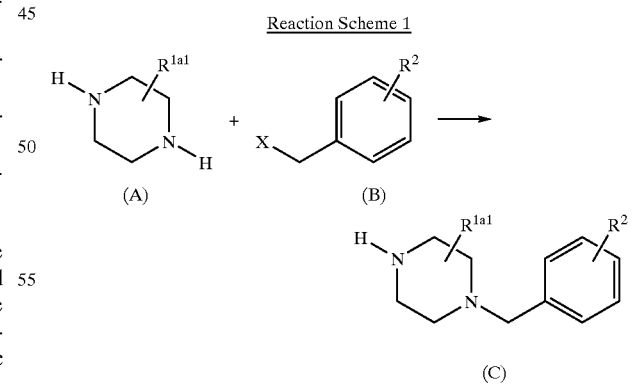

The compounds of formula (A) and formula (B) are commercially available, e.g., from Aldrich Chemical Co. or Sigma Chemical Co., or may be prepared according to methods known to those of ordinary skill in the art.

In general, the compounds of formula (C) are prepared by treating a compound of formula (A) in an organic solvent, such as methylene chloride, with an equimolar amount of a compound of formula (B). The reaction mixture is stirred for about 10 to 20 hours at ambient temperature. The reaction mixture is then concentrated to afford a residue which is dissolved in an organic solvent. The compound of formula (C) is isolated from the solution by standard isolation techniques, for example, by filtration, concentration and flash column chromatography.

B. Preparation of Compounds of Formula (Ga) and Formula (Gb)

Compounds of formula (Ga) and formula (Gb) are intermediates in the preparation of compounds of the invention. They are prepared as illustrated in the following Reaction Scheme 2 wherein each $R^{1a1}$ is independently selected from the group consisting of alkyl, cycloalkyl, cycloalkylalkyl, cycloalkylaminoalkyl, (cycloalkylalkyl)aminoalkyl, haloalkyl, alkenyl, alkynyl, aralkyl, aralkenyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, ureidoalkyl, monoalkylureidoalkyl, dialkylureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonylalkyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, heterocyclyl and heterocyclylalkyl (except that $R^{1a1}$ can not be aminoalkyl or monoalkylaminoalkyl unless appropriately protected):

Reaction Scheme 2

1.
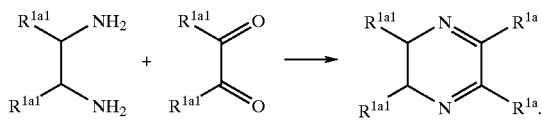
(D)   (E)   (F)

2a.
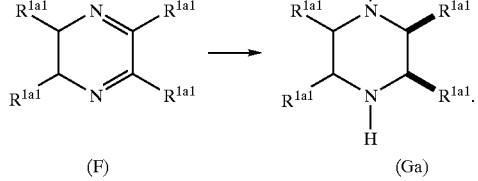
(F)   (Ga)

2b.
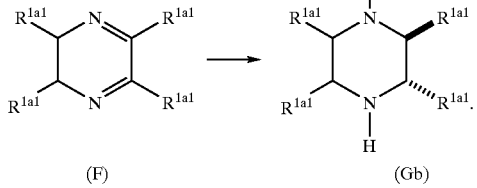
(F)   (Gb)

Compounds of formula (D) and formula (E) are commercially available, e.g., from Aldrich Chemical Co. or Sigma Chemical Co., or may be made from methods known to those of ordinary skill in the art.

In general, compounds of formula (Ga) and formula (Gb) are prepared by first treating a compound of formula (D) in an anhydrous aprotic solvent, such as anhydrous ether, with an equimolar amount of a compound of formula (E) in an anhydrous aprotic solvent, such as anhydrous ether, over a period of time, for example, over a two hour period. The resulting reaction mixture is stirred for about 2 to about 4 hours, preferably for about 3 hours, at ambient temperature. The compound of formula (F) is isolated from the reaction mixture by standard isolation techniques, such as concentration of the product and purification by vacuum distillation.

To a solution of a strong reducing agent, such as lithium aluminum hydride, in an anhydrous polar aprotic solvent, such as tetrahydrofuran, is added the compound of formula (F). The resulting mixture is stirred at ambient temperature for about 30 minutes to about 2 hours, preferably for about 1 hour. The mixture is then heated to reflux to complete the reaction. Upon completion, the compound of formula (Ga) is isolated from the reaction mixture by standard isolation techniques, such as quenching by water and a mild base, followed by filtration.

Alternatively, to a solution of formula (F) in a polar protic solvent, such as absolute ethanol, is added a solid alkaline metal, such as sodium metal over a period of time, such as over a 3 hour period. The resulting mixture is heated to reflux for about 2 to about 4 hours, preferably for about 3 hours. The compound of formula (Gb) is distilled from the reaction mixture by the addition of water to the reaction mixture. The distillate is then treated with an aqueous acid, such as hydrochloric acid, to form the salt of the compound of formula (Gb).

Compounds of formula (Ga) and formula (Gb) may then be treated with compounds of formula (B) in a manner similar to that described above in Reaction Scheme 1 to produce compounds of the invention wherein the relative orientation of the $R^{1a}$ substituents is fixed.

C. Preparation of Compounds of Formula (Ia)

The compounds of formula (Ia) are compounds of the invention and they are prepared as illustrated in the following Reaction Scheme 3 wherein each X is independently chloro or bromo; $R^{1a1}$ is one or more independently selected $R^{1a}$ substituents as described above in the Summary of the Invention for compounds of formula (Ia) (except that $R^{1a1}$ can not contain a primary or secondary amine unless appropriately protected); $R^2$, $R^4$ and $R^5$ are as described in the Summary of the Invention for compounds of formula (Ia) (except that $R^4$ and $R^5$ can not contain a primary or secondary amine unless adequately protected); and $R^{3a}$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl) aminoalkyl, alkoxycarbonylamino, (alkoxycarbonyl)(alkyl) amino, alkoxycarbonylaminoalkyl, (alkoxycarbonyl)(alkyl) aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl; and $R^4$ and $R^5$ are as described above in the Summary of the Invention:

Reaction Scheme 3

1.

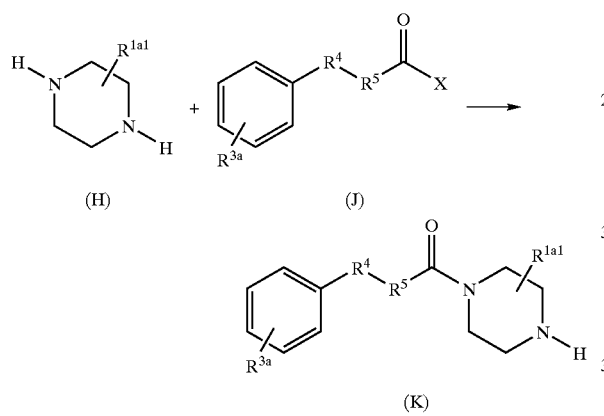

2.

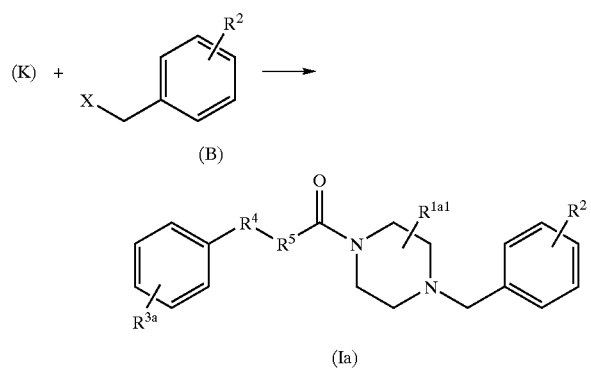

The compounds of formula (B), formula (H) and formula (J) are commercially available, for example, from Aldrich Chemical Co. or Sigma Chemical Co., or may be prepared according to methods known to those of ordinary skill in the art.

In general, compounds of formula (Ia) are prepared by the foregoing Reaction Scheme by first treating a compound of formula (H) in a polar solvent, such as methanol, with an equimolar amount of a compound of formula (J) in an anhydrous polar solvent, such as anhydrous ether. The resulting reaction mixture is stirred at ambient temperature for about 5 minutes to about 24 hours in the presence of an acid-scavenging base, such as triethylamine. The compound of formula (K) is then isolated from the reaction mixture by standard isolation techniques, such as organic phase extraction, evaporation of solvents and purification by flash column chromatography.

The compound of formula (K) in an aprotic polar solvent, such as tetrahydrofuran, is treated with an excess molar amount of a compound of formula (B) in the presence of a mild base, such as triethylamine and, optionally, a catalytic amount of sodium iodide. The resulting mixture is stirred at ambient temperature for about 1 to 5 days, preferably for about 2 days. The compound of formula (Ia) is then isolated from the reaction mixture by standard isolation techniques such as filtration, concentration of volatiles and purification by flash column chromatography.

Alternatively, compounds of formula (Ga) and formula (Gb), as prepared above in Reaction Scheme 2, may be used in place of compounds of formula (H) in this Reaction Scheme to produce compounds of the invention wherein the relative orientation of the $R^{1a}$ substituents is fixed.

D. Preparation of Compounds of Formula (Ia)

Compounds of formula (Ia) are compounds of the invention and they are prepared as illustrated in the following Reaction Scheme 4 wherein X is chloro, bromo or an activated ester; $P^1$ and $P^2$ are independently nitrogen-protecting groups, such as t-butoxycarbonyl ($P^1$ can also be hydrogen); $R^{1a}$, $R^2$, $R^4$ and $R^5$ are as described above in the Summary of the Invention; $R^{1b}$ is as described above in the Summary of the Invention for compounds of formula (Ic) and (Id); and $R^{3a}$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy) cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy) aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl) aminoalkyl, alkoxycarbonylamino, (alkoxycarbonyl)(alkyl) amino, alkoxycarbonylaminoalkyl, (alkoxycarbonyl)(alkyl) aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl:

Reaction Scheme 4

1.
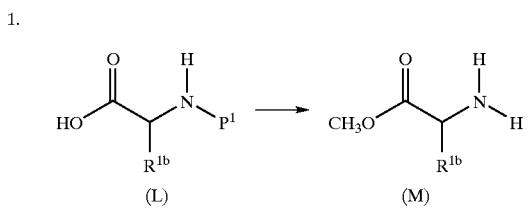

2.
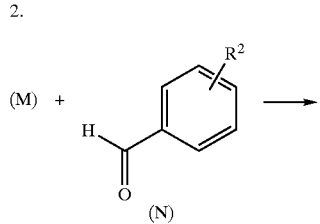

3.
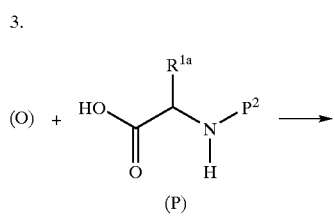

4.
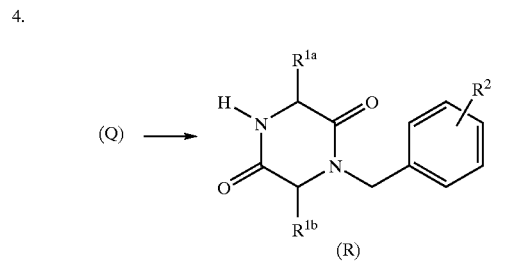

5.
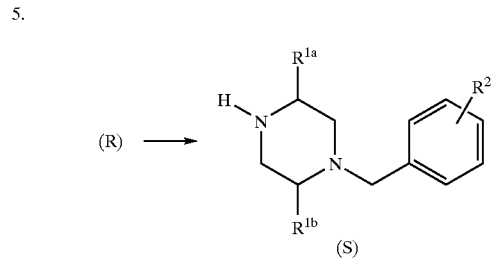

6.
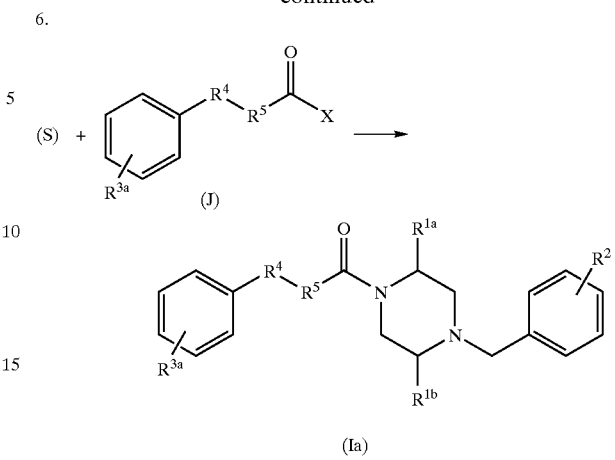

Compounds of formula (L), formula (N), formula (P) and formula (J) are commercially available, for example, from Aldrich Chemical Co. or Sigma Chemical Co., or may be prepared according to methods known to one of ordinary skill in the art.

Compounds of formula (L) wherein the $R^{1b}$ substituent contains an un-protected hydroxy group may be protected with the appropriate oxygen-protecting group prior to the synthesis of the compound of formula (M). Removal of the protecting group may be performed as desired.

In general, the compounds of formula (Ia) are prepared by first esterifying a compound of formula (L) by treating the compound with an excess molar amount of a lower alkanol, preferably methanol, in the presence of an acid, preferably hydrochloride gas, at about 0° C. to ambient temperature. The resulting mixture is then stirred at about 0° C. to reflux temperature, preferably at ambient temperature, for about 4 hours to about 18 hours. The mixture is then concentrated by removal of solvents to produce the compound of formula (M).

To a solution of the compound of formula (M) in an organic solvent, such as methanol, at about 0° C. to ambient temperature, is added an excess molar amount of a compound of formula (N), and then treated with a mild acid, such as acetic acid, and stirred at ambient temperature for about 2 hours to about 4 hours, preferably for about 3 hours, to form an intermediate imine. The imine is then reduced in situ by treatment with a reducing agent, such as sodium cyanoborohydride, to produce a compound of formula (O), which is isolated from the reaction mixture by standard isolation techniques, such as filtration and purification by flash column chromatography.

To a solution of a compound of formula (P) in a polar aprotic solvent, such as anhydrous tetrahydrofuran, is added an acid scavenging mild base, such as N-methylmorpholine, followed by the addition of an acid coupling reagent, such as isobutylchloroformate. The resulting mixture is stirred at about 0° C. to ambient temperature for about 15 minutes to about 2 hours, preferably for about 15 minutes at 0° C. and then for about an hour at ambient temperature, to form an intermediate active ester of the compound of formula (P). The intermediate is then treated in situ with a compound of formula (O) in anhydrous polar aprotic solvent, such as anhydrous tetrahydrofuran and the resulting mixture is stirred at ambient temperature for about 10 hours to about 24 hours, preferably for about 15 hours. The compound of formula (Q) is isolated from the reaction mixture by standard isolation techniques, such as concentration, organic phase separation and purification by flash column chromatography.

The compound of formula (Q) in an aprotic solvent, such as methylene chloride, at about 0° C., is then treated with a strong organic acid, such as trifluoroacetic acid, for a period of about 2 to about 4 hours, preferably for about 2 hours, to remove the protecting group on the nitrogen atom, followed by spontaneous cyclization to form the compound of formula (R), which is isolated from the reaction mixture by standard isolation techniques, such as neutralization with a mild base, filtration and concentration.

The compound of formula (R) in an anhydrous polar aprotic solvent, such as anhydrous tetrahydrofuran, at about 0° C. is treated with a strong reducing agent, such as lithium aluminum hydride. The resulting mixture is then heated to reflux for about 12 hours to about 24 hours, preferably for about 15 hours. The mixture is then cooled to ambient temperature and the reaction quenched with water, followed by aqeous base, preferably aqueous potassium hydroxide. The resulting mixture is allowed to stir at ambient temperature for about 30 minutes to an hour. The compound of formula (S) is then isolated from the reaction mixture by filtration and concentration.

The compound of formula (S) in a polar aprotic solvent, such as methylene chloride, in the presence of excess amount of an acid scavenging base, such as triethylamine, is added a slightly excess molar amount of a compound of formula (J) in a polar aprotic solvent, such as methylene chloride. The resulting mixture is stirred at ambient temperature for about 15 minutes to about 1 hour, preferably for about 15 minutes. The compound of formula (Ia) is then isolated from the reaction mixture by standard isolation techniques, such as extraction, concentration and flash column chromatography.

E. Preparation of Compounds of Formula (Ib)

Compounds of formula (Ib) are compounds of the invention and are prepared as illustrated below in Reaction Scheme 5 where X is chloro or bromo; $R^{1b}$ is as described above in the Summary of the Invention for compounds of formula (Ic) and formula (Id); and $R^2$ is as described above in the Summary of the Invention for compounds of formula (Ib); $R^{3a}$ is one or more substituents independently selected from the group consisting of hydrogen, halo, alkyl, alkoxy, aryloxy, haloalkyl, formyl, nitro, cyano, aralkoxy, haloalkoxy, cycloalkyl, alkenyl, alkynyl, aryl, aralkyl, aralkenyl, hydroxyalkyl, alkoxyalkyl, aryloxyalkyl, aralkoxyalkyl, amino, monoalkylamino, dialkylamino, aminoalkyl, monoalkylaminoalkyl, dialkylaminoalkyl, cycloalkylaminoalkyl, carboxy, alkoxycarbonyl, aryloxycarbonyl, aralkoxycarbonyl, carboxyalkyl, alkoxycarbonylalkyl, aryloxycarbonylalkyl, aminocarbonyl, monoalkylaminocarbonyl, dialkylaminocarbonyl, aminocarbonylalkyl, monoalkylaminocarbonylalkyl, dialkylaminocarbonylalkyl, arylsulfonyl, hydroxyalkoxy, aminoalkoxy, (monoalkylamino)aralkyl, aminoalkylamino, heterocyclylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, alkylsulfonylamino, arylcarbonylaminoalkyl, alkoxycarbonylalkylcarbonylaminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, (hydroxyalkoxy)carbonyl, (aminocarbonylalkyl)aminocarbonyl, (monoalkylaminocarbonylalkyl)aminocarbonyl, (carboxyalkyl)aminocarbonyl, (alkoxycarbonylalkyl)aminocarbonyl, (aminoalkyl)aminocarbonyl, (hydroxyalkyl)aminocarbonyl, dialkylaminocarbonyloxyalkyl, monoarylureido, monoaralkylureido, monohaloalkylureido, (monoalkyl)(monoaryl)ureido, diarylureido, (haloalkylcarbonyl)ureido, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, (alkoxyalkylcarbonyl)glycinamido, aminocarbonylglycinamido, (aminocarbonyl)(alkyl) glycinamido, (alkoxycarbonylalkylcarbonyl)(alkyl) glycinamido, (alkoxycarbonylaminoalkylcarbonyl) glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl; and $R^{4a}$ is —O— or —N($R^{7a}$)— where $R^{7a}$ is hydrogen, alkyl, aryl or aralkyl:

Reaction Scheme 5

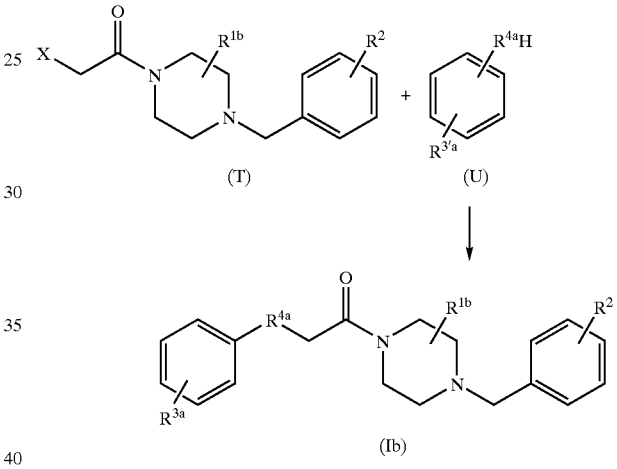

Compounds of formula (U) are commercially available, for example, from Aldrich Chemical Co. or Sigma Chemical Co., or may be prepared according to methods known to those of ordinary skill in the art. Compounds of formula (T) may be prepared according to the methods described herein for compounds of formula (C) or for compounds of formula (K), or by acylating the compounds of formula (C) as prepared herein by standard methods known to those of ordinary skill in the art.

In general, the compounds of formula (Ib) are prepared by the foregoing Reaction Scheme by first treating a compound of formula (T) in an anhydrous aprotic solvent, such as anhydrous dimethylformamide, with a slightly excess molar amount of a compound of formula (U) in the presence of a mild base, such as potassium carbonate. The resulting mixture is stirred at about 50° C. for about 10 hours to about 24 hours, preferably for about 15 hours. The compound of formula (Ib) is then isolated from the reaction mixture by standard isolation techniques, such as extraction, filtration and precipitation.

F. Preparation of Compounds of Formula (Ib)

Compounds of formula (Ib) may also be prepared as illustrated in the following Reaction Scheme 6 where X is chloro, bromo or an activated ester; $P^1$ is a nitrogen-protecting group, such as t-butoxycarbony; $R^{1b}$ is as described above in the Summary of the Invention for compounds of formula (Ic) and formula (Id); $R^{2a}$ is as described above in the Summary of the Invention for $R^2$ in compounds of formula (Ic) except that $R^{2a}$ can not be formyl or formylalkyl; $R^{3a}$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl; and $R^{4a}$ is —O— or —N($R^{7a}$)— where $R^{7a}$ is hydrogen, alkyl, aryl or aralkyl:

Reaction Scheme 6

1.

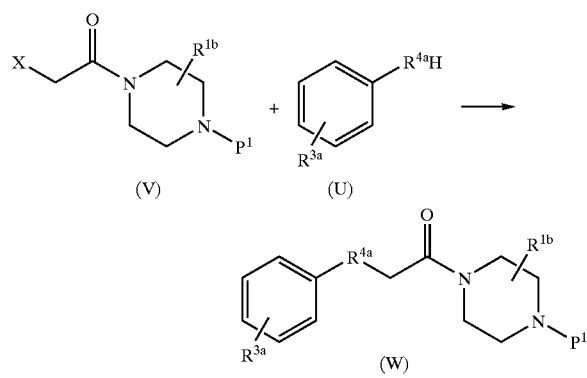

2.

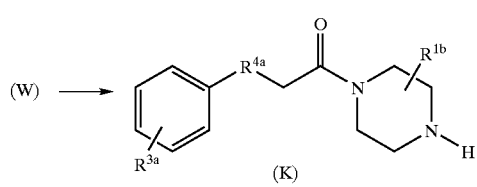

3.

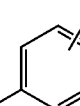

Compounds of formula (U) and formula (N) are commercially available, for example, from Aldrich Chemical Co. or Sigma Chemical Co., or may be prepared according to methods known to those of ordinary skill in the art. Compounds of formula (V) may be prepared according to the method described above for compounds of formula (K) in Reaction Scheme 3.

In general, compounds of formula (Ib) as prepared in the foregoing Reaction Scheme 6 are prepared by first treating a compound of formula (U) in an aprotic solvent, such as dimethylformamide, at about 0° C., with a strong base, such as potassium hexamethyldisilazane, to deprotonate the compound. The resulting mixture is stirred for about 20 minutes to an hour, preferably for about 20 minutes, at about 0° C. An equimolar amount of a compound of formula (V) in an aprotic solvent, such as dimethylformamide is then added to the mixture and the resulting mixture is stirred at ambient temperature for about 1 to 24 hours, preferably for about 2 hours. The compound of formula (W) is then isolated from the reaction mixture by standard isolation techniques, such as extraction and concentration.

The $P^1$ protecting group is then removed from the compound of formula (W) to form a compound of formula (K) by standard amine-deprotecting procedures, such as treating the compound of formula (W) with a strong acid, such as trifluoroacetic acid.

To a solution of the compound of formula (K) in a polar solvent, such as methanol, at about 0° C. to ambient temperature, was added an excess molar amount of a compound of formula (N), and then treated with a mild acid, such as acetic acid, and stirred at ambient temperature for about 2 hours to about 4 hours, preferably for about 3 hours, to form an intermediate imine. The imine is then reduced in situ by treatment with a reducing agent, such as sodium cyanoborohydride, to produce a compound of formula (Ib), which is isolated from the reaction mixture by standard isolation techniques, such as filtration and purification by flash column chromatography.

G. Preparation of Compounds of Formula (Ib)

Compounds of formula (Ib) may also be prepared as illustrated in the following Reaction Scheme 7 where $R^{1b}$ is as described above in the Summary of the Invention for compounds of formula (Ic) and formula (Id); and $R^2$ is as described above in the Summary of the Invention for the compounds of formula (Ib); and $R^{3a}$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl) amino, (cycloalkylalkyl)aminoalkyl, cyanoalkyl, alkenyl, alkynyl, aryl, aralkyl, aralkenyl, hydroxyalkyl, (hydroxy) aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl:

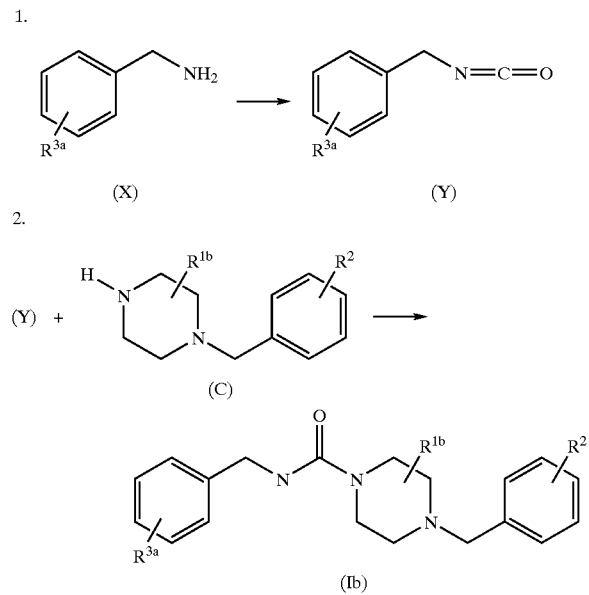

Compounds of formula (X) are commercially available, for example, from Aldrich Chemical Co. or Sigma Chemical Co., or may be prepared according to methods known to those of ordinary skill in the art. Compounds of formula (C) may be prepared according to methods described herein.

In general, the compounds of formula (Ib) prepared by this Reaction Scheme are prepared by first treating a compound of formula (X) in an organic solvent, such as toluene, with phosgene for a period of time from about 1 hour to about 24 hours, preferably for about 2 hours, at reflux temperature to form the isocyanate of formula (Y), which is isolated from the reaction mixture by standard isolation techniques, such as concentration and filtration.

The compound of formula (Y) in an anhydrous aprotic polar solvent, such as tetrahydrofuran, is then treated with an equimolar amount of a compound of formula (C). The resulting mixture is stirred at ambient temperature for about 10 hours to about 48 hours, preferably for about 20 hours. The compound of formula (Ib) is then isolated from the reaction mixture by standard isolation techniques, such as concentration and evaporation of solvents.

H. Preparation of Compounds of Formula (Ic)

Compounds of formula (Ic) are compounds of the invention and are prepared as illustrated in the following Reaction Scheme 8 where Y is bromo, chloro or iodo; and $R^{1b}$, $R^2$, $R^3$, $R^4$, $R^5$, $R^6$ and $R^9$ are as described above in the Summary of the Invention for compounds of formula (Ic):

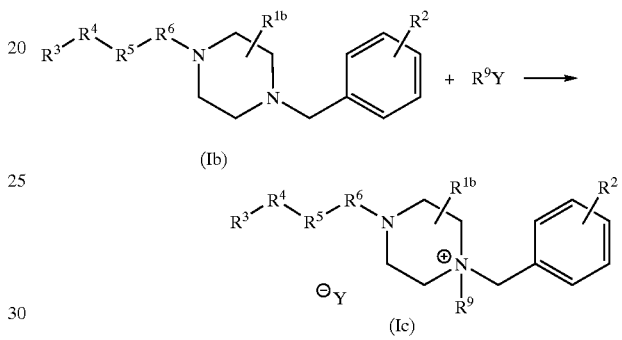

Compounds of formula (Ib) are prepared as disclosed herein and compounds of formula $R^9Y$ are commercially available, for example, Aldrich Chemical Co. or Sigma Chemical Co., or may be prepared according to methods known to those of ordinary skill in the art.

In general, compounds of formula (Ic) are prepared by first treating a compound of formula (Ib) in an non-polar organic solvent, such as toluene, with an excess molar amount of a compound of formula $R^9Y$. The resulting mixture is stirred at ambient temperature for about 1 to 10 days, preferably for about 6 days. The compound of formula (Ic) precipitates out of the solution as the quarternary salt and is isolated by standard isolation techniques such as filtration.

The counterion $^\ominus Y$ may be exchanged with other counterions by methods known to those of ordinary skill in the art.

In addition to the foregoing Reaction Schemes 1 through 8, other compounds of invention may be made by reactions known to one skilled in the art. For example, a compound of formula (Ia), formula (Ib), formula (Ic), or formula (Id), or any appropriately substituted starting material or intermediate thereof, wherein at least one $R^{1a}$ substituent or at least one $R^{1b}$ substituent is selected from the group consisting of hydroxyalkyl, hydroxyalkenyl, hydroxyalkynyl, (hydroxy) aralkyl, (hydroxy)cycloalkylalkyl, hydroxyalkylthioalkyl, and hydroxyalkylaminoalkyl, may be dissolved in an aprotic polar solvent, such as methylene chloride, in the presence of a mild acid scavenging base and then treated with a slightly excess molar amount of a sulfonyl halide, such as sulfonyl chloride, to form an intermediate compound containing a sulfonate leaving group. The compound may then be dissolved in an anhydrous aprotic solvent, such as dimethylformamide, and treated, in the presence of a mild base, with the appropriate nucleophilic reagent to form compounds of formula (Ia), formula (Ib) or formula (Ic), or any appropriately substituted starting material or intermediate thereof, wherein the $R^{1a}$ substituent or the $R^{1b}$ substituent (depending on the nucleophilic reagent utilized) may be selected from the group consisting of heterocyclylalkyl, monoalkylaminoalkyl, dialkylaminoalkyl, cycloalkylamino, cyanoalkyl, (cycloalkylalkyl)aminoalkyl, or hydroxyalkylthioalkyl.

Alternatively, a compound of formula (Ia), formula (Ib), formula (Ic), or formula (Id), or any appropriately substituted starting material or intermediate thereof, which contains a hydroxy group, such as hydroxyalkyl, hydroxyalkenyl, hydroxyalkynyl, (hydroxy)aralkyl, (hydroxy)cycloalkylalkyl, hydroxyalkylthioalkyl, and hydroxyalkylaminoalkyl, may be treated with a mild oxidizing agent, such as oxalyl chloride, which is dissolved in an inert organic solvent, such as methylene chloride, to which DMSO is added over a period of time at about −60° C. to about 0° C., preferably at about −50° C. The reaction mixture is stirred at about −60° C. to about 0° C. for about 15 minutes to about an hour, preferably for about 15 minutes, and then a mild base, such as triethylamine, is added to the mixture. The mixture is allowed to gradually warm to ambient temperature, at which point the oxidized compound (i.e., the corresponding aldehyde) of formula (Ia), formula (Ib), or formula (Ic) or formula (Id), or any appropriately substituted starting material or intermediate thereof, is isolated from the reaction mixture by standard isolation techniques.

Alternatively, a compound of formula (Ia), formula (Ib), formula (Ic) or formula (Id), or any appropriately substituted starting material or intermediate thereof, which contains an aldehyde or a ketone group, such as formyl, alkylcarbonyl or alkylcarbonylalkyl, may be treated with the appropriate organometallic reagent, such as an organomagnesium or organolithium, under standard Grignard synthesis reaction conditions to form the corresponding hydroxy-substituted compounds.

Alternatively, a compound of formula (Ia), formula (Ib), formula (Ic) or formula (Id), or any appropriately substituted starting material or intermediate thereof, which contains a hydroxy group, such as hydroxyalkyl, hydroxyalkenyl, hydroxyalkynyl, (hydroxy)aralkyl, (hydroxy) cycloalkylalkyl, hydroxyalkylthioalkyl, and hydroxyalkylaminoalkyl, in an anhydrous polar solvent, such as anhydrous ether, in the presence of a strong base, such as sodium hydride, may be treated with an alkyl halide, such as methyl iodide, at ambient temperatures, to form the corresponding alkoxy-substituted compounds.

Alternatively, a compound of formula (Ia), formula (Ib), formula (Ic) or formula (Id), or any appropriately substituted starting material or intermediate thereof, wherein at least one $R^{1a}$ substituent or at least one $R^{1b}$ substituent is formyl or formylalkyl, may be reacted with a primary or secondary amine, under the reductive amination conditions as described above for the preparation of the compounds of formula (O) or the compounds of formula (Ib) as prepared in Reaction Scheme 6 to form the corresponding compounds of formula (Ia), formula (Ib), formula (Ic) or formula (Id), or any appropriately substituted starting material or intermediate thereof, wherein the $R^{1a}$ substituent or the $R^{1b}$ substituent is monoalkylaminoalkyl, dialkylaminoalkyl, monoaralkylaminoalkyl, or hydroxyalkylaminoalkyl.

Alternatively, a compound of formula (Ia), formula (Ib), formula (Ic) or formula (Id), or any appropriately substituted starting material or intermediate thereof, which contains an ester group, such as an alkoxycarbonyl, aryloxycarbonyl or aralkoxycarbonyl group, may be subjected to standard basic hydrolysis conditions, to form the corresponding compound of formula (Ia), formula (Ib), formula (Ic) or formula (Id), or any appropriately substituted starting material or intermediate thereof, which contains an acid group, i.e. a carboxy group.

Alternatively, a compound of formula (Ia), formula (Ib), formula (Ic) or formula (Id), or any appropriately substituted starting material or intermediate thereof, wherein $R^6$ is —C(O)— may be reduced to the corresponding compound of formula (Ia), formula (Ib), formula (Ic) or formula (Id), or any appropriately substituted starting material or intermediate thereof, wherein $R^6$ is —CH$_2$— by methods known to those of ordinary skill in the art, for example, by the method described above for compounds of formula (S).

In addition, compounds of formula (Ia), formula (Ib), formula (Ic) or formula (Id), or any appropriately substituted starting material or intermediate thereof, wherein $R^6$ is —C(O)— may be converted to a compound of formula (Ia), formula (Ib), formula (Ic) or formula (Id), or any appropriately substituted starting material or intermediate thereof, wherein $R^6$ is —C(S)— by treatment with Lawesson's Reagent under standard conditions known to those of ordinary skill in the art.

In addition, compounds of formula (Ia), formula (Ib), formula (Ic) or formula (Id), or any appropriately substituted starting material or intermediate thereof, which contain an unoxidized sulfur atom may be oxidized with the appropriate sulfur oxidizing agent according to methods known to those skilled in the art, such as using hydrogen peroxide, to produce the corresponding compounds which contain a sulfinyl or a sulfonyl group in place thereof.

Alternatively, compounds of formula (Ia), formula (Ib), formula (Ic) or formula (Id), or any appropriately substituted starting material or intermediate thereof, which contain a carboxy group can be converted to compounds containing the corresponding amide group by first converting the carboxy group into an activated ester or mixed anhydride using, for example, isobutyl chloroformate in the presence of a mild base, such as N-methylmorpholine, in an aprotic solvent, such as THF, and then treating the ester with the appropriately substituted primary or secondard amine in an aprotic solvent, such as THF.

Alternatively, compounds of formula (Ia), formula (Ib), formula (Ic) or formula (Id), or any appropriately substituted starting material or intermediate thereof, which contain a cyano group can be converted to the compounds containing a hydroxyamidino group by reaction with the an hydroxyamine in a polar solvent, such as DMSO. The hydroxyamine may be prepared in situ by first treating the hydrochloride salt of the hydroxyamine with a base, such as triethylamine.

Alternatively, of formula (Ia), formula (Ib), formula (Ic) or formula (Id), or any appropriately substituted starting material or intermediate thereof, which contain a hydroxy group may be converted to the compounds containing the corresponding azide group by treating the compound with triphenylphosphine and an alkyl azodicarboxylate, for example, diethylazodicarboxylate, in an aprotic solvent, such as THF, and then displacing the activated oxygen so formed with an azide source, such as diphenylphosphorylazide, in an aprotic solvent, such as THF.

Alternatively, compounds of formula (Ia), formula (Ib), formula (Ic) or formula (Id), or any appropriately substituted starting material or intermediate thereof, which contain a —NH$_2$ group or a —R$_a$—NH$_2$ group may be converted to compounds containing a corresponding —R$_a$—N(H)—C(O)— group by reacting the compound with appropriately substituted acid halide under standard acylation conditions.

Alternatively, compounds of formula (Ia), formula (Ib), formula (Ic) or formula (Id), or any appropriately substituted starting material or intermediate thereof, which contain a acid halide group (—C(O)—X where X is halo) or an activated ester group can be converted to compounds containing the corresponding —C(O)—N(H)— group by reacting the compound with the appropriately substituted primary or secondary amine under standard acylation or amide bond formation conditions.

Alternatively, compounds of formula (Ia), formula (Ib), formula (Ic) or formula (Id), or any appropriately substituted starting material or intermediate thereof, which contains an primary or secondary amine group can be converted to compounds containing the corresponding aminoalkyl group in a manner similar to the conversion of formula (M) to formula (O) in Reaction Scheme 4. In particular, the amine is reacted with an appropriately substituted aldehyde to form the intermediate imine, which is then reduced by treatment with an appropriate reducing agent, such as sodium cyanoborohydride.

Alternatively, compounds of formula (Ia), formula (Ib), formula (Ic) or formula (Id), or any appropriately substituted starting material or intermediate thereof, which contain a primary or secondary amine can be converted to the compounds containing the corresponding ureido group by reacting the compound with phosgene in a manner similar to Reaction Scheme 7 above (in an aprotic solvent) to form the corresponding isocyanate, which is then reacted with the appropriately substituted primary or secondary amine.

In addition, all compounds of the invention that exist in free base form or free acid form may be converted to their pharmaceutically acceptable salts by treatment with the appropriate inorganic or organic acid, or by the appropriate inorganic or organic base. Salts of the compounds of the invention can also be converted to the free base form or to the free acid form or to another salt by methods known to those skilled in the art.

The following specific Preparations and Examples are provided as a guide to assist in the practice of the invention, and are not intended as a limitation on the scope of the invention.

In the following Preparation and Examples, all NMR data refers to $^1$H NMR spectrum data and is given in the format of "(multiplicity, number of hydrogens)". The yield of each of the reactions described herein is expressed as a percentage of the theoretical yield.

PREPARATION 1

Compounds of Formula (C)

A. To a solution of 2-methylpiperazine (0.10 g, 1 mmol) in CH$_2$Cl$_2$ (2 mL) was added 4-fluorobenzyl bromide (0.125 mL, 1 mmol). The resultant mixture was stirred at ambient temperature. After 15 hours, the mixture was concentrated in vacuo to afford a solid. This solid was dissolved in CH$_2$Cl$_2$ and washed sequentially with water, aqueous NaHCO$_3$ solution, then brine. The organic layer was dried over MgSO$_4$, filtered, and concentrated to an oil. Purification by flash column chromatography afforded 0.025 g (12% yield) of 1-(4-fluorobenzyl)-3-methylpiperazine, a compound of formula (C), as a colorless oil; NMR (CDCl$_3$) 7.3 (m, 2), 7.0 (m, 2), 3.4 (s, 2), 3.0–2.6 (m, 5), 2.0 (br s, 2), 1.6 (t, 1), 1.0 (d, 3) ppm.

B. In a similar manner, the following compounds of formula (C) were made:

(2R,5S)-1-(chloro)acetyl-4-(4-fluorobenzyl)-2,5-dimethylpiperazine-1-(4-fluorobenzyl)piperazine;

(trans)-1-(4-fluorobenzyl)-2,5-dimethylpiperazine;

(cis)-1-(4-fluorobenzyl)-2,3-dimethylpiperazine;

(trans)-1-(4-fluorobenzyl)-2,3-dimethylpiperazine; and (cis)-1-(4-fluorobenzyl)-3,5-dimethylpiperazine.

C. In a similar manner, other compounds of formula (C) are made.

PREPARATION 2

Compounds of Formula (F)

A. To a solution of ethylene diamine (13 g, 216 mmol) in anhydrous ether (600 mL) was added 2,3-butanedione (18.6 g, 216 mmol, in 200 mL anhydrous ether) dropwise over 2 hours. The resulting mixture was stirred at ambient temperature. After 3 hours, the clear solution was concentrated in vacuo to afford a brown oil. Purification by vacuum distillation afforded 16.6 g (70% yield) of 5,6-dimethyl-2,3-dihydropyrazine, a compound of formula (F), as clear, yellow oil; b.p. 60° C./16 mm Hg, NMR (CDCl$_3$) 3.3 (br s, 4), 2.1 (s, 6) ppm.

B. In a similar manner, other compounds of formula (F) are made.

PREPARATION 3

Compounds of Formula (Ga)

A. To a solution of lithium aluminum hydride (0.36 g, 10 mmol) in anhydrous tetrahydrofuran (50 mL) was carefully added 5,6-dimethyl-2,3-dihydropyrazine (1.0 g, 9 mmol, in 10 mL of anhydrous tetrahydrofuran). The resulting mixture was stirred at ambient temperature for 1 hour, then heated to reflux. After the reaction was completed, as determined by thin layer chromatographic analysis of reaction mixture, the reaction mixture was cooled to ambient temperature and quenched by sequential addition of 0.4 mL of water, 0.4 mL of 15% aqueous NaOH solution, then 1.2 mL of water. After brief shaking, the mixture was filtered through a fritted funnel. Filtrate was concentrated in vacuo to 0.92 g (90% yield) of (cis)-2,3-dimethylpiperazine, a compound of formula (Ga), as clear, yellow oil; NMR (CDCl$_3$) 2.7 (m, 4), 2.5 (m, 2), 0.9 (d, 6) ppm.

B. In a similar manner, other compounds of formula (Ga) are made.

PREPARATION 4

Compounds of Formula (Gb)

A. To a solution of 5,6-dimethyl-2,3-dihydropyrazine (2.3 g, 21 mmol) in absolute ethanol (60 mL) was added sodium metal (6.5 g, 280 mmol) in small portions over a 3 hour period. The resulting mixture was heated to reflux. After 3 hours at reflux, the product was distilled from the mixture while 200 mL of water was added gradually to reaction vessel. The distillate was treated with 1 N aqueous HCl solution and concentrated in vacuo to afford a semi-solid. Titration with acetone afforded 0.78 g (20% yield) of (trans)-2,3-dimethylpiperazine, a compound of formula (Gb), as an orange solid; NMR (DMSO-d$_6$) 9.8 (br s, 4), 3.5–3.2 (m, 6), 1.2 (s, 6) ppm.

B. In a similar manner, other compounds of formula (Gb) are made.

PREPARATION 5

Compounds of Formula (K)

A. To a solution of (cis)-2,6-dimethylpiperazine (0.115 g, 1.1 mmol) in methanol (35 mL) was added 4-chlorophenoxyacetyl chloride (0.205 g, 1.0 mmol, in solution of 6 mL of anhydrous ether). The resulting mixture was stirred at ambient temperature for 10 minutes and then triethylamine (0.10 mL, 0.72 mmol) was added. After 30 minutes, the mixture was concentrated in vacuo to afford an oily residue. This was taken up in ether and washed with saturated aqueous $NaHCO_3$ solution, then brine. The organic layer was separated, dried over $MgSO_4$, filtered and concentrated in vacuo to afford an oil. Purification by flash column chromatography afforded 0.202 g (80% yield) of (cis)-1-((4-chlorophenoxy)methyl)carbonyl-3,5-dimethylpiperazine, a compound of formula (K), as a clear, colorless oil; NMR ($CDCl_3$) 7.3 (d, 2), 6.9 (d, 2), 4.7 (d, 1), 4.6 (d, 1), 4.4 (d, 1), 3.8 (d, 1), 2.7 (m, 3), 2.2 (t, 1), 1.1 (m, 6) ppm.

B. In a similar manner, the following compounds of formula (I) were made:
- (3S,5S)-1-((4-chlorophenoxy)methyl)carbonyl-3,5-dimethylpiperazine; and
- (3R,5R)-1-((4-chlorophenoxy)methyl)carbonyl-3,5-dimethylpiperazine.

C. In a similar manner, other compounds of formula (K) are made.

PREPARATION 6

Compounds of Formula (M)

A. A solution of (2R)-3-benzyloxy-2-(N-(t-butoxycarbonyl)amino)propanoic acid (23 g, 78 mmol, $[\alpha]_D$ −4.4° (c=2, $H_2O$)) in methanol (250 mL) was cooled to 0° C. and HCl (g) bubbled into the solution until saturated. The resulting mixture was stirred at ambient temperature for 17 hours and then concentrated in vacuo to afford 17 g (100% yield) of (2R)-3-benzyloxy-2-aminopropanoic acid methyl ester, a compound of formula (M), as a white solid; NMR (DMSO-$d_6$) 8.7 (br s, 3), 7.4–7.3 (m, 5), 4.5 (q, 2), 4.4 (br s, 1), 3.8 (s, 2), 3.7 (s, 3) ppm.

B. In a similar manner, other compounds of formula (M) are made.

PREPARATION 7

Compounds of Formula (O)

A. A solution of (2R)-3-benzyloxy-2-aminopropanoic acid methyl ester (19 g, 78 mmol) in methanol (350 mL) under $N_2$ was cooled to 0° C. and acetic acid (2 g, pH 2) was added, followed by the addition of 4-fluorobenzaldehyde, a compound of formula (N) (12.5 mL, 117 mmol) and sodium cyanoborohydride (7.3 g, 117 mmol) and 3 Å molecular sieves (15 g). The resulting mixture was stirred at ambient temperature for 3 hours, then filtered through Celite (MeOH). The filtrate was concentrated in vacuo to afford a clear liquid. This was taken up in ethyl acetate and washed sequentially with 10% aqueous $Na_2CO_3$ solution, water, then brine. The organic phase was then dried over $MgSO_4$, filtered, and concentrated in vacuo. Purification by flash column chromatography on silica gel afforded 14.7 g (60% yield) of (2R)-3-benzyloxy-2-(N-(4-fluorobenzyl)amino)propanoic acid methyl ester, a compound of formula (O), as a clear, colorless oil; NMR ($CDCl_3$) 7.4–7.2 (m, 7), 7.0 (dd, 2), 4.5 (d, 2), 3.9–3.5 (m, 8) ppm, MS (LSIMS) 317.

B. In a similar manner, the following compounds of formula (O) were made:
- (2R)-2-(N-(4-fluorobenzyl)amino)propanoic acid methyl ester;
- (2S)-2-(N-(4-fluorobenzyl)amino)propanoic acid methyl ester;
- (2R)-2-(N-(4-fluorobenzyl)amino)-4-methylthiobutanoic acid methyl ester;
- (2R)-2-(N-(4-fluorobenzyl)amino)-3-methoxypropanoic acid methyl ester;
- (2R)-2-(N-(4-fluorobenzyl)amino)-3-((2-hydroxyethyl)thio)propanoic acid methyl ester; and
- (2R)-2-(N-(4-fluorobenzyl)amino)-3-methylbutanoic acid methyl ester.

C. In a similar manner, the following compounds of formula (O) are made:
- (2S)-2-(N-(4-fluorobenzyl)amino)-4-methylthiobutanoic acid methyl ester;
- (2S)-2-(N-(4-fluorobenzyl)amino)-3-methoxypropanoic acid methyl ester;
- (2S)-2-(N-(4-fluorobenzyl)amino)-3-((2-hydroxyethyl)thio)propanoic acid methyl ester;
- (2S)-2-(N-(4-fluorobenzyl)amino)-3-methylbutanoic acid methyl ester;
- (2R)-2-(N-(4-fluorobenzyl)amino)butanoic acid ethyl ester;
- (2S)-2-(N-(4-fluorobenzyl)amino)butanoic acid ethyl ester;
- (2R)-2-(N-(4-chlorobenzyl)amino)butanoic acid methyl ester;
- (2S)-2-(N-(4-chlorobenzyl)amino)butanoic acid methyl ester;
- (2R)-2-(N-(4-chlorobenzyl)amino)-4-methylthiobutanoic acid methyl ester;
- (2R)-2-(N-(4-chlorobenzyl)amino)-3-methoxypropanoic acid methyl ester;
- (2R)-2-(N-(4-chlorobenzyl)amino)-3-((2-hydroxyethyl)thio)propanoic acid methyl ester; and
- (2R)-2-(N-(4-chlorobenzyl)amino)-3-methylbutanoic acid methyl ester.

D. In a similar manner, other compounds of formula (O) are made.

PREPARATION 8

Compounds of Formula (Q)

A. To a solution of N-t-butoxycarbonyl-D-alanine (5.6 g, 30 mmol, $[\alpha]_D$ +23° (c=2, $CH_3CO_2H$)) in anhydrous tetrahydrofuran (150 mL) under $N_2$ at 0° C. was added N-methylmorpholine (3.0 g, 30 mmol), followed by the addition of isobutylchloroformate (3.7 mL, 30 mmol), resulting in the formation of a white solid. The resulting suspension was stirred at 0° C. for 15 minutes, and then at ambient temperature for 1 hour. A solution of (2R)-3-benzyloxy-2-(N-(4-fluorobenzyl)-amino)propanoic acid methyl ester (7.5 g, 24 mmol, in 50 mL of anhydrous tetrahydrofuran) was added to the mixture and the resulting mixture was stirred at ambient temperature. After 15 hours, the mixture was filtered through Celite (tetrahydrofuran).

The filtrate was concentrated in vacuo to afford a yellow liquid, which was dissolved in ethyl acetate, washed with water and then with brine. The organic phase was separated then dried over MgSO$_4$, filtered, and concentrated in vacuo. Purification by flash column chromatography on silica gel afforded 7.3 g (63% yield) of (2R)-3-benzyloxy-2-(N-(4-fluorobenzyl)-N-(((1S)-1-(t-butoxy-carbonylamino)ethyl)carbonyl)amino)propanoic acid methyl ester, a compound of formula (Q), as a clear oil; NMR (CDCl$_3$) 7.4–7.2 (m, 7), 7.0 (dd, 2), 5.3 (d, 2), 4.94,.3 (m, 5), 4.1–3.7 (m, 4), 1.6 (s, 9), 1.0 (d, 3) ppm.

B. In a similar manner, the following compounds of formula (Q) were made:

(2R)-2-(N-(4-fluorobenzyl)-N-(((1S)-1-(t-butoxycarbonylamino)ethyl)carbonyl)amino)propanoic acid methyl ester;

(2S)-2-(N-(4-fluorobenzyl)-N-(((1S)-1-(t-butoxycarbonylamino)ethyl)carbonyl)amino)propanoic acid methyl ester;

(2R)-2-(N-(4-fluorobenzyl)-N-(((1R)-1-(t-butoxycarbonylamino)ethyl)carbonyl)amino)propanoic acid methyl ester;

(2S)-2-(N-(4-fluorobenzyl)-N-(((1R)-1-(t-butoxycarbonylamino)ethyl)carbonyl)amino)propanoic acid methyl ester;

(2R)-2-(N-(4-fluorobenzyl)-N-(((1S)-1-(t-butoxycarbonylamino)ethyl)carbonyl)amino)-4-methylthiobutanoic acid methyl ester;

(2R)-2-(N-(4-fluorobenzyl)-N-(((1S)-1-(t-butoxycarbonylamino)ethyl)carbonyl)amino)-3-methoxypropanoic acid methyl ester;

(2R)-2-(N-(4-fluorobenzyl)-N-(((1S)-1-(t-butoxycarbonylamino)ethyl)carbonyl)amino)-3-((2-hydroxyethyl)thio)propanoic acid methyl ester;

(2R)-2-(N-(4-fluorobenzyl)-N-(((1S)-1-(t-butoxycarbonylamino)ethyl)carbonyl)amino)-3-methylbutanoic acid methyl ester; and (2R)-2-(N-(4-fluorobenzyl)-N-(((1S)-1-(t-butoxycarbonylamino)-2-(ethoxycarbonyl)ethyl)-carbonyl)amino)propanoic acid methyl ester.

C. In a similar manner, other compounds of formula (Q) are made.

PREPARATION 9

Compounds of Formula (R)

A. To a solution of (2R)-3-benzyloxy-2-(N-(4-fluorobenzyl)-N-(((1S)-1-(t-butoxy-carbonylamino)ethyl)carbonyl)amino)propanoic acid methyl ester (2.0 g, 4 mmol) in CH$_2$Cl$_2$ (25 mL) was cooled to 0° C. and trifluoroacetic acid (25 mL) was added dropwise over 2 hours. At the end of the addition, the ice bath was removed and the mixture was stirred at ambient temperature. After 2 hours, the mixture was concentrated in vacuo. The residual yellow oil was taken up in ethyl acetate and washed with 1 N aqueous NaHCO$_3$ solution. The organic layer was separated then dried over MgSO$_4$, filtered, and concentrated in vacuo to afford 1.2 g (83% yield) of (2R,5S)-1-(4-fluorobenzyl)-2-(benzyloxy)methyl-5-methylpiperazine-3,6-dione, a compound of formula (R), as a clear oil; NMR (CDCl$_3$) 7.4–7.2 (m, 7), 7.0 (dd, 2), 5.0 (1), 4.5–4.0 (m, 4), 3.9–3.5 (m, 4), 1.5 (d, 3) ppm, MS (LSIMS) 356.

B. In a similar manner, the following compounds of formula (R) were made:

(2R,5S)-1-(4-fluorobenzyl)-2,5-dimethylpiperazine-3,6-dione;

(2S,5S)-1-(4-fluorobenzyl)-2,5-dimethylpiperazine-3,6-dione;

(2R,5R)-1-(4-fluorobenzyl)-2,5-dimethylpiperazine-3,6-dione;

(2S,5R)-1-(4-fluorobenzyl)-2,5-dimethylpiperazine-3,6-dione;

(2R,5S)-1-(4-fluorobenzyl)-2-(2-methylthioethyl)-5-methylpiperazine-3,6-dione;

(2R,5S)-1-(4-fluorobenzyl)-2-(methoxymethyl)-5-methylpiperazine-3,6-dione;

(2R,5S)-1-(4-fluorobenzyl)-2-((2-hydroxyethyl)thiomethyl)-5-methylpiperazine-3,6-dione;

(2R,5S)-1-(4-fluorobenzyl)-2-(1-methylethyl)-5-methylpiperazine-3,6-dione; and (2R,5S)-1-(4-fluorobenzyl)-2-methyl-5-(ethoxycarbonyl)methylpiperazine-3,6-dione.

C. In a similar manner, other compounds of formula (R) are made:

PREPARATION 10

Compounds of Formula (S)

A. To a suspension of (2R,5S)-1-(4-fluorobenzyl)-2-(hydroxy)methyl-5-methylpiperazine-3,6-dione (2.0 g, 7.5 mmol) in anhydrous tetrahydrofuran (50 mL) under N$_2$ at 0° C. was carefully added lithium aluminum hydride (2.2 g, 60 mmol). The resulting suspension was heated to reflux. After 15 hours, the mixture was cooled to ambient temperature and carefully quenched with water (2 mL), then 1 N aqueous KOH solution (6 mL). The resulting suspension was stirred at ambient temperature for 30 minutes, then filtered through Celite (ethyl acetate). The filtrate was concentrated in vacuo to afford 1.6 g (90% yield) of (2R,5S)-1-(4-fluorobenzyl)-2-(hydroxy)methyl-5-methylpiperazine, a compound of formula (S), as a white solid; NMR (CDCl$_3$) 7.3 (dd, 2), 7.0 (dd, 2), 4.2–4.0 (m, 2), 3.5 (d, 1) 3.0 (m, 2), 2.7 (m, 2), 1.7 (m, 1), 1.0 (d, 3).

B. In a similar manner, the following compounds of formula (S) were made:

(2R,5S)-1-(4-fluorobenzyl)-2,5-dimethylpiperazine;

(2S,5S)-1-(4-fluorobenzyl)-2,5-dimethylpiperazine;

(2R,5R)-1-(4-fluorobenzyl)-2,5-dimethylpiperazine;

(2S,5R)-1-(4-fluorobenzyl)-2,5-dimethylpiperazine;

(2R,5S)-1-(4-fluorobenzyl)-2-(2-methylthioethyl)-5-methylpiperazine;

(2R,5S)-1-(4-fluorobenzyl)-2-(methoxymethyl)-5-methylpiperazine;

(2R,5S)-1-(4-fluorobenzyl)-2-((2-hydroxyethyl)thiomethyl)-5-methylpiperazine;

(2R,5S)-1-(4-fluorobenzyl)-2-(1-methylethyl)-5-methylpiperazine; and (2R,5S)-1-(4-fluorobenzyl)-2-methyl-5-(ethoxycarbonyl)methylpiperazine.

C. In a similar manner, other compounds of formula (S) are made.

PREPARATION 11

Compounds of Formula (W)

A. To a solution of 3,4,5-trimethoxyphenol (2.8 g, 15 mmol) in DMF (60 mL) at 0° C. was added potassium hexamethyldisilazide (32 mL, 16 mmol, 0.5 M solution in toluene). The resulting mixture was stirred at 0° C. After 20 minutes, 1-(chloro)acetyl-4-(t-butoxycarbonyl)-piperazine (4.6 g, 15 mmol, in 15 mL of DMF) was added and the mixture stirred at ambient temperature. After 2 hours the mixture was poured into water and extracted with ethyl acetate. The organic layer was separated, dried over $MgSO_4$, filtered and concentrated in vacuo to afford 6.5 g (100% yield) of 1-((3,4,5-trimethoxyphenoxy)methyl)carbonyl-4-(t-butoxycarbonyl)piperazine, a compound of formula (W), as a yellow solid; NMR ($CDCl_3$) 7.2 (m, 2), 4.6 (s, 2), 3.8 (m, 9), 3.6 (m, 4), 3.4 (m, 4), 1.5 (s, 9) ppm.

B. In a similar manner, the following compounds of formula (W) were made:

1-((4-chlorophenyl)methyl)carbonyl-4-(t-butoxycarbonyl)piperazine;

(3R)-1-((4-chlorophenyl)methyl)carbonyl-3-methyl-4-(t-butoxycarbonyl)piperazine;

(3S)-1-((4-chlorophenyl)methyl)carbonyl-3-methyl-4-(t-butoxycarbonyl)piperazine; and 1-((4-chlorophenyl)methyl)carbonyl-3-(2-((((4-chlorophenoxy)methyl)carbonyl)oxy)ethyl)-4-(t-butoxycarbonyl)piperazine.

C. In a similar manner, other compounds of formula (W) are made.

PREPARATION 12

Compounds of Formula (Y)

A. To a solution of 4-chlorobenzylamine (0.50 g, 3.5 mmol) in toluene (15 mL) was added phosgene (7.3 mL, 14 mmol, 1.93 M solution in toluene). The resulting mixture was stirred at ambient temperature for 15 minutes, then heated to reflux. After 2 hours at reflux, the mixture was cooled to ambient temperature and concentrated in vacuo to afford 0.70 g (100% yield) of 4-chlorobenzylisocyanate, a compound of formula (Y), as a yellow liquid; NMR ($CDCl_3$) 7.4–7.2 (m, 4), 4.4 (m, 2) ppm.

B. In a similar manner, other compounds of formula (Y) are made.

EXAMPLE 1

Compounds of Formula (Ia) and Formula (Ib)

A. To a solution of (2R,5S)-1-(4-fluorobenzyl)-2-(hydroxy)methyl-5-methylpiperazine (1.6 g, 6.7 mmol) in $CH_2Cl_2$ (30 mL) was added triethylamine (excess) and 4-chlorophenoxyacetyl chloride (1.5 g, 7.4 mmol, dropwise in 10 mL solution of $CH_2Cl_2$). The resultant mixture was stirred at ambient temperature. After 20 minutes, analysis by analytical TLC showed complete consumption of starting material had occurred. The mixture was concentrated of volatiles in vacuo and the residue taken up in $CH_2Cl_2$. This was washed with saturated aqueous $NaHCO_3$ solution, then water, then brine, dried over $MgSO_4$, filtered, and concentrated in vacuo. Purification by flash column chromatography on silica gel afforded 2.16 g (79% yield) of (2R,5R)-1-((4-chlorophenoxy)methyl)carbonyl-2-methyl-4-(4-fluorobenzyl)-5-((hydroxy)methyl)piperazine, as a solid yellow foam: NMR (DMSO-$d_6$) 7.7 (br s, 2), 7.3 (m, 4), 6.9 (d, 2), 5.0–4.2 (m, 5), 4.0–3.2 (m, 7), 1.2 (m, 3) ppm; MS (LSIMS) 406.

B. In a similar manner, other compounds of formula (Ia) were made:

1-((4-chlorophenoxy)methyl)carbonyl-4-(4-fluorobenzyl)-5-methylpiperazine, trifluoroacetic acid salt; NMR (DMSO-$d_6$) 7.6 (m, 2), 7.3 (m, 4), 6.9 (m, 2), 5.0–3.8 (m, 6), 3.5–2.8 (m, 5), 1.4 (m, 3) ppm;

4-(4-fluorobenzyl)-1-((4-chlorophenoxy)methyl)carbonyl-2-ethylpiperazine;

4-(4-fluorobenzyl)-1-((4-chlorophenoxy)methyl)carbonyl-3-methylpiperazine;

4-benzyl-1-((4-chlorophenoxy)methyl)carbonyl-2-phenylpiperazine;

(2R)-4-(4-fluorobenzyl)-1-((4-chlorophenoxy)methyl)carbonyl-2-(1-methylethyl)piperazine;

4-(4-fluorobenzyl)-1-((4-chlorophenoxy)methyl)carbonyl-2-(methoxymethyl)piperazine;

4-(4-fluorobenzyl)-1-((4-chlorophenoxy)methyl)carbonyl-2-ethylpiperazine-3-one;

4-(4-fluorobenzyl)-1-((4-chlorophenoxy)methyl)carbonyl-2-ethylpiperazine; NMR ($CDCl_3$) 7.3 (m, 4), 7.0 (t, 2), 6.9 (d, 2), 4.6 (s, 2), 4.4 (m, 1), 3.7 (m, 1), 3.4 (m, 2), 2.8 (m, 2), 2.0–1.7 (m, 5), 0.9 (m, 3) ppm;

(2S)-4-(4-fluorobenzyl)-1-((4-chlorophenoxy)methyl)carbonyl-2-(2-methylpropyl)piperazine;

(trans)-4-(4-fluorobenzyl)-1-((4-chlorophenoxy)methyl)carbonyl-2,5-dimethylpiperazine; NMR ($CDCl_3$) 7.3 (m, 4), 7.0 (t, 2), 6.9 (d, 2), 4.6 (m, 2), 4.2 (m, 1), 3.6–3.0 (m, 5), 2.7 (dd, 1), 2.2 (d, 1), 1.3 (m, 3), 0.9 (m, 3) ppm;

(2R)-4-(4-fluorobenzyl)-1-((4-chlorophenoxy)methyl)carbonyl-2-benzylpiperazine;

4-(benzyl)-1-((4-chlorophenoxy)methyl)carbonyl-2-phenylpiperazine-3-one;

4-(4-fluorobenzyl)-1-((4-chlorophenoxy)methyl)carbonyl-2-(2-hydroxyethyl)piperazine; NMR ($CDCl_3$) 7.3 (m, 4), 7.0 (t, 2), 6.9 (d, 2), 4.7 (m, 3), 3.8–3.2 (m,5), 2.8 (m, 2), 2.2 (m, 2), 2.0 (m, 2), 1.7 (m, 2) ppm;

(cis)-4-(4-fluorobenzyl)-1-((4-chlorophenoxy)methyl)carbonyl-2,6-dimethylpiperazine; NMR (DMSO-$d_6$) 7.6 (m, 2), 7.3 (m, 4), 6.9 (d, 2), 4.8 (m, 3), 4.4 (m, 3), 3.3 (d, 2), 3.0 (m, 2), 1.4 (m, 6) ppm;

4-(4-fluorobenzyl)-1-((4-chlorophenoxy)methyl)carbonyl-2-(1-methylpropyl)piperazine;

4-(4-fluorobenzyl)-1-((4-chlorophenoxy)methyl)carbonyl-2-methylpiperazine, hydrochloride salt;

(2R,5S)-4-(4-fluorobenzyl)-1-((4-chlorophenoxy)methyl)carbonyl-2,5-dimethylpiperazine; NMR ($CDCl_3$) 7.3 (m, 4), 7.0 (t, 2), 6.9 (d, 2), 4.6 (m, 2), 4.2 (m, 1), 3.6–3.0 (m, 5), 2.7 (dd, 1), 2.2 (d, 1), 1.3 (m, 3), 0.9 (m, 3) ppm;

(2R)-4-(4-fluorobenzyl)-1-((4-chlorophenoxy)methyl)carbonyl-2-(2-methylpropyl)piperazine;

4-(4-fluorobenzyl)-1-((4-chlorophenoxy)methyl)carbonyl-2-(butyl)piperazine;

(2R,5S)-4-(4-fluorobenzyl)-1-((4-chlorophenoxy)methyl)carbonyl-2-(2-hydroxyethyl)-5-methylpiperazine; NMR ($CDCl_3$) 7.3 (m, 4), 7.0 (t, 2), 6.9 (m, 2), 4.6 (m, 3), 3.5 (m, 5), 3.2 (dt, 1), 3.0 (m, 1), 2.8 (dd, 1), 2.2 (m, 2),1.6 (m, 2), 1.0 (d, 3) ppm;

(2S,5R)-4-(4-fluorobenzyl)-1-((4-chlorophenoxy)methyl)carbonyl-2,5-dimethylpiperazine; NMR ($CDCl_3$) 7.3 (m, 4), 7.0 (t, 2), 6.9 (d, 2), 4.6 (m, 2), 4.2 (m, 1), 3.6–3.0 (m, 5), 2.7 (dd, 1), 2.2 (d, 1), 1.3 (m, 3), 0.9 (m, 3) ppm;

(2S,5S)-4-(4-fluorobenzyl)-1-((4-chlorophenoxy)methyl)carbonyl-2,5-dimethylpiperazine, hydrochloride salt; NMR (DMSO-$d_6$) 7.6 (m, 2), 7.2 (m, 4), 6.9 (d, 2), 4.8 (m, 2), 4.4 (m, 1), 4.1 (t, 1), 3.9–2.9 (m, 6), 1.5–1.2 (m, 6) ppm;

(2R,5R)-4-(4-fluorobenzyl)-1-((4-chlorophenoxy)methyl)carbonyl-2,5-dimethylpiperazine, hydrochloride salt; NMR (DMSO-$d_6$) 7.6 (m, 2), 7.2 (m, 4), 6.9 (d, 2), 4.8 (m, 2), 4.4 (m, 1), 4.1 (t, 1), 3.9–2.9 (m, 6), 1.5–1.2 (m, 6) ppm;

4-(4-fluorobenzyl)-1-((4-chlorophenoxy)methyl)carbonyl-2-(1,1-dimethylethyl)piperazine;

(2S)-4-(4-fluorobenzyl)-1-((4-chlorophenoxy)methyl)carbonyl-2-(2-methylpropyl)piperazine;

(2R,5S)-4-(4-fluorobenzyl)-1-((4-chlorophenoxy)methyl)carbonyl-2-(2-(((4-chlorophenoxy)methyl)carbonyl)oxy)ethyl-5-methylpiperazine; NMR (CDCl$_3$) 7.2 (m, 6), 7.0 (m, 2), 6.8 (m, 4), 4.7–4.0 (m, 7), 3.6 (m, 2), 3.4 (m, 1), 3.1 (m, 1), 2.6 (m, 1), 2.3 (m, 2), 2.0 (m, 2), 1.0 (d, 3) ppm;

4-(4-fluorobenzyl)-1-((4-chlorophenoxy)methyl)carbonyl-3-(methoxycarbonyl)methylpiperazine;

(2S)-4-(4-fluorobenzyl)-1-((4-chlorophenoxy)methyl)carbonyl-2-propylpiperazine;

(cis)4-(4-fluorobenzyl)-1-((4-chlorophenoxy)methyl)carbonyl-2,3-dimethylpiperazine, hydrochloride salt; NMR (DMSO-$d_6$) 7.6 (m, 2), 7.2 (m, 4), 6.9 (m, 2), 5.0–4.1 (m, 6), 3.5–2.9 (m, 4), 1.5–1.2 (m, 6) ppm;

(2R)-4-(4-fluorobenzyl)-1-((4-chlorophenoxy)methyl)carbonyl-2-benzylpiperazine;

(2R)-4-(4-fluorobenzyl)-1-((4-chlorophenoxy)methyl)carbonyl-2-propylpiperazine; NMR (CDCl$_3$) 7.3 (m, 4), 7.0 (t, 2), 6.9 (d, 2), 4.6 (m, 2), 4.4 (m, 1), 3.7 (m, 1), 3.4 (m, 2), 3.0 (m, 1), 2.7 (m,2), 2.0–1.6 (m, 4), 1.2 (m, 2), 0.9 (m, 3) ppm;

4-(4-fluorobenzyl)-1-((4-chlorophenoxy)methyl)carbonyl-3-(ethoxycarbonyl)piperazine;

4-(4-fluorobenzyl)-1-((4-chlorophenoxy)methyl)carbonyl-3-(2-hydroxyethyl)piperazine; NMR (CDCl$_3$) 7.3 (m, 4), 7.0 (t, 2), 6.9 (dd, 2), 4.7 (d, 2), 4.0–3.4 (m, 8), 2.8 (m, 2), 2.3 (m, 1), 1.8 (m, 3) ppm;

4-(4-fluorobenzyl)-1-((4-chlorophenoxy)methyl)carbonyl-3-(hydroxymethyl)piperazine; NMR (CDCl$_3$) 7.3 (m, 4), 7.0 (t, 2), 6.9 (t, 2), 4.7 (d, 2), 3.9–3.2 (m, 7), 2.8–2.2 (m, 4) ppm;

(2S)-4-(4-fluorobenzyl)-1-((4-chlorophenoxy)methyl)carbonyl-2-butylpiperazine;

(2R,6R)-4-(4-fluorobenzyl)-1-((4-chlorophenoxy)methyl)carbonyl-2,6-dimethylpiperazine, hydrochloride salt; NMR (CDCl$_3$) 7.7 (br s, 2), 7.2 (m, 4), 6.8 (d, 2), 4.6 (s, 2), 4.4 (m, 3), 3.9 (m, 1), 3.5 (m, 1), 3.2 (m, 1), 2.8 (m, 2), 1.6 (s, 6) ppm;

(2S,6S)-4-(4-fluorobenzyl)-1-((4-chlorophenoxy)methyl)carbonyl-2,6-dimethylpiperazine, hydrochloride salt; NMR (CDCl$_3$) 7.7 (br s, 2), 7.2 (m, 4), 6.8 (d, 2), 4.6 (s, 2), 4.4 (m, 3), 3.9 (m, 1), 3.5 (m, 1), 3.2 (m, 1), 2.8 (m, 2), 1.6 (s, 6) ppm;

4-(4-fluorobenzyl)-1-(((4-chlorophenoxy)methyl)carbonyl)spiro[cyclopropane-1,2'-piperazine]; NMR (CDCl$_3$) 7.3 (m, 4), 7.0–6.8 (m, 4), 4.6 (m, 4), 2.8 (m, 2), 2.2–1.6 (m, 4) ppm;

4-(4-fluorobenzyl)-1-((4-chlorophenoxy)methyl)carbonyl-2-(trifluoromethyl)piperazine;

(2R,5S)-4-(4-fluorobenzyl)-1-((4-chlorophenoxy)methyl)carbonyl-2-methyl-5-(2-methylthio)ethylpiperazine, hydrochloride salt;

4-(4-fluorobenzyl)-1-((4-chlorophenoxy)methyl)carbonyl-3-((((4-chlorophenoxy)methyl)carbonyl)oxy)methylpiperazine;

(2S)-4-(4-fluorobenzyl)-1-((4-chlorophenoxy)methyl)carbonyl-2-propylpiperazine; NMR (CDCl$_3$) 7.3 (m, 4), 7.0 (t, 2), 6.9 (d, 2), 4.6 (s, 2), 3.8 (m, 2), 3.4 (m, 2), 3.2 (m, 2), 2.6 (m, 1), 2.4 (m, 1), 2.2 (m, 1), 1.6–1.3 (m, 4), 0.9 (m, 3) ppm;

(2R,5S)-4-(4-fluorobenzyl)-1-((4-chlorophenoxy)methyl)carbonyl-2-methyl-5-(1-methylethyl)piperazine; NMR (DMSO-$d_6$) 7.6 (m, 2), 7.3 (m, 4), 6.9 (d, 2), 5.0–4.2 (m, 6), 3.5–3.1 (m, 4), 2.2 (m, 1), 1.2 (d, 3), 0.9 (d, 6) ppm;

(2S)-4-(4-fluorobenzyl)-1-((4-chlorophenoxy)methyl)carbonyl-2-(2-methylpropyl)piperazine;

(2R,3R)4-(4-fluorobenzyl)-1-((4-chlorophenoxy)methyl)carbonyl-2,3-dimethylpiperazine, hydrochloride salt; NMR (DMSO-$d_6$) 7.8 (m, 2), 7.3 (m, 4), 6.9 (d, 2), 5.1–3.6 (m, 6), 3.2 (m, 4), 1.5–1.2 (m, 6) ppm;

(3S)-4-(4-fluorobenzyl)-1-((4-chlorophenoxy)methyl)carbonyl-3-butylpiperazine;

(3S)-4-(4-fluorobenzyl)-1-((4-chlorophenoxy)methyl)carbonyl-3-(1-methylpropyl)piperazine; (3R)4-(4-fluorobenzyl)-1-((4-chlorophenoxy)methyl)carbonyl-3-(2-methylpropyl)piperazine;

(3R)-4-(4-fluorobenzyl)-1-((4-chlorophenoxy)methyl)carbonyl-3-butylpiperazine;

(2R,5R)-4-(4-fluorobenzyl)-1-((4-chlorophenoxy)methyl)carbonyl-2-methyl-5-(benzyloxy)methylpiperazine; NMR (CDCl$_3$) 7.3 (m, 8), 6.8 (m, 5), 4.5 (m, 6), 3.6 (m, 5), 3.0 (m, 1), 2.7 (dd, 1), 2.3 (d, 1), 1.2 (d, 3) ppm;

4-(4-fluorobenzyl)-1-((4-chlorophenoxy)methyl)carbonyl-3-(2-hydroxyethyl)piperazine dihydrochloride salt;

(2R)4-(4-fluorobenzyl)-1-((4-chlorophenoxy)methyl)carbonyl-2-methylpiperazine hydrochloride salt;

(2R,5S)-4-(4-fluorobenzyl)-1-((4-chlorophenoxy)methyl)carbonyl-2-methyl-5-((4-acetylpiperazin-1-yl)methyl)piperazine;

4-(4-fluorobenzyl)-1-((4-chlorophenoxy)methyl)carbonyl-2-((trifluoroacetylamino)methyl)piperazine;

4-(4-fluorobenzyl)-1-((4-chlorophenoxy)methyl)carbonyl-3-(ethoxycarbonyl)methylpiperazine, hydrochloride salt;

(2R,5S)-4-(4-fluorobenzyl)-1-((4-chlorophenoxy)methyl)carbonyl-2,5-dimethylpiperazine, hydrochloride salt;

(trans)4-(4-fluorobenzyl)-1-((2-acetylamino-4-chlorophenoxy)methyl)carbonyl-2,5-dimethylpiperazine; NMR (DMSO-$d_6$) 9.5 (br s, 1), 8.1 (br s, 1), 7.7 (m, 2), 7.3 (m, 2), 7.0 (m, 2), 5.0 (m, 2), 4.3 (m, 3), 3.8–2.9 (m, 5), 2.1 (s,3), 1.2 (m, 6) ppm;

4-(4-fluorobenzyl)-1-((2-((acetylamino)methyl)-4-chlorophenoxy)methyl)carbonyl-2,5-methylpiperazine; NMR (CDCl$_3$) 7.3 (m, 3), 7.1 (dd, 1), 7.0 (t, 2), 6.7 (d, 1), 4.7 (m, 2), 4.2–3.4 (m, 10), 3.0 (br s, 1), 2.7 (dd, 1), 2.5 (q, 4), 2.2 (d, 1), 2.0 (m, 4), 1.3 (m, 3), 0.9 (m, 3) ppm;

4-(4-fluorobenzyl)-1-((4-chlorophenoxy)methyl)carbonyl-2-(((t-butoxycarbonyl)amino)methylpiperazine;

1-((4-chloro-2-(acetylamino)phenoxy)methyl)carbonyl-2-methyl-4-(4-fluorobenzyl)piperazine; NMR (DMSO-$d_6$) 10.9 (d, 1), 9.5 (s, 1), 8.1 (s, 1), 7.6 (d, 2), 7.3 (t, 2), 7.0 (m, 2), 5.0 (q, 2), 4.7 (m, 1), 4.3 (m, 2), 3.9–2.8 (m, 6), 2.1 (s, 3), 1.4 (d, 1.5), 1.3 (d, 1.5) ppm;

(trans)-1-((4-chloro-2-(propylcarbonylamino)phenoxy)methyl)carbonyl-2,5-dimethyl-4-(4-fluorobenzyl)piperazine; NMR (DMSO-$d_6$) 9.5 (d, 1), 8.2 (s, 1), 7.8 (t, 2), 7.3 (t, 2), 7.0 (dt, 2), 6.8 (dq, 1), 6.4 (d, 1), 5.2–4.3 (m, 5), 3.9–2.8 (m, 5), 1.8 (d, 3), 1.3 (m, 6) ppm;

(trans)-1-((4-chloro-2-(iso-propylcarbonylamino)phenoxy)methyl)carbonyl-2,5-dimethyl-4-(4-fluorobenzyl)piperazine; NMR (DMSO-$d_6$) 9.5 (d, 1), 8.2 (s, 1), 7.8 (t, 2), 7.3 (t, 2), 7.0 (m, 2), 5.2–4.3 (m, 5), 3.9–2.7 (m, 6), 1.4–1.1 (m, 12) ppm;

(trans)-1-((4-chloro-2-(methoxymethylcarbonylamino)phenoxy)methyl)carbonyl-2,5-dimethyl-4-(4-fluorobenzyl)piperazine; NMR (DMSO-$d_6$) 9.3 (s, 1), 8.2 (s, 1), 7.8 (t, 2), 7.3 (t, 2), 7.1 (m, 2), 5.3–4.2 (m, 5), 4.0 (s, 2), 3.9–2.8 (m, 8), 1.4–1.2 (m, 6) ppm;

(trans)-1-((4-chloro-2-(2-(methoxycarbonyl)ethylcarbonylamino)phenoxy)-methyl)carbonyl-2,5-dimethyl-4-(4-fluorobenzyl)piperazine; NMR (DMSO-$d_6$) 9.5 (s. 1), 8.1 (s, 1), 7.8 (t, 2), 7.3 (t, 2), 7.0 (m, 2), 5.2–4.2 (m, 5), 3.8 (q, 1), 3.7–3.2 (m, 5), 2.9–2.6 (m, 6), 1.4–1.2 (m, 6) ppm;

(trans)-1-((4-chloro-2-(2-(ethoxycarbonyl)ethylcarbonylamino)phenoxy)methyl)carbonyl-2,5-dimethyl-4-(4-fluorobenzyl)piperazine; NMR (DMSO-$d_6$) 9.6 (s. 1), 8.1 (s, 1), 7.8 (t, 2), 7.3 (t, 2), 7.0 (m, 2), 5.2–4.2 (m, 5), 4.0 (q, 2), 3.8 (q, 1), 3.6–3.2 (m, 3), 2.8–2.6 (m, 5), 1.4–1.2 (m, 9) ppm;

(trans)-1-((4-chloro-2-(methylsulfonylamino)phenoxy)methyl)carbonyl-2,5-dimethyl-4-(4-fluorobenzyl)piperazine; NMR (DMSO-$d_6$) 10.9 (d,1), 9.3 (s. 1), 7.7 (d, 2), 7.3–7.2 (m, 4), 7.0 (d, 1), 5.0 (m, 2), 4.7 (m, 1), 4.4 (m, 3), 3.9 (m, 1), 3.6 (m, 1), 3.4–2.8 (m, 6), 1.4 (d, 1.5), 1.2 (d, 1.5) ppm;

(trans)-1-((4-chloro-2-(bromomethylcarbonylamino)phenoxy)methyl)carbonyl-2,5-dimethyl-4-(4-fluorobenzyl)piperazine; NMR (CDCl$_3$) 10.0 (s. 1), 8.4 (s, 1), 7.3 (m, 2), 7.0 (m, 3), 6.9 (m, 1), 4.7 (m, 3), 4.0 (s, 2), 3.8–3.1 (m, 5), 2.7 (dd, 1), 2.2 (d, 1), 1.3 (brd, 3), 1.0 (br s, 3) ppm;

(trans)-((4-chloro-2-(ethylcarbonylamino)phenoxy)methyl)carbonyl-2,5-dimethyl-4-(4-fluorobenzyl)piperazine; NMR (CDCl$_3$) 9.4 (s, 1), 8.5 (s, 1), 7.3 (m, 2), 7.0 (m, 3), 6.8 (d, 1), 4.7 (m, 3), 3.5 (m,3), 3.1 (m,2), 2.7 (dd, 1), 2.5 (q, 1), 2.2 (d, 1), 1.3 (m, 6), 1.0 (m, 3) ppm;

(trans)-1-((4-chloro-2-(acetylaminomethyl)phenoxy)methyl)carbonyl-2,5-dimethyl-4-(4-fluorobenzyl)piperazine; NMR (CDCl$_3$) 8.0 (br s, 1), 7.3 (m, 3), 7.1 (dd, 1), 7.0 (m, 2), 6.8 (br d, 1), 4.7 (m, 3), 4.4 (d, 1), 3.8–3.0 (m, 6), 2.7 (m, 1), 2.2 (m, 1), 2.0 (s, 3), 1.3 (m, 3), 0.9 (m, 3) ppm;

(trans)-1-((4-chloro-2-(1-(methylsulfonyl)(methyl)aminoethyl)phenoxy)methyl)carbonyl-2,5-dimethyl-4-(4-fluorobenzyl)piperazine; NMR (CDCl$_3$) 7.3 (m, 4), 7.0 (t, 2), 6.8 (m, 1), 5.6 (q, 1), 4.7 (m, 3), 4.2 (m, 1), 3.7 (m, 1), 3.5 (q, 2), 3.2 (m, 1), 3.1 (m, 1), 2.8 (d, 3), 2.7 (d, 3), 2.3 (br d, 1), 1.6 (d, 3), 1.3 (m, 3), 0.9 (m, 3) ppm;

(trans)-1-((4-chloro-2-(1-(phenylsulfonyl)(methyl)aminoethyl)phenoxy)methyl)carbonyl-2,5-dimethyl-4-(4-fluorobenzyl)piperazine; NMR (CDCl$_3$) 7.6 (d, 2), 7.3 (m, 6), 6.9 (m, 2), 6.8 (t, 1), 5.6 (q, 1), 4.6 (m, 3), 4.2 (m, 1), 3.6 (m, 2), 3.4 (m, 1), 3.0 (m, 1), 2.6 (m, 4), 2.4 (s, 3), 2.3 (m, 1), 1.3 (m, 6), 0.9 (m, 3) ppm;

(trans)-1-((4-chloro-2-(1-(acetyl)(methyl)aminoethyl)phenoxy)methyl)carbonyl-2,5-dimethyl-4-(4-fluorobenzyl)piperazine; NMR (CDCl$_3$) 7.2 (m, 4), 7.0 (t, 2), 6.8 (m, 1), 6.0 (m, 1), 5.4 (q, 1), 4.6 (m, 3), 4.2 (m, 1), 3.5 (q, 2), 3.2 (m, 1), 3.0 (m, 1), 2.6 (m, 4), 2.2 (m, 3), 1.3 (m, 6), 0.9 (m, 3) ppm;

(trans)-1-(2-(4-chlorophenyl)-3-(methylsulfonylamino)propyl)carbonyl-2,5-dimethyl-4-(4-fluorobenzyl)piperazine; NMR (CDCl$_3$) 7.3 (t, 4), 7.2 (br d, 2), 7.0 (t, 2), 5.0 (br s, 1), 4.6 (br s, 1), 4.0 (m, 1), 3.4 (m, 5), 3.0 (m, 2), 2.8 (s, 3), 2.6 (m, 2), 2.2 (br d, 1), 1.3 (m, 3), 0.9 (m, 3) ppm;

(trans)-1-(2-(4-chlorophenyl)-3-(acetylamino)propyl)carbonyl-2,5-dimethyl-4-(4-fluorobenzyl)piperazine; NMR (CDCl$_3$) 7.3 (m, 4), 7.2 (br d, 2), 7.0 (t, 2), 5.2 (m, 1), 4.6 (brs, 1), 4.2 (m, 1), 3.8 (m, 1), 3.4 (m, 5), 3.0 (m, 1), 2.8 (s, 3), 2.6 (m, 2), 2.2 (m, 1), 1.2 (m, 3), 0.9 (m, 3) ppm;

(trans)-1-(2-(4-chlorophenyl)-2-(methylsulfonylamino)ethyl)carbonyl-2,5-dimethyl-4-(4-fluorobenzyl)piperazine; NMR (CDCl$_3$) 7.3 (m, 5), 7.0 (t, 2), 6.6 (m, 1), 4.9 (q, 1), 4.6 (m, 0.5), 4.2 (br d, 0.5), 3.8 (m, 1), 3.5 (m, 1), 3.4 (m, 1), 3.0 (m, 2), 2.7 (m, 6), 2.2 (m, 1), 1.2 (m, 3), 0.8 (m, 3) ppm;

(trans)-1-(2-(4-chlorophenyl)-2-(acetylamino)ethyl)carbonyl-2,5-dimethyl-4-(4-fluorobenzyl)piperazine; NMR (CDCl$_3$) 7.8 (m, 1), 7.3 (m, 5), 7.0 (t, 2), 5.3 (m, 1), 4.6 (m, 0.5), 4.1 (t, 0.5), 3.5 (m, 1), 3.4 (m, 1), 3.0 (m, 3), 2.6 (m, 2), 2.2 (m, 1), 2.0 (m, 4), 1.2 (m, 3), 0.8 (m, 3) ppm;

(trans)-1-((4-chloro-2-((4-(2,5-di(trifluoromethyl)phenylcarbonyl)piperazin-1-yl)methyl)phenoxy)methyl)carbonyl-2,5-dimethyl-4-(4-fluorobenzyl)piperazine; NMR (DMSO-$d_6$) 11.0 (m, 1), 8.1 (m, 2), 7.9 (t, 1), 7.7. (m, 1), 7.4 (d, 1), 7.3 (m, 2), 7.2 (m, 1), 5.4 (m, 1), 5.0 (m, 2), 4.4 (m, 6), 3.4 (m, 9), 3.0 (m, 1), 2.8 (m, 1), 1.4 (m, 3), 1.2 (m, 3) ppm;

(trans)-1-((4-chloro-2-((4-(benzylcarbonyl)piperazin-1-yl)methyl)phenoxy)methyl)-carbonyl-2,5-dimethyl-4-(4-fluorobenzyl)piperazine; NMR (DMSO-$d_6$) 11.0 (m, 1), 7.9 (t, 2), 7.7. (t, 1), 7.6., (s, 1), 7.5 (d, 1), 7.3 (m, 4), 7.2 (m, 3), 5.4 (m, 1), 5.0 (m, 2), 4.4 (m, 6), 3.7 (m, 2), 3.4 (m, 6), 3.0 (m, 2), 2.8 (m, 1), 1.4 (dd, 3), 1.2 (dd, 3) ppm;

(trans)-1-((4-chloro-2-((4-((2,3,4-trifluorophenyl)aminocarbonyl)piperazin-1-yl)methyl)phenoxy)methyl)carbonyl-2,5-dimethyl-4-(4-fluorobenzyl)piperazine; NMR (DMSO-$d_6$) 11.0 (m, 1), 9.0 (s, 1), 7.9 (t, 2), 7.7. (m, 1), 7.6 (s, 1), 7.5 (m, 1), 7.2 (m, 4), 5.4 (m, 1), 5.0 (m, 2), 4.4 (m, 6), 3.4 (m, 8), 3.1 (m, 2), 2.8 (m, 1), 1.4 (m, 3), 1.2 (m, 3) ppm;

(trans)-1-((4-chloro-2-((4-((2-fluorophenyl)aminocarbonyl)piperazin-1-yl)methyl)phenoxy)methyl)carbonyl-2,5-dimethyl-4-(4-fluorobenzyl)piperazine; NMR (DMSO-$d_6$) 11.0 (m, 1), 8.6 (s, 1), 7.9 (t, 2), 7.7. (m, 1), 7.6 (s, 1), 7.4 (d, 1), 7.3 (m, 1), 7.3 (t, 2), 7.2 (m, 3), 5.4 (m, 1), 5.0 (m, 2), 4.3 (m, 6), 3.4 (m, 9), 3.1 (m, 2), 2.8 (m, 1), 1.4 (dd, 3), 1.2 (dd, 3) ppm;

(trans)-1-((4-chloro-2-((N'-(2,6-difluorophenyl)ureido)phenoxy)methyl)carbonyl-2,5-dimethyl-4-(4-fluorobenzyl)piperazine; NMR (CDCl$_3$) 9.6 (br s, 1), 8.6 (s, 1), 7.4 (quin, 1), 7.3 (t, 2), 7.0 (m, 5), 6.9 (d, 1), 4.7 (m, 3), 4.1 (br s, 0.5), 3.8 (br s, 0.5), 3.5 (q, 2), 3.2 (m, 1), 3.0 (m, 1), 2.6 (dd, 1), 2.2 (d, 1), 1.2 (m, 3), 0.9 (m, 3) ppm;

(trans)-1-((4-chloro-2-(ethenylcarbonylamino)phenoxy)methyl)carbonyl-2,5-dimethyl-4-(4-fluorobenzyl)

piperazine; NMR (CDCl₃) 9.8 (d, 1), 8.6 (s, 1), 7.3 (m, 3), 7.0 (t, 3), 6.9 (d, 1), 6.4 (dd, 2), 5.8 (dd, 1), 4.7 (m, 3), 3.6 (m, 1), 3.5 (q, 2), 3.2 (m, 1), 3.0 (m, 1), 2.7 (dd, 1), 2.2 (dd, 1), 1.3 (m, 3), 0.9 (m, 3) ppm;

(trans)-1-((4-chloro-2-(cyclopropylcarbonylamino) phenoxy)methyl)carbonyl-2,5-dimethyl-4-(4-fluorobenzyl)piperazine; NMR (CDCl₃) 9.7 (br s, 1), 8.4 (s, 1), 7.3 (m, 2), 7.0 (m, 3), 6.8 (d, 1), 4.7 (m, 3), 3.7 (m, 1), 3.5 (q, 2), 3.1 (m, 2), 2.7 (dd, 1), 2.2 (dd, 1), 1.7 (m, 1), 1.3 (m, 3), 1.0 (m, 5), 0.8 (m, 2) ppm;

(trans)-1-((4-chloro-2-(cyclopentylcarbonylamino) phenoxy)methyl)carbonyl-2,5-dimethyl-4-(4-fluorobenzyl)piperazine; NMR (CDCl₃) 9.3 (br s, 1), 8.5 (s, 1), 7.3 (t, 2), 7.0 (m, 3), 6.8 (d, 1), 4.7 (m, 3), 3.7 (m, 1), 3.5 (q, 2), 3.1 (m, 2), 2.8 (quin, 1), 2.7 (dd, 1), 2.2 (dd, 1), 1.9 (m, 3), 1.8 (m, 1), 1.6 (m, 3), 1.3 (m, 3), 0.9 (m, 3) ppm;

(trans)-1-((4-chloro-2-((furan-2-yl)carbonylamino) phenoxy)methyl)carbonyl-2,5-dimethyl-4-(4-fluorobenzyl)piperazine; NMR (DMSO-d₆) 10.4 (br s, 1), 9.7 (br d, 1), 8.2 (br s, 1), 7.9 (s, 1), 7.7 (m, 2), 7.3 (m, 3), 7.2 (s, 2), 6.7 (d, 1), 5.3 (br d, 1), 5.0 (m, 2), 4.7 (m, 0.5), 4.5 (m, 0.5), 4.2 (m, 3), 3.6 (m, 1), 3.4 (m, 1), 2.8 (m, 1), 1.3 (m, 3), 1.2 (m, 3) ppm;

(trans)-1-((4-chloro-2-(phenylcarbonylamino)phenoxy) methyl)carbonyl-2,5-dimethyl-4-(4-fluorobenzyl) piperazine; NMR (CDCl₃) 10.0 (s, 1), 8.6 (s, 1), 8.1 (d, 2), 7.5 (m, 3), 7.3 (t, 2), 7.0 (t, 3), 6.8 (d, 1), 4.7 (m, 3), 3.7 (m, 1), 3.5 (q, 2), 3.1 (m, 2), 2.7 (dd, 1), 2.2 (dd, 1), 1.3 (m, 3), 0.9 (m, 3) ppm;

(trans)-1-(2-(4-chlorophenyl)-2-((ethoxycarbonylmethylcarbonylamino)ethyl) carbonyl-2,5-dimethyl-4-(4-fluorobenzyl)piperazine; NMR (CDCl₃) 8.6 (m, 1), 7.2 (s, 6), 7.0 (t, 2), 5.4 (m, 1), 4.2 (q, 2), 3.8 (m, 1), 3.5 (m, 1), 3.4 (m, 3), 3.0 (m, 3), 2.6 (m, 2), 2.2 (m, 2), 1.3. (m, 4.5), 1.1. (m, 1.5), 0.9 (dd, 1.5), 0.7 (dd, 1.5) ppm;

(trans)-1-(2-(4-chlorophenyl)-2-(N'-iso-propylureido) ethyl)carbonyl-2,5-dimethyl-4-(4-fluorobenzyl) piperazine; NMR (CDCl₃) 7.3 (m, 6), 7.0 (t, 2), 5.2 (t, 1), 4.6 (m, 0.5), 4.4 (m, 1), 4.2 (t, 0.5), 3.8 (m, 1), 3.5 (m, 1), 3.4 (m, 1), 3.0 (m, 3), 2.6 (m, 1), 2.2 (m, 1), 1.1 (m, 9), 0.9 (dd, 1.5), 0.8 (dd, 1.5) ppm;

(trans)-1-(2-(4-chlorophenyl)-2-(N'-(2-chloroethyl) ureido)ethyl)carbonyl-2,5-dimethyl-4-(4-fluorobenzyl) piperazine; NMR (CDCl₃) 7.3 (m, 6), 7.0 (t, 2), 5.2 (t, 2), 4.6 (m, 0.5), 4.2 (t, 0.5), 3.5 (m, 6), 3.0 (m, 4), 2.6 (m, 1), 2.2 (m, 1), 1.1 (m, 3), 0.9 (dd, 1.5), 0.8 (dd, 1.5) ppm;

(trans)-1-(2-(4-chlorophenyl)-2-((2-nitrophenyl) carbonylamino)ethyl)carbonyl-2,5-dimethyl-4-(4-fluorobenzyl)piperazine; NMR (CDCl₃) 8.1 (d, 1), 7.7 (q, 1), 7.6 (t, 2), 7.3 (m, 6), 7.0 (t, 2), 5.6 (m, 1), 4.6 (m, 0.5), 4.1 (t, 0.5), 3.7–3.2 (m, 3), 3.0 (m, 4), 2.6 (m, 1), 2.2 (m, 1), 1.2 (m, 3), 0.9 (m, 3) ppm;

(trans)-1-(2-(4-chlorophenyl)-2-((4-methoxyphenylmethyl)carbonylamino)ethyl)carbonyl-2,5-dimethyl-4-(4-fluorobenzyl)piperazine; NMR (CDCl₃) 7.3 (m, 8), 7.0 (t, 2), 6.9 (d, 2), 5.3 (m, 1), 4.6 (m, 0.5), 4.1 (t, 0.5), 3.8 (s, 3), 3.5 (m, 3), 3.4–2.8 (m, 6), 2.6 (m, 1), 2.2 (m, 1), 1.2 (m, 3), 0.8 (m, 3) ppm;

(trans)-1-(2-(4-chlorophenyl)-2-((2,4-dinitrophenyl) sulfonylamino)ethyl)carbonyl-2,5-dimethyl-4-(4-fluorobenzyl)piperazine; NMR (CDCl₃) 8.6 (s, 1), 8.2 (d, 1), 7.8 (m, 1), 7.3 (m, 4), 7.0 (t, 2), 6.9 (t, 2), 5.0 (m, 1), 4.6 (m, 0.5), 4.1 (m, 0.5), 3.5 (m, 1), 3.4 (m, 1), 3.0 (m, 5), 2.6 (m, 1), 2.2 (m, 1), 1.1 (m, 3), 0.8 (m, 3) ppm;

(trans)-1-(2-(4-chlorophenyl)-2-(cyclopropylcarbonylamino)ethyl)carbonyl-2,5-dimethyl-4-(4-fluorobenzyl)piperazine; NMR (CDCl₃) 7.3 (m, 6), 7.0 (t, 2), 5.2 (m, 1), 4.6 (m, 0.5), 4.2 (m, 0.5), 3.5 (m, 2), 3.4 (m, 1), 3.0 (m, 3), 2.6 (m, 2), 2.2 (m, 1), 1.5 (m, 1), 1.2 (m, 3), 0.9 (m, 3.5), 0.7 (m, 3.5) ppm;

(trans)-1-(2-(4-chlorophenyl)-2-((2-cyclopropylethyl) carbonylamino)ethyl)carbonyl-2,5-dimethyl-4-(4-fluorobenzyl)piperazine; NMR (CDCl₃) 7.3 (m, 6), 7.0 (t, 2), 5.4 (m, 1), 4.6 (m, 0.5), 4.2 (m, 0.5), 3.6 (m, 2), 3.4 (m, 1), 3.0 (m, 4), 2.6 (m, 1), 2.2 (m, 2), 1.6 (m, 10), 1.2 (m, 3), 1.1 (m, 2), 0.8 (m, 3) ppm;

(trans)-1-(2-(4-chlorophenyl)-3-((2-methylpropyl) carbonylamino)propyl)carbonyl-2,5-dimethyl-4-(4-fluorobenzyl)piperazine;; NMR (CDCl₃) 7.3 (d, 4), 7.2 (d, 2), 7.0 (t, 2), 6.0 (br s, 1), 4.6 (m, 0.5), 4.2 (m, 0.5), 3.6 (m, 2), 3.4 (m, 3), 3.0 (m, 2), 2.6 (m, 3), 2.2 (d, 1), 2.0 (m, 4), 1.2 (m, 3), 0.9 (m, 9) ppm;

(trans)-1-(2-(4-chlorophenyl)-3-(cyclopentylcarbonylamino)propyl)carbonyl-2,5-dimethyl-4-(4-fluorobenzyl)piperazine; NMR (CDCl₃) 7.3 (d, 4), 7.2 (d, 2), 7.0 (t, 2), 6.0 (br s, 1), 4.6 (m, 0.5), 4.2 (m, 0.5), 3.6 (m, 2), 3.4 (m, 3), 3.0 (m, 2), 2.6 (m, 3), 2.4 (m, 1), 2.2 (d, 1), 1.6 (m, 8), 1.1. (m, 4), 0.9 (m, 4) ppm;

(trans)-1-(2-(4-chlorophenyl)-3-(N'-(t-butyl)ureido) propyl)carbonyl-2,5-dimethyl-4-(4-fluorobenzyl) piperazine; NMR (CDCl₃) 7.3 (d, 4), 7.2 (d, 2), 7.0 (t, 2), 4.6 (m, 1.5), 4.2 (m, 0.5), 3.6 (m, 2), 3.4 (m, 4), 3.2 (m, 1), 3.0 (m, 1), 2.6 (m, 2), 2.2 (d, 1), 1.3 (s, 9), 1.2 (m, 3), 0.9 (m, 3) ppm;

(trans)-1-(2-(4-chlorophenyl)-3-(N'-(ethyl)ureido)propyl) carbonyl-2,5-dimethyl-4-(4-fluorobenzyl)piperazine; NMR (CDCl₃) 7.3 (d, 4), 7.2 (d, 2), 7.0 (t, 2), 5.1 (m, 1), 4.9 (m, 1), 4.6 (m, 0.5), 4.2 (m, 0.5), 3.6 (m, 2), 3.4 (m, 4), 3.2 (m, 3), 3.0 (m, 1), 2.6 (m, 3), 2.2 (m, 1), 1.1 (m, 6), 0.9 (m, 3) ppm;

(trans)-1-(2-(4-chlorophenyl)-3-(N'-(3-choropropyl) ureido)propyl)carbonyl-2,5-dimethyl-4-(4-fluorobenzyl)piperazine; NMR (CDCl₃) 7.3 (d, 4), 7.2 (d, 2), 7.0 (t, 2), 5.6 (br s, 1), 5.9 (s, 1), 4.6 (m, 0.5), 4.2 (m, 0.5), 3.6 (m, 5), 3.4 (m, 5), 3.2 (m, 1), 3.0 (m, 1), 2.6 (m, 3), 2.2 (d, 1), 2.0 (t, 2), 1.2 (m, 3), 0.9 (m, 3) ppm;

(trans)-1-(2-(4-chlorophenyl)-3-((morpholin-4-yl) carbonylamino)propyl)carbonyl-2,5-dimethyl-4-(4-fluorobenzyl)piperazine; NMR (CDCl₃) 7.3 (d, 4), 7.2 (d, 2), 7.0 (t, 2), 5.8 (br d, 1), 4.6 (m, 0.5), 4.2 (m, 0.5), 3.6 (m, 6), 3.4 (m, 4), 3.3 (t, 4), 3.0 (m, 2), 2.6 (m, 3), 2.2 (m, 1), 1.2 (m, 3), 0.9 (m, 3) ppm;

(trans)-1-((4-chloro-2-((N'-(methoxycarbonylmethylcarbonyl)-N'-(methyl) glycinamido)phenoxy)methyl)carbonyl-2,5-dimethyl-4-(4-fluorobenzyl)piperazine; NMR (CDCl₃) 9.6 (br s, 1), 8.4 (d, 1), 7.3 (dd, 2), 7.0 (t, 3), 6.8 (d, 1), 4.7 (m, 3), 4.3 (s, 2), 3.8 (s, 3), 3.6 (m, 4), 3.5 (m, 2), 3.1 (m, 4), 2.7 (dd, 1), 2.2 (d, 1), 1.3 (m, 3), 0.9 (m, 3) ppm;

(trans)-1-((4-chloro-2-((N'-(2-methoxycarbonylethyl) carbonyl-N'-(methyl)glycinamido)phenoxy)methyl) carbonyl-2,5-dimethyl-4-(4-fluorobenzyl)piperazine; NMR (CDCl₃) 9.6 (br s, 1), 8.4 (d, 1), 7.3 (dd, 2), 7.0 (t, 3), 6.8 (d, 1), 4.7 (m, 3), 4.3 (s, 3), 3.8 (s, 3), 3.6 (q, 2), 3.2 (s, 3), 3.1 (s, 2), 2.7 (m, 5), 2.2 (d, 1), 1.3 (m, 3), 0.9 (m, 3) ppm;

(trans)-1-((4-chloro-2-((N'-(3-methylbenzyl) aminocarbonyl-N'-(methyl)glycinamido)phenoxy) methyl)carbonyl-2,5-dimethyl-4-(4-fluorobenzyl) piperazine; NMR (CDCl$_3$) 9.6 (br s, 1), 8.4 (d, 1), 7.3 (dd, 2), 7.2 (t, 1), 7.0 (m, 6), 6.8 (d, 1), 5.4 (t, 1), 4.6 (m, 3), 4.4 (d, 2), 4.3 (s, 2), 3.8 (m, 1), 3.5 (q, 2), 3.1 (m, 5), 2.6 (m, 1), 2.3 (s, 3), 2.2 (d, 1), 1.3 (m, 3), 0.9 (m, 3) ppm;

(trans)-1-((4-chloro-2-((N'-(3-trifluoromethyl-4-fluorophenyl)carbonyl-N'-(methyl)glycinamido) phenoxy)methyl)carbonyl-2,5-dimethyl-4-(4-fluorobenzyl)piperazine; NMR (CDCl$_3$) 9.8 (br s, 1), 8.4 (d, 1), 8.1 (br s, 1), 7.6 (m, 2), 7.3 (dd, 2), 7.0 (m, 4), 6.8 (d, 1), 4.7 (m, 3), 4.3 (t, 2), 3.7 (m, 1), 3.6 (q, 2), 3.2 (s, 3), 3.1 (m, 2), 2.7 (m, 1), 2.2 (d, 1), 1.3 (m, 3), 0.9 (m, 3) ppm;

(trans)-1-((4-chloro-2-((N'-(4-methylbenzyl) aminocarbonyl-N'-(methyl)glycinamido)phenoxy) methyl)carbonyl-2,5-dimethyl-4-(4-fluorobenzyl) piperazine; NMR (CDCl$_3$) 9.6 (br s, 1), 8.4 (d, 1), 7.3 (m, 2), 7.2 (d, 2), 7.1 (d, 2), 7.0 (m, 3), 6.8 (d, 1), 5.4 (t, 1), 4.7 (m, 3), 4.4 (d, 2), 4.2 (d, 2), 3.8 (m, 1), 3.6 (q, 2), 3.1 (m, 5), 2.7 (m, 1), 2.3 (s, 3), 2.2 (d, 1), 1.3 (m, 3), 0.9 (m, 3) ppm;

(trans)-1-((4-chloro-2-((N'-(3-chlorophenyl)carbonyl-N'-(methyl)glycinamido)phenoxy)methyl)carbonyl-2,5-dimethyl-4-(4-fluorobenzyl)piperazine; NMR (CDCl$_3$) 9.9 (br s, 1), 8.4 (d, 1), 7.5 (s, 1), 7.3 (m, 5), 7.0 (t, 3), 6.8 (d, 1), 4.7 (m, 3), 4.4 (brs, 2), 4.1 (m, 1), 3.6 (m, 1), 3.5 (q, 2), 3.2 (m, 3), 3.0 (m, 1), 2.7 (dd, 1), 2.2 (d, 1), 1.3 (m, 3), 0.9 (m, 3) ppm;

(trans)-1-((4-chloro-2-((N'-(4-fluorobenzyl) aminocarbonyl-N'-(methyl)glycinamido)phenoxy) methyl)carbonyl-2,5-dimethyl-4-(4-fluorobenzyl) piperazine; NMR (CDCl$_3$) 9.7 (br s, 1), 8.4 (s, 1), 7.3 (m, 4), 7.0 (m, 5), 6.8 (d, 1), 5.5 (t, 1), 4.7 (m, 2), 4.4 (d, 2), 4.2 (m, 2), 3.6 (m, 1), 3.5 (q, 2), 3.1 (m, 5), 2.7 (m, 1), 2.2 (d, 1), 1.3 (m, 3), 0.9 (m, 3) ppm;

(trans)-1-((4-chloro-2-(N'-(methoxymethylcarbonyl) glycinamido)phenoxy)methyl)-carbonyl-2,5-dimethyl-4-(4-fluorobenzyl)piperazine; NMR (CDCl$_3$) 10.1 (br s, 1), 8.4 (d, 1), 7.3 (t, 3), 7.0 (t, 3), 6.8 (d, 1), 4.7 (m, 3), 4.2 (d, 2), 4.0 (s, 2), 3.6 (m, 1), 3.5 (q, 2), 3.4 (s, 3), 3.1 (m, 2), 2.7 (dd, 1), 2.2 (d, 1), 1.3 (m, 3), 0.9 (m, 3) ppm;

(trans)-1-((4-chloro-2-(N'-(ethoxycarbonylaminocarbonyl)-glycinamido) phenoxy)methyl)carbonyl-2,5-dimethyl-4-(4-fluorobenzyl)piperazine; NMR (CDCl$_3$) 9.9 (br s, 1), 8.4 (m, 2), 7.3 (m, 3), 7.0 (m, 3), 6.8 (d, 1), 4.7 (m, 3), 4.4 (m, 6), 3.6 (m, 1), 3.5 (q, 2), 3.1 (m, 2), 2.7 (dd, 1), 2.2 (d, 1), 1.3 (m, 6), 0.9 (m, 3) ppm;

(trans)-1-((4-chloro-2-(N'-(2-iodophenylcarbonyl) glycinamido)phenoxy)methyl)carbonyl-2,5-dimethyl-4-(4-fluorobenzyl)piperazine; NMR (CDCl$_3$) 10.4 (br s, 1), 8.4 (d, 1), 7.9 (d, 1), 7.5 (d, 1), 7.4 (t, 1), 7.3 (m, 2), 7.1 (t, 1), 7.0 (t, 3), 6.8 (m, 2), 4.7 (m, 3), 4.4 (d, 2), 3.6 (m, 1), 3.5 (q, 2), 3.1 (m, 2), 2.7 (dd, 1), 2.2 (d, 1), 1.3 (m, 3), 0.9 (m, 3) ppm;

(trans)-1-((4-chloro-2-(N'-(2,3-difluorophenylcarbonyl) glycinamido)phenoxy)-methyl)carbonyl-2,5-dimethyl-4-(4-fluorobenzyl)piperazine; NMR (CDCl$_3$) 10.3 (br s, 1), 8.4 (d, 1), 7.8 (t, 1), 7.5 (quin, 1), 7.3 (m, 3), 7.2 (m, 1), 7.0 (t, 3), 6.8 (d, 1), 4.7 (m, 3), 4.4 (d, 2), 3.6 (m, 1), 3.5 (q, 2), 3.1 (m, 2), 2.7 (dd, 1), 2.2 (d, 1), 1.3 (m, 3), 0.9 (m, 3) ppm;

(trans)-1-((4-chloro-2-(N'-((4-phenoxyphenyl) aminocarbonyl)glycinamido)phenoxy)-methyl) carbonyl-2,5-dimethyl-4-(4-fluorobenzyl)piperazine; NMR (CDCl$_3$) 9.9 (br s, 1), 8.3 (brs, 1), 7.3 (m, 6), 7.0 (t, 6), 6.8 (m, 3), 6.5 (m, 1), 4.7 (m, 3), 4.4 (m, 2), 3.6 (m, 1), 3.5 (q, 2), 3.1 (m, 2), 2.7 (dd, 1), 2.2 (d, 1), 1.3 (m, 3), 0.9 (m, 3) ppm;

(trans)-1-((4-chloro-2-(N'-(2,4-difluorophenylcarbonyl) glycinamido)phenoxy)methyl)-carbonyl-2,5-dimethyl-4-(4-fluorobenzyl)piperazine; NMR (CDCl$_3$) 10.3 (br s, 1), 8.4 (d, 1), 8.1 (q, 1), 7.5 (m, 1), 7.3 (m, 2), 7.0 (t, 3), 6.8 (m, 3), 4.7 (m, 3), 4.4 (d, 2), 3.6 (m, 1), 3.5 (q, 2), 3.1 (m, 2), 2.7 (dd, 1), 2.2 (d, 1), 1.3 (m, 3), 0.9 (m, 3) ppm;

(trans)-1-((4-chloro-2-((2-iodophenylcarbonyl) aminomethyl)phenoxy)methyl)carbonyl-2,5-dimethyl-4-(4-fluorobenzyl)piperazine; NMR (CDCl$_3$) 8.0 (m, 1), 7.8 (d, 1), 7.3 (m, 5), 7.2 (dd, 1), 7.0 (m, 3), 6.8 (d, 1), 4.8 (m, 3), 4.6 (d, 2), 4.4 (m, 0.5), 3.9 (m, 0.5), 3.5 (q, 2), 3.1 (m, 2), 2.6 (m, 1), 2.2 (m, 1), 1.3 (m, 3), 0.9 (m, 3) ppm;

(trans)-1-((4-chloro-2-((ethoxycarbonylmethylcarbonyl) aminomethyl)phenoxy)-methyl)carbonyl-2,5-dimethyl-4-(4-fluorobenzyl)piperazine; NMR (CDCl$_3$) 8.4 (br s, 1), 7.3 (m, 3), 7.2 (dd, 1), 7.0 (m, 2), 6.8 (d, 1), 4.8 (m, 3), 4.5 (d, 2), 4.2 (m, 3), 3.6 (m, 1), 3.5 (q, 2), 3.3 (s, 2), 3.1 (m, 1), 2.6 (m, 1), 2.2 (d, 1), 1.3 (m, 6), 0.9 (m, 3) ppm;

(trans)-1-((4-chloro-2-(N'-(3-chloropropyl)ureidomethyl) phenoxy)methyl)carbonyl-2,5-dimethyl-4-(4-fluorobenzyl)piperazine; NMR (CDCl$_3$) 7.3 (m, 3), 7.2 (dd, 1), 7.0 (m, 2), 6.8 (d, 1), 4.8 (m, 4), 4.4 (d, 2), 4.2 (m, 1), 3.6 (m, 5), 3.3 (m, 3), 3.1 (m, 1), 2.6 (m, 1), 2.2 (d, 1), 1.9 (quin, 2), 1.3 (m, 3), 0.9 (m, 3) ppm;

(trans)-1-((4-chloro-2-(N'-(2-fluoro-6-trifluoromethylphenyl)ureidomethyl)phenoxy)-methyl)carbonyl-2,5-dimethyl-4-(4-fluorobenzyl) piperazine; NMR (CDCl$_3$) 8.2 (m, 1), 7.3 (m, 6), 7.2 (dd, 1), 7.0 (t, 2), 6.8 (d, 1), 4.8 (m, 3), 4.4 (d, 2), 3.8 (m, 1), 3.5 (q, 2), 3.2 (m, 1), 3.1 (m, 1), 2.6 (m, 1), 2.2 (m, 1), 1.3 (m, 3), 0.9 (m, 3) ppm;

(trans)-1-((4-chloro-2-((3-fluorophenyl) carbonylaminomethyl)phenoxy)methyl)carbonyl-2,5-dimethyl-4-(4-fluorobenzyl)piperazine; NMR (CDCl$_3$) 8.6 (m, 1), 7.8 (t, 2), 7.3 (m, 4), 7.2 (dd, 1), 7.1 (dt, 1), 7.0 (t, 2), 6.8 (d, 1), 4.8 (m, 3), 4.6 (d, 2), 3.8 (m, 1), 3.5 (q, 2), 3.1 (m, 2), 2.6 (m, 1), 2.2 (d, 1), 1.3 (m, 3), 0.9 (m, 3) ppm;

(trans)-1-((4-chloro-2-(N'-(2-(ethoxycarbonyl)ethyl) ureidomethyl)phenoxy)-methyl)carbonyl-2,5-dimethyl-4-(4-fluorobenzyl)piperazine; NMR (CDCl$_3$) 7.3 (m, 3), 7.2 (dd, 1), 7.0 (t, 2), 6.9 (m, 1), 6.8 (d, 1), 5.1 (m, 1), 4.8 (m, 3), 4.4 (d, 2), 4.1 (q, 2), 3.6 (m, 2), 3.4 (m, 3), 3.2 (m, 1), 3.1 (m, 2), 2.7 (m, 1), 2.5 (t, 2), 2.2 (d, 1), 1.3 (m, 6), 0.9 (m, 3) ppm;

(trans)-1-((4-chloro-2-((2,5-di(trifluoromethyl)phenyl) carbonylaminomethyl)phenoxy)methyl)carbonyl-2,5-dimethyl-4-(4-fluorobenzyl)piperazine; NMR (CDCl$_3$) 8.9 (m, 1), 7.8 (m, 2), 7.2 (s, 1), 7.3 (m, 3), 7.2 (dd, 1), 7.0 (t, 2), 6.8 (d, 1), 4.8 (m, 3), 4.6 (d, 2), 4.4 (m, 0.5), 3.9 (m, 0.5), 3.5 (q, 2), 3.1 (m, 2), 2.6 (m, 1), 2.2 (m, 1), 1.3 (m, 3), 0.9 (m, 3) ppm; and (trans)-1-((4-chloro-2-(N'-(2-(phenyl)cyclopropyl) ureidomethyl)phenoxy)methyl)carbonyl-2,5-dimethyl- 4-(4-fluorobenzyl)piperazine; NMR (CDCl₃) 7.3 (m, 8), 7.0 (m, 3), 6.8 (d, 1), 4.9 (s, 1), 4.6 (d, 2), 4.4 (m, 2), 3.8 (m, 1), 3.5 (q, 2), 3.2 (m, 1), 3.0 (m, 1), 2.7 (m, 2), 2.2 (m, 1), 2.0 (m, 1), 1.3 (m, 5), 0.9 (m, 3) ppm.

C. In a similar manner, the following compounds of formula (Ib) were made:

1-(2-(4-chlorophenyl)ethenyl)carbonyl-4-(4-fluorobenzyl)piperazine;

1-(2-(4-chlorophenyl)ethyl)carbonyl-4-(4-fluorobenzyl)piperazine;

1-(1-(t-butoxycarbonyl)amino-2-(4-chlorophenyl)ethyl)carbonyl-4-(benzyl)piperazine;

1-(3-(t-butoxycarbonyl)amino-2-(4-chlorophenyl)propyl)carbonyl-4-(4-fluorobenzyl)piperazine; NMR (CDCl₃) 7.2 (m, 8), 4.8 (m, 1), 3.6–3.3 (m, 8), 2.6 (m, 2), 2.3 (m, 3), 2.1 (m, 1), 1.4 (s, 9) ppm;

1-(2-(3,4,5-trimethoxyphenyl)ethenyl)carbonyl-4-(4-fluorobenzyl)piperazine; NMR (CDCl₃) 7.6 (d, 1), 7.3 (m, 4), 6.7 (m, 3), 3.9–3.6 (m, 13), 3.5 (s, 2), 2.5 (m, 4) ppm;

1(1-(3,4-dimethoxyphenyl)-2-(4-chlorophenyl)ethenyl)carbonyl-4-(4-chlorobenzyl)piperazine;

1-(2-(3,4,5-trimethoxyphenyl)ethyl)carbonyl-4-(4-chlorobenzyl)piperazine;

1-(((acetyl)amino)(4-chlorophenyl)methyl)carbonyl-4-(4-fluorobenzyl)piperazine, hydrochloride salt.

D. In a similar manner, other compounds of formulae (Ia), (Ib), (Ic) and (Id) are made.

EXAMPLE 2

Compounds of Formula (Ib)

A. To a solution of (2R,5S)-1-(chloro)acetyl-4-(4-fluorobenzyl)-2,5-dimethylpiperazine (0.29 g, 1 mmol) in anhydrous DMF (5 mL) was added 4-hydroxy-3-methoxyphenylacetonitrile (0.20 g, 1.2 mmol) and potassium carbonate (0.28 g, 2 mmol, powdered). The resultant mixture was stirred at 50° C. After 15 hours analysis by analytical HPLC (HPLC on a C18 Vydac column with 20–70% acetonitrile in water gradient with 0.1% trifluoroacetic acid) showed complete consumption of starting material had occurred. The mixture was poured into water and extracted with three portions of ethyl acetate. The combined organic extracts were wished sequentially with 0.5 N aqueous KOH solution, water, then brine. It was then dried over MgSO₄, filtered and concentrated in vacuo to afford a yellow oil. This was dissolved in ethyl acetate and treated with a solution of HCl in anhydrous ether. Filtration of the resultant solid afforded 0.38 g (85% yield) of (2R,5S)-1-((4-(cyano)methyl-2-methoxyphenoxy)methyl)carbonyl-4-(4-chlorobenzyl)-2,5-dimethylpiperazine, hydrochloric acid salt as a white solid: NMR (DMSO-d₆) 11.5 (br s, 1), 7.6 (m, 4), 6.9 (m, 3), 4.8 (br s, 2), 4.4 (br s, 3), 4.0 (m, 1), 3.9 (s, 2), 3.8 (s, 3), 3.6 (m, 1), 3.3 (m, 2), 3.2–2.9 (m, 3) ppm.

B. In a similar manner, other compounds of formula (Ib) were made:

(trans)-1-((4-fluoro-3-chlorophenoxy)methyl)carbonyl-2,5-dimethyl-4-(4-fluorobenzyl)piperazine; NMR (DMSO-d₆) 10.4 (br d, 1), 7.7 (m, 2), 7.2 (m, 4), 6.9 (br s, 1), 5.0 (m, 1), 4.8 (m, 2), 4.3 (m, 3), 3.7 (m, 2), 3.3 (m, 2), 2.9 (m, 1), 1.4–1.2 (m, 6) ppm;

1-((2-acetylaminophenoxy)methyl)carbonyl-4-(4-fluorobenzyl)piperazine; NMR (DMSO-d₆) 10.6 (br s, 1), 9.4 (s, 1), 8.0 (d, 1), 7.8 (br s, 2), 7.2 (t, 2), 6.9 (m, 3), 5.0 (m, 3), 4.3 (m, 3), 3.8 (q, 1), 3.6 (brs, 1), 3.4 (m, 1), 2.8 (m, 1), 2.1 (s, 3), 1.3 (dd, 1), 1.2 (d, 3) ppm;

1-((3,4,5-trimethoxyphenoxy)methyl)carbonyl-2-(methoxycarbonyl)methyl-4-(4-fluorobenzyl)piperazine;

1-((3,4,5-trimethoxyphenoxy)methyl)carbonyl-2-(ethoxycarbonyl)-4-(4-fluorobenzyl)piperazine;

(cis)-1-((3,4,5-trimethoxyphenoxy)methyl)carbonyl-2,6-dimethyl-4-(4-fluorobenzyl)piperazine; NMR (CDCl₃) 7.3 (m, 2), 7.0 (t, 2), 6.2 (s, 2), 4.74.2 (m, 4), 3.8 (m, 9), 3.5 (s, 2), 2.6 (d, 2), 2.2 (dd, 2), 1.3 (m, 6) ppm;

1-((3,4,5-trimethoxyphenoxy)methyl)carbonyl-2-methyl-4-(4-fluorobenzyl)piperazine; NMR (CDCl₃) 7.3 (m, 2), 7.0 (t, 2), 6.2 (s, 2), 4.6 (s, 3), 4.4 (m, 1), 4.1 (m, 1), 3.8 (s, 6), 3.85 (s, 3), 3.5 (m, 2), 2.8 (d, 1), 2.6 (d, 1), 2.1 (m, 2), 1.3 (m, 3) ppm;

1-((4-chlorophenoxy)methyl)carbonyl-2-methyl-4-(4-fluorobenzyl)piperazine; NMR (CDCl₃) 7.3 (m, 4), 7.0 (t, 2), 6.9 (d, 2), 4.6 (s, 2), 4.4 (m, 1), 4.1 (m, 1), 3.7 (m, 1), 3.4 (m, 2), 2.8 (m, 1), 2.6 (d, 1), 2.0 (m, 2), 1.3 (m, 3) ppm;

1-((4-chlorophenoxy)methyl)carbonyl-3-methyl-4-(4-fluorobenzyl)piperazine; NMR (CDCl₃) 7.3 (m, 4), 7.0 (t, 2), 6.9 (d, 2), 4.6 (s, 2), 4.0 (m, 2), 3.7 (m, 1), 3.4–2.9 (m, 3), 2.7 (m, 1), 2.5 (m, 1), 2.1 (m, 1), 1.1 (m, 3) ppm;

(2S)-1-((4-chlorophenoxy)methyl)carbonyl-2-methyl-4-(4-fluorobenzyl)piperazine;

(2R)-1-((4-chlorophenoxy)methyl)carbonyl-2-methyl-4-(4-fluorobenzyl)piperazine; NMR (CDCl₃) 7.3 (m, 4), 7.0 (t, 2), 6.9 (d, 2), 4.6 (s, 2), 4.4 (m, 1), 4.1 (m, 1), 3.7 (m, 1), 3.4 (m, 2), 2.8 (m, 1), 2.6 (d, 1), 2.0 (m, 2), 1.3 (m, 3) ppm;

4-((4-chlorophenoxy)methyl)carbonyl-3-(((4-chlorophenyl)amino)carbonyl)methyl-1-(benzyl)piperazin-2-one;

1-((phenoxy)methyl)carbonyl-2-ethyl-4-(4-fluorobenzyl)piperazine;

1-((4-chlorophenoxy)methyl)carbonyl-2-hydroxymethyl-4-(4-fluorobenzyl)piperazine; NMR (CDCl₃) 7.3 (m, 4), 7.0 (t, 2), 6.9 (d, 2), 4.7–4.5 (m, 3), 4.2–3.3 (m, 5), 3.2–2.7 (m, 2), 2.3–2.0 (m, 4) ppm;

1-(1-(4-chlorophenoxy)-1-methylethyl)carbonyl-2-methyl-4-(4-fluorobenzyl)piperazine;

(2S,5R)-1-((4-chloro-3,5-dimethoxyphenoxy)methyl)carbonyl-2,5-dimethyl-4-(4-fluorobenzyl)piperazine; NMR (CDCl₃) 7.3 (m, 2), 7.0 (t, 2), 6.2 (s, 2), 4.6 (m, 34), 4.2 (m, 1), 3.8 (m, 6), 3.5 (m, 3), 3.0 (m, 1), 2.7 (dd, 1), 2.2 (d, 1), 1.3 (m, 4), 0.9 (m, 3) ppm;

(2R,5S)-1-((4-chloro-3,5-dimethoxyphenoxy)methyl)carbonyl-2,5-dimethyl-4-(4-fluorobenzyl)piperazine; NMR (CDCl₃) 7.3 (m, 2), 7.0 (t, 2), 6.2 (s, 2), 4.6 (m, 3), 4.2 (m, 1), 3.8 (m, 6), 3.5 (m, 3), 3.0 (m, 1), 2.7 (dd, 1), 2.2 (d, 1), 1.3 (m, 3), 0.9 (m, 3) ppm;

(trans)-1-((4-chloro-3,5-dimethoxyphenoxy)methyl)carbonyl-2,5-dimethyl-4-(4-fluorobenzyl)piperazine; NMR (CDCl₃) 7.3 (m, 2), 7.0 (t, 2), 6.3 (s, 2), 4.7 (m, 2), 4.2 (m, 1), 3.8 (s, 6), 3.5 (m, 4), 3.0 (m, 1), 2.7 (dd, 1), 2.2 (d, 1), 1.3 (m, 3), 0.9 (m, 3) ppm;

(2S,5R)-1-((4-bromo-3,5-dimethoxyphenoxy)methyl)carbonyl-2,5-dimethyl-4-(4-fluorobenzyl)piperazine, hydrochloride salt; NMR (DMSO-d₆) 10.7 (d, 1), 7.8 (m, 2), 7.3 (m, 2), 6.3 (s, 2), 4.9 (m, 2), 4.3 (m, 2), 4.0–2.8 (m, 12), 1.4–1.2 (m, 6) ppm;

(2S,5R)-1-((4-nitro-3-formylphenoxy)methyl)carbonyl-2,5-dimethyl-4-(4-fluorobenzyl)piperazine; NMR (CDCl₃) 10.4 (s, 1), 8.2 (d, 1), 7.3 (m, 4), 7.0 (t, 2), 4.8 (m, 3), 4.2–2.3 (m, 7), 1.3 (m 3), 1.0 (m, 3) ppm;

(trans)-1-((4-chloro-2-(aminocarbonyl)phenoxy)methyl)carbonyl-2,5-dimethyl-4-(4-fluorobenzyl)piperazine; NMR (CDCl₃) 9.2 (br s, 1), 8.2 (s, 1), 7.4 (m, 3), 7.0 (t, 2), 6.8 (d, 1), 5.9 (s, 1), 5.0–4.0 (m, 3), 3.8–3.0 (m, 5), 2.8 (d, 1), 2.3 (d, 1), 1.3 (m, 3), 1.0 (br s, 3) ppm;

(2R,5S)-1-((4-chloro-2-(aminocarbonyl)phenoxy)methyl)carbonyl-2,5-dimethyl-4-(4-fluorobenzyl)piperazine; NMR (CDCl₃) 9.2 (br s, 1), 8.2 (s, 1), 7.4 (m, 4), 7.0 (t, 2), 6.8 (d, 1), 5.8 (s, 1), 4.7 (m, 2), 3.7–3.1 (m, 5), 2.8 (d, 1), 2.3 (d, 1), 1.3 (d, 3), 1.0 (br s, 3) ppm;

(2R,5S)-1-((4-chlorophenoxy)methyl)carbonyl-2-methyl-5-((amino)carbonyloxy)methyl-4-(4-fluorobenzyl)piperazine;

(trans)-1-((4-chloro-3-nitrophenoxy)methyl)carbonyl-2,5-dimethyl-4-(4-fluorobenzyl)piperazine, hydrochloride salt; NMR (DMSO-d₆) 11 (br d, 1), 7.9 (br s, 1), 7.6 (m, 2), 7.3 (m, 4), 5.2 (d, 1), 5.0 (m, 2), 4.3 (m, 4), 4.0 (m, 1), 3.6 (m, 2), 1.3 (m, 6) ppm;

(trans)-1-((4-chloro-2-(hydroxymethyl)phenoxy)methyl)carbonyl-2,5-dimethyl-4-(4-fluorobenzyl)piperazine, hydrochloride salt; NMR (DMSO-d₆) 10.9 (br d, 1), 7.9 (br s, 2), 7.6 (m, 1), 7.3 (m, 4), 5.0 (m, 2), 4.5 (s, 2), 4.3 (m, 2), 3.7–3.3 (m, 6), 1.3 (m, 6) ppm;

(trans)-1-((4-chloro-2-aminophenoxy)methyl)carbonyl-2,5-dimethyl-4-(4-fluorobenzyl)piperazine, dihydrochloride salt; NMR (DMSO-d₆) 7.7 (br s, 3), 7.3 (m, 5), 5.2 (d, 1), 5.0 (m, 2), 4.7–4.2 (m, 4), 3.9–3.4 (m, 3), 1.3 (m, 6) ppm;

(trans)-1-((2-(aminocarbonyl)phenoxy)methyl)carbonyl-2,5-dimethyl-4-(4-fluorobenzyl)piperazine; NMR (CDCl₃) 9.1 (br s, 1), 8.2 (d, 1), 7.4 (dd, 1), 7.3 (br s, 2), 7.1 (t, 1), 7.0 (m, 2), 6.9 (d, 1), 5.8 (br s, 1), 4.7 (m, 2), 4.2 (m, 1), 3.7–3.4 (m, 3), 3.0 (br s, 1), 2.7 (br s, 1), 2.3 (d, 1), 1.3 (m, 3), 1.0 (m, 3) ppm;

(trans)-1-((4-chloro-2-amino-5-nitrophenoxy)methyl)carbonyl-2,5-dimethyl-4-(4-fluorobenzyl)piperazine, dihydrochloride salt; NMR (CDCl₃) 10.9 (br d, 1), 7.8 (m, 2), 7.5 (dd, 1), 7.3 (m, 2), 6.8 (s, 1), 5.0 (m, 3), 4.3–3.2 (m, 7), 1.4–1.2 (m, 6) ppm;

(trans)-1-((4-methyl-2-formylphenoxy)methyl)carbonyl-2,5-dimethyl-4-(4-fluorobenzyl)piperazine, hydrochloride salt; NMR (DMSO-d₆) 10.9 (br d, 1), 10.4 (s, 1), 7.9 (s, 2), 7.5 (m, 2), 7.3 (m, 2), 7.0 (d, 1), 5.2 (m, 1), 5.0 (m, 2), 4.6 (m, 1), 4.3 (m, 3), 3.6 (m, 2), 2.8 (m, 1), 2.5 (s, 3), 1.4–1.1 (m, 6) ppm;

(trans)-1-((4-chloro-2-formylphenoxy)methyl)carbonyl-2,5-dimethyl-4-(4-fluorobenzyl)piperazine; NMR (CDCl₃) 10.9 (brd, 1), 10.4 (s, 1), 7.8 (s, 1), 7.5 (dd, 1), 7.3 (dd, 2), 7.0 (m, 3), 4.8 (m, 3), 4.1 (m, 1), 3.5 (m, 3), 3.0 (br s, 1), 2.7 (dd, 1), 2.5 (d, 1), 1.3 (m, 3), 0.9 (m, 3) ppm;

(trans)-1-((2-methylphenoxy)methyl)carbonyl-2,5-dimethyl-4-(4-fluorobenzyl)piperazine hydrochloride salt; NMR (DMSO-d₆) 11.0 (d, 1), 7.8 (t, 2), 7.3 (t, 2), 7.1 (m, 2), 6.8 (m, 2), 4.9–3.3 (m, 9), 2.8 (t, 1), 2.2 (s, 3), 1.4–1.1 (m, 6) ppm;

(trans)-1-((2-(hydroxymethyl)phenoxy)methyl)carbonyl-2,5-dimethyl-4-(4-fluorobenzyl)piperazine, hydrochloride salt; NMR (DMSO-d₆) 11.0 (d, 1), 7.8 (t, 2), 7.3 (m, 3), 7.1 (t, 1), 6.9 (m, 2), 5.0–3.2 (m, 11), 2.8 (t, 1), 1.4–1.1 (m, 6) ppm;

(trans)-1-((3-chloro-5-methoxyphenoxy)methyl)carbonyl-2,5-dimethyl-4-(4-fluorobenzyl)piperazine, hydrochloride salt; NMR (DMSO-d₆) 10.8 (d, 1), 7.8 (m, 2), 7.3 (t, 2), 6.6 (s, 2), 6.5 (br s, 1), 5.0–3.2 (m, 12), 2.8 (m, 1), 1.4–1.2 (m, 6) ppm;

(trans)-1-((2-methoxy-5-nitrophenoxy)methyl)carbonyl-2,5-dimethyl-4-(4-fluorobenzyl)piperazine, hydrochloride salt; NMR (DMSO-d₆) 11.1 (d, 1), 7.9 (m, 2), 7.7 (br s, 1), 7.2 (m, 4), 5.2–3.3 (m, 12), 2.8 (t, 1), 1.4–1.2 (m, 6) ppm;

1-((phenoxy)methyl)carbonyl-2-methyl-4-(4-fluorobenzyl)piperazine; NMR (DMSO-d₆) 11 (br d, 1), 7.7 (m, 2), 7.3 (m, 4), 6.9 (m, 3), 4.9 (m, 3), 4.3 (m, 3), 4.0–2.8 (m, 5), 1.4 (d, 1.5), 1.2 (d, 1.5) ppm;

(trans)-1-((4-chlorophenylamino)methyl)carbonyl-2,5-dimethyl-4-(4-fluorobenzyl)piperazine; NMR (DMSO-d₆) 7.4 (dd, 2), 7.1 (m, 4), 6.6 (d, 2), 5.8 (t, 1), 4.5 (br s, 0.5), 4.0 (br m, 1.5), 3.8 (br m, 1), 3.8–3.3 (m, 3), 3.0 (m, 2), 2.6 (m, 1), 2.2 (d, 1), 1.1 (brd, 3), 0.9 (brd, 3) ppm;

(trans)-1-((4-chloro-3-nitrophenoxy)methyl)carbonyl-2-methyl-4-(4-fluorobenzyl)piperazine; NMR (DMSO-d₆) 11 (br d, 1), 7.7 (m, 4), 7.3 (m, 3), 5.0 (q, 2), 4.7 (m, 0.5), 4.4 (m, 2.5), 3.8 (m, 0.5), 3.6–2.9 (m, 6), 1.4 (d, 1.5), 1.3 (d, 1.5) ppm;

(trans)-1-((4-chloro-2-methylphenoxy)methyl)carbonyl-2,5-dimethyl-4-(4-fluorobenzyl)piperazine; NMR (DMSO-d₆) 10.8 (br d, 1), 7.9–6.8 (m, 7), 5.1–2.8 (m, 10), 2.2 (s, 3), 1.3 (m, 6) ppm;

(trans)-1-((4-chloro-2-(diethylamino)phenoxy)methyl)carbonyl-2,5-dimethyl-4-(4-fluorobenzyl)piperazine; NMR (CDCl₃) 7.3 (m, 2), 7.0 (t, 2), 6.8 (m, 3), 4.8 (br s, 3), 4.1 (br s, 1), 3.5 (q, 3), 3.2 (q, 4), 3.0 (br s, 1), 2.7 (dd, 1), 2.2 (d, 1), 1.3 (br s, 3), 1 (m, 9) 10 ppm;

(trans)-1-((4-chloro-2-hydroxyphenoxy)methyl)carbonyl-2,5-dimethyl-4-(4-fluorobenzyl)piperazine; NMR (CDCl₃) 7.3 (m, 2), 7.0–6.7 (m, 5), 4.9 (m, 0.5), 4.6 (br s, 2), 4.2 (m, 0.5), 3.6–3.2 (m, 3), 3.0 (br d, 1), 2.7 (br d, 1), 2.2 (d, 2), 1.3 (m, 3), 0.9 (m, 3) ppm;

1-((4-chloro-2-(hydroxymethyl)phenoxy)methyl)carbonyl-2-methyl-4-(4-fluorobenzyl)piperazine; NMR (DMSO-d₆) 10.8 (d, 1), 7.7 (m, 2), 7.3 (m, 4), 6.9 (d, 1), 5.0–4.3 (m, 6), 3.9–2.9 (m, 7), 1.4 (d, 1.5), 1.2 (d, 1.5) ppm;

(2R,5S)-1-((4-chloro-3-(hydroxymethyl)phenoxy)methyl)carbonyl-2,5-dimethyl-4-(4-fluorobenzyl)piperazine; NMR (CDCl₃) 7.3 (m, 4), 7.0–6.7 (m, 3), 4.7 (m, 4), 4.1 (m, 1), 20 3.5 (m, 2.5), 3.2 (m, 0.5), 3.0 (s, 1), 2.7 (dd, 1), 2.2 (d, 1), 2.1 (m, 1), 1.2 (m, 3), 0.9 (m, 3) ppm;

(trans)-1-((4-chloro-2-(ureidomethyl)phenoxy)methyl)carbonyl-2,5-dimethyl-4-(4-fluorobenzyl)piperazine; NMR (DMSO-d₆) 7.4 (m, 2), 7.1 (m, 4), 6.9 (d, 1), 6.4 (t, 1), 5.6 (s, 2), 5.0–4.0 (m, 4), 3.5 (m, 2), 3.3 (d, 2), 3.0 (m, 2), 2.2 (m, 2), 1.2 (br d , 3), 0.9 (br d, 25 3) ppm;

1-((4-chloro-2-aminophenoxy)methyl)carbonyl-2-methyl-4-(4-fluorobenzyl)piperazine; NMR (DMSO-d₆) 11.2 (br d, 1), 7.7 (m, 2), 7.3 (t, 2), 6.9 (m, 3), 5.0–4.2 (m, 5), 3.9 (m, 1), 3.6 (m, 1), 3.4 (m, 1), 3.0 (m, 3), 1.4 (d, 1.5), 1.3 (d, 1.5) ppm;

1-((4-chloro-3-aminophenoxy)methyl)carbonyl-2-methyl-4-(4-fluorobenzyl)piperazine; NMR (DMSO-d₆) 11.2 (br d, 1), 7.8 (br s, 2), 7.3 (t, 2), 7.0 (d, 1), 6.4 (s, 1), 6.2 (d, 1), 4.8–4.2 (m, 5), 4.0 (m, 1), 3.6 (m, 1), 3.4 (d, 1), 3.2–2.9 (m, 4), 1.3 (m, 3) ppm;

(2S)-1-((4-chloro-2-(ureido)phenoxy)methyl)carbonyl-2-methyl-4-(4-fluorobenzyl)piperazine; NMR (CDCl₃) 9.0 (s, 1), 8.2 (s, 1), 7.3 (t, 1), 7.0 (t, 3), 6.8 (q, 3), 5.0 (s, 2), 4.6 (dt, 2), 4.4 (d, 0.5), 3.7 (br s, 0.5), 3.4 (m, 2.5), 3.0 (t, 0.5), 2.8 (m, 1), 2.6 (d, 1), 2.1 (m, 3), 1.4 (d, 1.5),1.3 (d, 1.5) ppm;

(2R)-1-((4-chloro-2-(ureido)phenoxy)methyl)carbonyl-2-methyl-4-(4-fluorobenzyl)piperazine; NMR (CDCl$_3$) 9.0 (s, 1), 8.2 (s, 1), 7.3 (t, 1), 7.0 (t, 3), 6.8 (q, 3), 5.0 (s, 2), 4.6 (dt, 2), 4.4 (d, 0.5), 3.7 (br s, 0.5), 3.4 (m, 2.5), 3.0 (t, 0.5), 2.8 (m, 1), 2.6 (d, 1), 2.1 (m, 3), 1.4 (d, 1.5),1.3 (d, 1.5) ppm;

(trans)-1-((4-chloro-2-(ureido)phenoxy)methyl)carbonyl-2,5-dimethyl-4-(4-fluorobenzyl)piperazine; NMR (DMSO-d$_6$) 10.8 (br s, 1), 8.2 (br s, 2), 7.8 (br s, 2), 7.7 (br s, 1), 7.3 (m, 2), 6.8 (brs , 2), 5.2–4.3 (m, 5), 3.9–3.1 (m, 5), 2.8 (t, 1), 1.5–1.1 (m, 6) ppm;

(2R,5S)-1-((4-chloro-2-(ureido)phenoxy)methyl)carbonyl-2,5-dimethyl-4-(4-fluorobenzyl)piperazine; NMR (CDCl$_3$) 9.0 (s, 1), 8.3 (s, 1), 7.3 (t, 1), 7.0 (t, 3), 6.8 (m, 3), 5.0 (s, 2), 4.6 (m, 2), 4.2 (d, 0.5), 3.7–3.4 (m, 2.5), 3.2 (m, 2), 2.7 (d, 1), 2.5(m, 1), 2.2 (d, 1), 1.3 (br d, 3), 1.0 (br d, 3) ppm;

(trans)-1-((4-bromo-2-formylphenoxy)methyl)carbonyl-2,5-dimethyl-4-(4-fluorobenzyl)piperazine; NMR (CDCl$_3$) 10.4 (s, 1), 8.0 (s, 1), 7.6 (dd, 1), 7.3 (m, 2), 7.0 (m, 3), 4.8 (m, 3), 4.1 (brd, 1), 3.5 (m, 3), 3.0 (m, 1), 2.7 (dd, 1), 2.3 (d, 1), 1.3 (m, 3), 0.9 (m, 3) ppm;

1-((4-chloro-2-methoxycarbonylphenoxy)methyl)carbonyl-2-methyl-4-(4-fluorobenzyl)piperazine; NMR (DMSO-d$_6$) 11.0 (br d, 1), 7.7 (m, 3), 7.6 (dd, 1), 7.3 (t, 2), 7.0 (d, 1), 5.0 (dq, 2), 4.7 (m, 1), 4.4 (m, 3), 3.8 (m, 4), 3.4 (m, 2), 3.0 (m, 2), 1.4 (d, 1.5), 1.2 (d, 1.5) ppm;

(trans)-1-((4-chloro-2-methoxycarbonylphenoxy)methyl)carbonyl-2,5-dimethyl-4-(4-fluorobenzyl)piperazine; NMR (CDCl$_3$) 7.9 (br s, 2), 7.8 (s, 1), 7.4 (m, 1), 7.1 (t, 2), 7.0 (d, 1), 4.8 (m, 3), 4.4 (m, 2), 3.9 (m, 4), 3.5 (m, 2), 2.8 (m, 2), 1.6 (m, 3), 1.3 (m, 3) ppm;

1-((4-chloro-2-aminocarbonylphenoxy)methyl)carbonyl-2-methyl-4-(4-fluorobenzyl)piperazine; NMR (CDCl$_3$) 9.6 (br s, 1), 8.0 (s, 1), 7.6 (dd, 1), 7.4 (dd, 2), 7.2 (t, 2), 6.9 (d, 1), 5.0 (m, 3), 4.4 (m, 2), 4.0 (m, 1), 3.8 (m, 2), 3.6 (m, 1), 3.1 (m, 2), 2.9 (m, 1), 1.6 (d, 1.5), 1.4 (d, 1.5) ppm;

1-((4-chloro-2-(aminocarbonyl)phenylamino)methyl)carbonyl-2-methyl-4-(4-fluorobenzyl)piperazine; NMR (DMSO-d$_6$) 11.2 (br s, 1), 7.9 (br s, 1), 7.7 (m, 3), 7.2 (m, 2), 6.6 (d, 1), 4.8 (br s, 1), 4.4–3.9 (m, 6), 3.4 (d, 1), 3.0 (m, 3), 1.4 (m, 3) ppm;

(2R)-1-((4-chloro-2-aminocarbonylphenoxy)methyl)carbonyl-2-methyl-4-(4-fluorobenzyl)piperazine; NMR (CDCl$_3$) 9.1 (s, 1), 8.2 (s, 1), 7.4 (dd, 1), 7.3 (m, 3), 7.0 (t, 2), 6.8 (d, 1), 5.8 (br s, 1), 4.8 (m, 3), 3.5 (m, 3), 2.9 (d, 1), 2.7 (d, 1), 2.2 (m, 2), 1.4 (d, 1.5), 1.3 (d, 1.5) ppm;

1-((4-chloro-2-formylphenoxy)methyl)carbonyl-2-methyl-4-(4-fluorobenzyl)piperazine; NMR (DMSO-d$_6$) 11.0 (br d, 1), 10.4 (s, 1), 7.6 (m, 4), 7.3 (t, 2), 7.2 (d, 1), 5.2 (m, 2), 4.7 (m, 1), 4.3 (m, 3), 3.9 (m, 1), 3.6 (m, 1), 3.1 (m, 3), 1.5 (d, 1.5),1.3 (d, 1.5) ppm;

(2R,5S)-1-((4-chloro-2-formylphenoxy)methyl)carbonyl-2,5-dimethyl-4-(4-fluorobenzyl)piperazine; NMR (CDCl$_3$) 10.5 (s, 1), 7.8 (s, 1), 7.5 (d, 1), 7.3 (m, 2), 7.0 (t, 3), 4.8 (m, 3), 4.1 (m, 1), 3.5 (m, 3), 3.1 (br s, 1), 2.7 (dd, 1), 2.3 (dd, 1), 1.3 (m, 3), 0.9 (m, 3) ppm;

(2R)-1-((4-chloro-2-formylphenoxy)methyl)carbonyl-2-methyl-4-(4-fluorobenzyl)piperazine; NMR (CDCl$_3$) 10.4 (s, 1), 7.8 (s, 1), 7.5 (d, 1), 7.3 (m, 2), 7.0 (t, 3), 4.8 (br s, 2), 4.7 (m, 1), 4.2 (m, 1), 3.4 (m, 3), 3.1 (m, 1), 2.8 (br d, 1), 2.6 (br d, 1), 2.1 (m, 1), 2.0 (dd, 1), 1.3 (m, 3) ppm;

(trans)-1-((4-chloro-2-cyanophenoxy)methyl)carbonyl-2,5-dimethyl-4-(4-fluorobenzyl)piperazine; NMR (CDCl$_3$) 7.5 (dd, 1), 7.3 (m, 2), 7.0 (m, 4), 4.8 (m, 3), 4.1 (m, 1), 3.5 (m, 3), 3.0 (m, 1), 2.7 (m, 1), 2.2 (m, 1), 1.3 (m, 3), 0.8 (m, 3) ppm;

(trans)-1-((4-chloro-2-acetylphenoxy)methyl)carbonyl-2,5-dimethyl-4-(4-fluorobenzyl)piperazine; NMR (DMSO-d$_6$) 10.8 (br d, 1), 7.8 (s, 2), 7.5 (m, 2), 7.3 (m, 3), 7.2 (m, 1), 5.3 (m, 1), 5.0 (s, 2), 4.3 (m, 3), 4.0 (m, 1), 3.8–3.3 (m, 2), 2.8 (m, 1), 2.6 (s, 3), 1.4 (dd, 3), 1.3 (m, 3) ppm;

1-((2-(acetylamino)phenoxy)methyl)carbonyl-2-methyl-4-(4-fluorobenzyl)piperazine; NMR (DMSO-d$_6$) 11.0 (br s, 1), 9.4 (s, 1), 8.0 (d, 1), 7.6 (d, 2), 7.3 (t, 2), 7.0 (m, 3), 4.9 (q, 2), 4.7 (m, 1), 4.3 (m, 3), 3.9 (m, 1), 3.6–2.8 (m, 4), 2.1 (s, 3), 1.4 (d, 1.5), 1.3 (d, 1.5) ppm;

(trans)-1-((3-cyanophenoxy)methyl)carbonyl-2,5-dimethyl-4-(4-fluorobenzyl)piperazine; NMR (DMSO-d$_6$) 11.0 (br d, 1), 7.9 (s, 2), 7.5–7.3 (m, 6), 5.2 (d, 1), 4.9 (m, 2), 4.3 (m, 3), 3.6 (m, 2), 3.2 (m, 1), 2.8 (m, 1), 1.5–1.2 (m, 6) ppm;

(2R,5S)-1-((3-hydroxy-5-methylphenoxy)methyl)carbonyl-2,5-dimethyl-4-(4-fluorobenzyl)piperazine; NMR (DMSO-d$_6$)10.5 (br d, 1), 9.3 (s, 1), 7.8 (s, 2), 7.2 (m, 2), 6.2 (s, 2), 6.1 (s, 1), 4.7 (m, 4), 4.3 (m, 3), 3.8 (m, 1), 3.6 (m, 1), 2.8 (m, 1), 2.2 (s, 3), 1.4 (m, 3), 1.2 (m, 3) ppm;

(trans)-1-((4-methyl-2-aminophenoxy)methyl)carbonyl-2,5-dimethyl-4-(4-fluorobenzyl)piperazine; NMR (DMSO-d$_6$) 11.0 (br m, 1), 7.8 (s, 2), 7.2 (m, 5), 5.3 (m, 1), 5.0 (m, 2), 4.3 (m, 3), 4.0 (m, 1), 3.5 (m, 2), 2.8 (m, 1), 2.2 (s, 3), 1.3 (m, 6) ppm;

(trans)-1-((3-formylphenoxy)methyl)carbonyl-2,5-dimethyl-4-(4-fluorobenzyl)piperazine; NMR (DMSO-d$_6$) 11.0 (br d, 1), 10.0 (s, 1), 7.9 (s, 2), 7.5 (m, 2), 7.3 (m, 3), 6.9 (m, 1), 5.2 (m, 1), 4.9 (m, 2), 4.3 (m, 3), 4.0 (m, 1), 3.6 (m, 2), 2.8 (m, 1), 1.3 (m, 6) ppm;

(trans)-1-((4-methyl-2-acetylphenoxy)methyl)carbonyl-2,5-dimethyl-4-(4-fluorobenzyl)piperazine; NMR (CDCl$_3$) 7.5 (s, 1), 7.3(m, 3), 7.0 (t, 2), 6.8 (d, 1), 4.7 (m, 3), 4.2 (br d, 1), 3.6 (m, 1), 3.5 (q, 2), 3.0 (br s, 1), 2.7 (m, 4), 2.2 (m, 4), 1.3 (m, 3), 0.9 (m, 3) ppm;

(trans)-1-((2-methoxycarbonylphenoxy)methyl)carbonyl-2,5-dimethyl-4-(4-fluorobenzyl)piperazine; NMR (CDCl$_3$) 12.1 (s, 1), 7.8 (m, 3), 7.3 (br s, 1), 7.0 (br s, 4), 4.8 (m, 2), 4.3 (m, 3), 3.9 (m, 5), 3.6 (m, 1), 2.8 (m, 1), 2.4 (m, 1), 1.6 (m, 3), 1.3 (m, 3) ppm;

(trans)-1-((3-nitrophenoxy)methyl)carbonyl-2,5-dimethyl-4-(4-fluorobenzyl)piperazine; NMR (DMSO-d$_6$) 10.8 (brd, 1), 7.8 (m, 3), 7.7 (m, 1), 7.6 (t, 1), 7.4 (d, 1), 7.3 (t, 2), 5.2 (m, 1), 5.0 (m, 2), 4.7 (m, 1), 4.3 (m, 3), 4.0 (m, 1), 3.6 (m, 1), 2.8 (m, 1), 1.4 (m, 3), 1.3 (m, 3) ppm;

(trans)-1-((4-acetyl-2-(aminocarbonyl)phenoxy)methyl)carbonyl-2,5-dimethyl-4-(4-fluorobenzyl)piperazine; NMR (DMSO-d$_6$) 9.7 (br d, 1), 8.6 (s, 1), 8.5 (s, 1), 8.1 (d, 1), 7.8 (s, 1), 7.6 (br s, 3), 7.3 (t, 3), 5.4 (d, 1), 5.1 (m, 2), 4.6 (m, 1), 4.3 (s, 2), 4.2 (m, 1), 3.7 (m, 1), 3.4 (m, 1), 3.0 (m, 1), 2.6 (s, 3), 1.4 (m, 3), 1.2 (m, 3) ppm;

(trans)-1-((4-nitro-3-methylphenoxy)methyl)carbonyl-2,5-dimethyl-4-(4-fluorobenzyl)piperazine; NMR (DMSO-d$_6$) 11.2 (br d, 1), 8.0 (m, 3), 7.3 (m, 2), 7.0 (m, 2), 5.3 (d, 1), 5.0 (m, 2), 4.3 (m, 3), 3.7–3.3 (m, 2), 3.0 (m, 1), 2.8 (m, 1), 2.6 (s, 3), 1.4 (m, 3), 1.3 (m, 3) ppm;

(trans)-1-((5-nitro-2-methylphenoxy)methyl)carbonyl-2,5-dimethyl-4-(4-fluorobenzyl)piperazine; NMR (DMSO-d$_6$) 10.5 (br d, 1), 7.7 (m, 4), 7.4 (d, 1), 7.3 (t, 2), 5.3 (d, 1), 5.1 (m, 2), 4.7 (m, 1), 4.3 (m, 2), 3.9 (q, 1), 3.6 (brd, 1), 3.4 (m, 1), 2.9 (dd, 1), 2.3 (s, 3), 1.4 (m, 3), 1.3 (m, 3) ppm;

(trans)-1-((4-amino-3-nitrophenoxy)methyl)carbonyl-2,5-dimethyl-4-(4-fluorobenzyl)piperazine; NMR (DMSO-d$_6$) 11.2 (br d, 1), 7.9 (t, 2), 7.3 (m, 4), 7.0 (d, 1), 4.8 (m, 3), 4.3 (m, 3), 3.9 (m, 1), 3.6 (m, 1), 3.2 (m, 1), 2.8 (t, 1), 1.4 (dd, 3), 1.3 (dd, 3) ppm;

(trans)-1-((5-nitro-2-aminophenoxy)methyl)carbonyl-2,5-dimethyl-4-(4-fluorobenzyl)piperazine; NMR (DMSO-d$_6$) 11.2 (br d, 1), 7.9 (t, 2), 7.7 (d, 1), 7.6 (s, 1), 7.3 (t, 2), 6.7 (d, 1), 5.0 (m, 3), 4.7 (m, 1), 4.3 (m, 2), 4.0 (q, 1), 3.6 (m, 1), 3.3 (m, 1), 2.8 (t, 1), 1.4 (dd, 3), 1.3 (dd, 3) ppm;

(trans)-1-((2-aminophenoxy)methyl)carbonyl-2,5-dimethyl-4-(4-fluorobenzyl)piperazine; NMR (DMSO-d$_6$) 11.3 (m, 1), 7.9 (br s, 2), 7.8 (br m, 1), 7.3 (m, 4), 7.0 (t, 1), 5.3 (m, 1), 5.0 (m, 2), 4.6 (m, 1), 4.3 (m, 2), 3.6 (m, 3), 2.8 (m, 1), 1.3 (m, 6) ppm;

(trans)-1-((3-methoxyphenoxy)methyl)carbonyl-2,5-dimethyl-4-(4-fluorobenzyl)piperazine; NMR (DMSO-d$_6$) 10.5 (br d, 1), 7.8 (s, 2), 7.3 (m, 2), 7.1 (t, 1), 6.5 (m, 3), 4.8 (m, 2), 4.3 (m, 3), 3.8 (m, 1), 3.6 (m, 1), 3.4 (m, 2), 2.8 (t, 1), 1.4 (m, 3), 1.2 (m, 3) ppm;

(trans)-1-((4-methoxy-2-acetylphenoxy)methyl)carbonyl-2,5-dimethyl-4-(4-fluorobenzyl)piperazine; NMR (DMSO-d$_6$) 11.2 (br s, 1), 7.9 (br s, 2), 7.3 (m, 3), 7.1 (s, 2), 5.2 (d, 1), 4.9 (s, 2), 4.3 (m, 3), 3.9–3.4 (m, 9), 2.8 (m, 1), 1.4–1.2 (m, 6) ppm;

(trans)-1-((5-methoxy-2-acetylphenoxy)methyl)carbonyl-2,5-dimethyl-4-(4-fluorobenzyl)piperazine; NMR (DMSO-d$_6$) 11.2 (br d, 1), 7.9 (dd, 2), 7.6 (m, 1), 7.3 (t, 2), 6.6 (q, 2), 5.3 (d, 1), 5.0 (s, 2), 4.3 (m, 3), 3.8 (s, 3), 3.4 (m, 3), 2.8 (m, 1), 2.6 (s, 3), 1.5–1.2 (m, 6) ppm;

(trans)-1-((2-((2-hydroxyethyl)aminocarbonyl)phenoxy)methyl)carbonyl-2,5-dimethyl-4-(4-fluorobenzyl)piperazine; NMR (DMSO-d$_6$) 10.8 (br d, 1), 9.1 (br s, 1), 7.9 (d, 1), 7.8 (br s, 2), 7.4 (t, 1), 7.2 (m, 3), 7.0 (t, 1), 5.2 (d, 1), 5.0 (m, 2), 4.3 (m, 3), 3.9–3.4 (m, 7), 2.8 (dd, 1), 1.4–1.2 (m, 6) ppm;

(trans)-1-((2-((2-hydroxyethoxy)carbonyl)phenoxy)methyl)carbonyl-2,5-dimethyl-4-(4-fluorobenzyl)piperazine; NMR (DMSO-d$_6$) 10.0 (br s), 7.7 (m, 3), 7.4 (t, 1), 7.3 (t, 2), 7.0 (dd, 2), 5.0 (m, 2), 4.5 (m, 1), 4.2 (m, 5), 3.8 (q, 1), 3.6 (t, 2), 3.4 (m, 2), 2.9 (m, 1), 1.3 (m, 3), 1.2 (m, 3) ppm;

(trans)-1-((2-(2-hydroxyethoxy)phenoxy)methyl)carbonyl-2,5-dimethyl-4-(4-fluorobenzyl)piperazine; NMR (DMSO-d$_6$) 10.5 (br d, 1), 7.8 (t, 2), 7.3 (t, 2), 6.9 (m, 4), 4.8 (m, 3), 4.4 (m, 1), 4.3 (m, 2), 3.9 (m, 3), 3.6 (m, 3), 3.4 (m, 1), 2.8 (m, 1), 1.4 (m, 3), 1.2 (m, 3) ppm;

(trans)-1-((2-acetyl-4,5-dimethylphenoxy)methyl)carbonyl-2,5-dimethyl-4-(4-fluorobenzyl)piperazine; NMR (DMSO-d$_6$) 10.4 (br s, 1), 7.8 (m, 2), 7.4 (s, 1), 7.2 (t, 2), 6.8 (m, 1), 5.2 (d, 1), 4.9 (s, 2), 4.3 (m, 3), 3.8 (m, 1), 3.6 (m, 1), 3.4 (m, 1), 2.8 (m, 1), 2.6 (s, 3), 2.2 (s, 3), 2.1 (s, 3), 1.4 (m, 3), 1.2 (m, 3) ppm;

(trans)-1-((5-methoxy-2-(methoxycarbonyl)phenoxy)methyl)carbonyl-2,5-dimethyl-4-(4-fluorobenzyl)piperazine; NMR (DMSO-d$_6$) 11.0 (brd, 1), 7.9 (brs, 2), 7.7 (d, 1), 7.3 (m, 2), 6.6 (m, 2), 5.0 (m, 3), 4.3 (m, 3), 3.8 (s, 3), 3.7 (s, 3), 3.6 (m, 1), 3.4 (m, 2), 2.8 (dd, 1), 1.4 (dd, 3), 1.2 (dd, 3) ppm;

1-((4-chlorophenylamino)methyl)carbonyl-2-methyl-4-(4-fluorobenzyl)piperazine; NMR (DMSO-d$_6$) 7.4 (t, 2), 7.15 (t, 2), 7.1 (d, 2), 6.6 (d, 2), 5.8 (t, 1), 4.5 (m,.1), 4.2 (m, 1), 3.9 (m, 1), 3.7 (m, 1), 3.4 (m, 1), 3.3 (m, 1), 2.9 (m, 1), 2.8 (d, 1), 2.6 (d, 1), 2.0 (m, 2), 1.3 (d, 1.5), 1.1 (d, 1.5) ppm;

(trans)-1-((benzo[b]pyran-2-on-7-yloxy)methyl)carbonyl-2,5-dimethyl-4-(4-fluorobenzyl)piperazine; NMR (CDCl$_3$) 7.6 (d, 1), 7.4 (d, 1), 7.3 (m, 2), 7.0 (m, 3), 6.8 (s, 1), 6.3 (d, 1), 4.7 (m, 3), 4.1 (m, 1), 3.6 (m, 3), 3.0 (br s, 1), 2.7 (br d, 1), 2.2 (d, 1), 1.3 (m, 3), 1.0 (m, 3) ppm;

(trans)-1-((2-chloro-4-carboxyphenoxy)methyl)carbonyl-2,5-dimethyl-4-(4-fluorobenzyl)piperazine;

(trans)-1-((1-nitroso-3,6-di(hydroxysulfonyl)naphthalen-2-yloxy)methyl)carbonyl-2,5-dimethyl-4-(4-fluorobenzyl)piperazine;

(trans)-1-((2-nitroso-4-hydroxysulfonylnaphthalen-1-yloxy)methyl)carbonyl-2,5-dimethyl-4-(4-fluorobenzyl)piperazine; (trans)-1-((3,6-di(hydroxysulfonyl)naphthalen-1-yloxy)methyl)carbonyl-2,5-dimethyl-4-(4-fluorobenzyl)piperazine;

(trans)-1-((3-hydroxysulfonyl-6-aminonaphthalen-1-yloxy)methyl)carbonyl-2,5-dimethyl-4-(4-fluorobenzyl)piperazine;

(trans)-1-((3-hydroxysulfonyl-7-aminonaphthalen-1-yloxy)methyl)carbonyl-2,5-dimethyl-4-(4-fluorobenzyl)piperazine;

(trans)-1-((5-hydroxysulfonylquinolin-8-yloxy)methyl)carbonyl-2,5-dimethyl-4-(4-fluorobenzyl)piperazine;

(trans)-1-((2,3-dinitro-7-hydroxysulfonylnaphthalen-1-yloxy)methyl)carbonyl-2,5-dimethyl-4-(4-fluorobenzyl)piperazine;

(trans)-1-((2-carboxy-4-hydroxysulfonylphenoxy)methyl)carbonyl-2,5-dimethyl-4-(4-fluorobenzyl)piperazine;

(trans)-1-((2-amino-4-hydroxysulfonylphenoxy)methyl)carbonyl-2,5-dimethyl-4-(4-fluorobenzyl)piperazine;

(trans)-1-((4-formyl-2,6-di-t-butylphenoxy)methyl)carbonyl-2,5-dimethyl-4-(4-fluorobenzyl)piperazine;

(trans)-1-((4-(morpholin-4-yl)methyl-2,5-dimethylphenoxy)methyl)carbonyl-2,5-dimethyl-4-(4-fluorobenzyl)piperazine;

(trans)-1-((4-(methoxycarbonyl)-2,6-dichlorophenoxy)methyl)carbonyl-2,5-dimethyl-4-(4-fluorobenzyl)piperazine;

(trans)-1-((4-(hydroxysulfonyl)naphthalen-1-yloxy)methyl)carbonyl-2,5-dimethyl-4-(4-fluorobenzyl)piperazine;

(trans)-1-((3,6-di(hydroxysulfonyl)-8-aminonaphthalen-1-yloxy)methyl)carbonyl-2,5-dimethyl-4-(4-fluorobenzyl)piperazine;

(trans)-1-((2-carboxy-5-aminophenoxy)methyl)carbonyl-2,5-dimethyl-4-(4-fluorobenzyl)piperazine;

(trans)-1-((4-trifluromethyl-2,3,5,6-tetrafluorophenoxy)methyl)carbonyl-2,5-dimethyl-4-(4-fluorobenzyl)piperazine;

(trans)-1-((2-methoxy-4-formyl-5-(2-hydroxy-3-methoxy-5-formylphenyl)-phenoxy)methyl)carbonyl-2,5-dimethyl-4-(4-fluorobenzyl)piperazine;

(trans)-1-((4-carboxy-2,3,5,6-tetrafluorophenoxy)methyl)carbonyl-2,5-dimethyl-4-(4-fluorobenzyl)piperazine;

(trans)-1-((4-(adamant-1-yl)phenoxy)methyl)carbonyl-2,5-dimethyl-4-(4-fluorobenzyl)piperazine;

(trans)-1-((2-(adamant-1-yl)-4-methylphenoxy)methyl)carbonyl-2,5-dimethyl-4-(4-fluorobenzyl)piperazine;
(trans)-1-((2,4-di((1-methyl-1-phenyl)ethyl)phenoxy)methyl)carbonyl-2,5-dimethyl-4-(4-fluorobenzyl)piperazine;
(trans)-1-((2-acetyl-4-bromophenoxy)methyl)carbonyl-2,5-dimethyl-4-(4-fluorobenzyl)piperazine;
(trans)-1-((2-nitro-4-t-butylphenoxy)methyl)carbonyl-2,5-dimethyl-4-(4-fluorobenzyl)piperazine;
(trans)-1-((2-acetyl-4-chloro-5-methylphenoxy)methyl)carbonyl-2,5-dimethyl-4-(4-fluorobenzyl)piperazine;
(trans)-1-((2-acetyl-4-chloro-6-nitrophenoxy)methyl)carbonyl-2,5-dimethyl-4-(4-fluorobenzyl)piperazine;
(trans)-1-((2-acetyl-4,6-dibromophenoxy)methyl)carbonyl-2,5-dimethyl-4-(4-fluorobenzyl)piperazine;
(trans)-1-((2-formyl-4,6-di(t-butyl)phenoxy)methyl)carbonyl-2,5-dimethyl-4-(4-fluorobenzyl)piperazine;
(trans)-1-((3,5-dinitrophenoxy)methyl)carbonyl-2,5-dimethyl-4-(4-fluorobenzyl)piperazine;
(trans)-1-((2,6-dichloro-4-ethoxycarbonylphenoxy)methyl)carbonyl-2,5-dimethyl-4-(4-fluorobenzyl)piperazine;
(trans)-1-((2-ethoxycarbonyl-4-methylphenoxy)methyl)carbonyl-2,5-dimethyl-4-(4-fluorobenzyl)piperazine;
(trans)-1-((2-methoxy-6-(prop-3-enyl)phenoxy)methyl)carbonyl-2,5-dimethyl-4-(4-fluorobenzyl)piperazine;
(trans)-1-((3-fluoro-4-cyanophenoxy)methyl)carbonyl-2,5-dimethyl-4-(4-fluorobenzyl)piperazine;
(trans)-1-((2-acetyl-4-methyl-6-nitrophenoxy)methyl)carbonyl-2,5-dimethyl-4-(4-fluorobenzyl)piperazine;
(trans)-1-((2-methylbenzothiazol-5-yloxy)methyl)carbonyl-2,5-dimethyl-4-(4-fluorobenzyl)piperazine;
(trans)-1-((2-carboxy-4-(hydroxysulfonyl)phenoxy)methyl)carbonyl-2,5-dimethyl-4-(4-fluorobenzyl)piperazine;
(trans)-1-((4-(4-(trifluoromethyl)phenoxy)phenoxy)methyl)carbonyl-2,5-dimethyl-4-(4-fluorobenzyl)piperazine;
(trans)-1-((2-(1H-pyrazol-3-yl)-4-chloro-5-methylphenoxy)methyl)carbonyl-2,5-dimethyl-4-(4-fluorobenzyl)piperazine;
(trans)-1-((2-(1H-pyrazol-3-yl)-4-chlorophenoxy)methyl)carbonyl-2,5-dimethyl-4-(4-fluorobenzyl)piperazine;
(trans)-1-(((2-phenyl-4-oxo-7-hydroxy-4H-1-benzopyran-3-yl)oxy)methyl)carbonyl-2,5-dimethyl-4-(4-fluorobenzyl)piperazine;
(trans)-1-((2-chloro-3-trifluoromethylphenoxy)methyl)carbonyl-2,5-dimethyl-4-(4-fluorobenzyl)piperazine;
(trans)-1-((2-methoxy-4-(butoxymethyl)phenoxy)methyl)carbonyl-2,5-dimethyl-4-(4-fluorobenzyl)piperazine;
(trans)-1-((6-hydroxyquinolin-2-yloxy)methyl)carbonyl-2,5-dimethyl-4-(4-fluorobenzyl)piperazine;
(trans)-1-((2-methoxycarbonyl-6-methoxyphenoxy)methyl)carbonyl-2,5-dimethyl-4-(4-fluorobenzyl)piperazine;
(trans)-1-((2,5-di(t-butyl)-4-methoxyphenoxy)methyl)carbonyl-2,5-dimethyl-4-(4-fluorobenzyl)piperazine;
(trans)-1-((2-formyl-4-methylphenoxy)methyl)carbonyl-2,5-dimethyl-4-(4-fluorobenzyl)piperazine;
(trans)-1-((2-(2H-benzotriazol-2-yl)4-(2-hydroxyethyl)phenoxy)methyl)carbonyl-2,5-dimethyl-4-(4-fluorobenzyl)piperazine;
(trans)-1-((4-chlorophenoxy)methyl)carbonyl-2,5-dimethyl-4-(4-fluorobenzyl)piperazine;
(trans)-1-((2-(methylthio)phenoxy)methyl)carbonyl-2,5-dimethyl-4-(4-fluorobenzyl)piperazine;
(trans)-1-((3,5-di(t-butyl)-4-formylphenoxy)methyl)carbonyl-2,5-dimethyl-4-(4-fluorobenzyl)piperazine;
(trans)-1-((3,5-dibromo-4-methylphenoxy)methyl)carbonyl-2,5-dimethyl-4-(4-fluorobenzyl)piperazine;
(trans)-1-((2,6-diiodo-4-formylphenoxy)methyl)carbonyl-2,5-dimethyl-4-(4-fluorobenzyl)piperazine;
(trans)-1-((2-nitro-4-methoxycarbonylphenoxy)methyl)carbonyl-2,5-dimethyl-4-(4-fluorobenzyl)piperazine;
(trans)-1-((2-(ethoxycarbonyl)indol-5-yloxy)methyl)carbonyl-2,5-dimethyl-4-(4-fluorobenzyl)piperazine;
(trans)-1-((3-(2-carboxyethyl)phenoxy)methyl)carbonyl-2,5-dimethyl-4-(4-fluorobenzyl)piperazine;
(trans)-1-((2,6-dinitro-4-(carboxymethyl)phenoxy)methyl)carbonyl-2,5-dimethyl-4-(4-fluorobenzyl)piperazine;
(trans)-1-((2-nitro-3-carboxyphenoxy)methyl)carbonyl-2,5-dimethyl-4-(4-fluorobenzyl)piperazine;
(trans)-1-((6-carboxynaphthalen-2-yloxy)methyl)carbonyl-2,5-dimethyl-4-(4-fluorobenzyl)piperazine;
(trans)-1-((2,6-difluoro-4-ethylcarbonylphenoxy)methyl)carbonyl-2,5-dimethyl-4-(4-fluorobenzyl)piperazine;
(trans)-1-((2-(2-(methoxycarbonyl)ethyl)phenoxy)methyl)carbonyl-2,5-dimethyl-4-(4-fluorobenzyl)piperazine;
(trans)-1-((2-(prop-3-enyl)-4-acetylphenoxy)methyl)carbonyl-2,5-dimethyl-4-(4-fluorobenzyl)piperazine;
(trans)-1-(((3-oxo-2H-benzofuran-6-yl)oxy)methyl)carbonyl-2,5-dimethyl-4-(4-fluorobenzyl)piperazine;
(trans)-1-((2,4,6-tribromo-3,5-dimethylphenoxy)methyl)carbonyl-2,5-dimethyl-4-(4-fluorobenzyl)piperazine;
(trans)-1-((4-(heptylcarbonyl)phenoxy)methyl)carbonyl-2,5-dimethyl-4-(4-fluorobenzyl)piperazine;
(trans)-1-((2-carboxy-4-acetylphenoxy)methyl)carbonyl-2,5-dimethyl-4-(4-fluorobenzyl)piperazine;
(trans)-1-((2-nitro-4-phenylphenoxy)methyl)carbonyl-2,5-dimethyl-4-(4-fluorobenzyl)piperazine;
(trans)-1-((2-methoxy-4-(eth-2-enyl)phenoxy)methyl)carbonyl-2,5-dimethyl-4-(4-fluorobenzyl)piperazine;
(trans)-1-((2-chloro-4-methoxycarbonylphenoxy)methyl)carbonyl-2,5-dimethyl-4-(4-fluorobenzyl)piperazine;
(trans)-1-((2,6-diiodo-4-cyanophenoxy)methyl)carbonyl-2,5-dimethyl-4-(4-fluorobenzyl)piperazine;
(trans)-1-((2,6-diiodo-4-carboxyphenoxy)methyl)carbonyl-2,5-dimethyl-4-(4-fluorobenzyl)piperazine;
(trans)-1-(((2-phenyl-4-oxo-4H-1-benzopyran-5-yl)oxy)methyl)carbonyl-2,5-dimethyl-4-(4-fluorobenzyl)piperazine;
(trans)-1-(((2-phenyl-4-oxo-7-methoxy-4H-1-benzopyran-5-yl)oxy)methyl)carbonyl-2,5-dimethyl-4-(4-fluorobenzyl)piperazine;
(trans)-1-(((2-phenyl-4-oxo-7-methoxy-2,3-dihydro-4H-1-benzopyran-5-yl)oxy)methyl)carbonyl-2,5-dimethyl-4-(4-fluorobenzyl)piperazine;
(trans)-1-((4-octylcarbonylphenoxy)methyl)carbonyl-2,5-dimethyl-4-(4-fluorobenzyl)piperazine;
(trans)-1-(((4-phthalimid-1-ylphenoxy)methyl)carbonyl-2,5-dimethyl-4-(4-fluorobenzyl)piperazine;
(trans)-1-((3-(morpholin-4-yl)phenoxy)methyl)carbonyl-2,5-dimethyl-4-(4-fluorobenzyl)piperazine;

(trans)-1-((3-chloro-4-bromophenoxy)methyl)carbonyl-2,5-dimethyl-4-(4-fluorobenzyl)piperazine;
(trans)-1-(((2-oxo-7-methoxy-2H-1-benzopyran-8-yl)oxy)methyl)carbonyl-2,5-dimethyl-4-(4-fluorobenzyl)piperazine;
(trans)-1-((2-acetyl-5-fluorophenoxy)methyl)carbonyl-2,5-dimethyl-4-(4-fluorobenzyl)piperazine;
(trans)-1-((2-(1-methylcyclohex-1-yl)-4-methyl-6-(2-hydroxy-3-(1-methylcyclohex-1-yl)-5-methylbenzyl)phenoxy)methyl)carbonyl-2,5-dimethyl-4-(4-fluorobenzyl)piperazine;
(trans)-1-((2-formyl-3-methoxyphenoxy)methyl)carbonyl-2,5-dimethyl-4-(4-fluorobenzyl)piperazine;
(trans)-1-((2-amino-4-carboxyphenoxy)methyl)carbonyl-2,5-dimethyl-4-(4-fluorobenzyl)piperazine;
(trans)-1-((2-chloro-4-carboxy-6-methoxyphenoxy)methyl)carbonyl-2,5-dimethyl-4-(4-fluorobenzyl)piperazine;
(trans)-1-((2,6-dimethyl-4-carboxyphenoxy)methyl)carbonyl-2,5-dimethyl-4-(4-fluorobenzyl)piperazine;
(trans)-1-((2-methoxy-4-(2-(carboxy)ethyl)phenoxy)methyl)carbonyl-2,5-dimethyl-4-(4-fluorobenzyl)piperazine;
(trans)-1-((2,6-dimethoxy-4-(hydroxymethyl)phenoxy)methyl)carbonyl-2,5-dimethyl-4-(4-fluorobenzyl)piperazine;
(trans)-1-((2,6-dibromo-4-formylphenoxy)methyl)carbonyl-2,5-dimethyl-4-(4-fluorobenzyl)piperazine;
(trans)-1-((2-nitro-4-(ethoxycarbonyl)phenoxy)methyl)carbonyl-2,5-dimethyl-4-(4-fluorobenzyl)piperazine;
(trans)-1-((2-amino-4-(methoxycarbonyl)phenoxy)methyl)carbonyl-2,5-dimethyl-4-(4-fluorobenzyl)piperazine;
(trans)-1-((4-(2-(4-nitrophenyl)eth-2-enyl)phenoxy)methyl)carbonyl-2,5-dimethyl-4-(4-fluorobenzyl)piperazine;
(trans)-1-((2-acetyl-3,5-dimethoxyphenoxy)methyl)carbonyl-2,5-dimethyl-4-(4-fluorobenzyl)piperazine;
(trans)-1-((2,6-di(t-butyl)-4-(methoxycarbonyl)phenoxy)methyl)carbonyl-2,5-dimethyl-4-(4-fluorobenzyl)piperazine;
(trans)-1-((2-methoxy-4-(ethoxycarbonyl)phenoxy)methyl)carbonyl-2,5-dimethyl-4-(4-fluorobenzyl)piperazine;
(trans)-1-((2-cyclohexyl-4-chlorophenoxy)methyl)carbonyl-2,5-dimethyl-4-(4-fluorobenzyl)piperazine;
(trans)-1-((2,6-dimethyl-4-chlorophenoxy)methyl)carbonyl-2,5-dimethyl-4-(4-fluorobenzyl)piperazine;
(trans)-1-((2-methoxy-4-ethylphenoxy)methyl)carbonyl-2,5-dimethyl-4-(4-fluorobenzyl)piperazine;
(trans)-1-((4-n-butylphenoxy)methyl)carbonyl-2,5-dimethyl-4-(4-fluorobenzyl)piperazine;
(trans)-1-(((3-carboxy-1-bromonaphthalen-2-yl)oxy)methyl)carbonyl-2,5-dimethyl-4-(4-fluorobenzyl)piperazine;
(trans)-1-((2-bromo-4-nitro-6-formylphenoxy)methyl)carbonyl-2,5-dimethyl-4-(4-fluorobenzyl)piperazine;
(trans)-1-((2-formyl-4-chlorophenoxy)methyl)carbonyl-2,5-dimethyl-4-(4-fluorobenzyl)piperazine;
(trans)-1-((2,6-dichloro-4-(ethoxycarbonyl)phenoxy)methyl)carbonyl-2,5-dimethyl-4-(4-fluorobenzyl)piperazine;
(trans)-1-(((4-methyl-2-oxo-2H-1-benzopyran-6-yl)oxy)methyl)carbonyl-2,5-dimethyl-4-(4-fluorobenzyl)piperazine;
(trans)-1-((2,3-dibromo-4-formyl-6-methoxyphenoxy)methyl)carbonyl-2,5-dimethyl-4-(4-fluorobenzyl)piperazine;
(trans)-1-((4-(2-(4-nitrophenyl)eth-2-yl)phenoxy)methyl)carbonyl-2,5-dimethyl-4-(4-fluorobenzyl)piperazine;
(trans)-1-((2,4,6-tribromo-3-formylphenoxy)methyl)carbonyl-2,5-dimethyl-4-(4-fluorobenzyl)piperazine;
(trans)-1-((2-benzyl-4-chlorophenoxy)methyl)carbonyl-2,5-dimethyl-4-(4-fluorobenzyl)piperazine;
(trans)-1-((2-(bezothiazol-2-yl)phenoxy)methyl)carbonyl-2,5-dimethyl-4-(4-fluorobenzyl)piperazine;
(trans)-1-((2-nitro-6-fluorophenoxy)methyl)carbonyl-2,5-dimethyl-4-(4-fluorobenzyl)piperazine;
(trans)-1-((2-ethoxy-4-methylphenoxy)methyl)carbonyl-2,5-dimethyl-4-(4-fluorobenzyl)piperazine;
(trans)-1-((2-bromo-4,6-di(t-butyl)phenoxy)methyl)carbonyl-2,5-dimethyl-4-(4-fluorobenzyl)piperazine;
(trans)-1-((2-(pyrrolidin-1-yl)phenoxy)methyl)carbonyl-2,5-dimethyl-4-(4-fluorobenzyl)piperazine;
(trans)-1-((2-(morpholin-4-yl)phenoxy)methyl)carbonyl-2,5-dimethyl-4-(4-fluorobenzyl)piperazine;
(trans)-1-((2-(piperidin-1-yl)phenoxy)methyl)carbonyl-2,5-dimethyl-4-(4-fluorobenzyl)piperazine;
(trans)-1-((2-formyl-4-chloro-6-bromophenoxy)methyl)carbonyl-2,5-dimethyl-4-(4-fluorobenzyl)piperazine;
(trans)-1-(((4,7-dimethoxy-5-formylbenzofuran-6-yl)oxy)methyl)carbonyl-2,5-dimethyl-4-(4-fluorobenzyl)piperazine;
(trans)-1-(((2-oxo-4-methyl-8-nitro-2H-1-benzopyran-7-yl)oxy)methyl)carbonyl-2,5-dimethyl-4-(4-fluorobenzyl)piperazine;
(trans)-1-((2-methoxy-4-bromophenoxy)methyl)carbonyl-2,5-dimethyl-4-(4-fluorobenzyl)piperazine;
(trans)-1-((2-chloro-4-bromo-6-methylphenoxy)methyl)carbonyl-2,5-dimethyl-4-(4-fluorobenzyl)piperazine;
(trans)-1-((2,4-dimethyl-6-t-butylphenoxy)methyl)carbonyl-2,5-dimethyl-4-(4-fluorobenzyl)piperazine;
(trans)-1-(((2-nitro-4-(hydroxysulfonyl)naphthalen-1-yl)oxy)methyl)carbonyl-2,5-dimethyl-4-(4-fluorobenzyl)piperazine;
(trans)-1-(((3-(hydroxysulfonyl)-6-aminonaphthalen-1-yl)oxy)methyl)carbonyl-2,5-dimethyl-4-(4-fluorobenzyl)piperazine;
(trans)-1-(((3-(hydroxysulfonyl)-7-aminonaphthalen-1-yl)oxy)methyl)carbonyl-2,5-dimethyl-4-(4-fluorobenzyl)piperazine;
(trans)-1-(((3-(methoxycarbonyl)naphthalen-2-yl)oxy)methyl)carbonyl-2,5-dimethyl-4-(4-fluorobenzyl)piperazine;
(trans)-1-((2-carboxy-4-(hydroxysulfonyl)phenoxy)methyl)carbonyl-2,5-dimethyl-4-(4-fluorobenzyl)piperazine;
(trans)-1-((4-n-butylcarbonylphenoxy)methyl)carbonyl-2,5-dimethyl-4-(4-fluorobenzyl)piperazine;
(trans)-1-((3-ethoxyphenoxy)methyl)carbonyl-2,5-dimethyl-4-(4-fluorobenzyl)piperazine;
(trans)-1-((4-(((2-ethyl)hexoxy)carbonyl)phenoxy)methyl)carbonyl-2,5-dimethyl-4-(4-fluorobenzyl)piperazine;
(trans)-1-((4-((n-pentoxy)carbonyl)phenoxy)methyl)carbonyl-2,5-dimethyl-4-(4-fluorobenzyl)piperazine;
(trans)-1-((2-nitro-5-(methoxycarbonyl)phenoxy)methyl)carbonyl-2,5-dimethyl-4-(4-fluorobenzyl)piperazine;

(trans)-1-((2,4,6-tribromo-3-methylphenoxy)methyl) carbonyl-2,5-dimethyl-4-(4-fluorobenzyl)piperazine;
(trans)-1-((2-methoxy-5-methylphenoxy)methyl) carbonyl-2,5-dimethyl-4-(4-fluorobenzyl)piperazine;
(trans)-1-((3-methoxy-4-formylphenoxy)methyl) carbonyl-2,5-dimethyl-4-(4-fluorobenzyl)piperazine;
(trans)-1-((4-(2-(phenyl)eth-2-enyl)phenoxy)methyl) carbonyl-2,5-dimethyl-4-(4-fluorobenzyl)piperazine;
(trans)-1-((4-(1,2,4-triazol-1-yl)phenoxy)methyl) carbonyl-2,5-dimethyl-4-(4-fluorobenzyl)piperazine;
(trans)-1-((2-nitro-4-chloro-5-methylphenoxy)methyl) carbonyl-2,5-dimethyl-4-(4-fluorobenzyl)piperazine;
(trans)-1-((4-(n-hexoxycarbonyl)phenoxy)methyl) carbonyl-2,5-dimethyl-4-(4-fluorobenzyl)piperazine;
(trans)-1-((2-chloro-4-formyl-6-methoxyphenoxy) methyl)carbonyl-2,5-dimethyl-4-(4-fluorobenzyl) piperazine;
(trans)-1-((2-methoxy-4-(2-(ethoxycarbonyl)ethyl) phenoxy)methyl)carbonyl-2,5-dimethyl-4-(4-fluorobenzyl)piperazine;
(trans)-1-((2,3,4,6-tetrachlorophenoxy)methyl)carbonyl-2,5-dimethyl-4-(4-fluorobenzyl)piperazine;
(trans)-1-((2-((2-methylpropoxy)carbonyl)phenoxy) methyl)carbonyl-2,5-dimethyl-4-(4-fluorobenzyl) piperazine;
(trans)-1-((2-(n-butoxycarbonyl)phenoxy)methyl) carbonyl-2,5-dimethyl-4-(4-fluorobenzyl)piperazine;
(trans)-1-((4-(phenylamino)phenoxy)methyl)carbonyl-2,5-dimethyl-4-(4-fluorobenzyl)piperazine;
(trans)-1-((2-hydroxymethyl-4-chlorophenoxy)methyl) carbonyl-2,5-dimethyl-4-(4-fluorobenzyl)piperazine;
(trans)-1-((2-mercaptophenoxy)methyl)carbonyl-2,5-dimethyl-4-(4-fluorobenzyl)piperazine;
(trans)-1-((2-nitro-6-formylphenoxy)methyl)carbonyl-2,5-dimethyl-4-(4-fluorobenzyl)piperazine;
(trans)-1-((2,4-di(1-methylbutyl)phenoxy)methyl) carbonyl-2,5-dimethyl-4-(4-fluorobenzyl)piperazine;
(trans)-1-((3-trifluoromethyl-4-nitrophenoxy)methyl) carbonyl-2,5-dimethyl-4-(4-fluorobenzyl)piperazine;
(trans)-1-((2,6-dibromo-4-(methoxycarbonyl)phenoxy) methyl)carbonyl-2,5-dimethyl-4-(4-fluorobenzyl) piperazine;
(trans)-1-((2,4-dichloro-6-acetyl)methyl)carbonyl-2,5-dimethyl-4-(4-fluorobenzyl)piperazine;
(trans)-1-((2-methoxycarbonyl-4-methylphenoxy) methyl)carbonyl-2,5-dimethyl-4-(4-fluorobenzyl) piperazine;
(trans)-1-((2-formyl-4-bromo-6-methoxyphenoxy) methyl)carbonyl-2,5-dimethyl-4-(4-fluorobenzyl) piperazine;
(trans)-1-((2,6-diformyl-4-methylphenoxy)methyl) carbonyl-2,5-dimethyl-4-(4-fluorobenzyl)piperazine;
(trans)-1-((2,6-dinitro-4-carboxyphenoxy)methyl) carbonyl-2,5-dimethyl-4-(4-fluorobenzyl)piperazine;
(trans)-1-((2-nitro-4-acetylphenoxy)methyl)carbonyl-2,5-dimethyl-4-(4-fluorobenzyl)piperazine;
(trans)-1-((2-formyl-4-nitro-6-methoxyphenoxy)methyl) carbonyl-2,5-dimethyl-4-(4-fluorobenzyl)piperazine;
(trans)-1-((4-(aminocarbonyl)methylphenoxy)methyl) carbonyl-2,5-dimethyl-4-(4-fluorobenzyl)piperazine;
(trans)-1-((2-methoxycarbonyl-4-methoxyphenoxy) methyl)carbonyl-2,5-dimethyl-4-(4-fluorobenzyl) piperazine;
(trans)-1-(((2-phenyl-4-oxo-4H-1-benzopyran-6-yl)oxy) methyl)carbonyl-2,5-dimethyl-4-(4-fluorobenzyl) piperazine;
(trans)-1-((2-chloro-4-trifluoromethylphenoxy)methyl) carbonyl-2,5-dimethyl-4-(4-fluorobenzyl)piperazine;
(trans)-1-((2-carboxy-3-methyl-6-isopropylphenoxy) methyl)carbonyl-2,5-dimethyl-4-(4-fluorobenzyl) piperazine;
(trans)-1-(((5,7-dibromo-2-methylquinolin-8-yl)oxy) methyl)carbonyl-2,5-dimethyl-4-(4-fluorobenzyl) piperazine;
(trans)-1-(((5,7-dichloro-2-methylquinolin-8-yl)oxy) methyl)carbonyl-2,5-dimethyl-4-(4-fluorobenzyl) piperazine;
(trans)-1-((2,6-dinitrophenoxy)methyl)carbonyl-2,5-dimethyl-4-(4-fluorobenzyl)piperazine;
(trans)-1-((2-nitro-4-methoxyphenoxy)methyl)carbonyl-2,5-dimethyl-4-(4-fluorobenzyl)piperazine;
(trans)-1-((2-amino-4-(1,1-dimethylpropyl)phenoxy) methyl)carbonyl-2,5-dimethyl-4-(4-fluorobenzyl) piperazine;
(trans)-1-((2,6-diphenyl-4-aminophenoxy)methyl) carbonyl-2,5-dimethyl-4-(4-fluorobenzyl)piperazine;
(trans)-1-((2,4-dichloro-3-methyl-6-aminophenoxy) methyl)carbonyl-2,5-dimethyl-4-(4-fluorobenzyl) piperazine;
(trans)-1-(((2-oxo-4-(carboxy)methyl-2H-1-benzopyran-7-yl)oxy)methyl)carbonyl-2,5-dimethyl-4-(4-fluorobenzyl)piperazine;
(trans)-1-(((2-oxo-4-trifluoromethyl-2H-1-benzopyran-7-yl)oxy)methyl)carbonyl-2,5-dimethyl-4-(4-fluorobenzyl)piperazine;
(trans)-1-((2-t-butyl-4-methoxyphenoxy)methyl) carbonyl-2,5-dimethyl-4-(4-fluorobenzyl)piperazine;
(trans)-1-((2-formyl-6-methylphenoxy)methyl)carbonyl-2,5-dimethyl-4-(4-fluorobenzyl)piperazine;
(trans)-1-((2-methoxycarbonyl-4-acetylphenoxy)methyl) carbonyl-2,5-dimethyl-4-(4-fluorobenzyl)piperazine;
(trans)-1-((2-bromo-5-fluorophenoxy)methyl)carbonyl-2,5-dimethyl-4-(4-fluorobenzyl)piperazine;
(trans)-1-((2,4-di(1,1-dimethylpropyl)phenoxy)methyl) carbonyl-2,5-dimethyl-4-(4-fluorobenzyl)piperazine;
(trans)-1-((3-methyl-4-fluorophenoxy)methyl)carbonyl-2,5-dimethyl-4-(4-fluorobenzyl)piperazine;
(trans)-1-((2,3,4-trifluorophenoxy)methyl)carbonyl-2,5-dimethyl-4-(4-fluorobenzyl)piperazine;
(trans)-1-((2,5-difluorophenoxy)methyl)carbonyl-2,5-dimethyl-4-(4-fluorobenzyl)piperazine;
(trans)-1-((2-methyl-5-nitrophenoxy)methyl)carbonyl-2,5-dimethyl-4-(4-fluorobenzyl)piperazine;
(trans)-1-(((2-methyl-3-(ethoxycarbonyl)indol-5-yl)oxy) methyl)carbonyl-2,5-dimethyl-4-(4-fluorobenzyl) piperazine;
(trans)-1-((2-aminocarbonyl-4-acetylphenoxy)methyl) carbonyl-2,5-dimethyl-4-(4-fluorobenzyl)piperazine;
(trans)-1-((2,6-dinitro-3-t-butylphenoxy)methyl) carbonyl-2,5-dimethyl-4-(4-fluorobenzyl)piperazine;
(trans)-1-((2-fluoro-4-nitrophenoxy)methyl)carbonyl-2,5-dimethyl-4-(4-fluorobenzyl)piperazine;
(trans)-1-((2-carboxy-3-fluorophenoxy)methyl)carbonyl-2,5-dimethyl-4-(4-fluorobenzyl)piperazine;
(trans)-1-((2-(2-ethylhexoxy)carbonylphenoxy)methyl) carbonyl-2,5-dimethyl-4-(4-fluorobenzyl)piperazine;

(trans)-1-((2,4,6-tribromo-4-carboxyphenoxy)methyl)
carbonyl-2,5-dimethyl-4-(4-fluorobenzyl)piperazine;
(trans)-1-((4-(4-bromophenyl)phenoxy)methyl)carbonyl-
2,5-dimethyl-4-(4-fluorobenzyl)piperazine;
(trans)-1-((4-(4-carboxyphenyl)phenoxy)methyl)
carbonyl-2,5-dimethyl-4-(4-fluorobenzyl)piperazine;
(trans)-1-((2,3,6-trifluorophenoxy)methyl)carbonyl-2,5-
dimethyl-4-(4-fluorobenzyl)piperazine;
(trans)-1-((2,4,5-trifluorophenoxy)methyl)carbonyl-2,5-
dimethyl-4-(4-fluorobenzyl)piperazine;
(trans)-1-((2,4,6-trifluorophenoxy)methyl)carbonyl-2,5-
dimethyl-4-(4-fluorobenzyl)piperazine;
(trans)-1-((2-fluoro-5-trifluoromethylphenoxy)methyl)
carbonyl-2,5-dimethyl-4-(4-fluorobenzyl)piperazine;
(trans)-1-(((2,4-dinitronaphthalen-1-yl)oxy)methyl)
carbonyl-2,5-dimethyl-4-(4-fluorobenzyl)piperazine;
(trans)-1-(((3,6-di(hydroxysulfonyl)-8-aminonaphthalen-
1-yl)oxy)methyl)carbonyl-2,5-dimethyl-4-(4-
fluorobenzyl)piperazine;
(trans)-1-((2-acetyl-4-chlorophenoxy)methyl)carbonyl-2,
5-dimethyl-4-(4-fluorobenzyl)piperazine;
(trans)-1-((2,6-dimethyl-4-(1-(3,5-dimethyl-4-
hydoxyphenyl)-1-methylethyl)phenoxy)methyl)
carbonyl-2,5-dimethyl-4-(4-fluorobenzyl)piperazine;
(trans)-1-((4-(3-(4-hydroxyphenyl)hex-2-yl)phenoxy)
methyl)carbonyl-2,5-dimethyl-4-(4-fluorobenzyl)
piperazine;
(trans)-1-(((6-(hydroxysulfonyl)naphthalen-2-yl)oxy)
methyl)carbonyl-2,5-dimethyl-4-(4-fluorobenzyl)
piperazine;
(trans)-1-((2-chloro-4-methylphenoxy)methyl)carbonyl-
2,5-dimethyl-4-(4-fluorobenzyl)piperazine;
(trans)-1-((2-bromo-4,5-difluorophenoxy)methyl)
carbonyl-2,5-dimethyl-4-(4-fluorobenzyl)piperazine;
(trans)-1-((2-chloro-4-methoxyphenoxy)methyl)
carbonyl-2,5-dimethyl-4-(4-fluorobenzyl)piperazine;
(trans)-1-((2-methoxy-4-chlorophenoxy)methyl)
carbonyl-2,5-dimethyl-4-(4-fluorobenzyl)piperazine;
(trans)-1-((4-(2-(methoxycarbonyl)ethyl)phenoxy)
methyl)carbonyl-2,5-dimethyl-4-(4-fluorobenzyl)
piperazine;
(trans)-1-((2,6-diphenyl-4-nitrophenoxy)methyl)
carbonyl-2,5-dimethyl-4-(4-fluorobenzyl)piperazine;
(trans)-1-((2-amino-3-methylphenoxy)methyl)carbonyl-
2,5-dimethyl-4-(4-fluorobenzyl)piperazine;
(trans)-1-((2-methyl-4-fluorophenoxy)methyl)carbonyl-
2,5-dimethyl-4-(4-fluorobenzyl)piperazine;
(trans)-1-((2-methyl-4-iodophenoxy)methyl)carbonyl-2,
5-dimethyl-4-(4-fluorobenzyl)piperazine;
(trans)-1-((2-fluoro-6-methoxyphenoxy)methyl)
carbonyl-2,5-dimethyl-4-(4-fluorobenzyl)piperazine;
(trans)-1-((2-carboxy-3-isopropyl-6-methylphenoxy)
methyl)carbonyl-2,5-dimethyl-4-(4-fluorobenzyl)
piperazine;
(trans)-1-((2-carboxy-3,4,6-trichlorophenoxy)methyl)
carbonyl-2,5-dimethyl-4-(4-fluorobenzyl)piperazine;
(trans)-1-((2-carboxy-6-isopropylphenoxy)methyl)
carbonyl-2,5-dimethyl-4-(4-fluorobenzyl)piperazine;
(trans)-1-((2-(piperidin-1-yl)-4-methylphenoxy)methyl)
carbonyl-2,5-dimethyl-4-(4-fluorobenzyl)piperazine;
(trans)-1-(((2,3-dihydro-2,2-dimethylbenzofuran-7-yl)
oxy)methyl)carbonyl-2,5-dimethyl-4-(4-fluorobenzyl)
piperazine;
(trans)-1-((2,6-di(t-butyl)4-(1-methylpropyl)phenoxy)
methyl)carbonyl-2,5-dimethyl-4-(4-fluorobenzyl)
piperazine;
(trans)-1-((3-methyl-4-bromophenoxy)methyl)carbonyl-
2,5-dimethyl-4-(4-fluorobenzyl)piperazine;
(trans)-1-(((phenanthren-9-yl)oxy)methyl)carbonyl-2,5-
dimethyl-4-(4-fluorobenzyl)piperazine;
(trans)-1-((2-nitro-4-bromophenoxy)methyl)carbonyl-2,
5-dimethyl-4-(4-fluorobenzyl)piperazine;
(trans)-1-((2-fluoro-3-trifluoromethylphenoxy)methyl)
carbonyl-2,5-dimethyl-4-(4-fluorobenzyl)piperazine;
(trans)-1-((2-nitro-5-methoxyphenoxy)methyl)carbonyl-
2,5-dimethyl-4-(4-fluorobenzyl)piperazine;
(trans)-1-((2-chloro-4-aminophenoxy)methyl)carbonyl-2,
5-dimethyl-4-(4-fluorobenzyl)piperazine;
(trans)-1-((2-formyl-4-bromo-6-nitrophenoxy)methyl)
carbonyl-2,5-dimethyl-4-(4-fluorobenzyl)piperazine;
(trans)-1-((2-methoxy-4-(acetyl)methylphenoxy)methyl)
carbonyl-2,5-dimethyl-4-(4-fluorobenzyl)piperazine;
(trans)-1-((4-(5-mercaptotetrazol-1-yl)phenoxy)methyl)
carbonyl-2,5-dimethyl-4-(4-fluorobenzyl)piperazine;
(trans)-1-((2,4,6-triiodo-3-(2-carboxy)butylphenoxy)
methyl)carbonyl-2,5-dimethyl-4-(4-fluorobenzyl)
piperazine;
(trans)-1-((3-hydroxymethyl-4-nitrophenoxy)methyl)
carbonyl-2,5-dimethyl-4-(4-fluorobenzyl)piperazine;
(trans)-1-((2,3,5,6-tetrafluoro-4-(2,3,4,5,6-
pentafluorophenyl)phenoxy)methyl)carbonyl-2,5-
dimethyl-4-(4-fluorobenzyl)piperazine;
(trans)-1-((2-(benzotriazol-2-yl)-4,6-di(1,1-
dimethylpropyl)phenoxy)methyl)carbonyl-2,5-
dimethyl-4-(4-fluorobenzyl)piperazine;
(trans)-1-((2-phenyl-3-hydroxy-4-oxo-4H-1-benzopyran-
6-yl)oxy)methyl)carbonyl-2,5-dimethyl-4-(4-
fluorobenzyl)piperazine;
(trans)-1-((indanonyl)oxy)methyl)carbonyl-2,5-
dimethyl-4-(4-fluorobenzyl)piperazine;
(trans)-1-((2-nitro-4-(hydroxysulfonyl)phenoxy)methyl)
carbonyl-2,5-dimethyl-4-(4-fluorobenzyl)piperazine;
(trans)-1-((2-nitro-3-methylphenoxy)methyl)carbonyl-2,
5-dimethyl-4-(4-fluorobenzyl)piperazine;
(trans)-1-((4-(2,4-dinitrophenyl)aminophenoxy)methyl)
carbonyl-2,5-dimethyl-4-(4-fluorobenzyl)piperazine;
(trans)-1-((3-methyl-4-nitrophenoxy)methyl)carbonyl-2,
5-dimethyl-4-(4-fluorobenzyl)piperazine;
(trans)-1-((2,6-dibromo-4-nitrophenoxy)methyl)
carbonyl-2,5-dimethyl-4-(4-fluorobenzyl)piperazine;
(trans)-1-((2,6-diiodo-4-nitrophenoxy)methyl)carbonyl-
2,5-dimethyl-4-(4-fluorobenzyl)piperazine;
(trans)-1-((2-formyl-4-nitrophenoxy)methyl)carbonyl-2,
5-dimethyl-4-(4-fluorobenzyl)piperazine;
(trans)-1-((2-aminophenoxy)methyl)carbonyl-2,5-
dimethyl-4-(4-fluorobenzyl)piperazine;
(trans)-1-((2-amino-5-nitrophenoxy)methyl)carbonyl-2,
5-dimethyl-4-(4-fluorobenzyl)piperazine;
(trans)-1-((2-amino-5-methylphenoxy)methyl)carbonyl-
2,5-dimethyl-4-(4-fluorobenzyl)piperazine;
(trans)-1-((2-amino-4-chlorophenoxy)methyl)carbonyl-2,
5-dimethyl-4-(4-fluorobenzyl)piperazine;
(trans)-1-((2-amino-4-carboxyphenoxy)methyl)carbonyl-
2,5-dimethyl-4-(4-fluorobenzyl)piperazine;
(trans)-1-((2-amino-4-t-butylphenoxy)methyl)carbonyl-
2,5-dimethyl-4-(4-fluorobenzyl)piperazine;

(trans)-1-((2-amino-4-methylphenoxy)methyl)carbonyl-2,5-dimethyl-4-(4-fluorobenzyl)piperazine;
(trans)-1-((2-methyl-3-aminophenoxy)methyl)carbonyl-2,5-dimethyl-4-(4-fluorobenzyl)piperazine;
(trans)-1-((2-carboxy-5-aminophenoxy)methyl)carbonyl-2,5-dimethyl-4-(4-fluorobenzyl)piperazine;
(trans)-1-((3-methyl-4-aminophenoxy)methyl)carbonyl-2,5-dimethyl-4-(4-fluorobenzyl)piperazine;
(trans)-1-((2,5-dimethyl-4-aminophenoxy)methyl)carbonyl-2,5-dimethyl-4-(4-fluorobenzyl)piperazine;
(trans)-1-((2,6-dibromo-4-aminophenoxy)methyl)carbonyl-2,5-dimethyl-4-(4-fluorobenzyl)piperazine;
(trans)-1-((2-carboxy-4-aminophenoxy)methyl)carbonyl-2,5-dimethyl-4-(4-fluorobenzyl)piperazine;
(trans)-1-((2-aminocarbonylphenoxy)methyl)carbonyl-2,5-dimethyl-4-(4-fluorobenzyl)piperazine;
(trans)-1-((2-aminocarbonyl-4-chlorophenoxy)methyl)carbonyl-2,5-dimethyl-4-(4-fluorobenzyl)piperazine;
(trans)-1-((4-(2-aminoethyl)phenoxy)methyl)carbonyl-2,5-dimethyl-4-(4-fluorobenzyl)piperazine;
(trans)-1-((2,4,6-tri(dimethylamino)phenoxy)methyl)carbonyl-2,5-dimethyl-4-(4-fluorobenzyl)piperazine;
(trans)-1-((2-hydroxymethyl-6-methoxyphenoxy)methyl)carbonyl-2,5-dimethyl-4-(4-fluorobenzyl)piperazine;
(trans)-1-((2,3-dimethoxyphenoxy)methyl)carbonyl-2,5-dimethyl-4-(4-fluorobenzyl)piperazine;
(trans)-1-((4-(methoxycarbonyl)-5-methoxyphenoxy)methyl)carbonyl-2,5-dimethyl-4-(4-fluorobenzyl)piperazine;
(trans)-1-((2-methoxy-4-(methoxycarbonyl)phenoxy)methyl)carbonyl-2,5-dimethyl-4-(4-fluorobenzyl)piperazine;
(trans)-1-((2,6-dimethoxy-4-(prop-3-enyl)phenoxy)methyl)carbonyl-2,5-dimethyl-4-(4-fluorobenzyl)piperazine;
(trans)-1-((2-acetyl-5-methoxyphenoxy)methyl)carbonyl-2,5-dimethyl-4-(4-fluorobenzyl)piperazine;
(trans)-1-((2-acetyl-4-methoxyphenoxy)methyl)carbonyl-2,5-dimethyl-4-(4-fluorobenzyl)piperazine;
(trans)-1-((2-acetyl-3-methoxyphenoxy)methyl)carbonyl-2,5-dimethyl-4-(4-fluorobenzyl)piperazine;
(trans)-1-((2-methoxy-4-acetylphenoxy)methyl)carbonyl-2,5-dimethyl-4-(4-fluorobenzyl)piperazine;
(trans)-1-((2,6-dimethoxy-4-acetylphenoxy)methyl)carbonyl-2,5-dimethyl-4-(4-fluorobenzyl)piperazine;
(trans)-1-((2,6-di(t-butyl)phenoxy)methyl)carbonyl-2,5-dimethyl-4-(4-fluorobenzyl)piperazine;
(trans)-1-((2,4-di(t-butyl)phenoxy)methyl)carbonyl-2,5-dimethyl-4-(4-fluorobenzyl)piperazine;
(trans)-1-((3,5-di(t-butyl)phenoxy)methyl)carbonyl-2,5-dimethyl-4-(4-fluorobenzyl)piperazine;
(trans)-1-((2,6-di(isopropyl)phenoxy)methyl)carbonyl-2,5-dimethyl-4-(4-fluorobenzyl)piperazine;
(trans)-1-((2-methoxy-4-(ethoxycarbony)methylphenoxy)methyl)carbonyl-2,5-dimethyl-4-(4-fluorobenzyl)piperazine;
(trans)-1-((2-ethoxy-5-prop-2-enylphenoxy)methyl)carbonyl-2,5-dimethyl-4-(4-fluorobenzyl)piperazine;
(trans)-1-((2-methoxy-5-prop-2-enylphenoxy)methyl)carbonyl-2,5-dimethyl-4-(4-fluorobenzyl)piperazine;
(trans)-1-((2,6-di(1-methylpropyl)phenoxy)methyl)carbonyl-2,5-dimethyl-4-(4-fluorobenzyl)piperazine;
(trans)-1-((2,4-difluorophenoxy)methyl)carbonyl-2,5-dimethyl-4-(4-fluorobenzyl)piperazine;
(trans)-1-((2,6-diphenylphenoxy)methyl)carbonyl-2,5-dimethyl-4-(4-fluorobenzyl)piperazine;
(trans)-1-((2-nitro-3-trifluoromethylphenoxy)methyl)carbonyl-2,5-dimethyl-4-(4-fluorobenzyl)piperazine;
(trans)-1-((2-cyclopentphenoxy)methyl)carbonyl-2,5-dimethyl-4-(4-fluorobenzyl)piperazine;
(trans)-1-((4-cyclopentylphenoxy)methyl)carbonyl-2,5-dimethyl-4-(4-fluorobenzyl)piperazine;
(trans)-1-((2,3-difluorophenoxy)methyl)carbonyl-2,5-dimethyl-4-(4-fluorobenzyl)piperazine;
(trans)-1-((2-carboxy-6-aminophenoxy)methyl)carbonyl-2,5-dimethyl-4-(4-fluorobenzyl)piperazine;
(trans)-1-((2-amino-4-chloro-5-nitrophenoxy)methyl)carbonyl-2,5-dimethyl-4-(4-fluorobenzyl)piperazine;
(trans)-1-((3,4-difluorophenoxy)methyl)carbonyl-2,5-dimethyl-4-(4-fluorobenzyl)piperazine;
(trans)-1-((2-carboxy-6-chlorophenoxy)methyl)carbonyl-2,5-dimethyl-4-(4-fluorobenzyl)piperazine;
(trans)-1-((2,4-dicarboxyphenoxy)methyl)carbonyl-2,5-dimethyl-4-(4-fluorobenzyl)piperazine;
(trans)-1-((2,3-dimethoxy-5-formylphenoxy)methyl)carbonyl-2,5-dimethyl-4-(4-fluorobenzyl)piperazine;
(trans)-1-((2-bromo-4-fluorophenoxy)methyl)carbonyl-2,5-dimethyl-4-(4-fluorobenzyl)piperazine;
(trans)-1-((2,6-dichoro-4-fluorophenoxy)methyl)carbonyl-2,5-dimethyl-4-(4-fluorobenzyl)piperazine;
(trans)-1-((3-methyl-4-isopropylphenoxy)methyl)carbonyl-2,5-dimethyl-4-(4-fluorobenzyl)piperazine;
(trans)-1-(((fluoren-2-yl)oxy)methyl)carbonyl-2,5-dimethyl-4-(4-fluorobenzyl)piperazine;
(trans)-1-((2-diethylaminophenoxy)methyl)carbonyl-2,5-dimethyl-4-(4-fluorobenzyl)piperazine;
(trans)-1-((2-amino-3-nitrophenoxy)methyl)carbonyl-2,5-dimethyl-4-(4-fluorobenzyl)piperazine;
(trans)-1-(((2-oxo-3,4,8-trimethyl-2H-1-benzopyran-7-yl)oxy)methyl)carbonyl-2,5-dimethyl-4-(4-fluorobenzyl)piperazine;
(trans)-1-((2-acetyl-4-fluorophenoxy)methyl)carbonyl-2,5-dimethyl-4-(4-fluorobenzyl)piperazine;
(trans)-1-((2-fluoro-4-bromophenoxy)methyl)carbonyl-2,5-dimethyl-4-(4-fluorobenzyl)piperazine;
(trans)-1-((2-(methylcarbonyl)amino-5-methylphenoxy)methyl)carbonyl-2,5-dimethyl-4-(4-fluorobenzyl)piperazine;
(trans)-1-(((1-acetylnaphthalen-2-yl)oxy)methyl)carbonyl-2,5-dimethyl-4-(4-fluorobenzyl)piperazine;
(trans)-1-((2-methoxy-4-nitrophenoxy)methyl)carbonyl-2,5-dimethyl-4-(4-fluorobenzyl)piperazine;
(trans)-1-((3-methyl-5-isopropylphenoxy)methyl)carbonyl-2,5-dimethyl-4-(4-fluorobenzyl)piperazine;
(trans)-1-((2-methyl-4-formylphenoxy)methyl)carbonyl-2,5-dimethyl-4-(4-fluorobenzyl)piperazine;
(trans)-1-(((1-aminonaphthalen-2-yl)oxy)methyl)carbonyl-2,5-dimethyl-4-(4-fluorobenzyl)piperazine;
(trans)-1-((4-aminonaphthalen-1-yl)oxy)methyl)carbonyl-2,5-dimethyl-4-(4-fluorobenzyl)piperazine;
(trans)-1-((2-methoxy-4-(1,2-dihydroxyethyl)phenoxy)methyl)carbonyl-2,5-dimethyl-4-(4-fluorobenzyl)piperazine;
(trans)-1-(((3-(2-aminoethyl)indolin-5-yl)oxy)methyl)carbonyl-2,5-dimethyl-4-(4-fluorobenzyl)piperazine;

(trans)-1-(((5-chloroquinolin-8-yl)oxy)methyl)carbonyl-2,5-dimethyl-4-(4-fluorobenzyl)piperazine;
(trans)-1-((2-methoxy-4-(2-(amino)ethyl)phenoxy)methyl)carbonyl-2,5-dimethyl-4-(4-fluorobenzyl)piperazine;
(trans)-1-((4-(2-(amino)ethyl)phenoxy)methyl)carbonyl-2,5-dimethyl-4-(4-fluorobenzyl)piperazine;
(trans)-1-((2-methoxy-4-(2-(amino)ethyl)phenoxy)methyl)carbonyl-2,5-dimethyl-4-(4-fluorobenzyl)piperazine;
(trans)-1-((2,4-diaminophenoxy)methyl)carbonyl-2,5-dimethyl-4-(4-fluorobenzyl)piperazine;
(trans)-1-((4-aminophenoxy)methyl)carbonyl-2,5-dimethyl-4-(4-fluorobenzyl)piperazine;
(trans)-1-((2-(diethylamino)methyl-4-aminophenoxy)methyl)carbonyl-2,5-dimethyl-4-(4-fluorobenzyl)piperazine;
(trans)-1-((2-methyl-5-(2-aminobutyl)phenoxy)methyl)carbonyl-2,5-dimethyl-4-(4-fluorobenzyl)piperazine;
(trans)-1-((2-(benzotriazol-2-yl)-4-(1,1,3,3-tetramethylbutyl)phenoxy)methyl)carbonyl-2,5-dimethyl-4-(4-fluorobenzyl)piperazine;
(trans)-1-((2-nitro-4-bromo-6-fluorophenoxy)methyl)carbonyl-2,5-dimethyl-4-(4-fluorobenzyl)piperazine;
(trans)-1-((2-iodophenoxy)methyl)carbonyl-2,5-dimethyl-4-(4-fluorobenzyl)piperazine;
(trans)-1-((2-(2-carboxyethyl)phenoxy)methyl)carbonyl-2,5-dimethyl-4-(4-fluorobenzyl)piperazine;
(trans)-1-((2-carboxy-4-methylphenoxy)methyl)carbonyl-2,5-dimethyl-4-(4-fluorobenzyl)piperazine;
(trans)-1-((2,6-dibromo-3-carboxyphenoxy)methyl)carbonyl-2,5-dimethyl-4-(4-fluorobenzyl)piperazine;
(trans)-1-((2,6-dichloro-3-carboxyphenoxy)methyl)carbonyl-2,5-dimethyl-4-(4-fluorobenzyl)piperazine;
(trans)-1-((2-methoxy-4-carboxyphenoxy)methyl)carbonyl-2,5-dimethyl-4-(4-fluorobenzyl)piperazine;
(trans)-1-((2,6-dimethoxy-4-carboxyphenoxy)methyl)carbonyl-2,5-dimethyl-4-(4-fluorobenzyl)piperazine;
(trans)-1-((4-(2-carboxyethyl)phenoxy)methyl)carbonyl-2,5-dimethyl-4-(4-fluorobenzyl)piperazine;
(trans)-1-((2-(2-hydroxyethyl)phenoxy)methyl)carbonyl-2,5-dimethyl-4-(4-fluorobenzyl)piperazine;
(trans)-1-((3-(2-hydroxyethyl)phenoxy)methyl)carbonyl-2,5-dimethyl-4-(4-fluorobenzyl)piperazine;
(trans)-1-((4-(2-hydroxyethyl)phenoxy)methyl)carbonyl-2,5-dimethyl-4-(4-fluorobenzyl)piperazine;
(trans)-1-((2-methoxy-4-(2-hydroxyethyl)phenoxy)methyl)carbonyl-2,5-dimethyl-4-(4-fluorobenzyl)piperazine;
(trans)-1-((2,4-dibromo-6-formylphenoxy)methyl)carbonyl-2,5-dimethyl-4-(4-fluorobenzyl)piperazine;
(trans)-1-((2-fluoro-6-formylphenoxy)methyl)carbonyl-2,5-dimethyl-4-(4-fluorobenzyl)piperazine;
(trans)-1-((2,4-dichloro-6-formylphenoxy)methyl)carbonyl-2,5-dimethyl-4-(4-fluorobenzyl)piperazine;
(trans)-1-((2,4-diiodo-6-formylphenoxy)methyl)carbonyl-2,5-dimethyl-4-(4-fluorobenzyl)piperazine;
(trans)-1-((2-methoxy-6-formylphenoxy)methyl)carbonyl-2,5-dimethyl-4-(4-fluorobenzyl)piperazine;
(trans)-1-((2-ethoxy-6-formylphenoxy)methyl)carbonyl-2,5-dimethyl-4-(4-fluorobenzyl)piperazine;
(trans)-1-((2-formyl-5-(diethylamino)phenoxy)methyl)carbonyl-2,5-dimethyl-4-(4-fluorobenzyl)piperazine;
(trans)-1-((2-formyl-5-methoxyphenoxy)methyl)carbonyl-2,5-dimethyl-4-(4-fluorobenzyl)piperazine;
(trans)-1-((2-formyl-3,5-dimethoxyphenoxy)methyl)carbonyl-2,5-dimethyl-4-(4-fluorobenzyl)piperazine;
(trans)-1-((2-formyl-4-bromophenoxy)methyl)carbonyl-2,5-dimethyl-4-(4-fluorobenzyl)piperazine;
(trans)-1-((2-formyl-4-methoxyphenoxy)methyl)carbonyl-2,5-dimethyl-4-(4-fluorobenzyl)piperazine;
(trans)-1-(((4-methoxynapthalen-1-yl)oxy)methyl)carbonyl-2,5-dimethyl-4-(4-fluorobenzyl)piperazine;
(trans)-1-((2-carboxy-5,6-dimethoxyphenoxy)methyl)carbonyl-2,5-dimethyl-4-(4-fluorobenzyl)piperazine;
(trans)-1-((3-nitro-4-methoxyphenoxy)methyl)carbonyl-2,5-dimethyl-4-(4-fluorobenzyl)piperazine;
(trans)-1-(((fluoren-9-on-1-yl)oxy)methyl)carbonyl-2,5-dimethyl-4-(4-fluorobenzyl)piperazine;
(trans)-1-(((4-hydroxy-1,2,3,4-tetrahydronaphthalen-8-yl)oxy)methyl)carbonyl-2,5-dimethyl-4-(4-fluorobenzyl)piperazine;
(trans)-1-((2,3,4,5,6-pentabromophenoxy)methyl)carbonyl-2,5-dimethyl-4-(4-fluorobenzyl)piperazine;
(trans)-1-((2-methyl-3,4,5,6-tetrabromophenoxy)methyl)carbonyl-2,5-dimethyl-4-(4-fluorobenzyl)piperazine;
(trans)-1-((2,3,4-trichlorophenoxy)methyl)carbonyl-2,5-dimethyl-4-(4-fluorobenzyl)piperazine;
(trans)-1-((2-methyl-4-bromo-6-chlorophenoxy)methyl)carbonyl-2,5-dimethyl-4-(4-fluorobenzyl)piperazine;
(trans)-1-((2-chloro-4-fluorophenoxy)methyl)carbonyl-2,5-dimethyl-4-(4-fluorobenzyl)piperazine;
(trans)-1-((2,4,6-triiodophenoxy)methyl)carbonyl-2,5-dimethyl-4-(4-fluorobenzyl)piperazine;
(trans)-1-((2-formyl-4-chlorophenoxy)methyl)carbonyl-2,5-dimethyl-4-(4-fluorobenzyl)piperazine;
(trans)-1-((3-formylphenoxy)methyl)carbonyl-2,5-dimethyl-4-(4-fluorobenzyl)piperazine;
(trans)-1-(((1-bromonaphthalen-2-yl)oxy)methyl)carbonyl-2,5-dimethyl-4-(4-fluorobenzyl)piperazine;
(trans)-1-(((1,6-dibromonapthalen-2-yl)oxy)methyl)carbonyl-2,5-dimethyl-4-(4-fluorobenzyl)piperazine;
(trans)-1-(((1-nitrosonaphthalen-2-yl)oxy)methyl)carbonyl-2,5-dimethyl-4-(4-fluorobenzyl)piperazine;
(trans)-1-(((2,4-dichloronaphthalen-1-yl)oxy)methyl)carbonyl-2,5-dimethyl-4-(4-fluorobenzyl)piperazine;
(trans)-1-(((2-nitronaphthalen-1-yl)oxy)methyl)carbonyl-2,5-dimethyl-4-(4-fluorobenzyl)piperazine;
(trans)-1-(((2-carboxynaphthalen-1-yl)oxy)methyl)carbonyl-2,5-dimethyl-4-(4-fluorobenzyl)piperazine;
(trans)-1-(((2-methylnaphthalen-1-yl)oxy)methyl)carbonyl-2,5-dimethyl-4-(4-fluorobenzyl)piperazine;
(trans)-1-(((3-(hydroxysulfonyl)-7-(dimethylamino)naphthalen-1-yl)oxy)methyl)carbonyl-2,5-dimethyl-4-(4-fluorobenzyl)piperazine;
(trans)-1-(((4-methoxynaphthalen-1-yl)oxy)methyl)carbonyl-2,5-dimethyl-4-(4-fluorobenzyl)piperazine;
(trans)-1-(((1-formylnapthalen-2-yl)oxy)methyl)carbonyl-2,5-dimethyl-4-(4-fluorobenzyl)piperazine;
(trans)-1-(((1-carboxynaphthalen-1-yl)oxy)methyl)carbonyl-2,5-dimethyl-4-(4-fluorobenzyl)piperazine;
(trans)-1-(((1-amino-4-(hydroxysulfonyl)naphthalen-2-yl)oxy)methyl)carbonyl-2,5-dimethyl-4-(4-fluorobenzyl)piperazine;
(trans)-1-((4-(naphthalen-2-yl)aminophenoxy)methyl)carbonyl-2,5-dimethyl-4-(4-fluorobenzyl)piperazine;

(trans)-1-(((3-aminonaphthalen-2-yl)oxy)methyl)
carbonyl-2,5-dimethyl-4-(4-fluorobenzyl)piperazine;
(trans)-1-((2-fluoro-4-(carboxymethyl)phenoxy)methyl)
carbonyl-2,5-dimethyl-4-(4-fluorobenzyl)piperazine;
(trans)-1-((2-chloro-4-(carboxymethyl)phenoxy)methyl)
carbonyl-2,5-dimethyl-4-(4-fluorobenzyl)piperazine;
(trans)-1-((2-methoxy-4-(carboxymethyl)phenoxy)
methyl)carbonyl-2,5-dimethyl-4-(4-fluorobenzyl)
piperazine;
(trans)-1-((4-hydroxymethylphenxoy)methyl)carbonyl-2,
5-dimethyl-4-(4-fluorobenzyl)piperazine;
(trans)-1-((2-(hydroxymethyl)4-bromophenoxy)methyl)
carbonyl-2,5-dimethyl-4-(4-fluorobenzyl)piperazine;
(trans)-1-((2,6-di(hydroxymethyl)4-methylphenoxy)
methyl)carbonyl-2,5-dimethyl-4-(4-fluorobenzyl)
piperazine;
(trans)-1-((2-methoxy-4-(hydroxymethyl)phenoxy)
methyl)carbonyl-2,5-dimethyl-4-(4-fluorobenzyl)
piperazine;
(trans)-1-((4-mercaptophenoxy)methyl)carbonyl-2,5-
dimethyl-4-(4-fluorobenzyl)piperazine;
(trans)-1-(((2-carboxyindol-5-yl)oxy)methyl)carbonyl-2,
5-dimethyl-4-(4-fluorobenzyl)piperazine;
(trans)-1-(((3-carboxyindol-5-yl)oxy)methyl)carbonyl-2,
5-dimethyl-4-(4-fluorobenzyl)piperazine;
(trans)-1-(((indol-4-yl)oxy)methyl)carbonyl-2,5-
dimethyl-4-(4-fluorobenzyl)piperazine;
(trans)-1-(((indol-5-yl)oxy)methyl)carbonyl-2,5-
dimethyl-4-(4-fluorobenzyl)piperazine;
(trans)-1-((2-(benzoxazol-2-yl)phenoxy)methyl)
carbonyl-2,5-dimethyl-4-(4-fluorobenzyl)piperazine;
(trans)-1-(((2-methylquinolin-8-yl)oxy)methyl)carbonyl-
2,5-dimethyl-4-(4-fluorobenzyl)piperazine;
(trans)-1-(((5,7-dibromoquinolin-8-yl)oxy)methyl)
carbonyl-2,5-dimethyl-4-(4-fluorobenzyl)piperazine;
(trans)-1-(((5,7-diiodoquinolin-8-yl)oxy)methyl)
carbonyl-2,5-dimethyl-4-(4-fluorobenzyl)piperazine;
(trans)-1-(((5-nitroquinolin-8-yl)oxy)methyl)carbonyl-2,
5-dimethyl-4-(4-fluorobenzyl)piperazine;
(trans)-1-(((quinolin-5-yl)oxy)methyl)carbonyl-2,5-
dimethyl-4-(4-fluorobenzyl)piperazine;
(trans)-1-(((5-(hydroxysulfonyl)-7-iodoquinolin-8-yl)
oxy)methyl)carbonyl-2,5-dimethyl-4-(4-fluorobenzyl)
piperazine;
(trans)-1-(((2-phenyl-4-oxo-4H-1-benzopyran-7-yl)oxy)
methyl)carbonyl-2,5-dimethyl-4-(4-fluorobenzyl)
piperazine;
(trans)-1-((2-carboxy-2,5,7,8-tetramethyl-2,3-dihydro-1-
benzopyran-6-yl)oxy)methyl)carbonyl-2,5-dimethyl-
4-(4-fluorobenzyl)piperazine;
(trans)-1-(((2-oxo-3-chloro-4-methyl-2H-1-benzopyran-
7-yl)oxy)methyl)carbonyl-2,5-dimethyl-4-(4-
fluorobenzyl)piperazine;
(trans)-1-(((2-oxo-3-(diethylamino)methyl)-4-methyl-
2H-1-benzopyran-7-yl)oxy)methyl)carbonyl-2,5-
dimethyl-4-(4-fluorobenzyl)piperazine;
(trans)-1-(((2-oxo-6-methoxy-2H-1-benzopyran-7-yl)
oxy)methyl)carbonyl-2,5-dimethyl-4-(4-fluorobenzyl)
piperazine;
(trans)-1-(((2-oxo-2H-1-benzopyran-7-yl)oxy)methyl)
carbonyl-2,5-dimethyl-4-(4-fluorobenzyl)piperazine;
(trans)-1-((2-methoxy-4-formyl-6-bromophenoxy)
methyl)carbonyl-2,5-dimethyl-4-(4-fluorobenzyl)
piperazine;
(trans)-1-((2-methoxy-4-formyl-6-iodophenoxy)methyl)
carbonyl-2,5-dimethyl-4-(4-fluorobenzyl)piperazine;
(trans)-1-((2-methoxy-4-formylphenoxy)methyl)
carbonyl-2,5-dimethyl-4-(4-fluorobenzyl)piperazine;
(trans)-1-((2-ethoxy-4-formylphenoxy)methyl)carbonyl-
2,5-dimethyl-4-(4-fluorobenzyl)piperazine;
(trans)-1-((2-carboxy-4-formylphenoxy)methyl)
carbonyl-2,5-dimethyl-4-(4-fluorobenzyl)piperazine;
(trans)-1-((2,4-dichloro-6-nitrophenoxy)methyl)
carbonyl-2,5-dimethyl-4-(4-fluorobenzyl)piperazine;
(trans)-1-((2,4-dinitro-6-formylphenoxy)methyl)
carbonyl-2,5-dimethyl-4-(4-fluorobenzyl)piperazine;
(trans)-1-((2,4-dinitro-6-carboxyphenoxy)methyl)
carbonyl-2,5-dimethyl-4-(4-fluorobenzyl)piperazine;
(trans)-1-((2,4-dinitro-6-methylphenoxy)methyl)
carbonyl-2,5-dimethyl-4-(4-fluorobenzyl)piperazine;
(trans)-1-((2,5-dinitrophenoxy)methyl)carbonyl-2,5-
dimethyl-4-(4-fluorobenzyl)piperazine;
(trans)-1-((2-nitro-5-methylphenoxy)methyl)carbonyl-2,
5-dimethyl-4-(4-fluorobenzyl)piperazine;
(trans)-1-((2-nitro-4-chlorophenoxy)methyl)carbonyl-2,
5-dimethyl-4-(4-fluorobenzyl)piperazine;
(trans)-1-((2,4-dinitrophenoxy)methyl)carbonyl-2,5-
dimethyl-4-(4-fluorobenzyl)piperazine;
(trans)-1-((2-nitro-4-formylphenoxy)methyl)carbonyl-2,
5-dimethyl-4-(4-fluorobenzyl)piperazine;
(trans)-1-((2-nitro-4-formyl-6-methoxyphenoxy)methyl)
carbonyl-2,5-dimethyl-4-(4-fluorobenzyl)piperazine;
(trans)-1-((2-nitro-4-carboxyphenoxy)methyl)carbonyl-
2,5-dimethyl-4-(4-fluorobenzyl)piperazine;
(trans)-1-((2-nitro-4-methylphenoxy)methyl)carbonyl-2,
5-dimethyl-4-(4-fluorobenzyl)piperazine;
(trans)-1-((2,6-dinitro-4-methylphenoxy)methyl)
carbonyl-2,5-dimethyl-4-(4-fluorobenzyl)piperazine;
(trans)-1-((2-nitro-4-(carboxymethyl)phenoxy)methyl)
carbonyl-2,5-dimethyl-4-(4-fluorobenzyl)piperazine;
(trans)-1-((2,6-dichlorophenoxy)methyl)carbonyl-2,5-
dimethyl-4-(4-fluorobenzyl)piperazine;
(trans)-1-((3-methoxy-5-chlorophenoxy)methyl)
carbonyl-2,5-dimethyl-4-(4-fluorobenzyl)piperazine;
(trans)-1-((4-cyanophenoxy)methyl)carbonyl-2,5-
dimethyl-4-(4-fluorobenzyl)piperazine;
(trans)-1-((4-(1-methyl-1-phenylethyl)phenoxy)methyl)
carbonyl-2,5-dimethyl-4-(4-fluorobenzyl)piperazine;
(trans)-1-((3-(ethylamino)-4-methylphenoxy)methyl)
carbonyl-2,5-dimethyl-4-(4-fluorobenzyl)piperazine;
(trans)-1-(((2-acetylnaphthalen-1-yl)oxy)methyl)
carbonyl-2,5-dimethyl-4-(4-fluorobenzyl)piperazine;
(trans)-1-((2-(carboxymethyl)phenoxy)methyl)carbonyl-
2,5-dimethyl-4-(4-fluorobenzyl)piperazine;
(trans)-1-((4-(carboxymethyl)phenoxy)methyl)carbonyl-
2,5-dimethyl-4-(4-fluorobenzyl)piperazine;
(trans)-1-(((benzotriazol-1-yl)oxy)methyl)carbonyl-2,5-
dimethyl-4-(4-fluorobenzyl)piperazine;
(trans)-1-(((quinolin-2-yl)oxy)methyl)carbonyl-2,5-
dimethyl-4-(4-fluorobenzyl)piperazine;
(trans)-1-((4-formylphenoxy)methyl)carbonyl-2,5-
dimethyl-4-(4-fluorobenzyl)piperazine;
(trans)-1-((2,6-dimethoxy-4-formylphenoxy)methyl)
carbonyl-2,5-dimethyl-4-(4-fluorobenzyl)piperazine;
(trans)-1-((3,4-dimethoxyphenoxy)methyl)carbonyl-2,5-
dimethyl-4-(4-fluorobenzyl)piperazine;

(trans)-1-((2,4,6-tri(t-butyl)phenoxy)methyl)carbonyl-2,5-dimethyl-4-(4-fluorobenzyl)piperazine;
(trans)-1-((2,6-dimethoxy-4-(methoxycarbonyl)phenoxy)methyl)carbonyl-2,5-dimethyl-4-(4-fluorobenzyl)piperazine;
(trans)-1-((3-trifluoromethoxyphenoxy)methyl)carbonyl-2,5-dimethyl-4-(4-fluorobenzyl)piperazine;
(trans)-1-((2-methyl-5-aminophenoxy)methyl)carbonyl-2,5-dimethyl-4-(4-fluorobenzyl)piperazine;
(trans)-1-((4-(4-cyanophenyl)phenoxy)methyl)carbonyl-2,5-dimethyl-4-(4-fluorobenzyl)piperazine;
(trans)-1-((3-nitro-4-aminophenoxy)methyl)carbonyl-2,5-dimethyl-4-(4-fluorobenzyl)piperazine;
(trans)-1-((3-methylphenoxy)methyl)carbonyl-2,5-dimethyl-4-(4-fluorobenzyl)piperazine;
(trans)-1-((4-methylphenox)methyl)carbonyl-2,5-dimethyl-4-(4-fluorobenzyl)piperazine;
(trans)-1-((4-(methoxycarbonyl)methylphenoxy)methyl)carbonyl-2,5-dimethyl-4-(4-fluorobenzyl)piperazine;
(trans)-1-(((carbazol-2-yl)oxy)methyl)carbonyl-2,5-dimethyl-4-(4-fluorobenzyl)piperazine;
(trans)-1-(((2-oxo-1,3-benzothiol-2-on-6-yl)oxy)methyl)carbonyl-2,5-dimethyl-4-(4-fluorobenzyl)piperazine;
(trans)-1-(((2-phenyl-4-oxo-4H-1-benzopyran-3-yl)oxy)methyl)carbonyl-2,5-dimethyl-4-(4-fluorobenzyl)piperazine;
(trans)-1-(((2-oxo-4-methyl-2H-1-benzopyran-7-yl)oxy)methyl)carbonyl-2,5-dimethyl-4-(4-fluorobenzyl)piperazine;
(trans)-1-((4-nitrophenoxy)methyl)carbonyl-2,5-dimethyl-4-(4-fluorobenzyl)piperazine;
(trans)-1-((3-carboxy-4-aminophenoxy)methyl)carbonyl-2,5-dimethyl-4-(4-fluorobenzyl)piperazine;
(trans)-1-((2-methoxy-5-aminophenoxy)methyl)carbonyl-2,5-dimethyl-4-(4-fluorobenzyl)piperazine;
(trans)-1-(((2-phenyl-4-oxo-2,3-dihydro-4H-1-benzopyran-6-yl)oxy)methyl)carbonyl-2,5-dimethyl-4-(4-fluorobenzyl)piperazine;
(trans)-1-(((quinolin-6-yl)oxy)methyl)carbonyl-2,5-dimethyl-4-(4-fluorobenzyl)piperazine;
(trans)-1-((2,3-diaminophenoxy)methyl)carbonyl-2,5-dimethyl-4-(4-fluorobenzyl)piperazine;
(trans)-1-((4-(hydroxysulfonyl)phenoxy)methyl)carbonyl-2,5-dimethyl-4-(4-fluorobenzyl)piperazine;
(trans)-1-(((fluorenon-9-on-2-yl)oxy)methyl)carbonyl-2,5-dimethyl-4-(4-fluorobenzyl)piperazine;
(trans)-1-(((5,6,7,8-tetrahydronaphthalen-1-yl)oxy)methyl)carbonyl-2,5-dimethyl-4-(4-fluorobenzyl)piperazine;
(trans)-1-(((5,6,7,8-tetrahydronaphthalen-2-yl)oxy)methyl)carbonyl-2,5-dimethyl-4-(4-fluorobenzyl)piperazine;
(trans)-1-((2,4,6-tribromophenoxy)methyl)carbonyl-2,5-dimethyl-4-(4-fluorobenzyl)piperazine;
(trans)-1-((2,6-dibromo-4-cyanophenoxy)methyl)carbonyl-2,5-dimethyl-4-(4-fluorobenzyl)piperazine;
(trans)-1-((2-fluorophenoxy)methyl)carbonyl-2,5-dimethyl-4-(4-fluorobenzyl)piperazine;
(trans)-1-((2,3,5,6-tetrafluorophenoxy)methyl)carbonyl-2,5-dimethyl-4-(4-fluorobenzyl)piperazine;
(trans)-1-((2,6-difluorophenoxy)methyl)carbonyl-2,5-dimethyl-4-(4-fluorobenzyl)piperazine;
(trans)-1-((2,3-dichlorophenoxy)methyl)carbonyl-2,5-dimethyl-4-(4-fluorobenzyl)piperazine;
(trans)-1-((2,3,6-trichlorophenoxy)methyl)carbonyl-2,5-dimethyl-4-(4-fluorobenzyl)piperazine;
(trans)-1-((2-chloro-4,5-dimethylphenoxy)methyl)carbonyl-2,5-dimethyl-4-(4-fluorobenzyl)piperazine;
(trans)-1-((2,5-dichlorophenoxy)methyl)carbonyl-2,5-dimethyl-4-(4-fluorobenzyl)piperazine;
(trans)-1-((2-chloro-5-methylphenoxy)methyl)carbonyl-2,5-dimethyl-4-(4-fluorobenzyl)piperazine;
(trans)-1-((2-(methylcarbonyl)aminophenoxy)methyl)carbonyl-2,5-dimethyl-4-(4-fluorobenzyl)piperazine;
(trans)-1-((2-isopropoxyphenoxy)methyl)carbonyl-2,5-dimethyl-4-(4-fluorobenzyl)piperazine;
(trans)-1-((2-(benzyloxy)phenoxy)methyl)carbonyl-2,5-dimethyl-4-(4-fluorobenzyl)piperazine;
(trans)-1-((2-ethoxyphenoxy)methyl)carbonyl-2,5-dimethyl-4-(4-fluorobenzyl)piperazine;
(trans)-1-((2-phenylphenoxy)methyl)carbonyl-2,5-dimethyl-4-(4-fluorobenzyl)piperazine;
(trans)-1-((2-(methoxycarbonyl)phenoxy)methyl)carbonyl-2,5-dimethyl-4-(4-fluorobenzyl)piperazine;
(trans)-1-((2-(ethoxycarbonyl)phenoxy)methyl)carbonyl-2,5-dimethyl-4-(4-fluorobenzyl)piperazine;
(trans)-1-((2-acetylphenoxy)methyl)carbonyl-2,5-dimethyl-4-(4-fluorobenzyl)piperazine;
(trans)-1-((2-(ethylcarbonyl)phenoxy)methyl)carbonyl-2,5-dimethyl-4-(4-fluorobenzyl)piperazine;
(trans)-1-((2-(t-butyl)phenoxy)methyl)carbonyl-2,5-dimethyl-4-(4-fluorobenzyl)piperazine;
(trans)-1-((2-isopropylphenoxy)methyl)carbonyl-2,5-dimethyl-4-(4-fluorobenzyl)piperazine;
(trans)-1-((2-(1-methylpropyl)phenoxy)methyl)carbonyl-2,5-dimethyl-4-(4-fluorobenzyl)piperazine;
(trans)-1-((2,3-dimethylphenoxy)methyl)carbonyl-2,5-dimethyl-4-(4-fluorobenzyl)piperazine;
(trans)-1-((2,3,5-trimethylphenoxy)methyl)carbonyl-2,5-dimethyl-4-(4-fluorobenzyl)piperazine;
(trans)-1-((2,3,6-trimethylphenxoy)methyl)carbonyl-2,5-dimethyl-4-(4-fluorobenzyl)piperazine;
(trans)-1-((2,4-dimethylphenoxy)methyl)carbonyl-2,5-dimethyl-4-(4-fluorobenzyl)piperazine;
(trans)-1-((2,4,6-trimethoxy)methyl)carbonyl-2,5-dimethyl-4-(4-fluorobenzyl)piperazine;
(trans)-1-((2-methyl-5-isopropylphenoxy)methyl)carbonyl-2,5-dimethyl-4-(4-fluorobenzyl)piperazine;
(trans)-1-((2,5-dimethylphenoxy)methyl)carbonyl-2,5-dimethyl-4-(4-fluorobenzyl)piperazine;
(trans)-1-((2,5-dimethyl-4-(diethylamino)methylphenoxy)methyl)carbonyl-2,5-dimethyl-4-(4-fluorobenzyl)piperazine;
(trans)-1-((2-(t-butyl)-6-methylphenoxy)methyl)carbonyl-2,5-dimethyl-4-(4-fluorobenzyl)piperazine;
(trans)-1-((2,6-dimethoxyphenoxy)methyl)carbonyl-2,5-dimethyl-4-(4-fluorobenzyl)piperazine;
(trans)-1-((2-prop-3-enyl-6-methylphenoxy)methyl)carbonyl-2,5-dimethyl-4-(4-fluorobenzyl)piperazine;
(trans)-1-((2-prop-2-enylphenoxy)methyl)carbonyl-2,5-dimethyl-4-(4-fluorobenzyl)piperazine;
(trans)-1-((2-ethylphenoxy)methyl)carbonyl-2,5-dimethyl-4-(4-fluorobenzyl)piperazine;
(trans)-1-((2-n-propylphenoxy)methyl)carbonyl-2,5-dimethyl-4-(4-fluorobenzyl)piperazine;

(trans)-1-((3-fluorophenoxy)methyl)carbonyl-2,5-dimethyl-4-(4-fluorobenzyl)piperazine;
(trans)-1-((3,5-difluorophenoxy)methyl)carbonyl-2,5-dimethyl-4-(4-fluorobenzyl)piperazine;
(trans)-1-((3-chloro-4-fluorophenoxy)methyl)carbonyl-2,5-dimethyl-4-(4-fluorobenzyl)piperazine;
(trans)-1-((3,5-dichlorophenoxy)methyl)carbonyl-2,5-dimethyl-4-(4-fluorobenzyl)piperazine;
(trans)-1-((3-iodophenoxy)methyl)carbonyl-2,5-dimethyl-4-(4-fluorobenzyl)piperazine;
(trans)-1-((3-(phenylamino)phenoxy)methyl)carbonyl-2,5-dimethyl-4-(4-fluorobenzyl)piperazine;
(trans)-1-((3-(diethylamino)phenoxy)methyl)carbonyl-2,5-dimethyl-4-(4-fluorobenzyl)piperazine;
(trans)-1-((3-phenylphenoxy)methyl)carbonyl-2,5-dimethyl-4-(4-fluorobenzyl)piperazine;
(trans)-1-((3-acetylphenoxy)methyl)carbonyl-2,5-dimethyl-4-(4-fluorobenzyl)piperazine;
(trans)-1-((3-trifluoromethylphenoxy)methyl)carbonyl-2,5-dimethyl-4-(4-fluorobenzyl)piperazine;
(trans)-1-((3-t-butylphenoxy)methyl)carbonyl-2,5-dimethyl-4-(4-fluorobenzyl)piperazine;
(trans)-1-((3-isopropylphenoxy)methyl)carbonyl-2,5-dimethyl-4-(4-fluorobenzyl)piperazine;
(trans)-1-((3-methyl-4-acetylphenoxy)methyl)carbonyl-2,5-dimethyl-4-(4-fluorobenzyl)piperazine;
(trans)-1-((3,4-dimethylphenoxy)methyl)carbonyl-2,5-dimethyl-4-(4-fluorobenzyl)piperazine;
(trans)-1-((2-t-butyl-5-methylphenoxy)methyl)carbonyl-2,5-dimethyl-4-(4-fluorobenzyl)piperazine;
(trans)-1-((2-isopropyl-5-methylphenoxy)methyl)carbonyl-2,5-dimethyl-4-(4-fluorobenzyl)piperazine;
(trans)-1-((3-ethylphenoxy)methyl)carbonyl-2,5-dimethyl-4-(4-fluorobenzyl)piperazine;
(trans)-1-((2,6-dimethyl-4-bromophenoxy)methyl)carbonyl-2,5-dimethyl-4-(4-fluorobenzyl)piperazine;
(trans)-1-((2,6-dibromo-4-fluorophenoxy)methyl)carbonyl-2,5-dimethyl-4-(4-fluorobenzyl)piperazine;
(trans)-1-((2-bromo-4-chlorophenoxy)methyl)carbonyl-2,5-dimethyl-4-(4-fluorobenzyl)piperazine;
(trans)-1-((2-methyl-4-chlorophenoxy)methyl)carbonyl-2,5-dimethyl-4-(4-fluorobenzyl)piperazine;
(trans)-1-((2-isopropyl-4-chloro-5-methylphenoxy)methyl)carbonyl-2,5-dimethyl-4-(4-fluorobenzyl)piperazine;
(trans)-1-((4-(methylcarbonyl)aminophenoxy)methyl)carbonyl-2,5-dimethyl-4-(4-fluorobenzyl)piperazine;
(trans)-1-((4-ethoxyphenoxy)methyl)carbonyl-2,5-dimethyl-4-(4-fluorobenzyl)piperazine;
(trans)-1-((4-propoxyphenoxy)methyl)carbonyl-2,5-dimethyl-4-(4-fluorobenzyl)piperazine;
(trans)-1-((4-n-butoxyphenoxy)methyl)carbonyl-2,5-dimethyl-4-(4-fluorobenzyl)piperazine;
(trans)-1-((4-n-hexoxyphenoxy)methyl)carbonyl-2,5-dimethyl-4-(4-fluorobenzyl)piperazine;
(trans)-1-((4-n-heptoxyphenoxy)methyl)carbonyl-2,5-dimethyl-4-(4-fluorobenzyl)piperazine;
(trans)-1-((4-(propoxycarbonyl)phenoxy)methyl)carbonyl-2,5-dimethyl-4-(4-fluorobenzyl)piperazine;
(trans)-1-((4-(ethylcarbonyl)phenoxy)methyl)carbonyl-2,5-dimethyl-4-(4-fluorobenzyl)piperazine;
(trans)-1-((4-(1,1,3,3-tetramethylbutyl)phenoxy)methyl)carbonyl-2,5-dimethyl-4-(4-fluorobenzyl)piperazine;
(trans)-1-((4-(1,1-dimethylpropyl)phenoxy)methyl)carbonyl-2,5-dimethyl-4-(4-fluorobenzyl)piperazine;
(trans)-1-((4-(1-methylpropyl)phenoxy)methyl)carbonyl-2,5-dimethyl-4-(4-fluorobenzyl)piperazine;
(trans)-1-((2-methoxy-4-methylphenoxy)methyl)carbonyl-2,5-dimethyl-4-(4-fluorobenzyl)piperazine;
(trans)-1-((2-acetyl-4-methylphenoxy)methyl)carbonyl-2,5-dimethyl-4-(4-fluorobenzyl)piperazine;
(trans)-1-((2-(t-butyl)-4-methylphenoxy)methyl)carbonyl-2,5-dimethyl-4-(4-fluorobenzyl)piperazine;
-(trans)-1-((3-(ethylamino)4-methylphenoxy)methyl)carbonyl-2,5-dimethyl-4-(4-fluorobenzyl)piperazine;
(trans)-1-((4-(methoxycarbonyl)methylphenoxy)methyl)carbonyl-2,5-dimethyl-4-(4-fluorobenzyl)piperazine;
(trans)-1-((4-ethylphenoxy)methyl)carbonyl-2,5-dimethyl-4-(4-fluorobenzyl)piperazine;
(trans)-1-((4-n-propylphenoxy)methyl)carbonyl-2,5-dimethyl-4-(4-fluorobenzyl)piperazine;
(trans)-1-((2-carboxyphenoxy)methyl)carbonyl-2,5-dimethyl-4-(4-fluorobenzyl)piperazine;
(trans)-1-((2-carboxy-4,6-dibromophenoxy)methyl)carbonyl-2,5-dimethyl-4-(4-fluorobenzyl)piperazine;
(trans)-1-((2-carboxy-4,6-dichlorophenoxy)methyl)carbonyl-2,5-dimethyl-4-(4-fluorobenzyl)piperazine;
(trans)-1-((2-carboxy-4,6-diiodophenoxy)methyl)carbonyl-2,5-dimethyl-4-(4-fluorobenzyl)piperazine;
(trans)-1-((2-carboxy-6-methoxyphenoxy)methyl)carbonyl-2,5-dimethyl-4-(4-fluorobenzyl)piperazine;
(trans)-1-((2-carboxy-6-methylphenoxy)methyl)carbonyl-2,5-dimethyl-4-(4-fluorobenzyl)piperazine;
(trans)-1-((2-carboxy-5-chlorophenoxy)methyl)carbonyl-2,5-dimethyl-4-(4-fluorobenzyl)piperazine;
(trans)-1-((2-carboxy-5-methoxyphenoxy)methyl)carbonyl-2,5-dimethyl-4-(4-fluorobenzyl)piperazine;
(trans)-1-((2-carboxy-5-methylphenoxy)methyl)carbonyl-2,5-dimethyl-4-(4-fluorobenzyl)piperazine;
(trans)-1-((2-carboxy-4-bromophenoxy)methyl)carbonyl-2,5-dimethyl-4-(4-fluorobenzyl)piperazine;
(trans)-1-((2-carboxy-4-fluorophenoxy)methyl)carbonyl-2,5-dimethyl-4-(4-fluorobenzyl)piperazine;
(trans)-1-((2-carboxy-4-chlorophenoxy)methyl)carbonyl-2,5-dimethyl-4-(4-fluorobenzyl)piperazine;
(trans)-1-((2-carboxy-4-iodophenoxy)methyl)carbonyl-2,5-dimethyl-4-(4-fluorobenzyl)piperazine;
(trans)-1-((2-carboxy-4-methoxyphenoxy)methyl)carbonyl-2,5-dimethyl-4-(4-fluorobenzyl)piperazine;
(trans)-1-((2-chlorophenoxy)methyl)carbonyl-2,5-dimethyl-4-(4-fluorobenzyl)piperazine;
(trans)-1-((2,3,4-trichlorophenoxy)methyl)carbonyl-2,5-dimethyl-4-(4-fluorobenzyl)piperazine;
(trans)-1-((2,3,4,5,6-pentachlorophenoxy)methyl)carbonyl-2,5-dimethyl-4-(4-fluorobenzyl)piperazine;
(trans)-1-((2,4,5-trichlorophenoxy)methyl)carbonyl-2,5-dimethyl-4-(4-fluorobenzyl)piperazine;
(trans)-1-((3-methoxyphenoxy)methyl)carbonyl-2,5-dimethyl-4-(4-fluorobenzyl)piperazine;
(trans)-1-((3-(methoxycarbonyl)phenoxy)methyl)carbonyl-2,5-dimethyl-4-(4-fluorobenzyl)piperazine;
(trans)-1-((3-(ethoxycarbonyl)phenoxy)methyl)carbonyl-2,5-dimethyl-4-(4-fluorobenzyl)piperazine;
(trans)-1-((4-bromophenoxy)methyl)carbonyl-2,5-dimethyl-4-(4-fluorobenzyl)piperazine;

(trans)-1-((2,6-dimethyl-4-bromophenoxy)methyl)
carbonyl-2,5-dimethyl-4-(4-fluorobenzyl)piperazine;
(trans)-1-((3,5-dimethyl-4-bromophenoxy)methyl)
carbonyl-2,5-dimethyl-4-(4-fluorobenzyl)piperazine;
(trans)-1-((3-methyl-4-chlorophenoxy)methyl)carbonyl-
2,5-dimethyl-4-(4-fluorobenzyl)piperazine;
(trans)-1-((2-isopropyl-4-chloro-5-methylphenoxy)
methyl)carbonyl-2,5-dimethyl-4-(4-fluorobenzyl)
piperazine;
(trans)-1-((4-ethoxyphenoxy)methyl)carbonyl-2,5-
dimethyl-4-(4-fluorobenzyl)piperazine;
(trans)-1-((2-(t-butyl)-4-methylphenoxy)methyl)
carbonyl-2,5-dimethyl-4-(4-fluorobenzyl)piperazine;
(trans)-1-((3-formyl-4-nitrophenoxy)methyl)carbonyl-2,
5-dimethyl-4-(4-fluorobenzyl)piperazine;
(trans)-1-((2-methoxy-4-prop-3-enylphenoxy)methyl)
carbonyl-2,5-dimethyl-4-(4-fluorobenzyl)piperazine;
(trans)-1-((2-(1-phenylethyl)-4-chlorophenoxy)methyl)
carbonyl-2,5-dimethyl-4-(4-fluorobenzyl)piperazine;
(trans)-1-((4-(ethoxycarbonyl)methylphenoxy)methyl)
carbonyl-2,5-dimethyl-4-(4-fluorobenzyl)piperazine;
(trans)-1-((4-trifluoromethoxyphenoxy)methyl)carbonyl-
2,5-dimethyl-4-(4-fluorobenzyl)piperazine;
(trans)-1-((3-fluoro-4-chlorophenoxy)methyl)carbonyl-2,
5-dimethyl-4-(4-fluorobenzyl)piperazine;
(trans)-1-((2-fluoro-4-chlorophenoxy)methyl)carbonyl-2,
5-dimethyl-4-(4-fluorobenzyl)piperazine;
(trans)-1-(((7-methoxynaphthalen-2-yl)oxy)methyl)
carbonyl-2,5-dimethyl-4-(4-fluorobenzyl)piperazine;
(trans)-1-((2-benzyloxy-4-cyanophenoxy)methyl)
carbonyl-2,5-dimethyl-4-(4-fluorobenzyl)piperazine;
(trans)-1-((2-chloro-3,5-dimethoxyphenoxy)methyl)
carbonyl-2,5-dimethyl-4-(4-fluorobenzyl)piperazine;
(trans)-1-((2-bromo-3,5-dimethoxyphenoxy)methyl)
carbonyl-2,5-dimethyl-4-(4-fluorobenzyl)piperazine;
(trans)-1-((3,5-dimethoxy-4-bromophenoxy)methyl)
carbonyl-2,5-dimethyl-4-(4-fluorobenzyl)piperazine;
(trans)-1-((2,6-dibromo-3,5-dimethoxyphenoxy)methyl)
carbonyl-2,5-dimethyl-4-(4-fluorobenzyl)piperazine;
(trans)-1-((4-chlorophenoxy)methyl)carbonyl-2,5-
dimethyl-4-(4-fluorobenzyl)piperazine;
(trans)-1-((3-nitrophenoxy)methyl)carbonyl-2,5-
dimethyl-4-(4-fluorobenzyl)piperazine;
(trans)-1-((2-methyl-3-nitrophenoxy)methyl)carbonyl-2,
5-dimethyl-4-(4-fluorobenzyl)piperazine;
(trans)-1-((3,5-dimethoxyphenoxy)methyl)carbonyl-2,5-
dimethyl-4-(4-fluorobenzyl)piperazine;
(trans)-1-((2-nitro-3-carboxy-6-methylphenoxy)methyl)
carbonyl-2,5-dimethyl-4-(4-fluorobenzyl)piperazine;
(trans)-1-((3-cyanophenoxy)methyl)carbonyl-2,5-
dimethyl-4-(4-fluorobenzyl)piperazine;
(trans)-1-((2-methoxy-5-nitrophenoxy)methyl)carbonyl-
2,5-dimethyl-4-(4-fluorobenzyl)piperazine;
(trans)-1-((2-nitro-5-carboxyphenoxy)methyl)carbonyl-
2,5-dimethyl-4-(4-fluorobenzyl)piperazine;
(trans)-1-((3-(carboxymethyl)phenoxy)methyl)carbonyl-
2,5-dimethyl-4-(4-fluorobenzyl)piperazine;
(trans)-1-((2-methoxy-5-carboxyphenoxy)methyl)
carbonyl-2,5-dimethyl-4-(4-fluorobenzyl)piperazine;
(trans)-1-((4-(dimethylamino)methylphenoxy)methyl)
carbonyl-2,5-dimethyl-4-(4-fluorobenzyl)piperazine;
(trans)-1-((4-(2-(dimethylamino)ethylphenoxy)methyl)
carbonyl-2,5-dimethyl-4-(4-fluorobenzyl)piperazine;
(trans)-1-((3-carboxyphenoxy)methyl)carbonyl-2,
5dimethyl-4-(4-fluorobenzyl)piperazine;
(trans)-1-(((naphthalen-1-yl)oxy)methyl)carbonyl-2,5-
dimethyl-4-(4-fluorobenzyl)piperazine;
(trans)-1-(((5-aminonaphthalen-1-yl)oxy)methyl)
carbonyl-2,5-dimethyl-4-(4-fluorobenzyl)piperazine;
(trans)-1-((3-nitro-4-aminophenoxy)methyl)carbonyl-2,
5-dimethyl-4-(4-fluorobenzyl)piperazine;
(trans)-1-((2,6-di(t-butyl)-4-methylphenoxy)methyl)
carbonyl-2,5-dimethyl-4-(4-fluorobenzyl)piperazine;
(trans)-1-((3-carboxy-4-nitrophenoxy)methyl)carbonyl-
2,5-dimethyl-4-(4-fluorobenzyl)piperazine;
(trans)-1-((2-methyl-5-carboxyphenoxy)methyl)
carbonyl-2,5-dimethyl-4-(4-fluorobenzyl)piperazine;
(trans)-1-((2-nitro-4-aminophenoxy)methyl)carbonyl-2,
5-dimethyl-4-(4-fluorobenzyl)piperazine;
(trans)-1-((4-(benzyloxy)phenoxy)methyl)carbonyl-2,5-
dimethyl-4-(4-fluorobenzyl)piperazine;
(trans)-1-((4-(aminocarbonyl)phenoxy)methyl)carbonyl-
2,5-dimethyl-4-(4-fluorobenzyl)piperazine;
(trans)-1-((3,5-di(trifluoromethyl)phenoxy)methyl)
carbonyl-2,5-dimethyl-4-(4-fluorobenzyl)piperazine;
(trans)-1-((2,4-dibromophenoxy)methyl)carbonyl-2,5-
dimethyl-4-(4-fluorobenzyl)piperazine;
(trans)-1-((2,6-dibromo-4-methylphenoxy)methyl)
carbonyl-2,5-dimethyl-4-(4-fluorobenzyl)piperazine;
(trans)-1-((2,4-dichlorophenoxy)methyl)carbonyl-2,5-
dimethyl-4-(4-fluorobenzyl)piperazine;
(trans)-1-((3-methoxyphenoxy)methyl)carbonyl-2,5-
dimethyl-4-(4-fluorobenzyl)piperazine;
(trans)-1-((3,5-dimethyl-4-bromophenoxy)methyl)
carbonyl-2,5-dimethyl-4-(4-fluorobenzyl)piperazine;
(trans)-1-((3,5-dicarboxyphenoxy)methyl)carbonyl-2,5-
dimethyl-4-(4-fluorobenzyl)piperazine;
(trans)-1-((2-chloro-4-carboxyphenoxy)methyl)carbonyl-
2,5-dimethyl-4-(4-fluorobenzyl)piperazine;
(trans)-1-((2,6-dichloro-4-carboxyphenoxy)methyl)
carbonyl-2,5-dimethyl-4-(4-fluorobenzyl)piperazine;
(trans)-1-(((2-carboxyquinolin-4-yl)oxy)methyl)
carbonyl-2,5-dimethyl-4-(4-fluorobenzyl)piperazine;
(trans)-1-((2,6-dimethyl-4-formylphenoxy)methyl)
carbonyl-2,5-dimethyl-4-(4-fluorobenzyl)piperazine;
(trans)-1-((2,6-di(t-butyl)-4-carboxyphenoxy)methyl)
carbonyl-2,5-dimethyl-4-(4-fluorobenzyl)piperazine;
(trans)-1-((2-amino-5-carboxyphenoxy)methyl)carbonyl-
2,5-dimethyl-4-(4-fluorobenzyl)piperazine;
(trans)-1-((2,6-di(t-butyl)-4-(hydroxymethyl)phenoxy)
methyl)carbonyl-2,5-dimethyl-4-(4-fluorobenzyl)
piperazine;
(trans)-1-(((4-carboxyquinolin-2-yl)oxy)methyl)
carbonyl-2,5-dimethyl-4-(4-fluorobenzyl)piperazine;
(trans)-1-((3-nitro-4-chlorophenoxy)methyl)carbonyl-2,
5-dimethyl-4-(4-fluorobenzyl)piperazine;
(trans)-1-((3-ethyl-4-chloro-5-methylphenoxy)methyl)
carbonyl-2,5-dimethyl-4-(4-fluorobenzyl)piperazine;
(trans)-1-((3,5-di(methoxycarbonyl)phenoxy)methyl)
carbonyl-2,5-dimethyl-4-(4-fluorobenzyl)piperazine;
(trans)-1-((2-(morpholin-4-yl)methyl-4-carboxyphenoxy)
methyl)carbonyl-2,5-dimethyl-4-(4-fluorobenzyl)
piperazine;
(trans)-1-((2-methoxy-4-cyanophenoxy)methyl)
carbonyl-2,5-dimethyl-4-(4-fluorobenzyl)piperazine;

(trans)-1-((2-chloro-4-bromophenoxy)methyl)carbonyl-2,5-dimethyl-4-(4-fluorobenzyl)piperazine;
(trans)-1-((2-trifluoromethylphenoxy)methyl)carbonyl-2,5-dimethyl-4-(4-fluorobenzyl)piperazine;
(trans)-1-((2-methylphenoxy)methyl)carbonyl-2,5-dimethyl-4-(4-fluorobenzyl)piperazine;
(trans)-1-((2-methyl-4-acetylphenoxy)methyl)carbonyl-2,5-dimethyl-4-(4-fluorobenzyl)piperazine;
(trans)-1-((3-(dimethylamino)phenoxy)methyl)carbonyl-2,5-dimethyl-4-(4-fluorobenzyl)piperazine;
(trans)-1-((3-methyl-4-acetylphenoxy)methyl)carbonyl-2,5-dimethyl-4-(4-fluorobenzyl)piperazine;
(trans)-1-((3,5-dimethylphenoxy)methyl)carbonyl-2,5-dimethyl-4-(4-fluorobenzyl)piperazine;
(trans)-1-((4-phenylphenoxy)methyl)carbonyl-2,5-dimethyl-4-(4-fluorobenzyl)piperazine;
(trans)-1-((4-(ethoxycarbonyl)phenoxy)methyl)carbonyl-2,5-dimethyl-4-(4-fluorobenzyl)piperazine;
(trans)-1-((4-acetylphenoxy)methyl)carbonyl-2,5-dimethyl-4-(4-fluorobenzyl)piperazine;
(trans)-1-((4-benzylphenoxy)methyl)carbonyl-2,5-dimethyl-4-(4-fluorobenzyl)piperazine
(trans)-1-((2-methoxy-4-carboxyphenoxy)methyl)carbonyl-2,5-dimethyl-4-(4-fluorobenzyl)piperazine;
(trans)-1-(((3-carboxynaphthalen-2-yl)oxy)methyl)carbonyl-2,5-dimethyl-4-(4-fluorobenzyl)piperazine;
(trans)-1-((2-(hydroxymethyl)phenoxy)methyl)carbonyl-2,5-dimethyl-4-(4-fluorobenzyl)piperazine;
(trans)-1-(((quinolin-8-yl)oxy)methyl)carbonyl-2,5-dimethyl-4-(4-fluorobenzyl)piperazine;
(trans)-1-((3-aminophenoxy)methyl)carbonyl-2,5-dimethyl-4-(4-fluorobenzyl)piperazine;
(trans)-1-((4-(aminocarbonyl)phenoxy)methyl)carbonyl-2,5-dimethyl-4-(4-fluorobenzyl)piperazine;
(trans)-1-((3,5-dimethoxyphenoxy)methyl)carbonyl-2,5-dimethyl-4-(4-fluorobenzyl)piperazine;
(trans)-1-((2-(cyclohexyl)phenoxy)methyl)carbonyl-2,5-dimethyl-4-(4-fluorobenzyl)piperazine;
(trans)-1-(((quinolin-6-yl)oxy)methyl)carbonyl-2,5-dimethyl-4-(4-fluorobenzyl)piperazine;
(trans)-1-((2,4-dichloro-3-methylphenoxy)methyl)carbonyl-2,5-dimethyl-4-(4-fluorobenzyl)piperazine;
(trans)-1-((2,5-dimethylphenoxy)methyl)carbonyl-2,5-dimethyl-4-(4-fluorobenzyl)piperazine;
(trans)-1-((3-bromophenoxy)methyl)carbonyl-2,5-dimethyl-4-(4-fluorobenzyl)piperazine;
(trans)-1-((3-(methylcarbonyl)aminophenoxy)methyl)carbonyl-2,5-dimethyl-4-(4-fluorobenzyl)piperazine;
(trans)-1-((3-acetylphenoxy)methyl)carbonyl-2,5-dimethyl-4-(4-fluorobenzyl)piperazine;
(trans)-1-((3-trifluoromethylphenoxy)methyl)carbonyl-2,5-dimethyl-4-(4-fluorobenzyl)piperazine;
(trans)-1-((4-bromophenoxy)methyl)carbonyl-2,5-dimethyl-4-(4-fluorobenzyl)piperazine;
(trans)-1-((2-formylphenoxy)methyl)carbonyl-2,5-dimethyl-4-(4-fluorobenzyl)piperazine;
(trans)-1-((2-methoxy-5-formylphenoxy)methyl)carbonyl-2,5-dimethyl-4-(4-fluorobenzyl)piperazine;
(trans)-1-(((tropinon-yl)oxy)methyl)carbonyl-2,5-dimethyl-4-(4-fluorobenzyl)piperazine;
(trans)-1-((2-nitro-5-fluorophenoxy)methyl)carbonyl-2,5-dimethyl-4-(4-fluorobenzyl)piperazine;
(trans)-1-((2-nitro-5-formylphenoxy)methyl)carbonyl-2,5-dimethyl-4-(4-fluorobenzyl)piperazine;
(trans)-1-((3-formyl-4-nitrophenoxy)methyl)carbonyl-2,5-dimethyl-4-(4-fluorobenzyl)piperazine;
(trans)-1-((2-carboxy-5-nitrophenoxy)methyl)carbonyl-2,5-dimethyl-4-(4-fluorobenzyl)piperazine;
(trans)-1-((2-amino-4-nitrophenoxy)methyl)carbonyl-2,5-dimethyl-4-(4-fluorobenzyl)piperazine;
(trans)-1-((2-amino-3-carboxyphenoxy)methyl)carbonyl-2,5-dimethyl-4-(4-fluorobenzyl)piperazine;
(trans)-1-((2-nitro-4-aminophenoxy)methyl)carbonyl-2,5-dimethyl-4-(4-fluorobenzyl)piperazine;
(trans)-1-((2,6-dichloro-4-nitrophenoxy)methyl)carbonyl-2,5-dimethyl-4-(4-fluorobenzyl)piperazine;
(trans)-1-((3-fluoro-4-nitrophenoxy)methyl)carbonyl-2,5-dimethyl-4-(4-fluorobenzyl)piperazine;
(trans)-1-((2,3-difluoro-6-nitrophenoxy)methyl)carbonyl-2,5-dimethyl-4-(4-fluorobenzyl)piperazine;
(trans)-1-((2-chloro-4-nitrophenoxy)methyl)carbonyl-2,5-dimethyl-4-(4-fluorobenzyl)piperazine;
(trans)-1-((2-nitro-4-cyanophenoxy)methyl)carbonyl-2,5-dimethyl-4-(4-fluorobenzyl)piperazine;
(trans)-1-((2-bromo-4-methylphenoxy)methyl)carbonyl-2,5-dimethyl-4-(4-fluorobenzyl)piperazine;
(trans)-1-((3-chlorophenoxy)methyl)carbonyl-2,5-dimethyl-4-(4-fluorobenzyl)piperazine;
(trans)-1-((3,4-dichlorophenoxy)methyl)carbonyl-2,5-dimethyl-4-(4-fluorobenzyl)piperazine;
(trans)-1-((3,5-dichlorophenoxy)methyl)carbonyl-2,5-dimethyl-4-(4-fluorobenzyl)piperazine;
(trans)-1-((3,4,5-trimethylphenoxy)methyl)carbonyl-2,5-dimethyl-4-(4-fluorobenzyl)piperazine;
(trans)-1-((4-fluorophenoxy)methyl)carbonyl-2,5-dimethyl-4-(4-fluorobenzyl)piperazine;
(trans)-1-((3,5-dimethyl-4-chlorophenoxy)methyl)carbonyl-2,5-dimethyl-4-(4-fluorobenzyl)piperazine;
(trans)-1-((4-methoxyphenoxy)methyl)carbonyl-2,5-dimethyl-4-(4-fluorobenzyl)piperazine;
(trans)-1-((4-(methoxycarbonyl)phenoxy)methyl)carbonyl-2,5-dimethyl-4-(4-fluorobenzyl)piperazine;
(trans)-1-((4-trifluoromethylphenoxy)methyl)carbonyl-2,5-dimethyl-4-(4-fluorobenzyl)piperazine;
(trans)-1-((4-t-butylphenoxy)methyl)carbonyl-2,5-dimethyl-4-(4-fluorobenzyl)piperazine;
(trans)-1-((4-isopropylphenoxy)methyl)carbonyl-2,5-dimethyl-4-(4-fluorobenzyl)piperazine;
(trans)-1-(((naphthalen-2-yl)oxy)methyl)carbonyl-2,5-dimethyl-4-(4-fluorobenzyl)piperazine;
(trans)-1-(((6-bromonaphthalen-2-yl)oxy)methyl)carbonyl-2,5-dimethyl-4-(4-fluorobenzyl)piperazine;
(trans)-1-((3-(hydroxymethyl)phenoxy)methyl)carbonyl-2,5-dimethyl-4-(4-fluorobenzyl)piperazine;
(trans)-1-((2-methoxy-5-(hydroxymethyl)phenoxy)methyl)carbonyl-2,5-dimethyl-4-(4-fluorobenzyl)piperazine;
(trans)-1-(((1,3-benzodioxolan-5-yl)oxy)methyl)carbonyl-2,5-dimethyl-4-(4-fluorobenzyl)piperazine;
(trans)-1-((2,6-dimethyl-4-nitrophenoxy)methyl)carbonyl-2,5-dimethyl-4-(4-fluorobenzyl)piperazine;
(trans)-1-((2-nitrophenoxy)methyl)carbonyl-2,5-dimethyl-4-(4-fluorobenzyl)piperazine;
(trans)-1-((2-methoxy-4-(amino)methylphenoxy)methyl)carbonyl-2,5-dimethyl-4-(4-fluorobenzyl)piperazine (trans)-1-((3-(aminocarbonyl)phenoxy)methyl)carbonyl-2,5-dimethyl-4-(4-fluorobenzyl)piperazine;

(trans)-1-((3-(methoxycarbonyl)methylphenoxy)methyl)carbonyl-2,5-dimethyl-4-(4-fluorobenzyl)piperazine;

(trans)-1-((2-(4-phenylcarbonyl)-4-fluorophenoxy)methyl)carbonyl-2,5-dimethyl-4-(4-fluorobenzyl)piperazine;

(trans)-1-((2-(1-methyl)cyclohexyl-2,4-dimethylphenoxy)methyl)carbonyl-2,5-dimethyl-4-(4-fluorobenzyl)piperazine;

(trans)-1-((2-(benzyloxycarbonyl)phenoxy)methyl)carbonyl-2,5-dimethyl-4-(4-fluorobenzyl)piperazine;

(trans)-1-((2-(4-(methyl)phenylcarbonyl)-5-methoxyphenoxy)methyl)carbonyl-2,5-dimethyl-4-(4-fluorobenzyl)piperazine;

(trans)-1-((2-phenylcarbonyl-5-octoxyphenoxy)methyl)carbonyl-2,5-dimethyl-4-(4-fluorobenzyl)piperazine;

(trans)-1-((4-octylphenoxy)methyl)carbonyl-2,5-dimethyl-4-(4-fluorobenzyl)piperazine;

(trans)-1-((2-(2-(carboxy)phenylcarbonyl-5-di(n-butyl)aminophenoxy)methyl)carbonyl-2,5-dimethyl-4-(4-fluorobenzyl)piperazine;

(trans)-1-((2-phenylcarbonyl-5-methoxyphenoxy)methyl)carbonyl-2,5-dimethyl-4-(4-fluorobenzyl)piperazine;

(trans)-1-((2-methoxy-4-(3-hydroxyprop-2-enyl)phenoxy)methyl)carbonyl-2,5-dimethyl-4-(4-fluorobenzyl)piperazine;

(trans)-1-(((3-(phenylaminocarbonyl)naphthalen-2-yl)oxy)methyl)carbonyl-2,5-dimethyl-4-(4-fluorobenzyl)piperazine;

(trans)-1-(((6-(phenylcarbonyl)naphthalen-2-yl)oxy)methyl)carbonyl-2,5-dimethyl-4-(4-fluorobenzyl)piperazine;

(trans)-1-((2-((2-phenylethyl)carbonyl)phenoxy)methyl)carbonyl-2,5-dimethyl-4-(4-fluorobenzyl)piperazine;

(trans)-1-((4-((4-fluorophenyl)carbonyl)phenoxy)methyl)carbonyl-2,5-dimethyl-4-(4-fluorobenzyl)piperazine;

(trans)-1-((2-(phenylamino)carbonylphenoxy)methyl)carbonyl-2,5-dimethyl-4-(4-fluorobenzyl)piperazine;

(trans)-1-((2-phenylcarbonylphenoxy)methyl)carbonyl-2,5-dimethyl-4-(4-fluorobenzyl)piperazine;

(trans)-1-((2-phenylcarbonyl-4-chloro-5-methylphenoxy)methyl)carbonyl-2,5-dimethyl-4-(4-fluorobenzyl)piperazine;

(trans)-1-((4-(4-chlorophenyl)carbonylphenoxy)methyl)carbonyl-2,5-dimethyl-4-(4-fluorobenzyl)piperazine;

(trans)-1-((4-benzylcarbonyl)phenoxy)methyl)carbonyl-2,5-dimethyl-4-(4-fluorobenzyl)piperazine;

(trans)-1-((2-phenylcarbonyl-4-methylphenoxy)methyl)carbonyl-2,5-dimethyl-4-(4-fluorobenzyl)piperazine;

(trans)-1-((4-(2-methylcarbonylethyl)phenoxy)methyl)carbonyl-2,5-dimethyl-4-(4-fluorobenzyl)piperazine;

(trans)-1-((4-phenylcarbonylphenoxy)methyl)carbonyl-2,5-dimethyl-4-(4-fluorobenzyl)piperazine; and (trans)-1-((3-phenylcarbonylphenoxy)methyl)carbonyl-2,5-dimethyl-4-(4-fluorobenzyl)piperazine.

C. In a similar manner, the following compounds of formula (Ib) were made:

1-((3,4,5-trimethoxyphenoxy)methyl)carbonyl-4-(benzyl)piperazine; NMR (CDCl$_3$) 7.6 (m, 3), 7.5 (m, 4), 6.2 (s, 2), 4.6 (m, 4), 4.2 (m, 4), 3.8 (m, 9), 3.4 (m, 1), 2.6 (m, 1) ppm;

1-((3-methoxyphenoxy)methyl)carbonyl-4-(benzyl)piperazine; NMR (CDCl$_3$) 7.3 (m, 5), 6.5 (m, 4), 4.6 (s, 2), 3.8–3.5 (m, 9), 2.4 (m, 4) ppm;

1-((3,4-dimethoxyphenoxy)methyl)carbonyl-4-(benzyl)piperazine; NMR (CDCl$_3$) 7.8 (m, 2), 7.4 (m, 3), 6.8 (d, 1), 6.6 (d, 1), 6.4 (dd, 1), 4.8 (d, 2), 4.3 (m, 3), 4.0 (m, 1), 3.7 (s, 3), 3.65 (s, 3), 3.6–3.3 (m, 8), 3.2–2.9 (m, 3) ppm;

1-((phenoxy)methyl)carbonyl-4-(benzyl)piperazine and 1-(chloro)acetyl-4-(benzyl)piperazine; NMR (CDCl$_3$) 7.3 (m, 7), 7.0 (m, 3), 4.7 (s, 2), 3.6 (m, 6), 2.4 (m, 4) ppm;

1-((4-chlorophenoxy)methyl)carbonyl-4-(benzyl)piperazine and 1-(chloro)acetyl-4-(benzyl)piperazine; NMR (CDCl$_3$) 7.3 (m, 7), 6.9 (m, 2), 4.6 (s, 2), 3.6 (m, 6), 2.4 (m, 4) ppm;

1-((3-cyanophenoxy)methyl)carbonyl-4-(benzyl)piperazine; NMR (CDCl$_3$) 7.3 (m, 2), 7.0 (m, 4), 6.8 (m, 3), 4.4 (q, 2), 4.2 (d, 1), 3.9 (d, 2), 3.6 (m, 3), 3.0 (m, 3), 2.6 (m, 2) ppm;

1-((4-cyanophenoxy)methyl)carbonyl-4-(benzyl)piperazine; NMR (CDCl$_3$) 7.6 (m, 4), 7.4 (m, 3), 7.0 (d, 2), 4.9 (q, 2), 4.6 (d, 1), 4.3 (d, 2), 4.0 (d, 2), 3.6 (t, 1), 3.4 (d, 2), 3.0 (m, 2) ppm;

1-((3-(1-methylimidazolin-2yl)phenoxy)methyl)carbonyl-4-(benzyl)piperazine; NMR (CDCl$_3$) 7.5 (m, 6), 7.2 (m, 3), 5.0 (d, 2), 4.0 (m, 4), 3.3 (q, 4), 3.0 (m, 6) ppm;

1-((4-chloro-2-aminocarbonylphenoxy)methyl)carbonyl-4-(4-chlorobenzyl)piperazine; NMR (DMSO-d$_6$) 8.7 (s, 1), 7.8 (s, 1), 7.7 (s, 1), 7.6 (dd, 1), 7.4 (q, 3), 7.2 (d, 1), 5.0 (s, 2), 3.4 (br d, 4), 3.3 (s, 2), 2.4 (br d, 4) ppm;

1-((5-chloroquinolin-8-yloxy)methyl)carbonyl-4-(4-fluorobenzyl)piperazine; NMR (DMSO-d$_6$) 9.0 (s, 1), 8.5 (d, 1), 7.75 (dd, 1), 7.65 (d, 1), 7.4 (q, 2), 7.1 (d, 1), 5.1 (s, 2), 3.5 (m, 6), 2.4 (br d, 4) ppm;

1-((3-trifluoromethoxyphenoxy)methyl)carbonyl-4-(benzyl)piperazine;

1-(3-(3,4,5-trimethoxyphenoxy)propyl)carbonyl-4-(benzyl)piperazine;

1-(1-(3,4,5-trimethoxyphenoxy)propyl)carbonyl-4-(benzyl)piperazine;

1-(1-(3,4,5-trimethoxyphenoxy)pentyl)carbonyl-4-(benzyl)piperazine;

1-((4-methoxyphenoxy)methyl)carbonyl-4-(benzyl)piperazine;

1-((3,5-dimethoxyphenoxy)methyl)carbonyl-4-(benzyl)piperazine;

1-((3-chlorophenoxy)methyl)carbonyl-4-(benzyl)piperazine;

1-(1-(3,4,5-trimethoxyphenoxy)ethyl)carbonyl-4-(benzyl)piperazine;

1-((3,4-dichlorophenoxy)methyl)carbonyl-4-(benzyl)piperazine;

1-((3,5-dichlorophenoxy)methyl)carbonyl-4-(benzyl)piperazine;

1-((3,4,5-trimethylphenoxy)methyl)carbonyl-4-(benzyl)piperazine;

1-((4-nitrophenoxy)methyl)carbonyl-4-(benzyl)piperazine;

1-(1-(3,4,5-trimethoxyphenoxy)septyl)carbonyl-4-(benzyl)piperazine;

1-(-(3,4,5-trimethoxyphenoxy)-2-methylpropyl)carbonyl-4-(benzyl)piperazine;

1-(1-(3,4,5-trimethoxyphenoxy)butyl)carbonyl-4-(benzyl)piperazine;
1-((4-bromophenoxy)methyl)carbonyl-4-(benzyl)piperazine;
1-((4-fluorophenoxy)methyl)carbonyl-4-(benzyl)piperazine;
1-((4-trifluoromethylphenoxy)methyl)carbonyl-4-(benzyl)piperazine;
1-(((4-chlorophenyl)thio)methyl)carbonyl-4-(benzyl)piperazine;
1-((2-chlorophenoxy)methyl)carbonyl-4-(benzyl)piperazine;
1-((4-(benzyloxy)phenoxy)methyl)carbonyl-4-(benzyl)piperazine;
1-((4-(methoxycarbonyl)phenoxy)methyl)carbonyl-4-(benzyl)piperazine;
1-((4-(amino)phenoxy)methyl)carbonyl-4-(benzyl)piperazine;
1-((4-hydroxyphenoxy)methyl)carbonyl-4-(benzyl)piperazine;
1-((4-(1-methylethyl)phenoxy)methyl)carbonyl-4-(benzyl)piperazine;
1-((4-(2,2-dimethylethyl)phenoxy)methyl)carbonyl-4-(benzyl)piperazine;
1-((4-(acetyl)phenoxy)methyl)carbonyl-4-(benzyl)piperazine;
1-((napthalenyl-2-oxy)methyl)carbonyl-4-(benzyl)piperazine;
1-((4-chloro-3,5-dimethylphenoxy)methyl)carbonyl-4-(benzyl)piperazine;
1-((1,3-benzodioxolyl-5-oxy)methyl)carbonyl-4-(benzyl)piperazine;
1-((2,4,6-trichlorophenoxy)methyl)carbonyl-4-(benzyl)piperazine;
1-((2,3,4,5,6-pentafluorophenoxy)methyl)carbonyl-4-(benzyl)piperazine;
1-((2-(benzyloxy)-4-cyanophenoxy)methyl)carbonyl-4-(benzyl)piperazine;
1-((2-chloro-4-bromophenoxy)methyl)carbonyl-4-(benzyl)piperazine;
1-((3-bromophenoxy)methyl)carbonyl-4-(benzyl)piperazine;
1-((3,5-trifluoromethylphenoxy)methyl)carbonyl-4-(benzyl)piperazine;
1-(((5-oxo-6,7,8-trihydronaphthalen-1-yl)oxy)methyl)carbonyl-4-(benzyl)piperazine;
1-(((2-oxo-2H-1-benzopyran-4-yl)oxy)methyl)carbonyl-4-(benzyl)piperazine;
1-((2-cyanophenoxy)methyl)carbonyl-4-(benzyl)piperazine;
1-((4-methyl-3,5-dibromophenoxy)methyl)carbonyl-4-(benzyl)piperazine;
1-((quinolinyl-6-oxy)methyl)carbonyl-4-(benzyl)piperazine;
1-(((diphenyl)methoxy)methyl)carbonyl-4-(benzyl)piperazine;
1-((3-(morpholin-4-yl)phenoxy)methyl)carbonyl-4-(benzyl)piperazine;
1-((2-bromophenoxy)methyl)carbonyl-4-(4-chlorobenzyl)piperazine, hydrochloride salt;
1-((pyridinyl-3-oxy)methyl)carbonyl-4-(benzyl)piperazine;
1-((2-(benzyl)phenoxy)methyl)carbonyl-4-(benzyl)piperazine;
1-((4-(benzyl)phenoxy)methyl)carbonyl-4-(benzyl)piperazine;
1-((4-(formyl)phenoxy)methyl)carbonyl-4-(benzyl)piperazine;
1-((2-(prop-3-enyl)phenoxy)methyl)carbonyl-4-(4-chlorobenzyl)piperazine;
1-((2,6-dibromophenoxy)methyl)carbonyl-4-(4-chlorobenzyl)piperazine;
1-((benzothiazolyl-2-oxy)methyl)carbonyl-4-(4-chlorobenzyl)piperazine;
1-((4-cyclohexylphenoxy)methyl)carbonyl-4-(4-chlorobenzyl)piperazine;
1-((4-(benzyloxy)carbonylphenoxy)methyl)carbonyl-4-(4-chlorobenzyl)piperazine;
1-((5-chloroquinolinyl-8-oxy)methyl)carbonyl-4-(4-chlorobenzyl)piperazine;
1-((4-(imidazol-1-yl)phenoxy)methyl)carbonyl-4-(4-chlorobenzyl)piperazine;
1-((3-chloro-5-methoxyphenoxy)methyl)carbonyl-4-(4-chlorobenzyl)piperazine;
1-((4-carboxyphenoxy)methyl)carbonyl-4-(benzyl)piperazine;
1-((4-iodophenoxy)methyl)carbonyl-4-(4-chlorobenzyl)piperazine, hydrochloride salt; NMR (DMSO-$d_6$) 7.6 (m, 6), 6.8 (d, 2), 4.9 (d, 2), 4.4 (m, 3), 4.0 (m, 1), 3.6 (m, 1), 3.4–2.9 (m, 6) ppm;
1-((2-methoxyphenoxy)methyl)carbonyl-4-(4-chlorobenzyl)piperazine;
1-((2,6-dimethoxyphenoxy)methyl)carbonyl-4-(4-chlorobenzyl)piperazine;
1-((2-methylquinolinyl-4-oxy)methyl)carbonyl-4-(4-chlorobenzyl)piperazine;
1-(((2,3-dihydro-1H-inden-5-yl)oxy)methyl)carbonyl-4-(4-chlorobenzyl)piperazine;
1-((coumarin-4-yloxy)methyl)carbonyl-4-(4-chlorobenzyl)piperazine;
1-((4-chlorobenzyloxy)methyl)carbonyl-4-(4-chlorobenzyl)piperazine;
1-(((4-chlorophenyl)amino)methyl)carbonyl-4-(4-chlorobenzyl)piperazine, hydrochloride salt; NMR (DMSO-$d_6$) 11.4 (br s, 1), 7.6 (dd, 4), 7.1 (d, 2), 6.6 (d, 2), 4.4 (m, 4), 4.0 (m, 4), 3.6–2.9 (m, 4) ppm;
1-((4-chloronaphthalenyl-1-oxy)methyl)carbonyl-4-(4-chlorobenzyl)piperazine;
1-(((4-chlorophenyl)(methyl)amino)methyl)carbonyl-4-(4-chlorobenzyl)piperazine;
1-(((di(4-chloro)phenyl)methoxy)methyl)carbonyl-4-(chlorobenzyl)piperazine;
1-((3,5-dimethoxy-4-chlorophenoxy)methyl)carbonyl-4-(4-chlorobenzyl)piperazine; NMR (CDCl$_3$) 7.2 (q, 4), 6.2 (s, 2), 4.7 (s, 2), 3.9 (s, 6), 3.6 (m, 4), 3.5 (s, 2), 2.4 (m, 4) ppm;
1-((5,7-dichloroquinolinyl-8-oxy)methyl)carbonyl-4-(4-chlorobenzyl)piperazine;
1-((6-hydroxycoumarin-4-yloxy)methyl)carbonyl-4-(4-chlorobenzyl)piperazine;
1-((2-formylphenoxy)methyl)carbonyl-4-(4-chlorobenzyl)piperazine;
1-((3-fluoro-4-chlorophenoxy)methyl)carbonyl-4-(4-chlorobenzyl)piperazine, hydrochloride salt; NMR (DMSO-d$_6$) 11.8 (s, 1), 7.5 (m, 5), 7.1 (d, 1), 6.8 (d, 1), 5.0 (q, 2), 4.3 (m, 3), 3.9 (m, 1), 3.6–2.9 (m, 6) ppm;

1-((2-(hydroxymethyl)phenoxy)methyl)carbonyl-4-(4-chlorobenzyl)piperazine;

1-((2,4-dibromophenoxy)methyl)carbonyl-4-(4-chlorobenzyl)piperazine;

1-((2,4-dichlorophenoxy)methyl)carbonyl-4-(4-chlorobenzyl)piperazine;

1-((4-chloro-3-nitrophenoxy)methyl)carbonyl-4-(4-chlorobenzyl)piperazine; NMR (DMSO-d6) 7.6 (m, 6), 7.3 (d, 1), 5.0 (q, 2), 4.3 (m, 3), 3.9 (m, 1), 3.5–2.9 (m, 6) ppm;

1-((4-bromo-2-formylphenoxy)methyl)carbonyl-4-(4-chlorobenzyl)piperazine; NMR (DMSO-d$_6$) 11.4 (br s, 1), 7.8 (m, 2), 7.5 (m, 4), 7.2 (d, 1), 5.2 (q, 2), 4.4 (m, 3), 4.0 (m, 1), 3.6–2.9 (m, 6) ppm;

1-((2-methoxy-5-nitrophenoxy)methyl)carbonyl-4-(4-chlorobenzyl)piperazine;

1-((4-methylphenoxy)methyl)carbonyl-4-(4-chlorobenzyl)piperazine;

1-((4-bromo-2-chlorophenoxy)methyl)carbonyl-4-(4-chlorobenzyl)piperazine hydrochloride salt;

1-((2-methylphenoxy)methyl)carbonyl-4-(4-chlorobenzyl)piperazine hydrochloride salt;

1-((3,5-dimethoxyphenoxy)methyl)carbonyl-4-(4-chlorobenzyl)piperazine hydrochloride salt;

1-((2-aminocarbonyl-4-chlorophenoxy)methyl)carbonyl-4-(4-fluorobenzyl)piperazine; NMR (DMSO-d$_6$) 8.7 (br s, 1), 7.8 (s, 1), 7.7 (s, 1), 7.6 (dd, 1), 7.2 (m, 3), 7.2 (d, 1), 5.0 (s, 2), 3.5 (m, 6), 2.4 (m, 4) ppm;

1-((3,5-dimethoxy-4-bromophenoxy)methyl)carbonyl-4-(4-fluorobenzyl)piperazine; NMR (CDCl$_3$) 7.3 (m, 4), 6.2 (s, 2), 4.7 (s, 2), 3.9 (s, 6), 3.6 (m, 4), 3.5(s, 2), 2.4 (m, 4) ppm;

1-((3-formyl-4-nitrophenoxy)methyl)carbonyl-4-(4-fluorobenzyl)piperazine; NMR (CDCl$_3$) 10.5 (s, 1), 8.2 (d, 1), 7.3 (m, 6), 4.9 (s, 2), 3.6 (m, 2), 3.5 (m, 4), 2.4 (m, 4) ppm;

1-((2-chloro-4-carboxyphenoxy)methyl)carbonyl-4-(4-chlorobenzyl)piperazine;

1-((1-nitroso-3,6-di(hydroxysulfonyl)naphthalen-2-yloxy)methyl)carbonyl-4-(4-chlorobenzyl)piperazine;

1-((2-nitroso-4-hydroxysulfonylnaphthalen-1-yloxy)methyl)carbonyl-4-(4-chlorobenzyl)piperazine;

1-((3,6-di(hydroxysulfonyl)naphthalen-1-yloxy)methyl)carbonyl-4-(4-chlorobenzyl)piperazine;

1-((3-hydroxysulfonyl-6-aminonaphthalen-1-yloxy)methyl)carbonyl-4-(4-chlorobenzyl)piperazine;

1-((3-hydroxysulfonyl-7-aminonaphthalen-1-yloxy)methyl)carbonyl-4-(4-chlorobenzyl)piperazine;

1-(5-hydroxysulfonylquinolin-8-yloxy)methyl)carbonyl-4-(4-chlorobenzyl)piperazine;

1-((2,3-dinitro-7-hydroxysulfonylnaphthalen-1-yloxy)methyl)carbonyl-4-(4-chlorobenzyl)piperazine;

1-((2-carboxy-4-hydroxysulfonylphenoxy)methyl)carbonyl-4-(4-chlorobenzyl)piperazine;

1-((2-amino-4-hydroxysulfonylphenoxy)methyl)carbonyl-4-(4-chlorobenzyl)piperazine;

1-((4-formyl-2,6-di-t-butylphenoxy)methyl)carbonyl-4-(4-chlorobenzyl)piperazine;

1-((4-(morpholin-4-yl)methylphenoxy)methyl)carbonyl-4-(4-chlorobenzyl)piperazine;

1-((4-(methoxycarbonyl)-2,6-dichlorophenoxy)methyl)carbonyl-4-(4-chlorobenzyl)piperazine;

1-((4-(hydroxysulfonyl)naphthalen-1-yloxy)methyl)carbonyl-4-(4-chlorobenzyl)piperazine;

1-((3,6-di(hydoxysulfonyl)-8-aminonaphthalen-1-yloxy)methyl)carbonyl-4-(4-chlorobenzyl)piperazine;

1-((2-carboxy-5-aminophenoxy)methyl)carbonyl-4-(4-chlorobenzyl)piperazine;

1-((4-trifluromethyl-2,3,5,6-tetrafluorophenoxy)methyl)carbonyl-4-(4-chlorobenzyl)piperazine;

1-((2-methoxy-4-formyl-5-(2-hydroxy-3-methoxy-5-formylphenyl)phenoxy)methyl)carbonyl-4-(4-chlorobenzyl)piperazine;

1-((4-carboxy-2,3,5,6-tetrafluorophenoxy)methyl)carbonyl-4-(4-chlorobenzyl)piperazine;

1-((4-(adamant-1-yl)phenoxy)methyl)carbonyl-4-(4-chlorobenzyl)piperazine;

1-((2-(adamant-1-yl)-4-methylphenoxy)methyl)carbonyl-4-(4-chlorobenzyl)piperazine;

1-((2,4-di((1-methyl-1-phenyl)ethyl)phenoxy)methyl)carbonyl-4-(4-chlorobenzyl)piperazine;

1-((2-acetyl-4-bromophenoxy)methyl)carbonyl-4-(4-chlorobenzyl)piperazine;

1-((2-nitro-4-t-butylphenoxy)methyl)carbonyl-4-(4-chlorobenzyl)piperazine;

1-((2-acetyl-4-chloro-5-methylphenoxy)methyl)carbonyl-4-(4-chlorobenzyl)piperazine;

1-((2-acetyl-4-chloro-6-nitrophenoxy)methyl)carbonyl-4-(4-chlorobenzyl)piperazine;

1-((2-acetyl-4,6-dibromophenoxy)methyl)carbonyl-4-(4-chlorobenzyl)piperazine;

1-((2-formyl-4,6-di(t-butyl)phenoxy)methyl)carbonyl-4-(4-chlorobenzyl)piperazine;

1-((3,5-dinitrophenoxy)methyl)carbonyl-4-(4-chlorobenzyl)piperazine;

1-((2,6-dichloro-4-ethoxycarbonylphenoxy)methyl)carbonyl-4-(4-chlorobenzyl)piperazine;

1-((2-ethoxycarbonyl-4-methylphenoxy)methyl)carbonyl-4-(4-chlorobenzyl)piperazine;

1-((2-methoxy-6-(prop-3-enyl)phenoxy)methyl)carbonyl-4-(4-chlorobenzyl)piperazine;

1-((3-fluoro-4-cyanophenoxy)methyl)carbonyl-4-(4-chlorobenzyl)piperazine;

1-((2-acetyl-4-methyl-6-nitrophenoxy)methyl)carbonyl-4-(4-chlorobenzyl)piperazine;

1-((2-methylbenzothiazol-5-yloxy)methyl)carbonyl-4-(4-chlorobenzyl)piperazine;

1-((2-carboxy-4-(hydroxysulfonyl)phenoxy)methyl)carbonyl-4-(4-chlorobenzyl)piperazine;

1-((4-(4-(trifluoromethyl)phenoxy)phenoxy)methyl)carbonyl-4-(4-chlorobenzyl)piperazine;

1-((2-(1H-pyrazol-3-yl)-4-chloro-5-methylphenoxy)methyl)carbonyl-4-(4-chlorobenzyl)piperazine;

1-((2-(1H-pyrazol-3-yl)-4-chlorophenoxy)methyl)carbonyl-4-(4-chlorobenzyl)piperazine;

1-(((2-phenyl-4-oxo-7-hydroxy-4H-1-benzopyran-3-yl)oxy)methyl)carbonyl-4-(4-chlorobenzyl)piperazine;

1-((2-chloro-3-trifluoromethylphenoxy)methyl)carbonyl-4-(4-chlorobenzyl)piperazine;

1-((2-methoxy-4-(butoxymethyl)phenoxy)methyl)carbonyl-4-(4-chlorobenzyl)piperazine;

1-((6-hydroxyquinolin-2-yloxy)methyl)carbonyl-4-(4-chlorobenzyl)piperazine;

1-((2-methoxycarbonyl-6-methoxyphenoxy)methyl) carbony-4-(4-chlorobenzyl)piperazine;
1-((2,5-di(t-butyl)-4-methoxyphenoxy)methyl)carbonyl-4-(4-chlorobenzyl)piperazine;
1-((2-formyl-4-methylphenoxy)methyl)carbonyl-4-(4-chlorobenzyl)piperazine;
1-((2-(2H-benzotriazol-2-yl)-4-(2-hydroxyethyl)phenoxy)methyl)carbonyl-4-(4-chlorobenzyl)piperazine;
1-((4-chlorophenoxy)methyl)carbonyl-4-(4-chlorobenzyl)piperazine;
1-((2-(methylthio)phenoxy)methyl)carbonyl-4-(4-chlorobenzyl)piperazine;
1-((3,5-di(t-butyl)-4-formylphenoxy)methyl)carbonyl-4-(4-chlorobenzyl)piperazine;
1-((3,5-dibromo-4-methylphenoxy)methyl)carbonyl-4-(4-chlorobenzyl)piperazine;
1-((2,6-diiodo-4-formylphenoxy)methyl)carbonyl-4-(4-chlorobenzyl)piperazine;
1-((2-nitro-4-methoxycarbonylphenoxy)methyl) carbonyl-4-(4-chlorobenzyl)piperazine;
1-((2-(ethoxycarbonyl)indol-5-yloxy)methyl)carbonyl-4-(4-chlorobenzyl)piperazine;
1-((3-(2-carboxyethyl)phenoxy)methyl)carbonyl-4-(4-chlorobenzyl)piperazine;
1-((2,6-dinitro-4-(carboxymethyl)phenoxy)methyl) carbonyl-4-(4-chlorobenzyl)piperazine;
1-((2-nitro-3-carboxyphenoxy)methyl)carbonyl-4-(4-chlorobenzyl)piperazine;
1-((6-carboxynaphthalen-2-yloxy)methyl)carbonyl-4-(4-chlorobenzyl)piperazine;
1-((2,6-difluoro-4-ethylcarbonylphenoxy)methyl) carbonyl-4-(4-chlorobenzyl)piperazine;
1-((2-(2-(methoxycarbonyl)ethyl)phenoxy)methyl) carbonyl-4-(4-chlorobenzyl)piperazine;
1-((2-(prop-3-enyl)-4-acetylphenoxy)methyl)carbonyl-4-(4-chlorobenzyl)piperazine;
1-(((3-oxo-2H-benzofuran-6-yl)oxy)methyl)carbonyl-4-(4-chlorobenzyl)piperazine;
1-((2,4,6-tribromo-3,5-dimethylphenoxy)methyl) carbonyl-4-(4-chlorobenzyl)piperazine;
1-((4-(heptylcarbonyl)phenoxy)methyl)carbonyl-4-(4-chlorobenzyl)piperazine;
1-((2-carboxy-4-acetylphenoxy)methyl)carbonyl-4-(4-chlorobenzyl)piperazine;
1-((2-nitro-4-phenylphenoxy)methyl)carbonyl-4-(4-chlorobenzyl)piperazine;
1-((2-methoxy-4-(eth-2-enyl)phenoxy)methyl)carbonyl-4-(4-chlorobenzyl)piperazine;
1-((2-chloro-4-methoxycarbonylphenoxy)methyl) carbonyl-4-(4-chlorobenzyl)piperazine;
1-((2,6-diiodo-4-cyanophenoxy)methyl)carbonyl-4-(4-chlorobenzyl)piperazine;
1-((2,6-diiodo-4-carboxyphenoxy)methyl)carbonyl-4-(4-chlorobenzyl)piperazine;
1-(((2-phenyl-4-oxo-4H-1-benzopyran-5-yl)oxy)methyl) carbonyl-4-(4-chlorobenzyl)piperazine;
1-(((2-phenyl-4-oxo-7-methoxy-4H-1-benzopyran-5-yl) oxy)methyl)carbonyl-4-(4-chlorobenzyl)piperazine;
1-(((2-phenyl-4-oxo-7-methoxy-2,3-dihydro-4H-1-benzopyran-5-yl)oxy)methyl)carbonyl-4-(4-chlorobenzyl)piperazine;
1-((4-octylcarbonylphenoxy)methyl)carbonyl-4-(4-chlorobenzyl)piperazine;
1-(((4-phthalimid-1-ylphenoxy)methyl)carbonyl-4-(4-chlorobenzyl)piperazine;
1-((3-(morpholin-4-yl)phenoxy)methyl)carbonyl-4-(4-chlorobenzyl)piperazine;
1-((3-chloro-4-bromophenoxy)methyl)carbonyl-4-(4-chlorobenzyl)piperazine;
1-(((2-oxo-7-methoxy-2H-1-benzopyran-8-yl)oxy) methyl)carbonyl-4-(4-chlorobenzyl)piperazine;
1-((2-acetyl-5-fluorophenoxy)methyl)carbonyl-4-(4-chlorobenzyl)piperazine;
1-((2-(1-methylcyclohex-1-yl )4-methyl-6-(2-hydroxy-3-(1-methylcyclohex-1-yl)-5-methylbenzyl)phenoxy) methyl)carbonyl-4-(4-chlorobenzyl)piperazine;
1-((2-formyl-3-methoxyphenoxy)methyl)carbonyl-4-(4-chlorobenzyl)piperazine;
1-((2-amino-4-carboxyphenoxy)methyl)carbonyl-4-(4-chlorobenzyl)piperazine;
1-((2-chloro-4-carboxy-6-methoxyphenoxy)methyl) carbonyl-4-(4-chlorobenzyl)piperazine;
1-((2,6-dimethyl-4-carboxyphenoxy)methyl)carbonyl-4-(4-chlorobenzyl)piperazine;
1-((2-methoxy-4-(2-(carboxy)ethyl)phenoxy)methyl) carbonyl-4-(4-chlorobenzyl)piperazine;
1-((2,6-dimethoxy-4-(hydroxymethyl)phenoxy)methyl) carbonyl-4-(4-chlorobenzyl)piperazine;
1-((2,6-dibromo-4-formylphenoxy)methyl)carbonyl-4-(4-chlorobenzyl)piperazine;
1-((2-nitro-4-(ethoxycarbonyl)phenoxy)methyl)carbonyl-4-(4-chlorobenzyl)piperazine;
1-((2-amino-4-(methoxycarbonyl)phenoxy)methyl) carbonyl-4-(4-chlorobenzyl)piperazine;
1-((4-(2-(4-nitrophenyl)eth-2-enyl)phenoxy)methyl) carbonyl-4-(4-chlorobenzyl)piperazine;
1-((2-acetyl-3,5-dimethoxyphenoxy)methyl)carbonyl-4-(4-chlorobenzyl)piperazine;
1-((2,6-di(t-butyl)-4-(methoxycarbonyl)phenoxy)methyl) carbonyl-4-(4-chlorobenzyl)piperazine;
1-((2-methoxy-4-(ethoxycarbonyl)phenoxy)methyl) carbonyl-4-(4-chlorobenzyl)piperazine;
1-((2-cyclohexyl-4-chlorophenoxy)methyl)carbonyl-4-(4-chlorobenzyl)piperazine;
1-((2,6-dimethyl-4-chlorophenoxy)methyl)carbonyl-4-(4-chlorobenzyl)piperazine;
1-((2-methoxy-4-ethylphenoxy)methyl)carbonyl-4-(4-chlorobenzyl)piperazine;
1-((4-n-butylphenoxy)methyl)carbonyl-4-(4-chlorobenzyl)piperazine;
1-(((3-carboxy-1-bromonaphthalen-2-yl)oxy)methyl) carbonyl-4-(4-chlorobenzyl)piperazine;
1-((2-bromo-4-nitro-6-formylphenoxy)methyl)carbonyl-4-(4-chlorobenzyl)piperazine;
1-((2-formyl-4-chlorophenoxy)methyl)carbonyl-4-(4-chlorobenzyl)piperazine;
1-((2,6-dichloro-4-(ethoxycarbonyl)phenoxy)methyl) carbonyl-4-(4-chlorobenzyl)piperazine;
1-(((4-methyl-2-oxo-2H-1-benzopyran-6-yl)oxy)methyl) carbonyl-4-(4-chlorobenzyl)piperazine;
1-((2,3-dibromo-4-formyl-6-methoxyphenoxy)methyl) carbonyl-4-(4-chlorobenzyl)piperazine;
1-((4-(2-(4-nitrophenyl)eth-2-yl)phenoxy)methyl) carbonyl-4-(4-chlorobenzyl)piperazine;

1-((2,4,6-tribromo-3-formylphenoxy)methyl)carbonyl-4-(4-chlorobenzyl)piperazine;
1-((2-benzyl-4-chlorophenoxy)methyl)carbonyl-4-(4-chlorobenzyl)piperazine;
1-((2-(bezothiazol-2-yl)phenoxy)methyl)carbonyl-4-(4-chlorobenzyl)piperazine;
1-((2-nitro-6-fluorophenoxy)methyl)carbonyl-4-(4-chlorobenzyl)piperazine;
1-((2-ethoxy-4-methylphenoxy)methyl)carbonyl-4-(4-chlorobenzyl)piperazine;
1-((2-bromo-4,6-di(t-butyl)phenoxy)methyl)carbonyl-4-(4-chlorobenzyl)piperazine;
1-((2-(pyrrolidin-1-yl)phenoxy)methyl)carbonyl-4-(4-chlorobenzyl)piperazine;
1-((2-(morpholin-4-yl)phenoxy)methyl)carbonyl-4-(4-chlorobenzyl)piperazine;
1-((2-(piperidin-1-yl)phenoxy)methyl)carbonyl-4-(4-chlorobenzyl)piperazine;
1-((2-formyl-4-chloro-6-bromophenoxy)methyl)carbonyl-4-(4-chlorobenzyl)piperazine;
1-(((4,7-dimethoxy-5-formylbenzofuran-6-yl)oxy)methyl)carbonyl-4-(4-chlorobenzyl)piperazine;
1-(((2-oxo-4-methyl-8-nitro-2H-1-benzopyran-7-yl)oxy)methyl)carbonyl-4-(4-chlorobenzyl)piperazine;
1-((2-methoxy-4-bromophenoxy)methyl)carbonyl-4-(4-chlorobenzyl)piperazine;
1-((2-chloro-4-bromo-6-methylphenoxy)methyl)carbonyl-4-(4-chlorobenzyl)piperazine;
1-((2,4-dimethyl-6-t-butylphenoxy)methyl)carbonyl-4-(4-chlorobenzyl)piperazine;
1-(((2-nitro-4-(hydroxysulfonyl)naphthalen-1-yl)oxy)methyl)carbonyl-4-(4-chlorobenzyl)piperazine;
1-(((3-(hydroxysulfonyl)-6-aminonaphthalen-1-yl)oxy)methyl)carbonyl-4-(4-chlorobenzyl)piperazine;
1-(((3-(hydroxysulfonyl)-7-aminonaphthalen-1-yl)oxy)methyl)carbonyl-4-(4-chlorobenzyl)piperazine;
1-(((3-(methoxycarbonyl)naphthalen-2-yl)oxy)methyl)carbonyl-4-(4-chlorobenzyl)piperazine;
1-((2-carboxy-4-(hydroxysulfonyl)phenoxy)methyl)carbonyl-4-(4-chlorobenzyl)piperazine;
1-((4-n-butylcarbonylphenoxy)methyl)carbonyl-4-(4-chlorobenzyl)piperazine;
1-((3-ethoxyphenoxy)methyl)carbonyl-4-(4-chlorobenzyl)piperazine;
1-((4-(((2-ethyl)hexoxy)carbonyl)phenoxy)methyl)carbonyl-4-(4-chlorobenzyl)piperazine;
1-((4-((n-pentoxy)carbonyl)phenoxy)methyl)carbonyl-4-(4-chlorobenzyl)piperazine;
1-((2-nitro-5-(methoxycarbonyl)phenoxy)methyl)carbonyl-4-(4-chlorobenzyl)piperazine;
1-((2,4,6-tribromo-3-methylphenoxy)methyl)carbonyl-4-(4-chlorobenzyl)piperazine;
1-((2-methoxy-5-methylphenoxy)methyl)carbonyl-4-(4-chlorobenzyl)piperazine;
1-((3-methoxy-4-formylphenoxy)methyl)carbonyl-4-(4-chlorobenzyl)piperazine;
1-((4-(2-(phenyl)eth-2-enyl)phenoxy)methyl)carbonyl-4-(4-chlorobenzyl)piperazine;
1-((4-(1,2,4-triazol-1-yl)phenoxy)methyl)carbonyl-4-(4-chlorobenzyl)piperazine;
1-((2-nitro-4-chloro-5-methylphenoxy)methyl)carbonyl-4-(4-chlorobenzyl)piperazine;
1-((4-(n-hexoxycarbonyl)phenoxy)methyl)carbonyl-4-(4-chlorobenzyl)piperazine;
1-((2-chloro-4-formyl-6-methoxyphenoxy)methyl)carbonyl-4-(4-chlorobenzyl)piperazine;
1-((2-methoxy-4-(2-(ethoxycarbonyl)ethyl)phenoxy)methyl)carbonyl-4-(4-chlorobenzyl)piperazine;
1-((2,3,4,6-tetrachlorophenoxy)methyl)carbonyl-4-(4-chlorobenzyl)piperazine;
1-((2-((2-methylpropoxy)carbonyl)phenoxy)methyl)carbonyl-4-(4-chlorobenzyl)piperazine;
1-((2-(n-butoxycarbonyl)phenoxy)methyl)carbonyl-4-(4-chlorobenzyl)piperazine;
1-((4-(phenylamino)phenoxy)methyl)carbonyl-4-(4-chlorobenzyl)piperazine;
1-((2-hydroxymethyl-4-chlorophenoxy)methyl)carbonyl-4-(4-chlorobenzyl)piperazine;
1-((2-mercaptophenoxy)methyl)carbonyl-4-(4-chlorobenzyl)piperazine;
1-((2-nitro-6-formylphenoxy)methyl)carbonyl-4-(4-chlorobenzyl)piperazine;
1-((2,4-di(1-methylbutyl)phenoxy)methyl)carbonyl-4-(4-chlorobenzyl)piperazine;
1-((3-trifluoromethyl-4-nitrophenoxy)methyl)carbonyl-4-(4-chlorobenzyl)piperazine;
1-((2,6-dibromo-4-(methoxycarbonyl)phenoxy)methyl)carbonyl-4-(4-chlorobenzyl)piperazine;
1-((2,4-dichloro-6-acetyl)methyl)carbonyl-4-(4-chlorobenzyl)piperazine;
1-((2-methoxycarbonyl-4-methylphenoxy)methyl)carbonyl-4-(4-chlorobenzyl)piperazine;
1-((2-formyl-4-bromo-6-methoxyphenoxy)methyl)carbonyl-4-(4-chlorobenzyl)piperazine;
1-((2,6-diformyl-4-methylphenoxy)methyl)carbonyl-4-(4-chlorobenzyl)piperazine;
1-((2,6-dinitro-4-carboxyphenoxy)methyl)carbonyl-4-(4-chlorobenzyl)piperazine;
1-((2-nitro-4-acetylphenoxy)methyl)carbonyl-4-(4-chlorobenzyl)piperazine;
1-((2-formyl-4-nitro-6-methoxyphenoxy)methyl)carbonyl-4-(4-chlorobenzyl)piperazine;
1-((4-(aminocarbonyl)methylphenoxy)methyl)carbonyl-4-(4-chlorobenzyl)piperazine;
1-((2-methoxycarbonyl-4-methoxyphenoxy)methyl)carbonyl-4-(4-chlorobenzyl)piperazine;
1-(((2-phenyl-4-oxo-4H-1-benzopyran-6-yl)oxy)methyl)carbonyl-4-(4-chlorobenzyl)piperazine;
1-((2-chloro-4-trifluoromethylphenoxy)methyl)carbonyl-4-(4-chlorobenzyl)piperazine;
1-((2-carboxy-3-methyl-6-isopropylphenoxy)methyl)carbonyl-4-(4-chlorobenzyl)piperazine;
1-(((5,7-dibromo-2-methylquinolin-8-yl)oxy)methyl)carbonyl-4-(4-chlorobenzyl)piperazine;
1-(((5,7-dichloro-2-methylquinolin-8-yl)oxy)methyl)carbonyl-4-(4-chlorobenzyl)piperazine;
1-((2,6-dinitrophenoxy)methyl)carbonyl-4-(4-chlorobenzyl)piperazine;
1-((2-nitro-4-methoxyphenoxy)methyl)carbonyl-4-(4-chlorobenzyl)piperazine;
1-((2-amino-4-(1,1-dimethylpropyl)phenoxy)methyl)carbonyl-4-(4-chlorobenzyl)piperazine;
1-((2,6-diphenyl-4-aminophenoxy)methyl)carbonyl-4-(4-chlorobenzyl)piperazine;

1-((2,4-dichloro-3-methyl-6-aminophenoxy)methyl) carbonyl-4-(4-chlorobenzyl)piperazine;

1-(((2-oxo-4-(carboxy)methyl-2H-1-benzopyran-7-yl) oxy)methyl)carbonyl-4-(4-chlorobenzyl)piperazine;

1-(((2-oxo-4-trifluoromethyl-2H-1-benzopyran-7-yl)oxy) methyl)carbonyl-4-(4-chlorobenzyl)piperazine;

1-((2-t-butyl-4-methoxyphenoxy)methyl)carbonyl-4-(4-chlorobenzyl)piperazine;

1-((2-formyl-6-methylphenoxy)methyl)carbonyl-4-(4-chlorobenzyl)piperazine;

1-((2-methoxycarbonyl-4-acetylphenoxy)methyl) carbonyl-4-(4-chlorobenzyl)piperazine;

1-((2-bromo-5-fluorophenoxy)methyl)carbonyl-4-(4-chlorobenzyl)piperazine;

1-((2,4-di(1,1-dimethylpropyl)phenoxy)methyl)carbonyl-4-(4-chlorobenzyl)piperazine;

1-((3-methyl-4-fluorophenoxy)methyl)carbonyl-4-(4-chlorobenzyl)piperazine;

1-((2,3,4-trifluorophenoxy)methyl)carbonyl-4-(4-chlorobenzyl)piperazine;

1-((2,5-difluorophenoxy)methyl)carbonyl-4-(4-chlorobenzyl)piperazine;

1-((2-methyl-5-nitrophenoxy)methyl)carbonyl-4-(4-chlorobenzyl)piperazine;

1-(((2-methyl-3-(ethoxycarbonyl)indol-5-yl)oxy)methyl) carbonyl-4-(4-chlorobenzyl)piperazine;

1-((2-aminocarbonyl-4-acetylphenoxy)methyl)carbonyl-4-(4-chlorobenzyl)piperazine;

1-((2,6-dinitro-3-t-butylphenoxy)methyl)carbonyl-4-(4-chlorobenzyl)piperazine;

1-((2-fluoro-4-nitrophenoxy)methyl)carbonyl-4-(4-chlorobenzyl)piperazine;

1-((2-carboxy-3-fluorophenoxy)methyl)carbonyl-4-(4-chlorobenzyl)piperazine;

1-((2-(2-ethylhexoxy)carbonylphenoxy)methyl)carbonyl-4-(4-chlorobenzyl)piperazine;

1-((2,4,6-tribromo-4-carboxyphenoxy)methyl)carbonyl-4-(4-chlorobenzyl)piperazine;

1-((4-(4-bromophenyl)phenoxy)methyl)carbonyl-4-(4-chlorobenzyl)piperazine;

1-((4-(4-carboxyphenyl)phenoxy)methyl)carbonyl-4-(4-chlorobenzyl)piperazine;

1-((2,3,6-trifluorophenoxy)methyl)carbonyl-4-(4-chlorobenzyl)piperazine;

1-((2,4,5-trifluorophenoxy)methyl)carbonyl-4-(4-chlorobenzyl)piperazine;

1-((2,4,6-trifluorophenoxy)methyl)carbonyl-4-(4-chlorobenzyl)piperazine;

1-((2-fluoro-5-trifluoromethylphenoxy)methyl)carbonyl-4-(4-chlorobenzyl)piperazine;

1-(((2,4-dinitronaphthalen-1-yl)oxy)methyl)carbonyl-4-(4-chlorobenzyl)piperazine;

1-(((3,6-di(hydroxysulfonyl)-8-aminonaphthalen-1-yl) oxy)methyl)carbonyl-4-(4-chlorobenzyl)piperazine;

1-((2-acetyl-4-chlorophenoxy)methyl)carbonyl-4-(4-chlorobenzyl)piperazine;

1-((2,6-dimethyl-4-(1-(3,5-dimethyl-4-hydoxyphenyl)-1-methylethyl)phenoxy)methyl)carbonyl-4-(4-chlorobenzyl)piperazine;

1-((4-(3-(4-hydroxyphenyl)hex-2-yl)phenoxy)methyl) carbonyl-4-(4-chlorobenzyl)piperazine;

1-(((6-(hydroxysulfonyl)naphthalen-2-yl)oxy)methyl) carbonyl-4-(4-chlorobenzyl)piperazine;

1-((2-chloro-4-methylphenoxy)methyl)carbonyl-4-(4-chlorobenzyl)piperazine;

1-((2-bromo-4,5-difluorophenoxy)methyl)carbonyl-4-(4-chlorobenzyl)piperazine;

1-((2-chloro-4-methoxyphenoxy)methyl)carbonyl-4-(4-chlorobenzyl)piperazine;

1-((2-methoxy-4-chlorophenoxy)methyl)carbonyl-4-(4-chlorobenzyl)piperazine;

1-((4-(2-(methoxycarbonyl)ethyl)phenoxy)methyl) carbonyl-4-(4-chlorobenzyl)piperazine;

1-((2,6-diphenyl-4-nitrophenoxy)methyl)carbonyl-4-(4-chlorobenzyl)piperazine;

1-((2-amino-3-methylphenoxy)methyl)carbonyl-4-(4-chlorobenzyl)piperazine;

1-((2-methyl-4-fluorophenoxy)methyl)carbonyl-4-(4-chlorobenzyl)piperazine;

1-((2-methyl-4-iodophenoxy)methyl)carbonyl-4-(4-chlorobenzyl)piperazine;

1-((2-fluoro-6-methoxyphenoxy)methyl)carbonyl-4-(4-chlorobenzyl)piperazine;

1-((2-carboxy-3-isopropyl-6-methylphenoxy)methyl) carbonyl-4-(4-chlorobenzyl)piperazine;

1-((2-carboxy-3,4,6-trichlorophenoxy)methyl)carbonyl-4-(4-chlorobenzyl)piperazine;

1-((2-carboxy-6-isopropylphenoxy)methyl)carbonyl-4-(4-chlorobenzyl)piperazine;

1-((2-(piperidin-1-yl)-4-methylphenoxy)methyl) carbonyl-4-(4-chlorobenzyl)piperazine;

1-(((2,3-dihydro-2,2-dimethylbenzofuran-7-yl)oxy) methyl)carbonyl-4-(4-chlorobenzyl)piperazine;

1-((2,6-di(t-butyl)-4-(1-methylpropyl)phenoxy)methyl) carbonyl-4-(4-chlorobenzyl)piperazine;

1-((3-methyl-4-bromophenoxy)methyl)carbonyl-4-(4-chlorobenzyl)piperazine;

1-(((phenanthren-9-yl)oxy)methyl)carbonyl-4-(4-chlorobenzyl)piperazine;

1-((2-nitro-4-bromophenoxy)methyl)carbonyl-4-(4-chlorobenzyl)piperazine;

1-((2-fluoro-3-trifluoromethylphenoxy)methyl)carbonyl-4-(4-chlorobenzyl)piperazine;

1-((2-nitro-5-methoxyphenoxy)methyl)carbonyl-4-(4-chlorobenzyl)piperazine;

1-((2-chloro-4-aminophenoxy)methyl)carbonyl-4-(4-chlorobenzyl)piperazine;

1-((2-formyl-4-bromo-6-nitrophenoxy)methyl)carbonyl-4-(4-chlorobenzyl)piperazine;

1-((2-methoxy-4-(acetyl)methylphenoxy)methyl) carbonyl-4-(4-chlorobenzyl)piperazine;

1-((4-(5-mercaptotetrazol-1-yl)phenoxy)methyl) carbonyl-4-(4-chlorobenzyl)piperazine;

1-((2,4,6-triiodo-3-(2-carboxy)butylphenoxy)methyl) carbonyl-4-(4-chlorobenzyl)piperazine;

1-((3-hydroxymethyl-4-nitrophenoxy)methyl)carbonyl-4-(4-chlorobenzyl)piperazine;

1-((2,3,5,6-tetrafluoro-4-(2,3,4,5,6-pentafluorophenyl) phenoxy)methyl)carbonyl-4-(4-chlorobenzyl) piperazine;

1-((2-(benzotriazol-2-yl)4,6-di(1,1-dimethylpropyl) phenoxy)methyl)carbonyl-4-(4-chlorobenzyl) piperazine;

1-((2-phenyl-3-hydroxy-4-oxo-4H-1-benzopyran-6-yl) oxy)methyl)carbonyl-4-(4-chlorobenzyl)piperazine;

1-((indanonyl)oxy)methyl)carbonyl-4-(4-chlorobenzyl)piperazine;
1-((2-nitro-4-(hydroxysulfonyl)phenoxy)methyl)carbonyl-4-(4-chlorobenzyl)piperazine;
1-((2-nitro-3-methylphenoxy)methyl)carbonyl-4-(4-chlorobenzyl)piperazine;
1-((4-(2,4-dinitrophenyl)aminophenoxy)methyl)carbonyl-4-(4-chlorobenzyl)piperazine;
1-((3-methyl-4-nitrophenoxy)methyl)carbonyl-4-(4-chlorobenzyl)piperazine;
1-((2,6-dibromo-4-nitrophenoxy)methyl)carbonyl-4-(4-chlorobenzyl)piperazine;
1-((2,6-diiodo-4-nitrophenoxy)methyl)carbonyl-4-(4-chlorobenzyl)piperazine;
1-((2-formyl-4-nitrophenoxy)methyl)carbonyl-4-(4-chlorobenzyl)piperazine;
1-((2-aminophenoxy)methyl)carbonyl-4-(4-chlorobenzyl)piperazine;
1-((2-amino-5-nitrophenoxy)methyl)carbonyl-4-(4-chlorobenzyl)piperazine;
1-((2-amino-5-methylphenoxy)methyl)carbonyl-4-(4-chlorobenzyl)piperazine;
1-((2-amino-4-chlorophenoxy)methyl)carbonyl-4-(4-chlorobenzyl)piperazine;
1-((2-amino-4-carboxyphenoxy)methyl)carbonyl-4-(4-chlorobenzyl)piperazine;
1-((2-amino-4-t-butylphenoxy)methyl)carbonyl-4-(4-chlorobenzyl)piperazine;
1-((2-amino-4-methylphenoxy)methyl)carbonyl-4-(4-chlorobenzyl)piperazine;
1-((2-methyl-3-aminophenoxy)methyl)carbonyl-4-(4-chlorobenzyl)piperazine;
1-((2-carboxy-5-aminophenoxy)methyl)carbonyl-4-(4-chlorobenzyl)piperazine;
1-((3-methyl-4-aminophenoxy)methyl)carbonyl-4-(4-chlorobenzyl)piperazine;
1-((2,5-dimethyl-4-aminophenoxy)methyl)carbonyl-4-(4-chlorobenzyl)piperazine;
1-((2,6-dibromo-4-aminophenoxy)methyl)carbonyl-4-(4-chlorobenzyl)piperazine;
1-((2-carboxy-4-aminophenoxy)methyl)carbonyl-4-(4-chlorobenzyl)piperazine;
1-((2-aminocarbonylphenoxy)methyl)carbonyl-4-(4-chlorobenzyl)piperazine;
1-((2-aminocarbonyl-4-chlorophenoxy)methyl)carbonyl-4-(4-chlorobenzyl)piperazine;
1-((4-(2-aminoethyl)phenoxy)methyl)carbonyl-4-(4-chlorobenzyl)piperazine;
1-((2,4,6-tri(dimethylamino)phenoxy)methyl)carbonyl-4-(4-chlorobenzyl)piperazine;
1-((2-hydroxymethyl-6-methoxyphenoxy)methyl)carbonyl-4-(4-chlorobenzyl)piperazine;
1-((2,3-dimethoxyphenoxy)methyl)carbonyl-4-(4-chlorobenzyl)piperazine;
1-((4-(methoxycarbonyl)-5-methoxyphenoxy)methyl)carbonyl-4-(4-chlorobenzyl)piperazine;
1-((2-methoxy-4-(methoxycarbonyl)phenoxy)methyl)carbonyl-4-(4-chlorobenzyl)piperazine;
1-((2,6-dimethoxy-4-(prop-3-enyl)phenoxy)methyl)carbonyl-4-(4-chlorobenzyl)piperazine;
1-((2-acetyl-5-methoxyphenoxy)methyl)carbonyl-4-(4-chlorobenzyl)piperazine;
1-((2-acetyl-4-methoxyphenoxy)methyl)carbonyl-4-(4-chlorobenzyl)piperazine;
1-((2-acetyl-3-methoxyphenoxy)methyl)carbonyl-4-(4-chlorobenzyl)piperazine;
1-((2-methoxy-4-acetylphenoxy)methyl)carbonyl-4-(4-chlorobenzyl)piperazine;
1-((2,6-dimethoxy-4-acetylphenoxy)methyl)carbonyl-4-(4-chlorobenzyl)piperazine;
1-((2,6-di(t-butyl)phenoxy)methyl)carbonyl-4-(4-chlorobenzyl)piperazine;
1-((2,4-di(t-butyl)phenoxy)methyl)carbonyl-4-(4-chlorobenzyl)piperazine;
1-((3,5-di(t-butyl)phenoxy)methyl)carbonyl-4-(4-chlorobenzyl)piperazine;
1-((2,6-di(isopropyl)phenoxy)methyl)carbonyl-4-(4-chlorobenzyl)piperazine;
1-((2-methoxy-4-(ethoxycarbony)methylphenoxy)methyl)carbonyl-4-(4-chlorobenzyl)piperazine;
1-((2-ethoxy-5-prop-2-enylphenoxy)methyl)carbonyl-4-(4-chlorobenzyl)piperazine;
1-((2-methoxy-5-prop-2-enylphenoxy)methyl)carbonyl-4-(4-chlorobenzyl)piperazine;
1-((2,6-di(1-methylpropyl)phenoxy)methyl)carbonyl-4-(4-chlorobenzyl)piperazine;
1-((2,4-difluorophenoxy)methyl)carbonyl-4-(4-chlorobenzyl)piperazine;
1-((2,6-diphenylphenoxy)methyl)carbonyl-4-(4-chlorobenzyl)piperazine;
1-((2-nitro-3-trifluoromethylphenoxy)methyl)carbonyl-4-(4-chlorobenzyl)piperazine;
1-((2-cyclopentyphenoxy)methyl)carbonyl-4-(4-chlorobenzyl)piperazine;
1-((4-cyclopentylphenoxy)methyl)carbonyl-4-(4-chlorobenzyl)piperazine;
1-((2,3-difluorophenoxy)methyl)carbonyl-4-(4-chlorobenzyl)piperazine;
1-((2-carboxy-6-aminophenoxy)methyl)carbonyl-4-(4-chlorobenzyl)piperazine;
1-((2-amino-4-chloro-5-nitrophenoxy)methyl)carbonyl-4-(4-chlorobenzyl)piperazine;
1-((3,4-difluorophenoxy)methyl)carbonyl-4-(4-chlorobenzyl)piperazine;
1-((2-carboxy-6-chlorophenoxy)methyl)carbonyl-4-(4-chlorobenzyl)piperazine;
1-((2,4-dicarboxyphenoxy)methyl)carbonyl-4-(4-chlorobenzyl)piperazine;
1-((2,3-dimethoxy-5-formylphenoxy)methyl)carbonyl-4-(4-chlorobenzyl)piperazine;
1-((2-bromo-4-fluorophenoxy)methyl)carbonyl-4-(4-chlorobenzyl)piperazine;
1-((2,6-dichoro4-fluorophenoxy)methyl)carbonyl-4-(4-chlorobenzyl)piperazine;
1-((3-methyl-4-isopropylphenoxy)methyl)carbonyl-4-(4-chlorobenzyl)piperazine;
1-(((fluoren-2-yl)oxy)methyl)carbonyl-4-(4-chlorobenzyl)piperazine;
1-((2-diethylaminophenoxy)methyl)carbonyl-4-(4-chlorobenzyl)piperazine;
1-((2-amino-3-nitrophenoxy)methyl)carbonyl-4-(4-chlorobenzyl)piperazine;
1-(((2-oxo-3,4,8-trimethyl-2H-1-benzopyran-7-yl)oxy)methyl)carbonyl-4-(4-chlorobenzyl)piperazine;

1-((2-acetyl-4-fluorophenoxy)methyl)carbonyl-4-(4-chlorobenzyl)piperazine;
1-((2-fluoro-4-bromophenoxy)methyl)carbonyl-4-(4-chlorobenzyl)piperazine;
1-((2-(methylcarbonyl)amino-5-methylphenoxy)methyl) carbonyl-4-(4-chlorobenzyl)piperazine;
1-(((1-acetylnaphthalen-2-yl)oxy)methyl)carbonyl-4-(4-chlorobenzyl)piperazine;
1-((2-methoxy-4-nitrophenoxy)methyl)carbonyl-4-(4-chlorobenzyl)piperazine;
1-((3-methyl-5-isopropylphenoxy)methyl)carbonyl-4-(4-chlorobenzyl)piperazine;
1-((2-methyl-4-formylphenoxy)methyl)carbonyl-4-(4-chlorobenzyl)piperazine;
1-(((-aminonaphthalen-2-yl)oxy)methyl)carbonyl-4-(4-chlorobenzyl)piperazine;
1-((4-aminonaphthalen-1-yl)oxy)methyl)carbonyl-4-(4-chlorobenzyl)piperazine;
1-((2-methoxy-4-(1,2-dihydroxyethyl)phenoxy)methyl) carbonyl-4-(4-chlorobenzyl)piperazine;
1-(((3-(2-aminoethyl)indolin-5-yl)oxy)methyl)carbonyl-4-(4-chlorobenzyl)piperazine;
1-(((5-chloroquinolin-8-yl)oxy)methyl)carbonyl-4-(4-chlorobenzyl)piperazine;
1-((2-methoxy-4-(2-(amino)ethyl)phenoxy)methyl) carbony-1-4-(4-chlorobenzyl)piperazine;
1-((4-(2-(amino)ethyl)phenoxy)methyl)carbonyl-4-(4-chlorobenzyl)piperazine;
1-((2-methoxy-4-(2-(amino)ethyl)phenoxy)methyl) carbonyl-4-(4-chlorobenzyl)piperazine;
1-((2,4-diaminophenoxy)methyl)carbonyl-4-(4-chlorobenzyl)piperazine;
1-((4-aminophenoxy)methyl)carbonyl-4-(4-chlorobenzyl)piperazine;
1-((2-(diethylamino)methyl-4-aminophenoxy)methyl) carbonyl-4-(4-chlorobenzyl)piperazine;
1-((2-methyl-5-(2-aminobutyl)phenoxy)methyl) carbonyl-4-(4-chlorobenzyl)piperazine;
1-((2-(benzotriazol-2-yl)-4-(1,1,3,3-tetramethylbutyl) phenoxy)methyl)carbonyl-4-(4-chlorobenzyl) piperazine;
1-((2-nitro-4-bromo-6-fluorophenoxy)methyl)carbonyl-4-(4-chlorobenzyl)piperazine;
1-((2-iodophenoxy)methyl)carbonyl-4-(4-chlorobenzyl) piperazine;
1-((2-(2-carboxyethyl)phenoxy)methyl)carbonyl-4-(4-chlorobenzyl)piperazine;
1-((2-carboxy-4-methylphenoxy)methyl)carbonyl-4-(4-chlorobenzyl)piperazine;
1-((2,6-dibromo-3-carboxyphenoxy)methyl)carbonyl-4-(4-chlorobenzyl)piperazine;
1-((2,6-dichloro-3-carboxyphenoxy)methyl)carbonyl-4-(4-chlorobenzyl)piperazine;
1-((2-methoxy-4-carboxyphenoxy)methyl)carbonyl-4-(4-chlorobenzyl)piperazine;
1-((2,6-dimethoxy-4-carboxyphenoxy)methyl)carbonyl-4-(4-chlorobenzyl)piperazine;
1-((4-(2-carboxyethyl)phenoxy)methyl)carbonyl-4-(4-chlorobenzyl)piperazine;
1-((2-(2-hydroxyethyl)phenoxy)methyl)carbonyl-4-(4-chlorobenzyl)piperazine;
1-((3-(2-hydroxyethyl)phenoxy)methyl)carbonyl-4-(4-chlorobenzyl)piperazine;
1-((4-(2-hydroxyethyl)phenoxy)methyl)carbonyl-4-(4-chlorobenzyl)piperazine;
1-((2-methoxy-4-(2-hydroxyethyl)phenoxy)methyl) carbonyl-4-(4-chlorobenzyl)piperazine;
1-((2,4-dibromo-6-formylphenoxy)methyl)carbonyl-4-(4-chlorobenzyl)piperazine;
1-((2-fluoro-6-formylphenoxy)methyl)carbonyl-4-(4-chlorobenzyl)piperazine;
1-((2,4-dichloro-6-formylphenoxy)methyl)carbonyl-4-(4-chlorobenzyl)piperazine;
1-((2,4-diiodo-6-formylphenoxy)methyl)carbonyl-4-(4-chlorobenzyl)piperazine;
1-((2-methoxy-6-formylphenoxy)methyl)carbonyl-4-(4-chlorobenzyl)piperazine;
1-((2-ethoxy-6-formylphenoxy)methyl)carbonyl-4-(4-chlorobenzyl)piperazine;
1-((2-formyl-5-(diethylamino)phenoxy)methyl)carbonyl-4-(4-chlorobenzyl)piperazine;
1-((2-formyl-5-methoxyphenoxy)methyl)carbonyl-4-(4-chlorobenzyl)piperazine;
1-((2-formyl-3,5-dimethoxyphenoxy)methyl)carbonyl-4-(4-chlorobenzyl)piperazine;
1-((2-formyl-4-bromophenoxy)methyl)carbonyl-4-(4-chlorobenzyl)piperazine;
1-((2-formyl-4-methoxyphenoxy)methyl)carbonyl-4-(4-chlorobenzyl)piperazine;
1-(((4-methoxynapthalen-1-yl)oxy)methyl)carbonyl-4-(4-chlorobenzyl)piperazine;
1-((2-carboxy-5,6-dimethoxyphenoxy)methyl)carbonyl-4-(4-chlorobenzyl)piperazine;
1-((3-nitro-4-methoxyphenoxy)methyl)carbonyl-4-(4-chlorobenzyl)piperazine;
1-(((fluoren-9-on-1-yl)oxy)methyl)carbonyl-4-(4-chlorobenzyl)piperazine;
1-(((4-hydroxy-1,2,3,4-tetrahydronaphthalen-8-yl)oxy) methyl)carbonyl-4-(4-chlorobenzyl)piperazine;
1-((2,3,4,5,6-pentabromophenoxy)methyl)carbonyl-4-(4-chlorobenzyl)piperazine;
1-((2-methyl-3,4,5,6-tetrabromophenoxy)methyl) carbony-14-(4-chlorobenzyl)piperazine;
1-((2,3,4-trichlorophenoxy)methyl)carbonyl-4-(4-chlorobenzyl)piperazine;
1-((2-methyl-4-bromo-6-chlorophenoxy)methyl) carbonyl-4-(4-chlorobenzyl)piperazine;
1-((2-chloro-4-fluorophenoxy)methyl)carbonyl-4-(4-chlorobenzyl)piperazine;
1-((2,4,6-triiodophenoxy)methyl)carbonyl-4-(4-chlorobenzyl)piperazine;
1-((2-formyl-4-chlorophenoxy)methyl)carbonyl-4-(4-chlorobenzyl)piperazine;
1-((3-formylphenoxy)methyl)carbonyl-4-(4-chlorobenzyl)piperazine;
1-(((1-bromonaphthalen-2-yl)oxy)methyl)carbonyl-4-(4-chlorobenzyl)piperazine;
1-(((1,6-dibromonapthalen-2-yl)oxy)methyl)carbonyl-4-(4-chlorobenzyl)piperazine;
1-(((1-nitrosonaphthalen-2-yl)oxy)methyl)carbonyl-4-(4-chlorobenzyl)piperazine;
1-(((2,4-dichloronaphthalen-1-yl)oxy)methyl)carbonyl-4-(4-chlorobenzyl)piperazine;
1-(((2-nitronaphthalen-1-yl)oxy)methyl)carbonyl-4-(4-chlorobenzyl)piperazine;

1-(((2-carboxynaphthalen-1-yl)oxy)methyl)carbonyl-4-(4-chlorobenzyl)piperazine;
1-(((2-methylnaphthalen-1-yl)oxy)methyl)carbonyl-4-(4-chlorobenzyl)piperazine;
1-(((3-(hydroxysulfonyl)-7-(dimethylamino)naphthalen-1-yl)oxy)methyl)carbonyl-4-(4-chlorobenzyl)piperazine;
1-(((4-methoxynaphthalen-1-yl)oxy)methyl)carbonyl-4-(4-chlorobenzyl)piperazine;
1-(((1-formylnapthalen-2-yl)oxy)methyl)carbonyl-4-(4-chlorobenzyl)piperazine;
1-(((1-carboxynaphthalen-1-yl)oxy)methyl)carbonyl-4-(4-chlorobenzyl)piperazine;
1-(((1-amino-4-(hydroxysulfonyl)naphthalen-2-yl)oxy)methyl)carbonyl-4-(4-chlorobenzyl)piperazine;
1-((4-(naphthalen-2-yl)aminophenoxy)methyl)carbonyl-4-(4-chlorobenzyl)piperazine;
1-(((3-aminonaphthalen-2-yl)oxy)methyl)carbonyl-4-(4-chlorobenzyl)piperazine;
1-((2-fluoro-4-(carboxymethyl)phenoxy)methyl)carbonyl-4-(4-chlorobenzyl)piperazine;
1-((2-chloro-4-(carboxymethyl)phenoxy)methyl)carbonyl-4-(4-chlorobenzyl)piperazine;
1-((2-methoxy-4-(carboxymethyl)phenoxy)methyl)carbonyl-4-(4-chlorobenzyl)piperazine;
1-((4-hydroxymethylphenxoy)methyl)carbonyl-4-(4-chlorobenzyl)piperazine;
1-((2-(hydroxymethyl)-4-bromophenoxy)methyl)carbonyl-4-(4-chlorobenzyl)piperazine;
1-((2,6-di(hydroxymethyl)-4-methylphenoxy)methyl)carbonyl-4-(4-chlorobenzyl)piperazine;
1-((2-methoxy-4-(hydroxymethyl)phenoxy)methyl)carbonyl-4-(4-chlorobenzyl)piperazine;
1-((4-mercaptophenoxy)methyl)carbonyl-4-(4-chlorobenzyl)piperazine;
1-(((2-carboxyindol-5-yl)oxy)methyl)carbonyl-4-(4-chlorobenzyl)piperazine;
1-(((3-carboxyindol-5-yl)oxy)methyl)carbonyl-4-(4-chlorobenzyl)piperazine;
1-(((indol-4-yl)oxy)methyl)carbonyl-4-(4-chlorobenzyl)piperazine;
1-(((indol-5-yl)oxy)methyl)carbonyl-4-(4-chlorobenzyl)piperazine;
1-((2-(benzoxazol-2-yl)phenoxy)methyl)carbonyl-4-(4-chlorobenzyl)piperazine;
1-(((2-methylquinolin-8-yl)oxy)methyl)carbonyl-4-(4-chlorobenzyl)piperazine;
1-(((5,7-dibromoquinolin-8-yl)oxy)methyl)carbonyl-4-(4-chlorobenzyl)piperazine;
1-(((5,7-diiodoquinolin-8-yl)oxy)methyl)carbonyl-4-(4-chlorobenzyl)piperazine;
1-(((5-nitroquinolin-8-yl)oxy)methyl)carbonyl-4-(4-chlorobenzyl)piperazine;
1-(((quinolin-5-yl)oxy)methyl)carbonyl-4-(4-chlorobenzyl)piperazine;
1-(((5-(hydroxysulfonyl)-7-iodoquinolin-8-yl)oxy)methyl)carbonyl-4-(4-chlorobenzyl)piperazine;
1-(((2-phenyl-4-oxo-4H-1-benzopyran-7-yl)oxy)methyl)carbonyl-4-(4-chlorobenzyl)piperazine;
1-((2-carboxy-2,5,7,8-tetramethyl-2,3-dihydro-1-benzopyran-6-yl)oxy)methyl)carbonyl-4-(4-chlorobenzyl)piperazine;
1-(((2-oxo-3-chloro-4-methyl-2H-1-benzopyran-7-yl)oxy)methyl)carbonyl-4-(4-chlorobenzyl)piperazine;
1-(((2-oxo-3-(diethylamino)methyl)-4-methyl-2H-1-benzopyran-7-yl)oxy)methyl)carbonyl-4-(4-chlorobenzyl)piperazine;
1-(((2-oxo-6-methoxy-2H-1-benzopyran-7-yl)oxy)methyl)carbonyl-4-(4-chlorobenzyl)piperazine;
1-(((2-oxo-2H-1-benzopyran-7-yl)oxy)methyl)carbonyl-4-(4-chlorobenzyl)piperazine;
1-((2-methoxy-4-formyl-6-bromophenoxy)methyl)carbonyl-4-(4-chlorobenzyl)piperazine;
1-((2-methoxy-4-formyl-6-iodophenoxy)methyl)carbonyl-4-(4-chlorobenzyl)piperazine;
1-((2-methoxy-4-formylphenoxy)methyl)carbonyl-4-(4-chlorobenzyl)piperazine;
1-((2-ethoxy-4-formylphenoxy)methyl)carbonyl-4-(4-chlorobenzyl)piperazine;
1-((2-carboxy-4-formylphenoxy)methyl)carbonyl-4-(4-chlorobenzyl)piperazine;
1-((2,4-dichloro-6-nitrophenoxy)methyl)carbonyl-4-(4-chlorobenzyl)piperazine;
1-((2,4-dinitro-6-formylphenoxy)methyl)carbonyl-4-(4-chlorobenzyl)piperazine;
1-((2,4-dinitro-6-carboxyphenoxy)methyl)carbonyl-4-(4-chlorobenzyl)piperazine;
1-((2,4-dinitro-6-methylphenoxy)methyl)carbonyl-4-(4-chlorobenzyl)piperazine;
1-((2,5-dinitrophenoxy)methyl)carbonyl-4-(4-chlorobenzyl)piperazine;
1-((2-nitro-5-methylphenoxy)methyl)carbonyl-4-(4-chlorobenzyl)piperazine;
1-((2-nitro-4-chlorophenoxy)methyl)carbonyl-4-(4-chlorobenzyl)piperazine;
1-((2,4-dinitrophenoxy)methyl)carbonyl-4-(4-chlorobenzyl)piperazine;
1-((2-nitro-4-formylphenoxy)methyl)carbonyl-4-(4-chlorobenzyl)piperazine;
1-((2-nitro-4-formyl-6-methoxyphenoxy)methyl)carbonyl-4-(4-chlorobenzyl)piperazine;
1-((2-nitro-4-carboxyphenoxy)methyl)carbonyl-4-(4-chlorobenzyl)piperazine;
1-((2-nitro-4-methylphenoxy)methyl)carbonyl-4-(4-chlorobenzyl)piperazine;
1-((2,6-dinitro-4-methylphenoxy)methyl)carbonyl-4-(4-chlorobenzyl)piperazine;
1-((2-nitro-4-(carboxymethyl)phenoxy)methyl)carbonyl-4-(4-chlorobenzyl)piperazine;
1-((2,6-dichlorophenoxy)methyl)carbonyl-4-(4-chlorobenzyl)piperazine;
1-((3-methoxy-5-chlorophenoxy)methyl)carbonyl-4-(4-chlorobenzyl)piperazine;
1-((4-cyanophenoxy)methyl)carbonyl-4-(4-chlorobenzyl)piperazine;
1-((4-(1-methyl-1-phenylethyl)phenoxy)methyl)carbonyl-4-(4-chlorobenzyl)piperazine;
1-((3-(ethylamino)-4-methylphenoxy)methyl)carbonyl-4-(4-chlorobenzyl)piperazine;
1-(((2-acetylnaphthalen-1-yl)oxy)methyl)carbonyl-4-(4-chlorobenzyl)piperazine;
1-((2-(carboxymethyl)phenoxy)methyl)carbonyl-4-(4-chlorobenzyl)piperazine;
1-((4-(carboxymethyl)phenoxy)methyl)carbonyl-4-(4-chlorobenzyl)piperazine;

1-(((benzotriazol-1-yl)oxy)methyl)carbonyl-4-(4-chlorobenzyl)piperazine;
1-(((quinolin-2-yl)oxy)methyl)carbonyl-4-(4-chlorobenzyl)piperazine;
1-((4-formylphenoxy)methyl)carbonyl-4-(4-chlorobenzyl)piperazine;
1-((2,6-dimethoxy-4-formylphenoxy)methyl)carbonyl-4-(4-chlorobenzyl)piperazine;
1-((3,4-dimethoxyphenoxy)methyl)carbonyl-4-(4-chlorobenzyl)piperazine;
1-((2,4,6-tri(t-butyl)phenoxy)methyl)carbonyl-4-(4-chlorobenzyl)piperazine;
1-((2,6-dimethoxy-4-(methoxycarbonyl)phenoxy)methyl)carbonyl-4-(4-chlorobenzyl)piperazine;
1-((3-trifluoromethoxyphenoxy)methyl)carbonyl-4-(4-chlorobenzyl)piperazine;
1-((2-methyl-5-aminophenoxy)methyl)carbonyl-4-(4-chlorobenzyl)piperazine;
1-((4-(4-cyanophenyl)phenoxy)methyl)carbonyl-4-(4-chlorobenzyl)piperazine;
1-((3-nitro-4-aminophenoxy)methyl)carbonyl-4-(4-chlorobenzyl)piperazine;
1-((3-methylphenoxy)methyl)carbonyl-4-(4-chlorobenzyl)piperazine;
1-((4-methylphenox)methyl)carbonyl-4-(4-chlorobenzyl)piperazine;
1-((4-(methoxycarbonyl)methylphenoxy)methyl)carbonyl-4-(4-chlorobenzyl)piperazine;
1-(((carbazol-2-yl)oxy)methyl)carbonyl-4-(4-chlorobenzyl)piperazine;
1-(((2-oxo-1,3-benzothiol-2-on-6-yl)oxy)methyl)carbonyl-4-(4-chlorobenzyl)piperazine;
1-(((2-phenyl-4-oxo-4H-1-benzopyran-3-yl)oxy)methyl)carbonyl-4-(4-chlorobenzyl)piperazine;
1-(((2-oxo-4-methyl-2H-1-benzopyran-7-yl)oxy)methyl)carbonyl-4-(4-chlorobenzyl)piperazine;
1-((4-nitrophenoxy)methyl)carbonyl-4-(4-chlorobenzyl)piperazine;
1-((3-carboxy-4-aminophenoxy)methyl)carbonyl-4-(4-chlorobenzyl)piperazine;
1-((2-methoxy-5-aminophenoxy)methyl)carbonyl-4-(4-chlorobenzyl)piperazine;
1-(((2-phenyl-4-oxo-2,3-dihydro-4H-1-benzopyran-6-yl)oxy)methyl)carbonyl-4-(4-chlorobenzyl)piperazine;
1-(((quinolin-6-yl)oxy)methyl)carbonyl-4-(4-chlorobenzyl)piperazine;
1-((2,3-diaminophenoxy)methyl)carbonyl-4-(4-chlorobenzyl)piperazine;
1-((4-(hydroxysulfonyl)phenoxy)methyl)carbonyl-4-(4-chlorobenzyl)piperazine;
1-(((fluorenon-9-on-2-yl)oxy)methyl)carbonyl-4-(4-chlorobenzyl)piperazine;
1-(((5,6,7,8-tetrahydronaphthalen-1-yl)oxy)methyl)carbonyl-4-(4-chlorobenzyl)piperazine;
1-(((5,6,7,8-tetrahydronaphthalen-2-yl)oxy)methyl)carbonyl-4-(4-chlorobenzyl)piperazine;
1-((2,4,6-tribromophenoxy)methyl)carbonyl-4-(4-chlorobenzyl)piperazine;
1-((2,6-dibromo-4-cyanophenoxy)methyl)carbonyl-4-(4-chlorobenzyl)piperazine;
1-((2-fluorophenoxy)methyl)carbonyl-4-(4-chlorobenzyl)piperazine;
1-((2,3,5,6-tetrafluorophenoxy)methyl)carbonyl-4-(4-chlorobenzyl)piperazine;
1-((2,6-difluorophenoxy)methyl)carbonyl-4-(4-chlorobenzyl)piperazine;
1-((2,3-dichlorophenoxy)methyl)carbonyl-4-(4-chlorobenzyl)piperazine;
1-((2,3,6-trichlorophenoxy)methyl)carbonyl-4-(4-chlorobenzyl)piperazine;
1-((2-chloro-4,5-dimethylphenoxy)methyl)carbonyl-4-(4-chlorobenzyl)piperazine;
1-((2,5-dichlorophenoxy)methyl)carbonyl-4-(4-chlorobenzyl)piperazine;
1-((2-chloro-5-methylphenoxy)methyl)carbonyl-4-(4-chlorobenzyl)piperazine;
1-((2-(methylcarbonyl)aminophenoxy)methyl)carbonyl-4-(4-chlorobenzyl)piperazine;
1-((2-isopropoxyphenoxy)methyl)carbonyl-4-(4-chlorobenzyl)piperazine;
1-((2-(benzyloxy)phenoxy)methyl)carbonyl-4-(4-chlorobenzyl)piperazine;
1-((2-ethoxyphenoxy)methyl)carbonyl-4-(4-chlorobenzyl)piperazine;
1-((2-phenylphenoxy)methyl)carbonyl-4-(4-chlorobenzyl)piperazine;
1-((2-(methoxycarbonyl)phenoxy)methyl)carbonyl-4-(4-chlorobenzyl)piperazine;
1-((2-(ethoxycarbonyl)phenoxy)methyl)carbonyl-4-(4-chlorobenzyl)piperazine;
1-((2-acetylphenoxy)methyl)carbonyl-4-(4-chlorobenzyl)piperazine;
1-((2-(ethylcarbonyl)phenoxy)methyl)carbonyl-4-(4-chlorobenzyl)piperazine;
1-((2-(t-butyl)phenoxy)methyl)carbonyl-4-(4-chlorobenzyl)piperazine;
1-((2-isopropylphenoxy)methyl)carbonyl-4-(4-chlorobenzyl)piperazine;
1-((2-(1-methylpropyl)phenoxy)methyl)carbonyl-4-(4-chlorobenzyl)piperazine;
1-((2,3-dimethylphenoxy)methyl)carbonyl-4-(4-chlorobenzyl)piperazine;
1-((2,3,5-trimethylphenoxy)methyl)carbonyl-4-(4-chlorobenzyl)piperazine;
1-((2,3,6-trimethylphenxoy)methyl)carbonyl-4-(4-chlorobenzyl)piperazine;
1-((2,4-dimethylphenoxy)methyl)carbonyl-4-(4-chlorobenzyl)piperazine;
1-((2,4,6-trimethoxy)methyl)carbonyl-4-(4-chlorobenzyl)piperazine;
1-((2-methyl-5-isopropylphenoxy)methyl)carbonyl-4-(4-chlorobenzyl)piperazine;
1-((2,5-dimethylphenoxy)methyl)carbonyl-4-(4-chlorobenzyl)piperazine;
1-((2,5-dimethyl-4-(diethylamino)methylphenoxy)methyl)carbonyl-4-(4-chlorobenzyl)piperazine;
1-((2-(t-butyl)-6-methylphenoxy)methyl)carbonyl-4-(4-chlorobenzyl)piperazine;
1-((2,6-dimethoxyphenoxy)methyl)carbonyl-4-(4-chlorobenzyl)piperazine;
1-((2-prop-3-enyl-6-methylphenoxy)methyl)carbonyl-4-(4-chlorobenzyl)piperazine;
1-((2-prop-2-enylphenoxy)methyl)carbonyl-4-(4-chlorobenzyl)piperazine;

1-((2-ethylphenoxy)methyl)carbonyl-4-(4-chlorobenzyl)piperazine;
1-((2-n-propylphenoxy)methyl)carbonyl-4-(4-chlorobenzyl)piperazine;
1-((3-fluorophenoxy)methyl)carbonyl-4-(4-chlorobenzyl)piperazine;
1-((3,5-difluorophenoxy)methyl)carbonyl-4-(4-chlorobenzyl)piperazine;
1-((3-chloro-4-fluorophenoxy)methyl)carbonyl-4-(4-chlorobenzyl)piperazine;
1-((3,5-dichlorophenoxy)methyl)carbonyl-4-(4-chlorobenzyl)piperazine;
1-((3-iodophenoxy)methyl)carbonyl-4-(4-chlorobenzyl)piperazine;
1-((3-(phenylamino)phenoxy)methyl)carbonyl-4-(4-chlorobenzyl)piperazine;
1-((3-(diethylamino)phenoxy)methyl)carbonyl-4-(4-chlorobenzyl)piperazine;
1-((3-phenylphenoxy)methyl)carbonyl-4-(4-chlorobenzyl)piperazine;
1-((3-acetylphenoxy)methyl)carbonyl-4-(4-chlorobenzyl)piperazine;
1-((3-trifluoromethylphenoxy)methyl)carbonyl-4-(4-chlorobenzyl)piperazine;
1-((3-t-butylphenoxy)methyl)carbonyl-4-(4-chlorobenzyl)piperazine;
1-((3-isopropylphenoxy)methyl)carbonyl-4-(4-chlorobenzyl)piperazine;
1-((3-methyl-4-acetylphenoxy)methyl)carbonyl-4-(4-chlorobenzyl)piperazine;
1-((3,4-dimethylphenoxy)methyl)carbonyl-4-(4-chlorobenzyl)piperazine;
1-((2-t-butyl-5-methylphenoxy)methyl)carbonyl-4-(4-chlorobenzyl)piperazine;
1-((2-isopropyl-5-methylphenoxy)methyl)carbonyl-4-(4-chlorobenzyl)piperazine;
1-((3-ethylphenoxy)methyl)carbonyl-4-(4-chlorobenzyl)piperazine;
1-((2,6-dimethyl-4-bromophenoxy)methyl)carbonyl-4-(4-chlorobenzyl)piperazine;
1-((2,6-dibromo-4-fluorophenoxy)methyl)carbonyl-4-(4-chlorobenzyl)piperazine;
1-((2-bromo-4-chlorophenoxy)methyl)carbonyl-4-(4-chlorobenzyl)piperazine;
1-((2-methyl-4-chlorophenoxy)methyl)carbonyl-4-(4-chlorobenzyl)piperazine;
1-((2-isopropyl-4-chloro-5-methylphenoxy)methyl)carbonyl-4-(4-chlorobenzyl)piperazine;
1-((4-(methylcarbonyl)aminophenoxy)methyl)carbonyl-4-(4-chlorobenzyl)piperazine;
1-((4-ethoxyphenoxy)methyl)carbonyl-4-(4-chlorobenzyl)piperazine;
1-((4-propoxyphenoxy)methyl)carbonyl-4-(4-chlorobenzyl)piperazine;
1-((4-n-butoxyphenoxy)methyl)carbonyl-4-(4-chlorobenzyl)piperazine;
1-((4-n-hexoxyphenoxy)methyl)carbonyl-4-(4-chlorobenzyl)piperazine;
1-((4-n-heptoxyphenoxy)methyl)carbonyl-4-(4-chlorobenzyl)piperazine;
1-((4-(propoxycarbonyl)phenoxy)methyl)carbonyl-4-(4-chlorobenzyl)piperazine;
1-((4-(ethylcarbonyl)phenoxy)methyl)carbonyl-4-(4-chlorobenzyl)piperazine;
1-((4-(1,1,3,3-tetramethylbutyl)phenoxy)methyl)carbonyl-4-(4-chlorobenzyl)piperazine;
1-((4-(1,1-dimethylpropyl)phenoxy)methyl)carbonyl-4-(4-chlorobenzyl)piperazine;
1-((4-(1-methylpropyl)phenoxy)methyl)carbonyl-4-(4-chlorobenzyl)piperazine;
1-((2-methoxy-4-methylphenoxy)methyl)carbonyl-4-(4-chlorobenzyl)piperazine;
1-((2-acetyl-4-methylphenoxy)methyl)carbonyl-4-(4-chlorobenzyl)piperazine;
1-((2-(t-butyl)-4-methylphenoxy)methyl)carbonyl-4-(4-chlorobenzyl)piperazine;
1-((3-(ethylamino)-4-methylphenoxy)methyl)carbonyl-4-(4-chlorobenzyl)piperazine;
1-((4-(methoxycarbonyl)methylphenoxy)methyl)carbonyl-4-(4-chlorobenzyl)piperazine;
1-((4-ethylphenoxy)methyl)carbonyl-4-(4-chlorobenzyl)piperazine;
1-((4-n-propylphenoxy)methyl)carbonyl-4-(4-chlorobenzyl)piperazine;
1-((2-carboxyphenoxy)methyl)carbonyl-4-(4-chlorobenzyl)piperazine;
1-((2-carboxy-4,6-dibromophenoxy)methyl)carbonyl-4-(4-chlorobenzyl)piperazine;
1-((2-carboxy-4,6-dichlorophenoxy)methyl)carbonyl-4-(4-chlorobenzyl)piperazine;
1-((2-carboxy-4,6-diiodophenoxy)methyl)carbonyl-4-(4-chlorobenzyl)piperazine;
1-((2-carboxy-6-methoxyphenoxy)methyl)carbonyl-4-(4-chlorobenzyl)piperazine;
1-((2-carboxy-6-methylphenoxy)methyl)carbonyl-4-(4-chlorobenzyl)piperazine;
1-((2-carboxy-5-chlorophenoxy)methyl)carbonyl-4-(4-chlorobenzyl)piperazine;
1-((2-carboxy-5-methoxyphenoxy)methyl)carbonyl-4-(4-chlorobenzyl)piperazine;
1-((2-carboxy-5-methylphenoxy)methyl)carbonyl-4-(4-chlorobenzyl)piperazine;
1-((2-carboxy-4-bromophenoxy)methyl)carbonyl-4-(4-chlorobenzyl)piperazine;
1-((2-carboxy-4-fluorophenoxy)methyl)carbonyl-4-(4-chlorobenzyl)piperazine;
1-((2-carboxy-4-chlorophenoxy)methyl)carbonyl-4-(4-chlorobenzyl)piperazine;
1-((2-carboxy-4-iodophenoxy)methyl)carbonyl-4-(4-chlorobenzyl)piperazine;
1-((2-carboxy-4-methoxyphenoxy)methyl)carbonyl-4-(4-chlorobenzyl)piperazine;
1-((2-chlorophenoxy)methyl)carbonyl-4-(4-chlorobenzyl)piperazine;
1-((2,3,4-trichlorophenoxy)methyl)carbonyl-4-(4-chlorobenzyl)piperazine;
1-((2,3,4,5,6-pentachlorophenoxy)methyl)carbonyl-4-(4-chlorobenzyl)piperazine;
1-((2,4,5-trichlorophenoxy)methyl)carbonyl-4-(4-chlorobenzyl)piperazine;
1-((3-methoxyphenoxy)methyl)carbonyl-4-(4-chlorobenzyl)piperazine;
1-((3-(methoxycarbonyl)phenoxy)methyl)carbonyl-4-(4-chlorobenzyl)piperazine;

1-((3-(ethoxycarbonyl)phenoxy)methyl)carbonyl-4-(4-chlorobenzyl)piperazine;
1-((4-bromophenoxy)methyl)carbonyl-4-(4-chlorobenzyl)piperazine;
1-((2,6-dimethyl-4-bromophenoxy)methyl)carbonyl-4-(4-chlorobenzyl)piperazine;
1-((3,5-dimethyl-4-bromophenoxy)methyl)carbonyl-4-(4-chlorobenzyl)piperazine;
1-((3-methyl-4-chlorophenoxy)methyl)carbonyl-4-(4-chlorobenzyl)piperazine;
1-((2-isopropyl-4-chloro-5-methylphenoxy)methyl)carbonyl-4-(4-chlorobenzyl)piperazine;
1-((4-ethoxyphenoxy)methyl)carbonyl-4-(4-chlorobenzyl)piperazine;
1-((2-(-butyl)-4-methylphenoxy)methyl)carbonyl-4-(4-chlorobenzyl)piperazine;
1-((3-formyl-4-nitrophenoxy)methyl)carbonyl-4-(4-chlorobenzyl)piperazine;
1-((2-methoxy-4-prop-3-enylphenoxy)methyl)carbonyl-4-(4-chlorobenzyl)piperazine;
1-((2-(1-phenyethyl)-4-chlorophenoxy)methyl)carbonyl-4-(4-chlorobenzyl)piperazine;
1-((4-(ethoxycarbonyl)methylphenoxy)methyl)carbonyl-4-(4-chlorobenzyl)piperazine;
1-((4-trifluoromethoxyphenoxy)methyl)carbonyl-4-(4-chlorobenzyl)piperazine;
1-((3-fluoro-4-chlorophenoxy)methyl)carbonyl-4-(4-chlorobenzyl)piperazine;
1-((2-fluoro-4-chlorophenoxy)methyl)carbonyl-4-(4-chlorobenzyl)piperazine;
1-(((7-methoxynaphthalen-2-yl)oxy)methyl)carbonyl-4-(4-chlorobenzyl)piperazine;
1-((2-benzyloxy-4-cyanophenoxy)methyl)carbonyl-4-(4-chlorobenzyl)piperazine;
1-((2-chloro-3,5-dimethoxyphenoxy)methyl)carbonyl-4-(4-chlorobenzyl)piperazine;
1-((2-bromo-3,5-dimethoxyphenoxy)methyl)carbonyl-4-(4-chlorobenzyl)piperazine;
1-((3,5-dimethoxy-4-bromophenoxy)methyl)carbonyl-4-(4-chlorobenzyl)piperazine;
1-((2,6-dibromo-3,5-dimethoxyphenoxy)methyl)carbonyl-4-(4-chlorobenzyl)piperazine;
1-((4-chlorophenoxy)methyl)carbonyl-4-(4-chlorobenzyl)piperazine;
1-((3-nitrophenoxy)methyl)carbonyl-4-(4-chlorobenzyl)piperazine;
1-((2-methyl-3-nitrophenoxy)methyl)carbonyl-4-(4-chlorobenzyl)piperazine;
1-((3,5-dimethoxyphenoxy)methyl)carbonyl-4-(4-chlorobenzyl)piperazine;
1-((2-nitro-3-carboxy-6-methylphenoxy)methyl)carbonyl-4-(4-chlorobenzyl)piperazine;
1-((3-cyanophenoxy)methyl)carbonyl-4-(4-chlorobenzyl)piperazine;
1-((2-methoxy-5-nitrophenoxy)methyl)carbonyl-4-(4-chlorobenzyl)piperazine;
1-((2-nitro-5-carboxyphenoxy)methyl)carbonyl-4-(4-chlorobenzyl)piperazine;
1-((3-(carboxymethyl)phenoxy)methyl)carbonyl-4-(4-chlorobenzyl)piperazine;
1-((2-methoxy-5-carboxyphenoxy)methyl)carbonyl-4-(4-chlorobenzyl)piperazine;
1-((4-(dimethylamino)methylphenoxy)methyl)carbonyl-4-(4-chlorobenzyl)piperazine;
1-((4-(2-(dimethylamino)ethylphenoxy)methyl)carbonyl-4-(4-chlorobenzyl)piperazine;
1-((3-carboxyphenoxy)methyl)carbonyl-4-(4-chlorobenzyl)piperazine;
1-(((naphthalen-1-yl)oxy)methyl)carbonyl-4-(4-chlorobenzyl)piperazine;
1-(((5-aminonaphthalen-1-yl)oxy)methyl)carbonyl-4-(4-chlorobenzyl)piperazine;
1-((3-nitro-4-aminophenoxy)methyl)carbonyl-4-(4-chlorobenzyl)piperazine;
1-((2,6-di(t-butyl)-4-methylphenoxy)methyl)carbonyl-4-(4-chlorobenzyl)piperazine;
1-((3-carboxy-4-nitrophenoxy)methyl)carbonyl-4-(4-chlorobenzyl)piperazine;
1-((2-methyl-5-carboxyphenoxy)methyl)carbonyl-4-(4-chlorobenzyl)piperazine;
1-((2-nitro-4-aminophenoxy)methyl)carbonyl-4-(4-chlorobenzyl)piperazine;
1-((4-(benzyloxy)phenoxy)methyl)carbonyl-4-(4-chlorobenzyl)piperazine;
1-((4-(aminocarbonyl)phenoxy)methyl)carbonyl-4-(4-chlorobenzyl)piperazine;
1-((3,5-di(trifluoromethyl)phenoxy)methyl)carbonyl-4-(4-chlorobenzyl)piperazine;
1-((2,4-dibromophenoxy)methyl)carbonyl-4-(4-chlorobenzyl)piperazine;
1-((2,6-dibromo-4-methylphenoxy)methyl)carbonyl-4-(4-chlorobenzyl)piperazine;
1-((2,4-dichlorophenoxy)methyl)carbonyl-4-(4-chlorobenzyl)piperazine;
1-((3-methoxyphenoxy)methyl)carbonyl-4-(4-chlorobenzyl)piperazine;
1-((3,5-dimethyl-4-bromophenoxy)methyl)carbonyl-4-(4-chlorobenzyl)piperazine;
1-((3,5-dicarboxyphenoxy)methyl)carbonyl-4-(4-chlorobenzyl)piperazine;
1-((2-chloro-4-carboxyphenoxy)methyl)carbonyl-4-(4-chlorobenzyl)piperazine;
1-((2,6-dichloro-4-carboxyphenoxy)methyl)carbonyl-4-(4-chlorobenzyl)piperazine;
1-(((2-carboxyquinolin-4-yl)oxy)methyl)carbonyl-4-(4-chlorobenzyl)piperazine;
1-((2,6-dimethyl-4-formylphenoxy)methyl)carbonyl-4-(4-chlorobenzyl)piperazine;
1-((2,6-di(t-butyl)-4-carboxyphenoxy)methyl)carbonyl-4-(4-chlorobenzyl)piperazine;
1-((2-amino-5-carboxyphenoxy)methyl)carbonyl-4-(4-chlorobenzyl)piperazine;
1-((2,6-di(t-butyl)-4-(hydroxymethyl)phenoxy)methyl)carbonyl-4-(4-chlorobenzyl)piperazine;
1-(((4-carboxyquinolin-2-yl)oxy)methyl)carbonyl-4-(4-chlorobenzyl)piperazine;
1-((3-nitro-4-chlorophenoxy)methyl)carbonyl-4-(4-chlorobenzyl)piperazine;
1-((3-ethyl-4-chloro-5-methylphenoxy)methyl)carbonyl-4-(4-chlorobenzyl)piperazine;
1-((3,5-di(methoxycarbonyl)phenoxy)methyl)carbonyl-4-(4-chlorobenzyl)piperazine;
1-((2-(morpholin-4-yl)methyl-4-carboxyphenoxy)methyl)carbonyl-4-(4-chlorobenzyl)piperazine;

1-((2-methoxy-4-cyanophenoxy)methyl)carbonyl-4-(4-chlorobenzyl)piperazine;
1-((2-chloro-4-bromophenoxy)methyl)carbonyl-4-(4-chlorobenzyl)piperazine;
1-((2-trifluoromethylphenoxy)methyl)carbonyl-4-(4-chlorobenzyl)piperazine;
1-((2-methylphenoxy)methyl)carbonyl-4-(4-chlorobenzyl)piperazine;
1-((2-methyl-4-acetylphenoxy)methyl)carbonyl-4-(4-chlorobenzyl)piperazine;
1-((3-(dimethylamino)phenoxy)methyl)carbonyl-4-(4-chlorobenzyl)piperazine;
1-((3-methyl-4-acetylphenoxy)methyl)carbonyl-4-(4-chlorobenzyl)piperazine;
1-((3,5-dimethylphenoxy)methyl)carbonyl-4-(4-chlorobenzyl)piperazine;
1-((4-phenylphenoxy)methyl)carbonyl-4-(4-chlorobenzyl)piperazine;
1-((4-(ethoxycarbonyl)phenoxy)methyl)carbonyl-4-(4-chlorobenzyl)piperazine;
1-((4-acetylphenoxy)methyl)carbonyl-4-(4-chlorobenzyl)piperazine;
1-((4-benzylphenoxy)methyl)carbonyl-4-(4-chlorobenzyl)piperazine;
1-((2-methoxy-4-carboxyphenoxy)methyl)carbonyl-4-(4-chlorobenzyl)piperazine;
1-(((3-carboxynaphthalen-2-yl)oxy)methyl)carbonyl-4-(4-chlorobenzyl)piperazine;
1-((2-(hydroxymethyl)phenoxy)methyl)carbonyl-4-(4-chlorobenzyl)piperazine;
1-(((quinolin-8-yl)oxy)methyl)carbonyl-4-(4-chlorobenzyl)piperazine;
1-((3-aminophenoxy)methyl)carbonyl-4-(4-chlorobenzyl)piperazine;
1-((4-(aminocarbonyl)phenoxy)methyl)carbonyl-4-(4-chlorobenzyl)piperazine;
1-((3,5-dimethoxyphenoxy)methyl)carbonyl-4-(4-chlorobenzyl)piperazine;
1-((2-(cyclohexyl)phenoxy)methyl)carbonyl-4-(4-chlorobenzyl)piperazine;
1-(((quinolin-6-yl)oxy)methyl)carbonyl-4-(4-chlorobenzyl)piperazine;
1-((2,4-dichloro-3-methylphenoxy)methyl)carbonyl-4-(4-chlorobenzyl)piperazine;
1-((2,5-dimethylphenoxy)methyl)carbonyl-4-(4-chlorobenzyl)piperazine;
1-((3-bromophenoxy)methyl)carbonyl-4-(4-chlorobenzyl)piperazine;
1-((3-(methylcarbonyl)aminophenoxy)methyl)carbonyl-4-(4-chlorobenzyl)piperazine;
1-((3-acetylphenoxy)methyl)carbonyl-4-(4-chlorobenzyl)piperazine;
1-((3-trifluoromethylphenoxy)methyl)carbonyl-4-(4-chlorobenzyl)piperazine;
1-((4-bromophenoxy)methyl)carbonyl-4-(4-chlorobenzyl)piperazine;
1-((2-formylphenoxy)methyl)carbonyl-4-(4-chlorobenzyl)piperazine;
1-((2-methoxy-5-formylphenoxy)methyl)carbonyl-4-(4-chlorobenzyl)piperazine;
1-(((tropinon-yl)oxy)methyl)carbonyl-4-(4-chlorobenzyl)piperazine;
1-((2-nitro-5-fluorophenoxy)methyl)carbonyl-4-(4-chlorobenzyl)piperazine;
1-((2-nitro-5-formylphenoxy)methyl)carbonyl-4-(4-chlorobenzyl)piperazine;
1-((3-formyl-4-nitrophenoxy)methyl)carbonyl-4-(4-chlorobenzyl)piperazine;
1-((2-carboxy-5-nitrophenoxy)methyl)carbonyl-4-(4-chlorobenzyl)piperazine;
1-((2-amino-4-nitrophenoxy)methyl)carbonyl-4-(4-chlorobenzyl)piperazine;
1-((2-amino-3-carboxyphenoxy)methyl)carbonyl-4-(4-chlorobenzyl)piperazine;
1-((2-nitro-4-aminophenoxy)methyl)carbonyl-4-(4-chlorobenzyl)piperazine;
1-((2,6-dichloro-4-nitrophenoxy)methyl)carbonyl-4-(4-chlorobenzyl)piperazine;
1-((3-fluoro-4-nitrophenoxy)methyl)carbonyl-4-(4-chlorobenzyl)piperazine;
1-((2,3-difluoro-6-nitrophenoxy)methyl)carbonyl-4-(4-chlorobenzyl)piperazine;
1-((2-chloro-4-nitrophenoxy)methyl)carbonyl-4-(4-chlorobenzyl)piperazine;
1-((2-nitro-4-cyanophenoxy)methyl)carbonyl-4-(4-chlorobenzyl)piperazine;
1-((2-bromo-4-methylphenoxy)methyl)carbonyl-4-(4-chlorobenzyl)piperazine;
1-((3-chlorophenoxy)methyl)carbonyl-4-(4-chlorobenzyl)piperazine;
1-((3,4-dichlorophenoxy)methyl)carbonyl-4-(4-chlorobenzyl)piperazine;
1-((3,5-dichlorophenoxy)methyl)carbonyl-4-(4-chlorobenzyl)piperazine;
1-((3,4,5-trimethylphenoxy)methyl)carbonyl-4-(4-chlorobenzyl)piperazine;
1-((4-fluorophenoxy)methyl)carbonyl-4-(4-chlorobenzyl)piperazine;
1-((3,5-dimethyl-4-chlorophenoxy)methyl)carbonyl-4-(4-chlorobenzyl)piperazine;
1-((4-methoxyphenoxy)methyl)carbonyl-4-(4-chlorobenzyl)piperazine;
1-((4-(methoxycarbonyl)phenoxy)methyl)carbonyl-4-(4-chlorobenzyl)piperazine;
1-((4-trifluoromethylphenoxy)methyl)carbonyl-4-(4-chlorobenzyl)piperazine;
1-((4-t-butylphenoxy)methyl)carbonyl-4-(4-chlorobenzyl)piperazine;
1-((4-isopropylphenoxy)methyl)carbonyl-4-(4-chlorobenzyl)piperazine;
1-(((naphthalen-2-yl)oxy)methyl)carbonyl-4-(4-chlorobenzyl)piperazine;
1-(((6-bromonaphthalen-2-yl)oxy)methyl)carbonyl-4-(4-chlorobenzyl)piperazine;
1-((3-(hydroxymethyl)phenoxy)methyl)carbonyl-4-(4-chlorobenzyl)piperazine;
1-((2-methoxy-5-(hydroxymethyl)phenoxy)methyl)carbonyl-4-(4-chlorobenzyl)piperazine;
1-(((1,3-benzodioxolan-5-yl)oxy)methyl)carbonyl-4-(4-chlorobenzyl)piperazine;
1-((2,6-dimethyl-4-nitrophenoxy)methyl)carbonyl-4-(4-chlorobenzyl)piperazine;
1-((2-nitrophenoxy)methyl)carbonyl-4-(4-chlorobenzyl)piperazine;

1-((2-methoxy-4-(amino)methylphenoxy)methyl)
carbonyl-4-(4-chlorobenzyl)piperazine;

1-((3-(aminocarbonyl)phenoxy)methyl)carbonyl-4-(4-chlorobenzyl)piperazine;

1-((3-(methoxycarbonyl)methylphenoxy)methyl)
carbonyl-4-(4-chlorobenzyl)piperazine;

1-((2-(4-phenylcarbonyl)-4-fluorophenoxy)methyl)
carbonyl-2,5-dimethyl-4-(4-fluorobenzyl)piperazine;

1-((2-(-methyl)cyclohexyl-2,4-dimethylphenoxy)methyl)
carbonyl-2,5-dimethyl-4-(4-fluorobenzyl)piperazine;

1-((2-(benzyloxycarbonyl)phenoxy)methyl)carbonyl-4-(4-fluorobenzyl)piperazine;

1-((2-(4-(methyl)phenylcarbonyl)-5-methoxyphenoxy)
methyl)carbonyl-4-(4-fluorobenzyl)piperazine;

1-((2-phenylcarbonyl-5-octoxyphenoxy)methyl)
carbonyl-4-(4-fluorobenzyl)piperazine;

1-((4-octylphenoxy)methyl)carbonyl-4-(4-fluorobenzyl)
piperazine;

1-((2-(2-(carboxy)phenylcarbonyl-5-di(n-butyl)
aminophenoxy)methyl)carbonyl-4-(4-fluorobenzyl)
piperazine;

1-((2-phenylcarbonyl-5-methoxyphenoxy)methyl)
carbonyl-4-(4-fluorobenzyl)piperazine;

1-((2-methoxy-4-(3-hydroxyprop-2-enyl)phenoxy)
methyl)carbonyl-4-(4-fluorobenzyl)piperazine;

1-(((3-(phenylaminocarbonyl)naphthalen-2-yl)oxy)
methyl)carbonyl-4-(4-fluorobenzyl)piperazine;

1-(((6-(phenylcarbonyl)naphthalen-2-yl)oxy)methyl)
carbonyl-4-(4-fluorobenzyl)piperazine;

1-((2-((2-phenylethyl)carbonyl)phenoxy)methyl)
carbonyl-4-(4-fluorobenzyl)piperazine;

1-((4-((4-fluorophenyl)carbonyl)phenoxy)methyl)
carbonyl-4-(4-fluorobenzyl)piperazine;

1-((2-(phenylamino)carbonylphenoxy)methyl)carbonyl-4-(4-fluorobenzyl)piperazine;

1-((2-phenylcarbonylphenoxy)methyl)carbonyl-4-(4-fluorobenzyl)piperazine;

1-((2-phenylcarbonyl-4-chloro-5-methylphenoxy)
methyl)carbonyl-4-(4-fluorobenzyl)piperazine;

1-((4-(4-chlorophenyl)carbonylphenoxy)methyl)
carbonyl-4-(4-fluorobenzyl)piperazine;

1-((4-benzylcarbonyl)phenoxy)methyl)carbonyl-4-(4-fluorobenzyl)piperazine;

1-((2-phenylcarbonyl-4-methylphenoxy)methyl)
carbonyl-4-(4-fluorobenzyl)piperazine;

1-((4-(2-methylcarbonylethyl)phenoxy)methyl)carbonyl-4-(4-fluorobenzyl)piperazine;

1-((4-phenylcarbonylphenoxy)methyl)carbonyl-4-(4-fluorobenzyl)piperazine; and 1-((3-phenylcarbonylphenoxy)methyl)carbonyl-4-(4-fluorobenzyl)piperazine;

D. In a similar manner, other compounds of formulae (Ia), (Ib), (Ic) and (Id) are made.

EXAMPLE 3

Compounds of Formula (Ia) and Formula (Ib)

A. To a solution of 1-((3,4,5-trimethoxyphenoxy)methyl)carbonylpiperazine (0.22 g, 0.70 mmol) in 1% acetic acid in methanol (6 mL) was added 4-cyanobenzaldehyde (0.33 g, 2.5 mmol) and sodium cyanoborohydride (0.093 g, 1.4 mmol). The resultant mixture was stirred at ambient temperature for 1.5 hours and the mixture was then concentrated of volatiles in vacuo. Residue was taken up in ethyl acetate and washed with saturated aqueous $NaHCO_3$ solution, water, and then brine. The organic layer was separated, dried over $MgSO_4$, filtered and concentrated in vacuo to afford a yellow oil. Purification by flash column chromatography on silica gel afforded 0.21 g of 1-((3,4,5-trimethoxyphenoxy)methyl)carbonyl-4-(4-cyanobenzyl)piperazine, a compound of formula (Ib) as a clear oil: NMR ($CDCl_3$) 7.6 (d, 2), 7.4 (d, 2), 6.2 (s, 2), 4.6 (s, 2), 3.8 (s, 6), 3.75 (s, 3), 3.6 (m, 4), 3.5 (s, 2), 2.2 (m, 4) ppm.

B. In a similar manner, other compounds of formula (Ib) were made:

1-((3,4,5-trimethoxyphenoxy)methyl)carbonyl-4-(3,4-dimethoxybenzyl)piperazine;

1-((3,4,5-trimethoxyphenoxy)methyl)carbonyl-4-(4-methoxybenzyl)piperazine;

1-((3,4,5-trimethoxyphenoxy)methyl)carbonyl-4-(3-chlorobenzyl)piperazine;

1-((3,4,5-trimethoxyphenoxy)methyl)carbonyl-4-(3-trifluoromethylbenzyl)piperazine;

1-((3,4,5-trimethoxyphenoxy)methyl)carbonyl-4-(2,3-dimethyl-4-methoxybenzyl)piperazine;

1-((3,4,5-trimethoxyphenoxy)methyl)carbonyl-4-(3-phenoxybenzyl)piperazine;

1-((3,4,5-trimethoxyphenoxy)methyl)carbonyl-4-(4-(dimethylamino)benzyl)piperazine;

1-((3,4,5-trimethoxyphenoxy)methyl)carbonyl-4-(4-(methylthio)benzyl)piperazine;

1-((3,4,5-trimethoxyphenoxy)methyl)carbonyl-4-(4-methoxy 3-methylbenzyl)piperazine;

1-((3,4,5-trimethoxyphenoxy)methyl)carbonyl-4-(2-chlorobenzyl)piperazine;

1-((3,4,5-trimethoxyphenoxy)methyl)carbonyl-4-(3-nitrobenzyl)piperazine;

1-((3,4,5-trimethoxyphenoxy)methyl)carbonyl-4-(4-hydroxybenzyl)piperazine;

1-((3,4,5-trimethoxyphenoxy)methyl)carbonyl-4-(3,5-dibromo-4-hydroxybenzyl)piperazine;

1-((3,4,5-trimethoxyphenoxy)methyl)carbonyl-4-(2-fluorobenzyl)piperazine;

1-((3,4,5-trimethoxyphenoxy)methyl)carbonyl-4-(4-fluorobenzyl)piperazine; NMR ($CDCl_3$) 7.3 (m, 2), 7.0 (m, 2), 6.2 (s, 2), 4.6 (s, 2), 3.9 (m, 9), 3.6 (m, 4), 3.4 (s, 2), 2.4 (m, 4) ppm;

1-((3,4,5-trimethoxyphenoxy)methyl)carbonyl-4-(4-bromobenzyl)piperazine; NMR ($CDCl_3$) 7.4 (d, 2), 7.2 (d, 2), 6.2 (s, 2), 4.6 (s, 2), 3.85 (s, 6), 3.75 (s, 3), 3.6 (m, 4), 3.4 (s, 2), 2.4 (m, 4) ppm;

1-((3,4,5-trimethoxyphenoxy)methyl)carbonyl-4-(2-bromobenzyl)piperazine;

1-((3,4,5-trimethoxyphenoxy)methyl)carbonyl-4-(3-fluorobenzyl)piperazine;

1-((3,4,5-trimethoxyphenoxy)methyl)carbonyl-4-(3-bromobenzyl)piperazine;

1-((3,4,5-trimethoxyphenoxy)methyl)carbonyl-4-(3-cyanobenzyl)piperazine;

1-((3,4,5-trimethoxyphenoxy)methyl)carbonyl-4-(2,4-difluorobenzyl)piperazine;

1-((3,4,5-trimethoxyphenoxy)methyl)carbonyl-4-(2,3-difluorobenzyl)piperazine;

1-((3,4,5-trimethoxyphenoxy)methyl)carbonyl-4-(3,4-difluorobenzyl)piperazine; NMR ($CDCl_3$) 7.3–7.0 (m, 3), 6.2 (s, 2), 4.6 (s, 2), 3.85 (s, 6), 3.75 (s, 3), 3.6 (m, 4), 3.5 (s, 2), 2.4 (m, 4) ppm;

1-((3,4,5-trimethoxyphenoxy)methyl)carbonyl-4-(2,6-difluorobenzyl)piperazine;

1-((3,4,5-trimethoxyphenoxy)methyl)carbonyl-4-(4-chlorobenzyl)piperazine; NMR (CDCl$_3$) 7.2 (m, 4), 6.2 (s, 2), 4.6 (s, 2), 3.85 (s, 6), 3.75 (s, 3), 3.6 (m, 4), 3.5 (s, 2), 2.4 (m, 4) ppm;

1-((3,4,5-trimethoxyphenoxy)methyl)carbonyl-4-(3-chloro-4-fluorobenzyl)piperazine;

1-((3,4,5-trimethoxyphenoxy)methyl)carbonyl-4-(4-trifluoromethylbenzyl)piperazine;

1-((3,4,5-trimethoxyphenoxy)methyl)carbonyl-4-(4-nitrobenzyl)piperazine;

1-((3,4,5-trimethoxyphenoxy)methyl)carbonyl-4-(4-fluorobenzyl)piperazine;

1-((3,4,5-trimethoxyphenoxy)methyl)carbonyl-4-(2,5-difluorobenzyl)piperazine;

1-((3,4,5-trimethoxyphenoxy)methyl)carbonyl-4-(3-nitro-4-hydroxybenzyl)piperazine;

1-((4-chlorophenoxy)methyl)carbonyl-4-(4-fluorobenzyl)piperazine; NMR (CDCl$_3$) 7.2 (m, 4), 7.0 (t, 2), 6.8 (d, 2), 4.6 (s, 2), 3.6 (m, 4), 3.4 (s, 2), 2.4 (m, 4) ppm;

1-((4-chlorophenoxy)methyl)carbonyl-4-(4-chlorobenzyl)piperazine; NMR (CDCl$_3$) 7.2 (m, 6), 6.8 (d, 2), 4.6 (s, 2), 3.6 (m, 4), 3.5 (s, 2), 2.4 (m, 4) ppm;

1-((3,4,5-trimethoxyphenoxy)methyl)carbonyl-4-(3-(benzyloxy)benzyl)piperazine;

1-((4-chlorophenoxy)methyl)carbonyl-4-(3,4,5-trimethoxybenzyl)piperazine;

C. In a similar manner, the following compounds of formula (Ia) were made:

(3S)-1-((4-chlorophenoxy)methyl)carbonyl-3-methyl-4-(4-fluorobenzyl)piperazine; NMR (CDCl$_3$) 7.3 (m, 4), 7.0 (t, 2), 6.9 (d, 2), 4.6 (s, 2), 4.0 (m, 2), 3.7 (m, 1), 3.4–2.9 (m, 3), 2.7 (m, 1), 2.5 (m, 1), 2.1 (m, 1), 1.1 (m, 3) ppm;

(3R)-1-((4-chlorophenoxy)methyl)carbonyl-3-methyl-4-(4-fluorobenzyl)piperazine; NMR (CDCl$_3$) 7.3 (m, 4), 7.0 (t, 2), 6.9 (d, 2), 4.6 (s, 2), 4.0 (m, 2), 3.7 (m, 1), 3.4–2.9 (m, 3), 3.2 (m, 1), 3.0 (m, 1), 2.7 (m, 1), 2.5 (m, 1), 2.1 (m, 1), 1.1 (m, 3) ppm;

1-((4-chlorophenoxy)methyl)carbonyl-3-(2-((((4-chlorophenoxy)methyl)carbonyl)oxy)ethyl)-4-(4-fluorobenzyl)piperazine;

1-((4-chlorophenoxy)methyl)carbonyl-2-hydroxyethyl-4-(4-fluorobenzyl)piperazine, dihydrochloride salt;

1-((4-chlorophenoxy)methyl)carbonyl-2-(2-((2-methylpropyl)amino)ethyl)-4-(4-fluorobenzyl)piperazine; NMR (CDCl$_3$) 7.1 (m, 4), 6.9 (t, 2), 6.7 (d, 2), 4.6 (s, 2), 4.4 (d, 1), 3.6 (d, 1), 3.3 (m, 3), 2.7–2.3 (m, 6), 2.0–1.7 (m, 5), 0.8 (t, 6) ppm;

1-((4-chlorophenoxy)methyl)carbonyl-2-(2-((4-fluorobenzyl)amino)ethyl)-4-(4-fluorobenzyl)piperazine, hydrochloride salt;

1-((4-chlorophenoxy)methyl)carbonyl-2-(2-((2-hydroxyethyl)amino)ethyl)-4-(4-fluorobenzyl)piperazine;

1-((4-chlorophenoxy)methyl)carbonyl-2-(2-((methyl)amino)ethyl)-4-(4-fluorobenzyl)piperazine;

1-((4-chlorophenoxy)methyl)carbonyl-3-(2-((4-fluorobenzyl)amino)ethyl)-4-(4-fluorobenzyl)piperazine, hydrochloride salt;

1-((4-chlorophenoxy)methyl)carbonyl-3-(2-((methyl)amino)ethyl)-4-(4-fluorobenzyl)piperazine;

1-((4-chlorophenoxy)methyl)carbonyl-3-(2-((2-hydroxyethyl)amino)ethyl)-4-(4-fluorobenzyl)piperazine;

1-((4-chlorophenoxy)methyl)carbonyl-3-(2-((2-methylpropyl)amino)ethyl)-4-(4-fluorobenzyl)piperazine;

(trans)-1-((4-chloro-2-(((ethyl)amino)methyl)phenoxy)methyl)carbonyl-2,5-dimethyl-4-(4-fluorobenzyl)piperazine; NMR (CDCl$_3$) 7.3 (m, 4), 7.0 (d, 2), 6.9 (t, 1), 6.4 (br s, 2), 5.0–4.6 (m, 3), 4.0 (m, 3), 3.7–3.2 (m, 4), 3.0–2.7 (m, 3), 2.2 (m, 1), 1.3 (m, 6), 1.0 (br d, 3) ppm;

(trans)-1-((4-chloro-2-(((diethyl)amino)methyl)phenoxy)methyl)carbonyl-2,5-dimethyl-4-(4-fluorobenzyl)piperazine; NMR (CDCl$_3$) 7.5 (d, 1), 7.3 (m, 2), 7.2 (dd, 1), 7.0 (t, 2), 6.8 (d, 1), 4.7 (m, 3), 4.2 (m, 1), 3.6–3.4 (m, 4), 3.2 (m, 1), 3.0 (m, 1), 2.7 (dd, 1), 2.6 (q, 2), 2.2 (d, 1), 1.3 (m, 3), 1.0 (m, 9) ppm;

(trans)-1-((4-chloro-2-(((cyclopropyl)amino)methyl)phenoxy)methyl)carbonyl-2,5-dimethyl-4-(4-fluorobenzyl)piperazine; NMR (CDCl$_3$) 7.3 (m, 4), 7.0 (d, 2), 6.8 (t, 1), 4.8–4.0 (m, 6), 3.7–3.2 (m, 3), 3.0 (br s, 1), 2.7 (d, 1), 2.2 (m, 2), 1.3 (m, 3), 0.9 (m, 3), 0.5 (m, 4) ppm;

(trans)-1-((4-chloro-2-(((dimethyl)amino)methyl)phenoxy)methyl)carbonyl-2,5-dimethyl-4-(4-fluorobenzyl)piperazine; NMR (CDCl$_3$) 7.3 (m, 4), 7.1 (dd, 1), 7.0 (t, 2), 6.8 (d, 1), 4.7 (m, 3), 4.1 (m, 1), 3.6–3.4 (m, 4), 3.0 (br s, 1), 2.7 (dd, 1), 2.2 (m, 8), 1.3 (m, 3), 0.9 (m, 3) ppm;

(trans)-1-((4-chloro-2-(((methyl)amino)methyl)phenoxy)methyl)carbonyl-2,5-dimethyl-4-(4-fluorobenzyl)piperazine; NMR (CDCl$_3$) 7.3 (m, 4), 7.1 (dd, 1), 7.0 (t, 2), 6.8 (d, 1), 4.7 (m, 2), 4.1 (m, 1), 3.7–3.4 (m, 5), 3.0 (br s, 1), 2.7 (dd, 1), 2.4 (s, 3), 2.2 (m, 2), 1.3 (m, 3), 0.9 (m, 3) ppm;

(trans)-1-((4-chloro-2-((amino)methyl)phenoxy)methyl)carbonyl-2,5-dimethyl-4-(4-fluorobenzyl)piperazine; NMR (CDCl$_3$) 7.3 (m, 4), 7.1 (dd, 1), 7.0 (t, 2), 6.7 (d, 1), 4.7 (m, 2), 3.8 (d, 1), 3.5 (m, 4), 3.0 (br s, 1), 2.7 (dt, 1), 2.2 (d, 1), 1.3 (m, 3), 0.9 (m, 3) ppm;

(trans)-1-((4-chloro-2-((4-methylpiperazin-1-yl)methyl)phenoxy)methyl)carbonyl-2,5-dimethyl-4-(4-fluorobenzyl)piperazine; NMR (CDCl$_3$) 7.3 (m, 4), 7.1 (dd, 1), 7.0 (t, 2), 6.8 (d, 1), 4.7 (m, 4), 4.2 (m, 1), 3.8 (m, 1), 3.6–3.0 (m, 8), 2.9 (t, 1), 2.7 (m, 1), 2.5–2.2 (m, 6), 1.3 (m, 3), 0.9 (m, 3) ppm;

(trans)-1-((4-chloro-2-((piperazin-1-yl)methyl)phenoxy)methyl)carbonyl-2,5-dimethyl-4-(4-fluorobenzyl)piperazine; NMR (DMSO-d$_6$) 7.9 (m, 3), 7.7 (s, 2), 7.4 (t, 1), 7.2 (m, 2), 5.4 (d, 1), 5.0 (m, 2), 4.3 (m, 4), 3.6–3.1 (m, 12), 2.8 (m, 1), 1.5–1.0 (m, 6) ppm;

(trans)-1-((4-chloro-2-(((2-hydroxyethyl)amino)methyl)phenoxy)methyl)carbonyl-2,5-dimethyl-4-(4-fluorobenzyl)piperazine; NMR (CDCl$_3$) 7.3 (m, 4), 7.1 (dd, 1), 7.0 (t, 2), 6.7 (d, 1), 4.7 (m, 2), 4.2–3.4 (m, 6), 3.0 (br s, 2), 2.7 (m, 4), 2.2 (d, 2), 1.3 (m, 3), 0.9 (m, 3) ppm;

(trans)-1-((4-chloro-2-((morpholin-4-yl)methyl)phenoxy)methyl)carbonyl-2,5-dimethyl-4-(4-fluorobenzyl)piperazine; NMR (CDCl$_3$) 7.3 (m, 3), 7.1 (dd, 1), 7.0 (t, 2), 6.7 (d, 1), 4.7 (m, 2), 4.1–3.4 (m, 11), 3.0 (br s, 1), 2.7 (dd, 1), 2.5 (t, 4), 2.2 (d, 1), 1.3 (m, 3), 0.9 (m, 3) ppm;

(trans)-1-((4-chloro-2-(ethylaminomethyl)phenoxy)
methyl)carbonyl-2,5-dimethyl-4-(4-fluorobenzyl)
piperazine; NMR (CDCl$_3$) 7.3 (m, 3), 7.2 (dd, 1), 7.0 (t,
2), 6.8 (m, 1), 4.7 (m, 2), 4.1 (m, 1), 3.8 (s, 2), 3.6 (m,
1), 3.5 (q, 2), 3.0 (m, 1), 2.7 (m, 3), 2.6 (q, 2), 1.3 (m,
3), 1.1 (t, 3), 1.0 (m, 6) ppm;

(trans)-1-((4-chloro-2-((ethyl)(1-methylbutyl)
aminomethyl)phenoxy)methyl)carbonyl-2,5-dimethyl-
4-(4-fluorobenzyl)piperazine; NMR (DMSO-d$_6$) 7.9
(m, 1), 7.7 (m, 2), 7.5 (m, 1), 7.2 (m, 3), 5.1 (m, 1), 4.6
(d, 1), 4.3 (m, 2), 3.7–2.8 (m, 6), 2.5 (s, 2), 1.5–1.2 (m,
19), 0.8 (s, 3) ppm;

(trans)-1-((4-chloro-2-(benzylamino)phenoxy)methyl)
carbonyl-2,5-dimethyl-4-(4-fluorobenzyl)piperazine;
NMR (CDCl$_3$) 7.3 (m, 7), 7.0 (t, 2), 6.7 (d, 1), 6.6 (m,
2), 4.7 (d, 4), 4.4 (s, 2), 4.2–3.0 (m, 8), 2.6 (dd, 1), 2.2
(d, 1), 1.3 (m, 3), 0.9 (m, 3) ppm;

(trans)-1-((4-chloro-2-((1-methylbutyl)amino)phenoxy)
methyl)carbonyl-2,5-dimethyl-4-(4-fluorobenzyl)
piperazine; NMR (DMSO-d$_6$) 7.9 (m, 2), 7.3 (t, 2), 7.1
(m, 1), 6.9 (d, 2), 5.2 (d, 1), 4.9 (m, 2), 4.6 (m, 1),
4.5–3.2 (m, 6), 2.8 (t, 1), 2.5 (s, 1), 1.7–1.2 (m, 9), 0.9
(d, 6) ppm;

(trans)-1-((4-chloro-2-((cyclopropylmethyl)
aminomethyl)phenoxy)methyl)carbonyl-2,5-dimethyl-
4-(4-fluorobenzyl)piperazine; NMR (CDCl$_3$) 7.3 (m,
3), 7.1 (dd, 1), 7.0 (t, 2), 6.8 (br d, 1), 4.7 (m, 2), 3.8
(s, 2), 3.6 (m, 1), 3.5 (q, 2), 3.0 (m, 2), 2.7 (dd, 1), 2.4
(m, 3), 2.2 (d, 1), 1.3 (m, 3), 0.9 (m, 4), 0.4 (m, 2), 0.1
(m, 2) ppm;

(trans)-1-((4-chloro-2-(phenylaminomethyl)phenoxy)
methyl)carbonyl-2,5-dimethyl-4-(4-fluorobenzyl)
piperazine; NMR (DMSO-d$_6$) 7.8 (m, 2), 7.4 (m, 8), 7.2
(m, 2), 5.4 (d, 1), 5.0 (m, 2), 4.7 (m, 1), 4.5 (s, 2), 4.3
(m, 2), 3.9–3.4 (m, 4), 1.4 (m, 3), 1.2 (m, 3) ppm;

(trans)-1-((4-chloro-2-(1-((methyl)(ethyl)amino)ethyl)
phenoxy)methyl)carbonyl-2,5-dimethyl-4-(4-
fluorobenzyl)piperazine; NMR (CDCl$_3$) 7.4 (s, 1), 7.3
(m, 2), 7.1 (dd, 1), 7.0 (t, 2), 6.8 (br d, 1), 4.6 (br s, 3),
4.0 (m, 2), 3.6 (d, 1), 3.4 (d, 1), 3.0 (m, 1), 2.7 (dd, 1),
2.5 (d q, 1), 2.4 (d q, 1), 2.2 (s, 3), 1.3 (m, 6), 1.0 (m,
6) ppm;

(trans)-1-((4-chloro-2-(1-(dimethylamino)ethyl)phenoxy)
methyl)carbonyl-2,5-dimethyl-4-(4-fluorobenzyl)
piperazine; NMR (CD$_3$OD) 7.6 (m, 3), 7.5 (d, 1), 7.3
(m, 3), 5.1 (m, 3), 4.4 10 (m, 2), 3.8 (dd, 2), 3.6 (m, 1),
3.4 (m, 1), 3.0 (m, 1), 2.6 (m, 7), 1.6 (m, 6), 1.3 (m, 3)
ppm;

(2R)-1-((4-chloro-2-((4-t-butoxycarbonylpiperazin-1-yl)
methyl)phenoxy)methyl)carbonyl-2-methyl-4-(4-
fluorobenzyl)piperazine; NMR (CDCl$_3$) 7.3 (m, 3), 7.0
(t, 2), 6.8 (d, 1), 4.7 (m, 2), 4.4 (m, 1), 3.5 (m, 10), 3.0
(m, 1), 2.8 (m, 1), 2.6 (m, 2), 1.4 (m, 12), 1.2 (m, 3) 1
5 ppm;

(trans)-1-((4-chloro-2-((4-t-butoxycarbonylpiperazin-1-
yl)methyl)phenoxy)methyl)carbonyl-2,5-dimethyl-4-
(4-fluorobenzyl)piperazine; NMR (DMSO-d$_6$) 7.8 (m,
2), 7.6 (s, 1), 7.5 (m, 1), 7.3 (t, 2), 7.2 (m, 1), 5.4 (d, 1),
5.0 (m, 2), 4.7 (m, 1), 4.3 (m, 6), 4.0 (m, 2), 3.8–3.1 (m,
8), 2.9 (m, 1), 1.4 (m, 12), 1.2 (m, 3) ppm;

1-((4-chloro-2-(morpholin-4-ylmethyl)phenoxy)methyl)
carbonyl-2-methyl-4-(4-fluorobenzyl)piperazine;
NMR (DMSO-d$_6$) 11.5 (br d, 1), 10.6 (m, 1), 7.7 (m, 2),
7.6 (s, 1), 7.5 (dd, 1), 7.3 (t, 2), 7.2 (d, 1), 5.2 (q d, 2),
4.7 (m, 1), 4.4 (m, 4), 3.9–3.7 (m, 4), 3.5 (m, 1), 3.4 (m,
4), 3.0 (m, 4), 2.8 (m, 1), 1.5 (d, 1.5), 1.3 (d, 1.5) ppm;
and D. In a similar manner, the following compound of formula (Id) was prepared:

1-((4-chlorophenoxy)methyl)carbonyl-2-methyl-4-(2-bromothienyl)methylpiperazine; NMR (CDCl$_3$) 7.2 (d, 2), 6.8 (dd, 3), 6.6 (d, 1), 4.6 (s, 2), 3.6 (s, 4), 3.5 (t, 2), 2.4 (q, 4) ppm.

E. In a similar manner, other compounds of formulae (Ia), (Ib), (Ic) and (Id) are made.

EXAMPLE 4

Compounds of Formula (Ia)

A. To a solution of (2R,5R)-1-((4-chlorophenoxy)methyl) carbonyl-2-methyl-4-(4-fluorobenzyl)-5-((hydroxy)methyl) piperazine (0.17 g, 0.42 mmol) in CH$_2$Cl$_2$ (50 mL) at 0° C. was added triethylamine (excess) and methane sulfonyl chloride (0.050 mL, 0.5 mmol). The resultant mixture was stirred at 0° C. until consumption of alcohol was observed by TLC analysis. The mixture was concentrated of volatiles in vacuo. Residue was taken up in anhydrous DMF (5 mL) and K$_2$CO$_3$ (excess) added, followed by tetrazole (0.050 g, 0.71 mmol). The resulting mixture was stirred at ambient temperature for 3 days and filtered. The filtrate was concentrated in vacuo and the residue taken up in ethyl acetate. This was washed with water then brine, then dried over MgSO$_4$ and concentrated in vacuo to afford a yellow oil. Purification by flash column chromatography on silica gel afforded 25 mg of (2R,5R)-1-((4-chlorophenoxy)methyl)carbonyl-2-methyl-4-(4-fluorobenzyl)-5-((tetrazolyl)methyl)piperazine as a white solid: NMR (CDCl$_3$) 7.3 (m, 5), 7.0 (m, 4), 4.8–4.1 (m, 5), 3.8 (m, 3), 3.2 (m, 2), 2.8 (dd, 1), 2.5 (dd, 1), 1.4 (d, 3) ppm, MS (ESI) 458.

B. In a similar manner, the following compounds of formula (Ia) were made:

(2R,5R)-1-((4-chlorophenoxy)methyl)carbonyl-2-methyl-4-(4-fluorobenzyl)-5-((1,2,4-triazol-2-yl) methyl)piperazine; NMR (CDCl$_3$) 7.9 (s, 1), 7.3(m, 5), 6.9 (m, 4), 4.7 (m, 3), 4.4–3.4 (m, 5), 3.1–2.7 (m, 2), 2.4 (t, 1), 2.0 (d, 1), 1.2 (m, 3) ppm;

(2R,5S)-1-((4-chlorophenoxy)methyl)carbonyl-2-methyl-4-(4-fluorobenzyl)-5-((morpholin-4-yl)methyl) piperazine; NMR (CDCl$_3$) 7.3 (m, 4), 7.0 (t, 2), 6.8 (d, 2), 4.7–4.1 (m, 5), 3.9–3.4 (m, 9), 3.2–2.7 (m, 3), 2.3 (m, 2), 2.0 (m, 1), 1.2 (m, 3) ppm;

(2R,5R)-1-((4-chlorophenoxy)methyl)carbonyl-2-methyl-4-(4-fluorobenzyl)-5-((piperazin-1-yl)methyl) piperazine;

(2R,5S)-1-((4-chlorophenoxy)methyl)carbonyl-2-methyl-4-(4-fluorobenzyl)-5-((diethylamino)methyl) piperazine; NMR (CDCl$_3$) 7.3 (m, 4), 7.0 (t, 2), 6.9 (d, 2), 4.7 (m, 3), 3.9–3.4 (m, 4), 2.8–2.3 (m, 7), 1.2 (m, 3), 0.9 (t, 6) ppm;

(2R,5S)-1-((4-chlorophenoxy)methyl)carbonyl-2-methyl-4-(4-fluorobenzyl)-5-(((ethyl)amino)methyl) piperazine; NMR (CDCl$_3$) 7.3 (m, 4), 7.0 (t, 2), 6.9 (d, 2), 4.7 (m, 3), 4.2–3.4 (m, 5), 2.8–2.3 (m, 6),1.3–1.0 (m, 6) ppm;

(2R,5S)-1-((4-chlorophenoxy)methyl)carbonyl-2-methyl-4-(4-fluorobenzyl)-5-((4-methylpiperazin-1-yl) methyl)piperazine; NMR (CDCl$_3$) 7.3 (m, 4), 7.0 (t, 2), 6.9 (d, 2), 4.7 (m, 3), 3.9–3.4 (m, 4), 2.8–2.2 (m, 14), 1.2 (m, 3) ppm;

1-((4-chlorophenoxy)methyl)carbonyl-4-(4-fluorobenzyl)-3-(2-(4-(t-butoxycarbonyl)-piperazin-1-yl)ethyl)piperazine, hydrochloride salt (2R,5S)-1-((4-chlorophenoxy)methyl)carbonyl-2-methyl-4-(4-fluorobenzyl)-5-((dimethylamino)methyl)piperazine (2R,5S)-1-((4-chlorophenoxy)methyl)carbonyl-2-methyl-4-(4-fluorobenzyl)-5-(((cyclopropyl)amino)methyl)piperazine (2R,5S)-1-((4-chlorophenoxy)methyl)carbonyl-2-methyl-4-(4-fluorobenzyl)-5-((cyano)methyl)piperazine; NMR (CDCl$_3$) 7.3 (m, 4), 7.0 (m, 4), 4.6 (m, 4), 4.2–3.2 (m, 4), 2.6–2.2 (m, 4), 1.2 (m, 3) ppm;

(2R,5S)-1-((4-chlorophenoxy)methyl)carbonyl-2-methyl-4-(4-fluorobenzyl)-5-((((cyclopropyl)methyl)amino)methyl)piperazine;

(2R,5R)-1-((4-chlorophenoxy)methyl)carbonyl-2-methyl-4-(4-fluorobenzyl)-5-(((2-hydroxyethyl)thio)methyl)piperazine; NMR (CDCl$_3$) 7.3 (m, 4), 7.0 (t, 2), 6.8 (d, 2), 4.7 (m, 3), 4.1–3.5 (m, 5), 3.1–2.3 (m, 8), 1.3 (m, 3) ppm;

(trans)-1-((4-chloro-2-(imidazol-1-ylmethyl)phenoxy)methyl)carbonyl-2,5-dimethyl-4-(4-fluorobenzyl)piperazine; NMR (DMSO-d$_6$) 11.3 (m, 1), 9.4 (s, 1), 7.9 (s, 3), 7.6 (s, 2), 7.4 (m, 1), 7.3 (m, 3), 7.1 (m, 1), 5.4 (m, 2), 4.9 (m, 1), 4.2 (m, 2), 3.8–3.2 (m, 6), 2.7 (m, 1), 1.4–1.2 (m, 6) ppm;

(trans)-1-((4-chloro-2-(1-(imidazol-1-yl)ethyl)phenoxy)methyl)carbonyl-2,5-dimethyl-4-(4-fluorobenzyl)piperazine; NMR (CDCl$_3$) 7.6 (s, 1), 7.3 (m, 2), 7.2 (dd, 1), 7.0 (m, 5), 6.8 (d, 1), 5.8 (q, 1), 4.6 (m, 3), 4.2 (m, 1), 3.5 (q, 2), 3.2 (m, 1), 3.0 (m, 1), 2.7 (dd, 1), 2.2 (dd, 1), 2.0 (br s, 1), 1.8 (dd, 3), 1.3 (m, 3), 0.9 (m, 3) ppm;

(trans)-1-((4-chloro-2-(triazol-1-ylmethyl)phenoxy)methyl)carbonyl-2,5-dimethyl-4-(4-fluorobenzyl)piperazine; NMR (CDCl$_3$) 8.4 (s, 1), 7.9 (s, 1), 7.3 (m, 3), 7.0 (t, 2), 6.8 (d, 1), 5.4 (s, 2), 4.6 (m, 3), 4.2 (m, 1), 3.5 (q, 2), 3.2 (m, 1), 3.0 (m, 1), 2.9 (dd, 1), 2.2 (dd, 1), 1.3 (m, 3), 0.9 (m, 3) ppm; and (trans)-1-((4-chloro-2-(tetrazol-1-ylmethyl)phenoxy)methyl)carbonyl-2,5-dimethyl-4-(4-fluorobenzyl)piperazine; NMR (CDCl$_3$) 9.4 (s, 1), 7.4 (s, 1), 7.3 (m, 3), 7.0 (t, 2), 6.8 (d, 1), 5.6 (s, 2), 4.7 (m, 3), 4.2 (m, 1), 3.5 (q, 2), 3.2 (m, 1), 3.0 (m, 1), 2.9 (dd, 1), 2.2 (dd, 1), 1.3 (m, 3), 0.9 (m, 3) ppm.

C. In a similar manner, other compounds of formulae (Ia), (Ib), (Ic) and (Id) are made.

EXAMPLE 5

Compounds of Formula (Ia)

A. To a solution of oxalyl chloride (0.62 g, 5 mmol) in CH$_2$Cl$_2$ (20 mL) at −50° C. was added DMSO (0.85 g, 11 mmol, in solution of 5 mL of CH$_2$Cl$_2$) over 2 minutes. 4-(4-fluorobenzyl)-1-((4-chlorophenoxy)methyl)carbonyl-3-(2-hydroxyethyl)piperazine (1.85 g, 4.5 mmol, in solution of 5 mL of CH$_2$Cl$_2$) was added. The resulting mixture was stirred at −50° C. for 15 minutes, then triethylamine (2.3 g, 22 mmol) was added. After 5 minutes at −50° C., the mixture was gradually warmed to ambient temperature. At that time the mixture was diluted with CH$_2$Cl$_2$ and washed with water, then brine. The organic layer was then dried over MgSO$_4$ and concentrated in vacuo to afford 1.7 g of 4-(4-fluorobenzyl)-1-((4-chlorophenoxy)methyl)carbonyl-3-((formyl)methyl)piperazine as a yellow oil; NMR (CDCl$_3$) 9.8 (d, 1) 7.3 (m, 4), 7.0 (m, 4), 4.6 (m, 3), 3.8–3.2 (m, 7), 2.7–2.2 (m, 4) ppm.

B. In a similar manner, the following compounds of formula (Ia) were made:

4-(4-fluorobenzyl)-1-((4-chlorophenoxy)methyl)carbonyl-3-((acetyl)methyl)piperazine, hydrochloride salt; NMR (CDCl$_3$) 7.3 (m, 4), 6.9 (m, 4), 4.6 (m, 2), 3.8–3.3 (m, 7), 2.4 (m, 4), 2.1 (d, 3) ppm; and (2R,5S)-4-(4-fluorobenzyl)-1-((4-chlorophenoxy)methyl)carbonyl-2-methyl-5-formylpiperazine.

C. In a similar manner, other compounds of formulae (Ia), (Ib), (Ic) and (Id) are made.

EXAMPLE 6

Compounds of Formula (Ia)

A. To a solution of 4-(4-fluorobenzyl)-1-((4-chlorophenoxy)methyl)carbonyl-3-((formyl)methyl)piperazine (0.31 g, 0.77 mmol) in anhydrous THF (20 mL) was added methyl magnesium bromide (0.26 mL, 0.77 mmol, 3.0 M solution in ether). The resultant mixture was stirred overnight at ambient temperature. At that time the mixture was poured into 5% aqueous NH$_4$Cl solution and extracted with two portions of ether. The combined organic extracts were washed with brine, then dried over MgSO$_4$, filtered and concentrated in vacuo to afford a yellow oil. Purification by flash column chromatography on silica gel afforded 0.29 g of 4-(4-fluorobenzyl)-1-((4-chlorophenoxy)methyl)carbonyl-3-(2-hydroxypropyl)piperazine, as a clear, colorless oil, which was converted to its hydrochloride salt; NMR (CDCl$_3$) 7.6 (m, 2), 7.2 (m, 4), 6.9 (m, 2), 4.7 (m, 2), 4.4–3.0 (m, 10), 2.4–1.4 (m, 2), 1.3–1.0 (m, 3) ppm.

B. In a similar manner, the following compounds of formula (Ia) were made:

4-(4-fluorobenzyl)-1-((4-chlorophenoxy)methyl)carbonyl-3-(2-hydroxy-2-phenylethyl)piperazine; NMR (CDCl$_3$) 7.3 (m, 9), 7.0 (t, 2), 6.8 (d, 2), 4.9 (m, 1), 4.8 (m, 2), 4.1 (m, 1), 3.8–3.3 (m, 6), 2.8 (m, 2), 2.2 (m, 1), 2.0 (m, 2) ppm;

4-(4-fluorobenzyl)-1-((4-chlorophenoxy)methyl)carbonyl-3-(2-hydroxypentyl)piperazine; NMR (CDCl$_3$) 7.8 (m, 2), 7.3 (m, 4), 6.9 (d, 2), 4.8 (d, 2), 4.5–3.0 (m, 16) 2.2–1.2 (m, 8), 0.9 (m, 3) ppm;

4-(4-fluorobenzyl)-1-((4-chlorophenoxy)methyl)carbonyl-3-(2-hydroxybut-4-enyl)piperazine; NMR (CDCl$_3$) 7.3 (m, 4), 7.0 (t, 2), 6.8 (d, 2), 5.7 (m, 1), 5.2 (dd, 1), 5.1 (t, 1), 4.6 (m, 2), 4.2–3.3 (m, 7), 2.9 (m, 2), 2.4 (m, 1), 1.9–1.5 (m, 2) ppm;

4-(4-fluorobenzyl)-1-((4-chlorophenoxy)methyl)carbonyl-3-(2-hydroxy-2-(4-methylphenyl)-ethyl)piperazine;

(2R,5R)-4-(4-fluorobenzyl)-1-((4-chlorophenoxy)methyl)carbonyl-2-methyl-5-(1-hydroxyprop-2-enyl)piperazine, hydrochloride salt; NMR (DMSO-d$_6$) 10.1 (b s, 1), 7.6 (m, 2), 7.3 (d, 4), 6.9 (d, 2), 6.1 (m, 1), 5.9 (m, 1), 5.4 (m, 2), 4.8 (m, 2), 4.4 (m, 4), 3.7–3.1 (m, 5), 1.1 (m, 3) ppm;

(2R,5R)-4-(4-fluorobenzyl)-1-((4-chlorophenoxy)methyl)carbonyl-2-methyl-5-(1-hydroxybutyl)piperazine, hydrochloride salt; NMR (DMSO-d$_6$) 10.3 (b s, 1), 7.6 (m, 2), 7.3 (m, 4), 6.9 (d, 2), 5.6 (m, 1), 4.9 (m, 2), 4.4 (m, 3), 3.9–3.1 (m, 5), 1.4 (m, 4), 1.1 (d, 3), 0.8 (t, 3) ppm;

4-(4-fluorobenzyl)-1-((4-chlorophenoxy)methyl)carbonyl-3-(2-hydroxybut-4-ynyl)piperazine;

4-(4-fluorobenzyl)-1-((4-chlorophenoxy)methyl)carbonyl-3-(2-hydroxy-2-cyclohexylethyl)-piperazine;

(2R,5R)-4-(4-fluorobenzyl)-1-((4-chlorophenoxy)methyl)carbonyl-2-methyl-5-(1-hydroxyethyl)piperazine, hydrochloride salt; NMR (DMSO-d$_6$) 10.3 (b s, 1), 7.6 (m, 2), 7.3(m, 4), 6.9 (d, 2), 5.6 (b s, 1), 4.9 (m, 2), 4.6–4.0 (m, 6), 3.2 (m, 3), 1.2 (d, 3), 1.1 (d, 3) ppm;

(2R,5R)4-(4-fluorobenzyl)-1-((4-chlorophenoxy)methyl)carbonyl-2-methyl-5-(1-hydroxy-1-(phenyl)methyl)piperazine, hydrochloride salt;

4-(4-fluorobenzyl)-1-((4-chlorophenoxy)methyl)carbonyl-5-(2-hydroxy-2-methylpropyl)-piperazine;

(trans)-1-((4-chloro-2-(1-hydroxyethyl)phenoxy)methyl)carbonyl-2,5-dimethyl-4-(4-fluorobenzyl)piperazine; NMR (CDCl$_3$) 7.3 (m, 3), 7.2–6.8 (m, 4), 5.1 (m, 1), 4.7 (m, 2), 4.2–3.0 (m, 9), 2.7 (dd, 1), 2.3 (d, 1), 1.5 (d, 3), 1.3 (br m, 3), 0.9 (br m, 3) ppm;

1-((4-chlorophenoxy)methyl)carbonyl-2-(1-hydroxyethyl)-4-(4-fluorobenzyl)piperazine; NMR (CDCl$_3$) 7.2 (m, 4), 7.0 (m, 2), 6.8 (dd, 2), 4.7 (m, 3), 4.2 (m, 1), 3.8 (m, 1), 3.4 (s, 2), 3.2 (m, 1), 2.3 (dd, 1), 2.1 (m, 1), 1.1 (m, 3) ppm;

1-((4-chlorophenoxy)methyl)carbonyl-2-(2-hydroxypropyl)-4-(4-fluorobenzyl)piperazine; NMR (DMSO-d$_6$) 7.6 (br s, 2), 7.3 (d, 4), 6.9 (q, 2), 4.9 (m, 3), 4.3 (m, 3), 3.9 (m, 3), 3.3. (m, 2), 3.0 (m, 1), 2.2 (t, 1), 1.8 (m, 1), 1.5 (m, 1), 1.1 (d, 1.5), 1.0 (d, 1.5) ppm; and 1-((4-chlorophenoxy)methyl)carbonyl-2-(2-hydroxybut-3-enyl)-4-(4-fluorobenzyl)piperazine; NMR (DMSO-d$_6$) 7.6 (dt, 2), 7.3 (m, 4), 6.9 (t, 2), 5.8 (m, 1), 5.2 (dd, 1), 5.0 (dt, 2), 4.8 (dt, 1), 4.4 (m, 2), 3.9 (m, 1), 3.4 (m, 3), 3.0 (m, 3), 2.2 (m, 1), 1.8 (m, 1), 1.6 (m, 1) ppm.

C. In a similar manner, other compounds of formulae (Ia), (Ib), (Ic) and (Id) are made.

EXAMPLE 7

Compounds of Formula (Ia)

A. To a solution of 4-(4-fluorobenzyl)-1-((4-chlorophenoxy)methyl)carbonyl-3-(2-hydroxy-2-phenylethyl)piperazine (0.051 g, 0.11 mmol) in anhydrous ether (5 mL) was added sodium hydride (0.006 g, 0.15 mmol). The resultant mixture was stirred at ambient temperature for 30 minutes, then methyl iodide (0.016 g, 0.11 mmol) was added. Once thin layer chromatography analysis showed complete consumption of 4-(4-fluorobenzyl)-1-((4-chlorophenoxy)methyl)carbonyl-3-(2-hydroxy-2-phenylethyl)piperazine had occurred, the mixture was poured into water and extracted with two portions of ether. The combined organic extracts were dried over MgSO$_4$, filtered and concentrated in vacuo to afford 0.046 g of 4-(4-fluorobenzyl)-1-((4-chlorophenoxy)methyl)carbonyl-3-(2-methoxy-2-phenylethyl)piperazine as a yellow oil: NMR (CDCl$_3$) 7.3 (m, 9), 7.0 (m, 2), 6.9 (m, 2), 4.8 (m, 3), 4.2 (m, 2), 3.9–3.2 (m, 5), 3.1 (d, 2), 3.0 (s, 1), 2.9 (s, 1), 2.6 (m, 1), 2.4 (m, 1), 1.9 (m, 1) ppm.

B. In a similar manner, other compounds of the invention were made:

(2R,5R)-4-(4-fluorobenzyl)-1-((4-chlorophenoxy)methyl)carbonyl-2-methyl-5-((methoxy)-methyl)piperazine; NMR (CDCl$_3$) 7.3 (m, 4), 7.0 (t, 2), 6.9 (d, 2), 4.6 (m, 3), 3.8–3.1 (m, 9), 3.0 (br s, 1), 2.7 (dd, 1), 2.3 (t, 1), 1.2 (m, 3) ppm;

4-(4-fluorobenzyl)-1-((4-chlorophenoxy)methyl)carbonyl-2-(2-(methoxy)ethyl)piperazine; NMR (CDCl$_3$) 7.3 (m, 4), 7.0 (t, 2), 6.9 (d, 2), 4.7 (m, 3), 4.1 (m, 1), 3.7 (m, 1), 3.4–3.2 (m, 6), 2.8 (m, 3), 2.0 (m, 4) ppm;

4-(4-fluorobenzyl)-1-((4-chlorophenoxy)methyl)carbonyl-3-(ethoxycarbonyl)methylpiperazine-2-one;

4-(4-fluorobenzyl)-1-((4-chlorophenoxy)methyl)carbonylpiperazine-2-one;

4-(4-fluorobenzyl)-1-((4-chlorophenoxy)methyl)carbonyl-3-((methoxy)methyl)piperazine; NMR (CDCl$_3$) 7.3 (m, 4), 7.0 (t, 2), 6.9 (dd, 2), 4.7 (d, 2), 3.9–3.3 (m, 11), 2.6 (m, 2), 2.2 (m, 1) ppm;

4-(4-fluorobenzyl)-1-((4-chlorophenoxy)methyl)carbonyl-3-(2-(methoxy)ethyl)piperazine; NMR (CDCl$_3$) 7.3 (m, 4), 7.0 (t, 2), 6.9 (dd, 2), 4.7 (d, 2), 3.8–3.3 (m, 11), 2.6 (m, 2), 2.2 (m, 1), 1.8 (m, 2) ppm;

4-(4-fluorobenzyl)-1-(2-(4-chlorophenoxy)ethyl)piperazin-2-one; NMR (CDCl$_3$) 7.3 (m, 4), 7.0 (t, 2), 6.8 (d, 2), 4.2 (t, 2), 3.8 (t, 2), 3.5 (m, 4), 3.2 (s, 2), 2.6 (t, 2) ppm;

4-(4-fluorobenzyl)-1-(2-(4-chlorophenoxy)ethyl)-3-((ethoxycarbonyl)methyl)piperazin-2-one, hydrochloride salt; NMR (CDCl$_3$) 7.2 (m, 2), 7.1 (m, 4), 6.8 (d, 2), 4.2 (m, 9), 3.5 (m, 5), 2.9 (br s, 1), 1.3 (t, 3) ppm;

(trans)-1-((4-chloro-2-methoxyphenoxy)methyl)carbonyl-2,5-dimethyl-4-(4-fluorobenzyl)piperazine; NMR (CDCl$_3$) 7.3 (m, 2), 7.0–6.8 (m, 5), 4.7 (br m, 2.5), 4.2 (br s, 0.5), 3.8 (s, 3), 3.6–3.2 (m, 4), 3.0 (br s, 1), 2.7 (m, 1), 2.2 (d, 1), 1.2 (br m, 3), 1.9 (br m, 3) ppm; and (trans)-1-((5-chloro-2-methoxyphenoxy)methyl)carbonyl-2,5-dimethyl-4-(4-fluorobenzyl)piperazine; NMR (CDCl$_3$) 7.3 (m, 2), 7.0–6.8 (m, 5), 4.7 (br m, 2.5), 4.2 (br s, 0.5), 3.8 (s, 3), 3.6–3.2 (m, 4), 3.0 (br s, 1), 2.7 (m, 1), 2.2 (d, 1), 1.2 (br m, 3), 1.9 (br m, 3) ppm.

C. In a similar manner, other compounds of formulae (Ia), (Ib), (Ic) and (Id) are made.

EXAMPLE 8

Compounds of Formula (Ia)

A. To a solution of 4-chlorobenzylisocyanate (0.59 g, 3.5 mmol) in anhydrous THF (15 mL) at 0° C. was added 1-(4-chlorobenzyl)piperazine (0.74 g, 3.5 mmol). The resultant mixture was stirred at ambient temperature. After 20 hours the mixture was concentrated of volatiles. The resulting solid was washed with ethyl acetate and dried in vacuo to afford 0.72 g of 1-(((4-chlorobenzyl)amino)carbonyl)-4-(4-chlorobenzyl)piperazine as a white solid; NMR (CDCl$_3$) 7.4 (m, 4), 7.3 (m, 2), 7.2 (m, 2), 4.4–4.1 (m, 6), 3.6 (m, 4), 3.0 (m, 2) ppm.

B. In a similar manner, other compounds of formula (Ia) were made:

4-(4-fluorobenzyl)-1-((4-chlorophenoxy)methyl)carbonyl-2-(N'-methylureido)-amino)methyl)piperazine; NMR (CDCl$_3$) 7.2 (m, 4), 7.0 (t, 2), 6.8 (dd, 2), 5.7 (br s, 1), 5.2 (m, 1), 5.0 (m, 1), 4.8–2.0 (m, 15) ppm;

4-(4-fluorobenzyl)-1-((4-chlorophenoxy)methyl)carbonyl-2-(N'-(ethoxycarbonylmethyl)ureido)methyl)piperazine; NMR (DMSO-d$_6$) 7.3 (m, 4), 7.1 (t, 2), 6.8 (d, 2), 6.5 (t, 2), 4.8 (m, 2), 4.1–1.8 (m, 15), 1.1 (m, 3) ppm;

(trans)-1-((4-chloro-2-((aminocarbonyl)glycinamido)phenoxy)methyl)carbonyl-2,5-dimethyl-4-(4- fluorobenzyl)piperazine; NMR (CDCl$_3$) 9.8 (br s, 1), 8.3 (s, 1), 7.3 (m, 2), 7.0 (m, 3), 6.8 (d, 1), 6.0 (br s, 1), 5.0 (m, 2), 4.8 (m, 2), 4.1 (m, 3), 3.6 (m, 3), 3.1 (m, 2), 2.7 (d, 1), 2.3 (d, 1), 0.9 (m, 6) ppm;

(trans)-1-((4-chloro-2-((aminocarbonyl)(methyl) glycinamido)phenoxy)methyl)carbonyl-2,5-dimethyl-4-(4-fluorobenzyl)piperazine; NMR (DMSO-d$_6$) 9.8 (br m, 1), 9.4 (s, 1), 8.2 (s, 1), 7.6 (m, 2), 7.3 (m, 2), 7.0 (m, 2), 6.0 (br m, 2), 5.0 (m, 3), 4.3 (br m, 3), 4.0 (s, 2), 3.7–3.2 (m, 4), 2.8 (s, 3), 1.3 (m, 3), 1.2 (m, 3) ppm;

(trans)-1-((4-chloro-2-(N'-ethyluredio)phenoxy)methyl) carbonyl-2,5-dimethyl-4-(4-fluorobenzyl)piperazine; NMR (CDCl$_3$) 8.8 (s, 1), 8.4 (s, 1), 7.3 (m, 2), 7.0 (m, 2), 6.8 (m, 3), 4.7 (m, 2), 4.1 (m, 2), 3.6–3.3 (m, 4), 3.0 (br s, 1), 2.7 (dd, 1), 2.2 (d, 1), 1.3 (m, 5), 0.9 (m, 6) ppm;

(trans)-1-((4-chloro-2-(N'-(2,4-dichlorophenyl)ureido) phenoxy)methyl)carbonyl-2,5-dimethyl-4-(4-fluorobenzyl)piperazine; NMR (DMSO-d$_6$) 10.4 (br d, 1), 9.2 (s, 1), 9.1 (s, 1), 8.2 (s, 1), 8.1 (d, 1), 7.7 (m, 2), 7.3 (m, 3), 6.9 (m, 2), 5.0 (m, 2), 4.7 (m, 1), 4.3 (m, 3), 3.8 (q, 1), 3.6 (m, 1), 3.4 (m, 1), 2.9 (t, 1), 1.4 (m, 3), 1.2 (m, 3) ppm;

(trans)-1-((4-chloro-2-(N'-(4-nitrophenyl)ureido) phenoxy)methyl)carbonyl-2,5-dimethyl-4-(4-fluorobenzyl)piperazine; NMR (CDCl$_3$) 9.1 (s, 1), 8.4 (s, 1), 8.3 (s, 1), 8.2 (s, 1), 7.9 (d, 1), 7.8 (d, 1), 7.3 (m, 3), 7.0 (t, 2), 6.8 (d, 1), 6.7 (m, 1), 4.7 (m, 2), 3.6 (m, 4), 3.1 (m, 1), 2.8 (m, 1), 2.3 (d, 1), 1.4 (m, 3), 1.0 (m, 3) ppm;

(trans)-1-((4-chloro-2-(N'-(4-methylphenyl)ureido) phenoxy)methyl)carbonyl-2,5-dimethyl-4-(4-fluorobenzyl)piperazine; NMR (DMSO-d$_6$) 10.5 (br d, 1), 9.6 (s, 1), 8.5 (d, 1), 8.2 (s, 1), 7.8 (m, 2), 7.3 (m, 4), 7.1 (d, 2), 6.9 (s, 1), 5.0 (m, 2), 4.3 (m, 3), 3.9 (s, 1), 3.6 (m, 1), 3.4 (m, 1), 2.8 (dd, 1), 2.2 (s, 3), 1.4 (m, 3), 1.2 (m, 3) ppm;

(trans)-1-((4-chloro-2-(N'-benzylureido)phenoxy)methyl) carbonyl-2,5-dimethyl-4-(4-fluorobenzyl)piperazine; NMR (CDCl$_3$) 9.0 (s, 1), 8.4 (s, 1), 7.3 (m, 8), 7.0 (t, 2), 6.8 (q, 2), 5.6 (t, 1), 4.6 (m, 4), 3.6 (m, 3), 3.0 (m, 1), 2.7 (m, 1), 2.2 (m, 2), 1.3 (m, 3), 0.9 (m, 3) ppm;

(trans)-1-((4-chloro-2-(1-(N-methyl-N'-ethylureido) ethyl)phenoxy)methyl)carbonyl-2,5-dimethyl-4-(4-fluorobenzyl)piperazine; NMR (CDCl$_3$) 7.3 (m, 4), 7.0 (t, 2), 6.8 (d, 1), 5.6 (m, 1), 5.4 (br d, 1) 4.7 (m, 2), 3.5 (q, 2), 3.2 (m, 4), 3.0 (m, 1), 2.7 (m, 4), 2.2 (d, 1), 1.4 (d, 3), 1.3 (m, 9), 0.9 (m, 3) ppm;

(trans)-1-((4-chloro-2-(oxazol-2-ylaminomethyl) phenoxy)methyl)carbonyl-2,5-dimethyl-4-(4-fluorobenzyl)piperazine; NMR (CDCl$_3$) 7.3 (m, 3), 7.2 (dd, 1), 7.0 (t, 2), 6.8 (d, 1), 4.7 (m, 3), 4.4 (s, 2), 4.3 (t, 2), 3.9 (m, 1), 3.8 (t, 2), 3.5 (q, 2), 3.3 (m, 1), 3.0 (m, 1), 2.7 (dd, 1), 2.2 (d, 1), 1.3 (m, 3), 0.9 (m, 3) ppm;

(trans)-1-(2-(4-chlorophenyl)-3-(ureido)propyl)carbonyl-2,5-dimethyl-4-(4-fluorobenzyl)piperazine; NMR (DMSO-d$_6$) 7.3 (m, 4), 7.2 (m, 2), 7.1 (t, 2), 5.8 (br s, 1), 5.4 (br s, 2), 4.0 (m, 1), 3.4 (m, 2), 3.2 (m, 3), 2.9 (m, 1), 2.5 (m, 2), 2.1 (m, 1), 1.1 (m, 3), 0.8 (m, 3) ppm;

(trans)-1-(2-(4-chlorophenyl)-2-(ureido)ethyl)carbonyl-2,5-dimethyl-4-(4-fluorobenzyl)piperazine; NMR (DMSO-d$_6$) 7.3 (m, 5), 7.1 (t, 2), 6.6 (q, 1), 5.6 (br s, 2), 5.0 (m, 1), 4.4 (m, 0.5), 4.0 (m, 0.5), 3.5 (m, 2), 3.3 (m, 2), 2.8 (m, 2), 2.7 (m, 1), 2.5 (m, 1), 2.1 (d, 1), 1.2 (m, 3), 0.8 (m, 3) ppm;

(trans)-1-((4-chloro-2-((N'-(3-methoxyphenyl)ureido) phenoxy)methyl)carbonyl-2,5-dimethyl-4-(4-fluorobenzyl)piperazine; NMR (DMSO-d$_6$) 10.2 (br s, 1), 9.5 (s, 1), 8.5 (br s, 1), 8.2 (s, 1), 7.7 (m, 2), 7.2 (m, 4), 7.0 (s, 3), 6.5 (dd, 1), 5.0 (m, 2), 4.3 (m, 3), 3.7 (m, 5), 3.4 (m, 1), 2.9 (m, 1), 1.4 (s, 3), 1.2 (s, 3) ppm; and (trans)-1-((4-chloro-2-((N'-(trichloromethylcarbonyl) ureido)phenoxy)methyl)carbonyl-2,5-dimethyl-4-(4-fluorobenzyl)piperazine; NMR (CDCl$_3$) 10.5 (s, 1), 9.0 (m, 1), 8.3 (s, 1), 7.3 (m, 2), 7.0 (m, 4), 4.8 (m, 3), 4.2 (m, 1), 3.6 (m, 2), 3.4 (m, 1), 3.0 (m, 1), 2.7 (dd, 1), 2.2 (d, 1), 1.3 (m, 3), 0.9 (m, 3) ppm.

C. In a similar manner, other compounds of formulae (Ia), (Ib), (Ic) and (Id) are made.

EXAMPLE 9

Compounds of Formula (Ia)

A. To a solution of (cis)-1-((4-chlorophenoxy)methyl) carbonyl-3,5-dimethylpiperazine (0.20 g, 0.71 mmol) in anhydrous THF (2 mL) was added 4-fluorobenzyl-bromide (0.11 mL, 0.85 mmol), diisopropylethylamine (0.15 mL, 0.85 mmol) and sodium iodide (0.042 g, 0.28 mmol). The resultant mixture was stirred at ambient temperature for 2 days. At that time the mixture was poured into ether and washed with 5% aqueous NaHCO$_3$ solution, then brine. The organic layer was dried over MgSO$_4$, filtered, and concentrated in vacuo to afford a yellow oil. Purification by flash column chromatography on silica gel afforded 0.17 g of (cis)-1-((4-chlorophenoxy)methyl)carbonyl-3,5-dimethyl-4-(4-fluorobenzyl)piperazine as a pink oil; which was converted to its hydrochoride salt; NMR (CDCl$_3$) 7.6 (m, 2), 7.3 (m, 4), 7.0–6.8 (m, 2), 5.0–2.8 (m, 10), 1.5–1.3 (m, 6) ppm.

B. In a similar manner, the following compounds of formula (Ia) were made:

1-((4-chlorophenoxy)methyl)carbonyl-2-((((cyclopropyl) methyl)amino)methyl)-4-(4-fluorobenzyl)piperazine; NMR (CDCl$_3$) 7.3 (m, 4), 7.0 (t, 2), 6.8 (d, 2), 4.5 (s, 2), 3.4 (m, 4), 3.0 (m, 1), 2.5 (m, 4), 2.2 (t, 1), 2.0 (m, 2), 1.6 (s, 2), 0.8 (m, 1), 0.5 (m, 2), 0.1 (m, 2) ppm;

(3R,5R)-4-(4-fluorobenzyl)-1-((4-chlorophenoxy) methyl)carbonyl-3,5-dimethylpiperazine, hydrochloride salt; NMR (CDCl$_3$) 13.3 (m,1), 7.9 (q, 2), 7.2 (m, 4), 6.9 (d, 2), 6.8 (d, 2), 4.8–3.3 (m, 10), 1.7 (d, 3), 1.2–1.0 (m, 3) ppm;

(3S,5S)-4-(4-fluorobenzyl)-1-((4-chlorophenoxy)methyl) carbonyl-3,5-dimethylpiperazine, hydrochloride salt; NMR (CDCl$_3$) 13.3 (m,1), 7.9 (q, 2), 7.2 (m, 4), 6.9 (d, 2), 6.8 (d, 2), 4.8–3.3 (m, 10), 1.7 (d, 3), 1.2–1.0 (m, 3) ppm;

1-((4-chlorophenoxy)methyl)carbonyl-2-(((4-fluorobenzyl)amino)methyl)-4-(4-fluorobenzyl) piperazine;

1-((4-chlorophenoxy)methyl)carbonyl-2-(((methyl) amino)methyl)-4-(4-fluorobenzyl)piperazine: NMR CDCl$_3$) 7.3 (m, 4), 7.0 (t, 2), 6.8 (d, 2), 4.5 (q, 2), 3.6 (m, 4), 3.1 (m, 2), 2.8 (m, 3), 2.6 (s, 3), 2.5–2.3 (m, 3) ppm; and 1-((4-chlorophenoxy)methyl)carbonyl-3-trifluoromethyl-4-(4-fluorobenzyl)piperazine; NMR (CDCl$_3$) 7.3 (m, 4), 7.0 (t, 2), 6.8 (dd, 2), 4.6 (m, 2), 4.2 (m, 1), 3.8 (m, 3), 3.6 (dd, 1), 3.3 (m, 2), 3.0 (m, 1), 2.6 (m, 1) ppm.

C. In a similar manner, other compounds of formulae (Ia), (Ib), (Ic) and (Id) are made.

EXAMPLE 10

Compounds of Formula (Ic)

A. To a solution of 1-((3,4,5-trimethoxyphenoxy)methyl) carbonyl-4-(benzyl)piperazine (0.15 g, 0.37 mmol) in toluene (10 mL) was added iodomethane (0.15 mL, 2.2 mmol). The resultant mixture was stirred at ambient temperature for 4 days. At that time the solid precipitate was filtered and washed with ether to afford 0.019 g of 1-((3,4,5-trimethoxyphenoxy)methyl)carbonyl-4-methyl-4-(benzyl) piperazinium iodide as a white solid; NMR (DMSO-$d_6$) 7.6 (s, 5), 6.3 (s, 2), 4.8 (s, 2), 4.7 (s, 2), 4.2 (d, 1), 4.0 (d, 1), 3.8 (s, 6), 3.6–3.3 (m, 9), 3.1 (s, 3) ppm.

B. In a similar manner, other compounds of formula (Ic) were made:

1-((3,4,5-trimethoxyphenoxy)methyl)carbonyl-4-methyl-4-(4-fluorobenzyl)piperazinium iodide; NMR (DMSO-$d_6$) 7.6 (dt, 2), 7.4 (t, 2), 6.3 (s, 2), 4.8 (s, 2), 4.7 (s, 2), 4.2 (d, 1), 4.0 (d, 1), 3.8 (s, 6), 3.6–3.3 (m, 9), 3.0 (s, 3) ppm;

1-((3,4,5-trimethoxyphenoxy)methyl)carbonyl-4-(prop-2-enyl)-4-(4-fluorobenzyl)piperazinium bromide; NMR (DMSO-$d_6$) 7.6 (dt, 2), 7.4 (t, 2), 6.2 (m, 3), 5.75 (d, 1), 5.65 (d, 1), 4.8 (s, 2), 4.7 (s, 2), 4.2–3.3 (m, 19) ppm;

1-((3,4,5-trimethoxyphenoxy)methyl)carbonyl-4-benzyl-4-(4-fluorobenzyl)piperazinium bromide; NMR (DMSO-$d_6$) 7.7–7.1 (m, 9), 6.2 (s, 2), 4.8 (m, 6), 4.0–3.3 (m, 17) ppm; and 1-((3,4,5-trimethoxyphenoxy)methyl)carbonyl-2,4-dimethyl-4-(4-fluorobenzyl)piperazinium iodide; NMR (DMSO-$d_6$) 7.6 (m, 2), 7.2 (m4), 7.0 (d, 2), 4.9 (s, 2), 4.6 (s, 2), 3.6–3.3 (m, 7), 3.1 (s, 2), 2.9 (s, 1), 1.2 (m, 3) ppm.

C. In a similar manner, other compounds of formula (Ic) are made.

EXAMPLE 11

Compounds of Formula (Ia)

A. To a solution of 1-((3,4,5-trimethoxyphenoxy)methyl)carbonyl-2-(methoxycarbonyl)methyl-4-(4-fluorobenzyl)piperazine (0.20 g, 0.42 mmol) in a methanol/water solution (20 mL, 3:1) was added lithium hydroxide, monohydrate (0.40 mL, 9.5 mmol). The resultant mixture was stirred at ambient temperature for 30 min. At that time HPLC analysis showed complete conversion had occurred. The mixture was poured into ethyl acetate and washed sequentially with an aqueous acetic acid/water solution (pH <4), water, and brine. The organic layer was separated, dried over MgSO$_4$, filtered and concentrated in vacuo to afford 0.060 g of 1-((3,4,5-trimethoxyphenoxy)methyl)carbonyl-2-(carboxy)methyl-4-(4-fluorobenzyl)piperazine as a white solid; NMR (CDCl$_3$) 7.4 (m, 2), 7.1 (m, 2), 6.2 (m, 2), 5.1 (m, 1), 4.7 (m, 3), 4.0 (m, 2), 3.8 (d, 9), 3.3–3.1 (m, 4), 2.6 (m, 2), 2.4 (m, 2) ppm, MS (ESI) 476.

B. In a similar manner, the following compounds of the invention were made:

1-((4-chlorophenoxy)methyl)carbonyl-3-(carboxy)methyl-4-(4-fluorobenzyl)piperazine; NMR (DMSO-$d_6$) 7.4 (t, 2), 7.3 (d, 2), 7.1 (t, 2), 6.9 (d, 2), 4.7 (m, 2), 4.0 (d, 2), 3.7 (m, 2), 3.5 (m, 3), 3.2 (m, 1), 2.8–2.4 (m, 3) ppm;

1-((4-chloro-2-carboxyphenoxy)methyl)carbonyl-2-methyl-4-(4-fluorobenzyl)piperazine; NMR (CDCl$_3$) 8.0 (s, 1), 7.4 (dd, 1), 7.3 (m, 3), 7.0 (t, 1), 6.9 (d, 1), 5.0 (m, 2), 4.6 (m, 1), 4.3 (m, 1), 3.7 (m, 1), 3.4 (m, 2), 2.8 (d, 1), 2.6 (m, 1), 2.1 (m, 1), 1.4 (d, 1.5), 1.3 (d, 1.5) ppm; and (trans)-1-((4-chloro-2-carboxyphenoxy)methyl)carbonyl-2,5-dimethyl-4-(4-fluorobenzyl)piperazine; NMR (CDCl$_3$) 9.4 (br s, 1), 8.0 (m, 1), 7.5 (m, 3), 7.2 (m, 2), 7.0 (d, 1), 5.0 (m, 2), 4.6 (m, 1), 4.3 (m, 3), 3.7 (m, 2), 3.4 (m, 1), 3.3 (m, 1), 1.4–1.3 (m, 6) ppm.

C. In a similar manner, other compounds of formulae (Ia), (Ib), (Ic) and (Id) are made.

EXAMPLE 12

Compounds of Formula (Ia)

A. To a solution of lithium aluminum hydride (0.29 g, 7 mmol) in a solution of anhydrous THF (16 mL) was added 1-((4-chlorophenoxy)methyl)carbonyl-4-(4-fluorobenzyl)piperazine (0.36 g, 1.0 mmol, in 3 mL of THF). The resultant mixture was stirred at ambient temperature for 9 hours. At that time 0.3 mL of water and 0.3 mL of 15% aqueous NaOH solution were added and the resulting mixture stirred at ambient temperature. After 18 hours, the mixture was filtered through a short column of Celite (THF) and the filtrate concentrated in vacuo to afford 0.12 g of 1-(2-(4-chlorophenoxy)ethyl)-4-(4-fluorobenzyl)piperazine as a clear oil; NMR (CDCl$_3$) 7.2 (m, 4), 7.0 (m, 2), 6.8 (m, 2), 4.0 (m, 2), 3.4 (m, 2), 2.8–2.4 (m, 10) ppm.

B. In a similar manner, other compounds of formulae (Ia), (Ib), (Ic) and (Id) are made.

EXAMPLE 13

Compounds of Formula (Ib)

A. To a solution of 1-(1-(t-butoxycarbonyl)amino-2-(4-chlorophenyl)ethyl)carbonyl-4-(benzyl)piperazine (0.20 g, 0.44 mmol) in a solution of CH$_2$Cl$_2$ (3 mL) was added trifluoroacetic acid (3 mL). The resultant mixture was stirred at ambient temperature. After 18 hours, the mixture was concentrated in vacuo to afford a yellow oil. This was dissolved in ethyl acetate and washed with an aqueous NaHCO$_3$ solution. The organic layer was separated, dried over MgSO$_4$, filtered and concentrated in vacuo to afford 0.17 g of a clear, colorless film. This was dissolved in ether and treated with an ethereal solution of HCl, resulting in formation of a white precipitate. Concentration afforded 0.18 g of 1-(1-amino-2-(4-chlorophenyl)ethyl)carbonyl-4-(benzyl)piperazine as a white solid; NMR (CDCl$_3$) 7.4 (m, 7), 7.1 (m, 2), 4.0 (t, 1), 3.7–3.1 (m, 4), 2.8 (m, 2), 2.4–2.2 (m, 5), 1.8 (m, 1) ppm.

B. In a similar manner, the following compounds of formula (Ib) were made:

1-(3-amino-2-(4-chlorophenyl)propyl)carbonyl-4-(4-chlorobenzyl)piperazine; NMR (CDCl$_3$) 7.2 (m, 8), 3.8 (s, 3), 3.6–3.3 (m, 8), 3.0 (m, 2), 2.6 (dq, 2), 2.4–2.1 (m, 4) ppm; and 1-(1-amino-2-(4-chlorophenyl)ethyl)carbonyl-4-(4-chlorobenzyl)piperazine; NMR (CDCl$_3$) 7.3 (m, 6), 7.1 (d, 2), 4.0 (t, 1), 3.6–3.1 (m, 6), 2.8 (dq, 2), 2.6 (brs, 2), 2.4 (m, 3), 1.8 (m, 1) ppm.

C. In a similar manner, the following compounds of formula (Ia) were made:

(trans)-1-((4-chloro-2-(aminomethyl)phenoxy)methyl) carbonyl-2,5-dimethyl-4-(4-fluorobenzyl)piperazine; NMR (CDCl$_3$) 7.3 (m, 3), 7.2 (dd, 1), 7.0 (t, 2), 6.8 (br d, 1), 4.7 (m, 2), 3.9 (s, 2), 3.5 (m, 3), 3.0 (br s, 1), 2.7 (m, 1), 2.2 (m, 4), 1.3 (m, 3), 0.9 (m, 3) ppm;

(trans)-1-((4-chloro-2-(glycinamido)phenoxy)methyl) carbonyl-2,5-dimethyl-4-(4-fluorobenzyl)piperazine; NMR (CDCl$_3$) 10.1 (s, 1), 8.5 (s, 1), 7.3 (t, 3), 7.0 (t, 3), 6.8 (d, 1), 4.7 (m, 3), 4.2–3.4 (m, 5), 3.2 (m, 1), 3.0 (br s, 1), 2.7 (dd, 1), 2.2 (d, 1), 1.3 (m, 3), 0.9 (m, 3) ppm;

(2R,5S)-1-((4-chloro-2-(glycinamido)phenoxy)methyl) carbonyl-2,5-dimethyl-4-(4-fluorobenzyl)piperazine; NMR (DMSO-$d_6$) 10.0 (s, 1), 8.2 (m, 3), 7.6 (s, 1), 7.3 (m, 2), 7.1 (dd, 1), 6.9 (m, 1), 5.2–4.2 (m, 5), 3.8–2.9 (m, 7), 1.2 (m, 6) ppm;

(2R)-1-((4-chloro-2-(glycinamido)phenoxy)methyl) carbonyl-2-methyl-4-(4-fluorobenzyl)piperazine; NMR (DMSO-$d_6$) 11.4 (br s, 1), 10.0 (s, 1), 8.3 (br s, 2), 8.1 (s, 1), 7.8 (m, 2), 7.4 (t, 2), 7.1 (d, 1), 7.0 (d, 1) 5.0 (q, 2), 4.7 (m, 1), 4.3 (m, 3), 3.9 (m, 3), 3.6 (m, 1), 3.1 (m, 3), 1.5 (d, 1.5), 1.3 (d, 1.5) ppm;

(trans)-1-((4-chloro-2-((N'-methylglycinamido) phenoxy) methyl)carbonyl-2,5-dimethyl-4-(4-fluorobenzyl) piperazine; NMR (CDCl$_3$) 9.9 (s, 1), 8.5 (s, 1), 7.3 (m, 3), 7.0 (m, 3), 6.8 (d, 1), 4.7 (m, 3), 4.2–3.9 (m, 1), 3.6–3.3 (m, 5), 3.0 (br s, 1), 2.7 (dd, 1), 2.5 (s, 3), 2.3 (d, 1), 1.3 (m, 3), 1.0 (m, 3) ppm;

(trans)-1-((4-chloro-2-(alaninamido)phenoxy)methyl) carbonyl-2,5-dimethyl-4-(4-fluorobenzyl)piperazine; NMR (CDCl$_3$) 10.2 (s, 1), 8.5 (s, 1), 7.3 (m, 3), 7.0 (m, 3), 6.8 (d, 1), 4.7 (m, 3), 4.2–3.9 (m, 1), 3.6–3.2 (m, 5), 3.0 (m, 1), 2.7 (dd, 1), 2.2 (d, 1), 1.4 (d, 3), 1.3 (m, 3), 1.0 (br s, 3) ppm;

(trans)-1-((4-chloro-2-(1-(methylamino)ethyl)phenoxy) methyl)carbonyl-2,5-dimethyl-4-(4-fluorobenzyl) piperazine; NMR (CDCl$_3$) 7.3 (m, 3), 7.1 (dd, 1), 7.0 (t, 2), 6.8 (br d, 1), 4.7 (m, 3), 4.0 (q, 2), 3.6 (q, 2), 3.2 (m, 1), 3.0 (m, 1), 2.7 (dd, 1), 2.3 (m, 4), 1.3 (m, 6), 0.9 (m, 3) ppm;

(trans)-1-((4-chloro-2-((methylamino)(phenyl)methyl) phenoxy)methyl)carbonyl-2,5-dimethyl-4-(4-fluorobenzyl)piperazine; NMR (CDCl$_3$) 7.6 (br d, 1), 7.4–7.1 (m, 8), 7.0 (t, 2), 6.8 (m, 1), 5.0 (d, 1), 4.6 (m, 3), 4.2 (m, 1), 3.5 (t, 1), 3.4–3.0 (m, 4), 2.8 (m, 1), 2.4 (s, 3), 2.2 (m, 1), 1.2 (m, 3), 0.8 (m, 3) ppm;

(2R)-1-((4-chloro-2-((piperazin-1-yl)methyl)phenoxy) methyl)carbonyl-2-methyl-4-(4-fluorobenzyl) piperazine; NMR (DMSO-$d_6$) 9.2 (br s, 1), 7.6 (m, 4), 7.3 (t, 2), 7.2 (d, 1), 5.2 (dd, 1), 5.0 (d, 1), 4.8 (m, 1), 4.4 (d, 4), 3.9 (d, 1), 3.4 (m, 11), 1.4 (d, 1.5), 1.2 (d, 1.5) ppm;

(2R,5S)-1-((4-chloro-2-((piperazin-1-yl)methyl) phenoxy)methyl)carbonyl-2,5-dimethyl-4-(4-fluorobenzyl)piperazine; NMR (DMSO-$d_6$) 9.8 (br s, 1), 9.2 (br s, 1), 7.6 (s, 3), 7.5 (dd, 1), 7.3 (t, 2), 7.2 (d, 1), 5.4 (m, 1), 5.0 (m, 3), 4.7 (m, 1), 4.5 (s, 2), 4.3 (m, 3), 3.7–3.1 (m, 11), 1.4–1.1 (m, 6) ppm;

(trans)-1-((4-chloro-2-((piperazin-1-yl)methyl)phenoxy) methyl)carbonyl-2,5-dimethyl-4-(4-fluorobenzyl) piperazine; NMR (DMSO-$d_6$) 11.3 (br d, 1), 9.7 (m, 2), 7.9 (m, 2), 7.7 (m, 2), 7.4–7.2 (m, 3), 5.4 (m, 1), 5.0 (m, 2), 4.6 (m, 1), 4.2 (m, 3), 3.8–3.2 (m, 10), 2.8 (dd, 1), 1.7 (m, 3), 1.4 (dd, 3), 1.2 (m, 3) ppm;

(trans)-1-(2-(4-chlorophenyl)-3-(amino)propyl)carbonyl-2,5-dimethyl-4-(4-fluorobenzyl)piperazine; NMR (CDCl$_3$) 7.3 (m, 4), 7.2 (d, 2), 7.0 (t, 2), 4.8 (m, 1), 4.2 (m, 1), 3.9 (m, 1), 3.5–3.2 (m, 3), 2.9 (m, 3), 2.6 (m, 2), 2.2 (m, 1), 1.2 (m, 3), 0.8 (m, 3) ppm; and (trans)-1-(2-(4-chlorophenyl)-2-(amino)ethyl)carbonyl-2, 5-dimethyl-4-(4-fluorobenzyl)piperazine; NMR (CDCl$_3$) 7.3 (m, 6), 7.0 (t, 2), 4.7 (m, 0.5), 4.5 (m, 1), 4.2 (d, 0.5), 3.5 (q, 2), 3.2 (m, 1), 3.0 (m, 1), 2.6 (m, 2), 2.5 (m, 2), 2.2 (m, 1), 1.2 (m, 3), 0.9 (m, 3) ppm.

D. In a similar manner, other compounds of formulae (Ia), (Ib), (Ic) and (Id) are made.

EXAMPLE 14

Compounds of Formula (Ia)

A. To a solution of (trans)-1-((4-chloro-2-carboxyphenoxy)methyl)carbonyl-2,5-dimethyl-4-(4-fluorobenzyl)piperazine (0.217 g, 0.50 mmol) in a solution of tetrahydroduran (5 mL) at 0° C. was added isobutyl chloroformate (0.075 g, 0.55 mmol) and N-methylmorpholine (0.0556 g, 0.55 mmol). The resulting mixture was stirred at 0° C. for 20 min, resulting in formation of a white precipitate. A solution of methylamine in tetrahydrofuran (0.25 mL, 2.0 M, 0.50 mmol) was then added and the mixture stirred for 30 min more, at which time it was concentrated of volatiles in vacuo. The resulting residue was dissolved in ethyl acetate and washed with water, then brine, dried over MgSO$_4$, filtered and concentrated to 0.208 g of a foam. This was dissolved in ethyl acetate and treated with 1 M ethereal HCl solution (excess). The resulting solid was collected by filtration and washed with ethyl acetate. Drying in vacuo afforded 0.19 g of (trans)-1-((4-chloro-2-(methylaminocarbonyl)phenoxy) methyl)carbonyl-2,5-dimethyl-4-(4-fluorobenzyl)piperazine as a white solid; NMR (DMSO-$d_6$) 10.8 (br d, 1), 9.2 (br s, 1), 7.8 (s, 2), 7.7 (m, 1), 7.6 (m, 1), 7.3 (m, 3), 5.4 (d, 1), 5.0 (m, 2), 4.7 (m, 1), 4.3 (m, 3), 4.0 (m, 1), 3.6 (m, 2), 2.8 (s, 3), 1.4 (m, 3), 1.3 (m, 3) ppm.

B. In a similar manner, the following compounds of formula (Ia) were made:

(trans)-1-((4-chloro-2-((aminocarbonylmethyl) aminocarbonyl)phenoxy)methyl)carbonyl-2,5-dimethyl-4-(4-fluorobenzyl)piperazine; NMR (DMSO-$d_6$) 9.4 (br s, 1), 7.8 (s, 1), 7.6 (dd, 1), 7.4 (m, 2), 7.2 (d, 1), 7.1 (t, 2), 7.0 (s, 1), 5.3 (m, 1), 5.0 (m, 2), 4.4 (m, 1), 4.0 (m, 1), 3.8 (d, 2), 3.5 (m, 2), 3.0 (m, 1), 2.7 (m, 1), 2.2 (brd, 1), 1.2 (brd, 3), 0.9 (brd, 3) ppm;

(trans)-1-((4-chloro-2-((2-aminoethyl)aminocarbonyl) phenoxy)methyl)carbonyl-2,5-dimethyl-4-(4-fluorobenzyl)piperazine; NMR (CDCl$_3$) 9.4 (br s, 1), 8.2 (s, 1), 7.3 (m, 3), 7.0 (t, 2), 6.8 (d, 1), 4.7 (m, 3), 4.2 (m, 1) 3.6 (m, 5), 3.1 (m, 3), 2.7 (br d, 1), 2.3 (d, 1), 1.3 (br d, 3), 1.0 (m, 2) ppm;

(trans)-1-((4-chloro-2-((4-aminocarbonylphenyl) aminocarbonyl)phenoxy)methyl)carbonyl-2,5-dimethyl-4-(4-fluorobenzyl)piperazine; NMR (DMSO-$d_6$) 11.4 (s, 1), 7.9 (m, 5), 7.7 (d, 1), 7.4 (m, 3), 7.1 (t, 2), 5.4 (d, 1), 5.1 (m, 2), 4.6 (br s, 1), 4.0 (m, 1), 3.5 (m, 3), 3.0 (m, 1), 2.2 (m, 1), 1.3 (m, 3), 0.9 (m, 3) ppm; and (trans)-1-(2-(4-chlorophenyl)-3-(t-butoxycarbonylamino) propyl)carbonyl-2,5-dimethyl-4-(4-fluorobenzyl) piperazine; NMR (CDCl$_3$) 7.3 (m, 4), 7.2 (d, 2), 7.0 (t, 2), 4.8 (br s, 1), 4.6 (m, 1), 4.0 (m, 1), 3.4 (m, 6), 3.0 (m, 1), 2.6 (m, 2), 2.1 (m, 1), 1.4 (s, 9), 1.2 (m, 3), 0.9 (m, 3) ppm.

C. In a similar manner, other compounds of formulae (Ia), (Ib), (Ic) and (Id) are prepared.

EXAMPLE 15

Compounds of Formula (Ia)

A. To a solution of hydroxylamine, hydrochloride (0.17 g, 2.5 mmol) in DMSO (3 mL) was added triethylamine (0.252 g, 2.5 mmol). The mixture was stirred at ambient temperature for 10 minutes, then filtered and washed with THF. The filtrate was concentrated in vacuo to remove the THF then treated with (trans)-1-((4-chloro-2-cyanophenoxy)methyl)carbonyl-2,5-dimethyl-4-(4-fluorobenzyl)piperazine (0.200 g, 0.48 mmol). The resulting mixture was heated to 75° C. for 20 hours. At that time the mixture was diluted with water and extracted with ethyl acetate. The organic extract was washed with water, then brine, dried over $MgSO_4$, filtered concentrated in vacuo to afford 0.21 g of an oil. 0.030 g of this oil was dissolved in ethyl acetate and treated with 1 M ethereal HCl solution (excess). The resulting solid was collected by filtration and washed with ethyl acetate. Drying in vacuo afforded 0.027 g of (trans)-1-((4-chloro-2-(hydroxyamidino)phenoxy)methyl)carbonyl-2,5-dimethyl-4-(4-fluorobenzyl)piperazine as a white solid; NMR ($CDCl_3$) 7.6 (s, 1), 7.3 (t, 2), 7.2 (dd, 1), 7.0 (t, 2), 6.7 (br d, 1), 6.1 (brs, 2), 4.7 (m, 3), 3.7 (br d, 1), 3.5 (q, 2), 3.2 (m, 1), 3.0 (m, 1), 2.7 (m, 1), 2.2 (t, 1), 1.3 (m, 3), 0.9 (m, 3) ppm.

B. In a similar manner, other compounds of formulae (Ia), (Ib), (Ic) and (Id) are made.

EXAMPLE 16

Compounds of Formula (Ia)

A. To a solution of 4-(4-fluorobenzyl)-1-((4-chlorophenoxy)methyl)carbonyl-2-(2-hydroxyethyl)piperazine (0.134 g, 0.33 mmol) and triphenylphosphine (0.100 g) in THF (6 mL) at 0° C. was added diethyl azodicarboxylate (0.060 mL) and diphenylphosphoryl azide (0.081 mL). The mixture was stirred at ambient temperature for 2 days, then concentrated of volatiles in vacuo. Purification by flash column chromatography on silica gel afforded 0.047 g of 1-((4-chlorophenoxy)methyl)carbonyl-2-(2-azidoethyl)-4-(4-fluorobenzyl)piperazine as a clear, colorless oil; NMR ($CDCl_3$) 7.3 (m, 4), 7.0 (t, 2), 6.9 (d, 2), 4.7 (m, 3), 4.4 (br d, 1), 4.3 (m, 1), 4.1 (m, 1), 3.5–3.1 (m, 4), 2.8 (d, 1), 2.7 (d, 1), 2.1 (m, 2), 1.8 (m, 1) ppm.

B. In a similar manner, the compounds of formula (Ia), (Ib), (Ic) and (Id) are made.

EXAMPLE 17

Compounds of Formula (Ia)

A. To a solution of (trans)-1-((4-chloro-2-aminophenoxy)methyl)carbonyl-2,5-dimethyl-4-(4-fluorobenzyl)piperazine (0.169 g, 0.416 mol) in 10 mL of methylene chloride was added phthallic anhydride (0.074 g, 0.499 mol) and several 4 Å molecular sieves. The mixture was stirred at ambient temperature for 3 hours, then at 70° C. for 3 hours. At that time the mixture was cooled to 0° C. and treated with oxalyl chloride (0.064 g, 0.499 mol). This was stirred at ambient temperature for 3 hours then partitioned between methylene chloride and water. The organic layer was concentrated to give an oil. Purification by flash column chromatography on silica gel afforded 0.058 g of a clear oil. This was dissolved in ethyl acetate and treated with 1 M ethereal HCl solution (excess). The resulting solid was collected by filtration and washed with ethyl acetate. Drying in vacuo afforded 0.045 g of (trans)-1-((4-chloro-2-(phthalimido)phenoxy)methyl)carbonyl-2,5-dimethyl-4-(4-fluorobenzyl)piperazine as a white solid; NMR ($CDCl_3$) 7.9 (m, 2), 7.8 (m, 2), 7.4 (d, 1), 7.3 (m, 3), 7.05 (d, 1), 7.0 (t, 2), 4.6 (m, 3), 4.0 (m, 1), 3.5 (m, 1), 3.4 (m, 2), 2.9 (m, 1), 2.6 (m, 1), 2.2 (m, 1), 1.2 (m, 3), 0.9 (m, 3) pppm.

B. In a similar manner, the following compound of formula (Ia) was made:

(trans)-1-((4-chloro-2-(maleimido)phenoxy)methyl)carbonyl-2,5-dimethyl-4-(4-fluorobenzyl)piperazine;

NMR ($CDCl_3$) 7.3 (m, 6), 7.0 (t, 2), 6.8 (s, 1), 4.6 (m, 3), 4.0 (m, 1), 3.5 (q, 2), 3.2 (m, 1), 3.0 (br s, 1), 2.6 (dd, 1), 2.2 (br d, 1), 1.2 (m, 3), 0.9 (m, 3) ppm.

C. In a similar manner, compound of formula (Ia), (Ib), (Ic) and (Id) are made.

EXAMPLE 18

This example illustrates the preparation of representative pharmaceutical compositions for oral administration containing a compound of the invention, or a pharmaceutically acceptable salt thereof, e.g., 1-((2-methylphenoxy)methyl)carbonyl-4-(4-chlorobenzyl)piperazine hydrochloride salt:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 19

This example illustrates the preparation of a representative pharmaceutical formulation for parenteral administration containing a compound of the invention, or a pharmaceutically acceptable salt thereof, e.g., 4-(4-fluorobenzyl)-1-((2-((acetylamino)methyl)4-chlorophenoxy)methyl)carbonyl-2,5-methylpiperazine:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 20

This example illustrates the preparation of a representative pharmaceutical composition in suppository form containing a compound of the invention, or a pharmaceutically acceptable salt thereof, e.g., 4-(4-fluorobenzyl)-1-((4-chlorophenoxy)methyl)carbonyl-2-(2-hydroxyethyl)piperazine:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 21

This example illustrates the preparation of a representative pharmaceutical formulation for insufflation containing a compound of the invention, or a pharmaceutically acceptable salt thereof, e.g., (2R,5R)-4-(4-fluorobenzyl)-1-((4-chlorophenoxy)methyl)carbonyl-2,5-dimethylpiperazine:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 22

This example illustrates the preparation of a representative pharmaceutical formulation in nebulized form containing a compound of the invention, or a pharmaceutically acceptable salt thereof, e.g., 1-(((4-chlorophenyl)amino)methyl)carbonyl-4-(4-chlorobenzyl)piperazine:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 23

This example illustrates the preparation of a representative pharmaceutical formulation in aerosol form containing a compound of the invention, or a pharmaceutically acceptable salt thereof, e.g., 1-((4-chloro-2-(((ethyl)amino)methyl)phenoxy)methyl)carbonyl-2,5-dimethyl-4-(4-fluorobenzyl)piperazine:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

In the following examples, 293MR cells are utilized. These are human embryonic kidney cells (HEK293) which were stably transfected to express human CCR1 receptor by the following procedure: HEK293 cells were obtained from the American Type Culture Collection (ATCC CRL 1573). Human CCR1 cDNA was provided through collaboration with Dr. Stephen Peiper of the University of Louisville, Ky. The CCR1 gene was subcloned using standard techniques (see, e.g., *Molecular Cloning: A Laboratory Manual*, 2nd Edition, Cold Spring Harbor Laboratory Press, 1989) into a standard plasmid containing the SV40 promoter and enhancer. The plasmid also contained hygromycin and puromycin resistance genes. Calcium phosphate transfection standard protocols were used to insert the plasmid into the HEK293 cells. Cells were selected for stable expression of CCR1 using hygromycin and puromycin selection. Cells were tested for the ability to bind $^{125}$I-labelled RANTES or MIP-1α with high affinity.

EXAMPLE 24

In Vitro Assay: Calcium Flux

Since the CCR1 receptor, in common with other seven transmembrane G-protein coupled receptors, responds to the binding of its ligand, e.g., MIP-1α and RANTES, by mobilizing free intracellular calcium, one can measure biological activity by calcium flux assays using the fluorescent dye Fura 2. In the following assay, the ability of the compounds of the invention to block this biologic response is measured.

Protocol:

1) Two flasks of 293MR cells were detached, washed and resuspended in Hanks $Ca^{2+}$ (50 mL Hanks, 1.0 mL 1 M Hepes, 1.6 mL 500 mM $CaCl_2$, pH 7.4). The cells were washed twice in this media.
2) The cells were counted CCR1=$28\times10^6$ cells made to $2\times10^6$ cells/mL by suspending into 14 mL Hanks $Ca^{2+}$.
3) To 10 mL of the cells ($20\times10^6$) was added 30 mL of media (containing 50 μg of Fura in 50 μL of DMSO). Final cell concentration was $1.0\times10^6$ cells/mL. Final Fura concentration was 1.25 μM.
4) The cells were incubated at 37° C. for 30 minutes in the presence (or absence) of increasing concentrations of compounds of the invention. Cells were washed as above to remove free Fura. Cells were resuspended at $1\times10^6$ cells/mL. Cells were then aliquoted (2.0 mL) in a cuvette and placed in a spectrofluorimeter. The cells were then stimulated with either MIP-1α or RANTES (Peprotech Inc.) and $Ca^{2+}$ release was measured in the spectrofluorimeter.
5) The data were corrected for nM $Ca^{2+}$ released by adding 100 μL of 0.1% Triton X-100 (for maximum values) followed by 100 μL of 500 mM EGTA, pH 8.5 (for minimum values).

The compounds of the invention, when tested in this assay, demonstrated the ability to inhibit the $Ca^{2+}$ mobilization in response to binding of MIP-1α and RANTES to the CCR1 receptor.

EXAMPLE 25

In Vitro Assay

The assays were performed in a microphysiometer to investigate the functional activity of the antagonist of interest. The microphysiometer assesses cellular response through the use of a silicon-based potentiometric sensor that can measure small changes on solution pH (Hafeman et al., *Science* (1988), Vol. 240, pp. 1182–1185; Parce et al., *Science* (1989), Vol. 246, pp. 243–247). It has been shown that the microphysiometer can be used for measuring metabolic rates of living cells (Parce at al., 1989). The activation of cell membrane receptors can alter the rate of extracellular acidification (Owicki et al., *Proc. Natl. Acad. Sci.* (1990), Vol. 87, pp. 4007–4011). The following assay demonstrates that activation of CCR1 receptors endogenously expressed on human THP-1 cells with MIP-1α and RANTES induced physiological changes resulting in an increase in metabolic rates and that the compounds of the invention inhibit this effect in a dose-dependent manner.

Materials:

1. Cytosensor Capsule Kit (Molecular Devices Cat #R8013).
2. Agarose Entrapment Medium (Molecular Devices Cat #R8023)
3. Cytosensor Modified RPMI 1640 Medium, low buffered (Molecular Devices Cat #R8023)
4. Cytosensor Sterilant Kit (Molecular Devices Cat#R8017)
5. Reference Electrode Maintenance Kit (Molecular Devices Cat#0310-2805)
6. MIP-1α or RANTES (Peprotech Inc.) working solution: 10 μM in Modified RPMI 1640 medium (Molecular Devices Cat#R8016) supplemented with 1 mg/mL BSA (bovine serum albumin),100 units/mL penicillin, and 100 μg/mL streptomycin). This working solution is hereinafter referred to as "modified culture medium".
7. MCP-1 working solution: 10 μM in modified culture medium.
8. Compounds of the invention stock solution: 1 mM in DMSO (stored at ambient temperature).
9. Cell Culture:
   a. THP-1 (ATCC Cat #TIB202)
   b. Tissue culture medium: RPMI 1640 supplemented with 10% FBS (fetal bovine serum). This medium is hereinafter referred to as "growth medium".

Assay Procedure:

THP-1 cells were grown in T-25 $cm^2$ flasks in growth medium at 37° C., 5.0% $CO_2$, 95% air to a cell density of $1\times10^6$ cells/mL. The cells were harvested by centrifugation (5 minutes at 20 G) and resuspended in modified growth medium. Trypan blue dye exclusion cell count was performed and cells were ≧90% viable. Cells were centrifuged again, the supernatant was removed, and the resulting pellet was resuspended to final cell concentration of $1\times10^6/0.1$ mL. Agarose cell entrapment reagent was melted and placed into a 37° C. water bath. Cell suspension was prepared: 0.15 mL of the THP-1 cells were added to a 1.5 mL centrifuge tube with 50 μL of the melted agarose solution. Addition to the capsule cups: the capsule cups were placed in a 12 well microtiter plate, a spacer was added to the capsule cup, and 7 μL of cell/agarose suspension was pipetted into the center of the cup. After three minutes, 1 mL of modified growth medium was pipetted to the outside of the capsule cup, and 200 μL of modified growth medium was pipetted to the inside. The capsule insert was then placed into the cup with sterile forceps and 500 μL of modified culture medium was pipetted into the insert. Completed capsule were loaded into the chambers of the microphysiometer. The chambers were perfused at a rate of 100 μL/minute with modified culture medium. The pump cycle was 50 seconds on and 40 seconds off. Multiple data points representing metabolic rate were taken and used as baseline. Cells were exposed to the compounds of the invention for 30 minutes prior to addition of chemokine agonists at a final concentration of 10 nM. Treated and non-treated cells were challenged with agonist for 100 seconds and data was collected.

When tested in this assay, the compounds of the invention demonstrated the ability to inhibit the activation of the CCR1 receptor by MIP-1α or RANTES.

EXAMPLE 26

In Vitro Assay

In Vitro Assay for CCR1 Receptor Antagonists

This assay demonstrates the affinities of the compounds of the invention for binding to the CCR1 receptor. The binding affinities of the compounds for the CCR1 receptor were determined by their abilities to compete with $^{125}$I-MIP-1α or $^{125}$I-RANTES for binding to the CCR1 receptor.

Reagents and Solutions:

MIP-1α and RANTES (Peprotech Inc.)

Cells: 293MR cells ($K_D$=1–3 nM and $B_{max}$=2–3 $\times10^6$ sites/cell) were detached by trypsinization and plated into flasks at least 48 hours prior to the experiment.

Ligand: $^{125}$I-MIP-1α and $^{125}$I-RANTES from New England Nuclear (specific activity is 2200 Ci/mmol, 25 μCi/vial) was reconstituted in 1 mL H$_2$O.

Assay buffer: 130 mM NaCl, 5 mM KCl, 1 mM MnCl$_2$, 50 mM Tris, 30 μg/ml bacitracin, 0.1% BSA, pH 7.4.

Wash buffer: Phosphate buffer solution (PBS)

Compounds of the Invention: The stock solution of the compounds was 1 mM in 100% DMSO. The highest concentration in the assay was 10 μM and may vary depending on the potency of the compounds. A serial 1:3 dilution from the highest concentration was made with assay buffer. Six concentrations of each compound were usually being screened to generate a dose curve from which the K$_i$ value was determined.

Assay Procedure:

Assays were performed in 96-well v-bottom microtiter plates in a total volume of 100 μl.

293MR cells was detached from T225 cm$^2$ flask in PBS by shaking. The cells were washed once in PBS and resuspended in the assay buffer to about 1.1×10$^5$ cells/mL. Cells (about 8000 cells/assay) were incubated with either $^{125}$I-MIP-1α or $^{125}$I-RANTES (about 15,000–20,000 cpm/assay) in the presence and absence of different concentrations of compounds at ambient temperature for 30–40 minutes.

The reactions were terminated by harvesting through a GF/B filter plate presoaked with 0.3% PEI (Sigma # P-3143) plus 0.5% BSA and washing 5 times with cold PBS. The radioactivities in each well were determined by scintilation counting following addition of 50 μl of scintillation fluid.

The nonspecific binding was defined by the binding in the presence of 100 nM of unlabeled MIP-1α or RANTES. The CCR1 receptor concentration used in the assay was 0.4 nM and $^{125}$I-MIP-1α or $^{125}$I-RANTES was 0.06 nM. The concentrations of compounds in the assay is typically from 10 μM to 30 nM in 1:3 dilution and the concentrations for more potent compounds were lower depending on the potency.

Calculations:

The dose curves of each compound with 6 concentration points were generated and IC$_{50}$ values were determined by fitting the data to the log-logit equation (linear) with an EXCEL spread-sheet. The K$_i$ values were then calculated by dividing the IC$_{50}$ by 1.025, to correct for concentration of labelled ligand.

The compounds of the invention, when tested in this assay, demonstrated their affinity to bind to the CCR1 receptor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of the following formula (Ia):

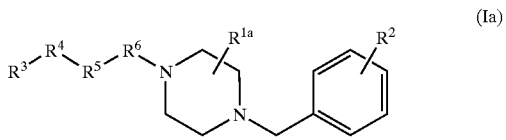

wherein:
R$^{1a}$ is one or more substituents independently selected from the group consisting of oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;

R$^2$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl) aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkylalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl)aminocarbonyl, (monoalkylaminocarbonylalkyl)aminocarbonyl, (carboxyalkyl)aminocarbonyl, (alkoxycarbonylalkyl)aminocarbonyl, (aminoalkyl)aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

$R^4$ is $C(R^8)_2$—;

$R^5$ is an alkylene chain or an alkylidene chain;

$R^6$ is —C(O)—; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl;

as a single stereoisomer or a mixture thereof; or a pharmaceutically acceptable salt thereof.

2. The compound of claim 1 wherein:

$R^5$ is methylene; and each $R^8$ is independently selected from the group consisting of hydrogen, alkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, alkylcarbonylaminoalkyl, cycloalkylcarbonylaminoalkyl, alkoxycarbonylaminoalkyl, heterocyclylcarbonylaminoalkyl, arylsulfonylamino, alkylsulfonylaminoalkyl, ureido, monoalkylureido, monohaloalkylureido, ureidoalkyl, monoalkylureidoalkyl, monohaloalkylureidoalkyl, aminoalkyl, monoalkylaminoalkyl, and dialkylaminoalkyl.

3. The compound of claim 2 wherein:

$R^{1a}$ is one or more substituents independently selected from the group consisting of halo, alkyl, cycloalkyl cycloalkylaminoalkyl, haloalkyl, hydroxyalkyl, hydroxyalkenyl, hydroxyalkynyl, (hydroxy)aralkyl, cyanoalkyl, haloalkylcarbonylaminoalkyl, alkoxyalkyl, aralkoxyalkyl, alkylthioalkyl, hydroxyalkylthioalkyl, aminoalkyl, monoalkylaminoalkyl, dialkylaminoalkyl, monoarylaminoalkyl, monoaralkylaminoalkyl, azidoalkyl, monoalkylureidoalkyl, (alkoxycarbonylalkyl)ureidoalkyl, hydroxyalkylaminoalkyl, aryloxyalkylcarbonyloxyalkyl, aralkoxyalkylcarbonyloxyalkyl, alkylcarbonylalkyl, alkoxycarbonyl, alkoxycarbonylalkyl, and heterocyclylalkyl;

$R^2$ is one or more substituents independently selected from the group consisting of hydrogen and halo;

$R^3$ is phenyl optionally substituted by one or more substituents independently selected from the group consisting of hydrogen, hydroxy, halo, alkyl, alkoxy, haloalkyl, hydroxyalkoxy, haloalkyl, formyl, nitro, cyano, aminoalkoxy, cycloalkyl, cycloalkylaminoalkyl, aralkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, alkylsulfonylamino, aminoalkyl, monoalkylaminoalkyl, dialkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, dialkylaminocarbonylalkyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, alaninamido, heterocyclyl and heterocyclylalkyl.

4. The compound of claim 3 wherein:

$R^{1a}$ is one or more substituents independently selected from the group consisting of alkyl, cycloalkyl, hydroxyalkyl, hydroxyalkenyl, cyanoalkyl, alkoxyalkyl, monoalkylaminoalkyl, azidoalkyl, monoalkylureidoalkyl, aryloxyalkylcarbonyloxyalkyl, and heterocyclylalkyl;

$R^2$ is one or more substituents independently selected from the group consisting of hydrogen, chloro or fluoro;

$R^3$ is phenyl substituted by one or more substituents independently selected from the group consisting of hydroxy, halo, alkyl, alkoxy, formyl, nitro, cyano, aminoalkoxy, cycloalkylaminoalkyl, hydroxyalkyl, (monoalkylamino)aralkyl, alkoxyalkyl, amino, monoalkylamino, dialkylamino, monoaralkylamino, alkylcarbonylamino, alkenylcarbonylamino cycloalkylcarbanylamino, arylcarbonylamino, heterocyclylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylalkylcarbonylaminoalkyl, alkylsulfonylaminoalkyl, (alkylsulfonyl)(alkyl)aminoalkyl, arylsulfonylaminoalkyl, (arylsulfonyl)(alkyl)aminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)(alkyl)glycinamido, (monoarylaminocarbonyl)glycinamido, (monoarylaminocarbonyl)(alkyl)glycinamido, alaninamido, heterocyclyl and heterocyclylalkyl.

5. The compound of claim 4 wherein:

$R^{1a}$ is one or more substituents independently selected from the group consisting of alkyl and hydroxyalkyl;

$R^2$ is one or more substituents independently selected from the group consisting of hydrogen, chloro or fluoro;

$R^3$ is phenyl substituted by one or more substituents independently selected from the group consisting of halo, alkyl, alkoxy, formyl, nitro, cycloalkylaminoalkyl, hydroxyalkyl, amino, alkylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, (alkylsulfonyl)(alkyl)aminoalkyl, alkylcarbonyl, aminocarbonyl, monoalkylaminocarbonyl, monoarylaminocarbonyl, (aminocarbonylalkyl) aminocarbonyl, (aminoalkyl)aminocarbonyl, hydroxyamidino, ureido, (haloalkylcarbonyl)ureido, ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylaminoalkylcarbonyl)glycinamido, alaninamido, and heterocyclylalkyl.

6. The compound of claim 5 wherein:

$R^2$ is 4-fluoro;

$R^3$ is phenyl substituted at the 4-position with chloro and optionally substituted at the 2-position by aminocarbonyl, ureido, or glycinamido; and one $R^6$ is hydrogen and the other $R^8$ is selected from the group consisting of amino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, alkylcarbonylaminoalkyl, cycloalkylcarbonylaminoalkyl, alkoxycarbonylaminoalkyl, heterocyclylcarbonylaminoalkyl, arylsulfonylamino, alkylsulfonylaminoalkyl, ureido, monoalkylureido, monohaloalkylureido, ureidoalkyl, monoalkylureidoalkyl, monohaloalkylureidoalkyl, and aminoalkyl.

7. A compound selected from the group consisting of the following compounds:

(trans)-1-(2-(4-chlorophenyl)-3-(methylsulfonylamino) propyl)carbonyl-2,5-dimethyl-4-(4-fluorobenzyl) piperazine;

(trans)-1-(2-(4-chlorophenyl)-3-(acetylamino)propyl) carbonyl-2,5-dimethyl-4-(4-fluorobenzyl)piperazine;

(trans)-1-(2-(4-chlorophenyl)-2-(methylsulfonylamino) ethyl)carbonyl-2,5-dimethyl-4-(4-fluorobenzyl) piperazine;

(trans)-1-(2-(4-chlorophenyl)-2-(acetylamino)ethyl) carbonyl-2,5-dimethyl-4-(4-fluorobenzyl)piperazine;

(trans)-1-(2-(4-chlorophenyl)-2-(amino)ethyl)carbonyl-2,5-dimethyl-4-(4-fluorobenzyl)piperazine;

(trans)-1-(2-(4-chlorophenyl)-2-(ureido)ethyl)carbonyl-2,5-dimethyl-4-(4-fluorobenzyl)piperazine;

(trans)-1-(2-(4-chlorophenyl)-3-(ureido)propyl)carbonyl-2,5-dimethyl-4-(4-fluorobenzyl)piperazine;

(trans)-1-(2-(4-chlorophenyl)-3-(amino)propyl)carbonyl-2,5-dimethyl-4-(4-fluorobenzyl)piperazine;

(trans)-1-(2-(4-chlorophenyl)-3-(t-butoxycarbonylamino) propyl)carbonyl-2,5-dimethyl-4-(4-fluorobenzyl) piperazine;

(trans)-1-(2-(4-chlorophenyl)-2-((ethoxycarbonylmethylcarbonylamino)ethyl) carbonyl-2 5-dimethyl-4-(4-fluorobenzyl)piperazine;

(trans)-1-(2-(4-chlorophenyl)-2-(N'-iso-propylureido) ethyl)carbonyl-2,5-dimethyl-4-(4-fluorobenzyl) piperazine;

(trans)-1-(2-(4-chlorophenyl)-2-(N'-(2-chloroethyl) ureido)ethyl)carbonyl-2,5-dimethyl-4-(4-fluorobenzyl) piperazino;

(trans)-1-(2-(4-chlorophenyl)-2-((2-nitrophenyl) carbonylamino)ethyl)carbonyl-2,5-dimethyl-4-(4-fluorobenzyl)piperazine;

(trans)-1-(2-(4-chlorophenyl)-2-((4-methoxyphenylmethyl)carbonylamino)ethyl)carbonyl-2,5-dimethyl-4-(4-fluorobenzyl)piperazine;

(trans)-1-(2-(4-chlorophenyl)-2-((2,4-dinitrophenyl) sulfonylamino)ethyl)carbonyl-2,5-dimethyl-4-(4-fluorobenzyl)piperazine;

(trans)-1-(2-(4-chlorophenyl)-2-(cyclopropylcarbonylamino)ethyl)carbonyl-2,5-dimethyl-4-(4-fluorobenzyl)piperazine;

(trans)-1-(2-(4-chlorophenyl)-2-((2-cyclopropylethyl) carbonylamino)ethyl)carbonyl-2,5-dimethyl-4-(4-fluorobenzyl)piperazine;

(trans)-1-(2-(4-chlorophenyl)-3-((2-methylpropyl) carbonylamino)propyl)carbonyl-2,5-dimethyl-4-(4-fluorobenzyl)piperazine;

(trans)-1-(2-(4-chlorophenyl)-3-(cyclopentylcarbonylamino)propyl)carbonyl-2,5-dimethyl-4-(4-fluorobenzyl)piperazine;

(trans)-1-(2-(4-chlorophenyl)-3-(N'-(t-butyl)ureido) propyl)carbonyl-2,5-dimethyl-4-(4-fluorobenzyl) piperazine;

(trans)-1-(2-(4-chlorophenyl)-3-(N'-(ethyl)ureido)propyl) carbonyl-2,5-dimethyl-4-(4-fluorobenzyl)piperazine;

(trans)-1-(2-(4-chlorophenyl)-3-(N'-(3-choropropyl) ureido)propyl)carbonyl-2,5-dimethyl-4-(4-fluorobenzyl)piperazine; and (trans)-1-(2-(4-chlorophenyl)-3-((morpholin-4-yl) carbonylamino)propyl)carbonyl-2,5-dimethyl-4-(4-fluorobenzyl)piperazine.

8. A compound of the following formula (Ic):

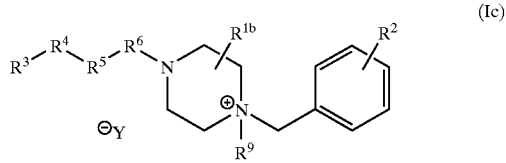

(Ic)

wherein:

Y is a pharmaceutically acceptable counterion:

$R^{1b}$ is one or more substituents independently selected from the group consisting of hydrogen, oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl) aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;

$R^2$ is one or more substituents independently selected from the group consisting of hydrogen, hydroxy, hydroxysulfonyl, halo, alkyl mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl) aminoalkyl, alkoxycarbonylamino, (alkoxycarbonyl) (alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy) aralkyl, (monoalkylamino)aralkyl, (hydroxyalkyl) hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl) (alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl) aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl) aminoalkyl, arylsulfonylaminoalkyl, (arylsulfonyl) (alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy) carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl) aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

$R^4$ is $—C(R^8)_2—$;

$R^5$ is an alkylene chain or an alkylidene chain;

$R^6$ is $—C(O)—$;

each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl) (alkyl)amino, aralkylcarbonylamino, (aralkylcarbonyl) (alkyl)amino, alkylcarbonylaminoalkyl, cycloalkylcarbonylaminoalkyl, alkoxycarbonylaminoalkyl, (alkylcarbonyl)(alkyl) aminoalkyl, aralkylcarbonylaminoalkyl, heterocyclylcarbonylaminoalkyl, (aralkylcarbonyl)

(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl; and $R^9$ is alkyl, aralkyl, haloalkyl, hydroxyalkyl, alkoxyalkyl, carboxyalkyl, alkoxycarbonylalkyl, alkylcarbonylalkyl, alkylcarbonylaminoalkyl, aminocarbonylalkyl, monoalkylaminocarbonylalkyl, dialkylaminocarbonylalkyl, heterocyclylalkyl, or cycloalkylalkyl;

as a single stereoisomer or a mixture thereof; or a pharmaceutically acceptable salt thereof.

9. The compound of claim 8 wherein:

$R^5$ is methylene; and each $R^8$ is independently selected from the group consisting of hydrogen, alkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, alkylcarbonylaminoalkyl, cycloalkylcarbonylaminoalkyl, alkoxycarbonylaminoalkyl, heterocyclylcarbonylaminoalkyl, arylsulfonylamino, alkylsulfonylaminoalkyl, ureido, monoalkylureido, monohaloalkylureido, ureidoalkyl, monoalkylureidoalkyl, monohaloalkylureidoalkyl, aminoalkyl, monoalkylaminoalkyl, and dialkylaminoalkyl.

10. The compound of claim 9 wherein:

$R^{1b}$ is one or more substituents independently selected from the group consisting of halo, alkyl, cycloalkyl, cycloalkylaminoalkyl, haloalkyl, hydroxyalkyl, hydroxyalkenyl, hydroxyalkynyl, (hydroxy)aralkyl, cyanoalkyl, haloalkylcarbonylaminoalkyl, alkoxyalkyl, aralkoxyalkyl, alkylthioalkyl, hydroxyalkylthioalkyl, aminoalkyl, monoalkylaminoalkyl, dialkylaminoalkyl, monoarylaminoalkyl, monoaralkylaminoalkyl, azidoalkyl, monoalkylureidoalkyl, (alkoxycarbonylalkyl)ureidoalkyl, hydroxyalkylaminoalkyl, aryloxyalkylcarbonyloxyalkyl, aralkoxyalkylcarbonyloxyalkyl, alkylcarbonylalkyl, alkoxycarbonyl, alkoxycarbonylalkyl, and heterocyclylalkyl;

$R^2$ is one or more substituents independently selected from the group consisting of hydrogen and halo;

$R^3$ is phenyl optionally substituted by one or more substituents independently selected from the group consisting of hydrogen, hydroxy, halo, alkyl, alkoxy, hydroxyalkoxy, haloalkyl, formyl, nitro, cyano, aminoalkoxy, cycloalkyl, cycloalkylaminoalkyl, aralkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, alkylsulfonylamino, aminoalkyl, monoalkylaminoalkyl, dialkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, dialkylaminocarbonylalkyl, hydroxyamidino, ureido, monoalkylureido, monoarylureido, monoarylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, alaninamido, heterocyclyl and heterocyclylalkyl.

11. The compound of claim 10 wherein:

$R^{1b}$ is one or more substituents independently selected from the group consisting of alkyl, cycloalkyl, hydroxyalkyl, hydroxyalkenyl, cyanoalkyl, alkoxyalkyl, monoalkylaminoalkyl, azidoalkyl, monoalkylureidoalkyl, aryloxyalkylcarbonyloxyalkyl, and heterocyclylalkyl;

$R^2$ is one or more substituents independently selected from the group consisting of hydrogen, chloro or fluoro;

$R^3$ is phenyl substituted by one or more substituents independently selected from the group consisting of hydroxy, halo, alkyl, alkoxy, formyl, nitro, cyano, aminoalkoxy, cycloalkylaminoalkyl, hydroxyalkyl, (monoalkylamino)aralkyl, alkoxyalkyl, amino, monoalkylamino, dialkylamino, monoaralkylamino, alkylcarbonylamino, alkenylcarbonylamino, cycloalkylcarbonylamino arylcarbonylamino, heterocyclylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylalkylcarbonylaminoalkyl, alkylsulfonylaminoalkyl, (alkylsulfonyl)(alkyl)aminoalkyl, arylsulfonylaminoalkyl, (arylsulfonyl)(alkyl)aminoalkyl, carboxy, alkoxycarbonyl, alkylcarbonyl, (hydroxyalkoxy)carbonyl, aminocarbonyl, monoalkylaminocarbonyl, monoarylaminocarbonyl, (aminocarbonylalkyl)aminocarbonyl, (aminoalkyl)aminocarbonyl, (hydroxyalkyl)aminocarbonyl, hydroxyamidino, ureido, monoalkylureido, monoarylureido, monoaralkylureido, (monoalkyl)(monoaryl)ureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)(alkyl)glycinamido, (monoarylaminocarbonyl)glycinamido, (monoarylaminocarbonyl)(alkyl)glycinamido, alaninamido, heterocyclyl and heterocyclylalkyl.

12. The compound of claim 11 wherein:

$R^{1b}$ is one or more substituents independently selected from the group consisting of alkyl and hydroxyalkyl;

$R^2$ is one or more substituents independently selected from the group consisting of hydrogen, chloro or fluoro;

$R^3$ is phenyl substituted by one or more substituents independently selected from the group consisting of halo, alkyl, alkoxy, formyl, nitro, cycloalkylaminoalkyl, hydroxyalkyl, amino, alkylcarbonylamino, haloalkylcarbonylamino, alkoxyalkylcarbonylamino, alkoxycarbonylalkylcarbonylamino, alkylsulfonylamino, aminoalkyl, monoalkylaminoalkyl, dialkylaminoalkyl, (alkylsulfonyl)(alkyl)aminoalkyl, alkylcarbonyl, aminocarbonyl, monoalkylaminocarbonyl, monoarylaminocarbonyl, (aminocarbonylalkyl)aminocarbonyl, (aminoalkyl)aminocarbonyl, hydroxyamidino, ureido, (haloalkylcarbonyl)ureido, ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylaminoalkylcarbonyl)glycinamido, alaninamido, and heterocyclylalkyl.

13. The compound of claim 12 wherein:

$R^2$ is 4-fluoro;

$R^3$ is phenyl substituted at the 4-position with chloro and optionally substituted at the 2-position by aminocarbonyl, ureido, or glycinamido; and one $R^8$ is hydrogen and the other $R^8$ is selected from the group consisting of amino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, alkylcarbonylaminoalkyl, cycloalkylcarbonylaminoalkyl, alkoxycarbonylaminoalkyl, heterocyclylcarbonylaminoalkyl, arylsulfonylamino, alkylsulfonylaminoalkyl, ureido, monoalkylureido, monohaloalkylureido, ureidoalkyl, monoalkylureidoalkyl, monohaloalkylureidoalkyl, and aminoalkyl.

14. A pharmaceutical composition useful in treating an inflammatory disorder in a human in need of such treatment, which composition comprises a therapeutically effective amount of a compound of formula (Ia):

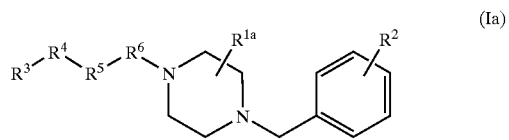

wherein:

$R^{1a}$ is one or more substituents independently selected from the group consisting of oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;

$R^2$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkylalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

R³ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl)aminocarbonyl, (monoalkylaminocarbonylalkyl)aminocarbonyl, (carboxyalkyl)aminocarbonyl, (alkoxycarbonylalkyl)aminocarbonyl, (aminoalkyl)aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

R⁴ is —C(R⁸)₂—;

R⁵ is an alkylene chain or an alkylidene chain;

R⁶ is —C(O)—; and each R⁸ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl;

as a single stereoisomer or a mixture thereof; or a pharmaceutically acceptable salt thereof; and a pharmaceutically acceptable excipient.

15. A pharmaceutical composition useful in treating an inflammatory disorder in a human in need of such treatment, which composition comprises a therapeutically effective amount of a compound of formula (Ib):

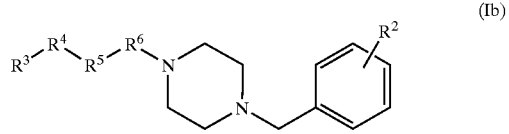

wherein:

R² is one or more substituents independently selected from the group consisting of hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl arylcarbonyl, aralkylcarbonyl, (hydroxyalkoxy)carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl)aminocarbonyl, (monoalkylaminocarbonylalkyl)aminocarbonyl, (carboxyalkyl)aminocarbonyl, (alkoxycarbonylalkyl)aminocarbonyl, (aminoalkyl)aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

$R^4$ is —C($R^8$)$_2$—;

$R^5$ is an alkylene chain or an alkylidene chain;

$R^6$ is —C(O)—; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl;

as a single stereoisomer or a mixture thereof; or a pharmaceutically acceptable salt thereof; and
a pharmaceutically acceptable excipient.

16. A pharmaceutical composition useful in treating an inflammatory disorder in a human in need of such treatment, which composition comprises a therapeutically effective amount of a compound of formula (Ic):

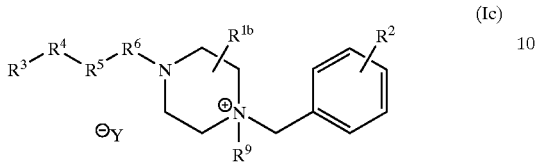

(Ic)

wherein:
Y is a pharmaceutically acceptable counterion:
$R^{1b}$ is one or more substituents independently selected from the group consisting of hydrogen, oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;
$R^2$ is one or more substituents independently selected from the group consisting of hydrogen, hydroxy, hydroxysulfonyl halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl) aminoalkyl, alkoxycarbonylamino, (alkoxycarbonyl)(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;
$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl) aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl)

aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

$R^4$ is $-C(R^8)_2-$;

$R^5$ is an alkylene chain or an alkylidene chain;

$R^6$ is $-C(O)-$;

each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl) (alkyl)amino, aralkylcarbonylamino, (aralkylcarbonyl) (alkyl)amino, alkylcarbonylaminoalkyl, cycloalkylcarbonylaminoalkyl, alkoxycarbonylaminoalkyl, (alkylcarbonyl)(alkyl) aminoalkyl, aralkylcarbonylaminoalkyl, heterocyclylcarbonylaminoalkyl, (aralkylcarbonyl) (alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl; and $R^9$ is alkyl, aralkyl, haloalkyl, hydroxyalkyl, alkoxyalkyl, carboxyalkyl, alkoxycarbonylalkyl, alkylcarbonylalkyl, alkylcarbonylaminoalkyl, aminocarbonylalkyl, monoalkylaminocarbonylalkyl, dialkylaminocarbonylalkyl, hetereocyclylalkyl, or cycloalkylalkyl;

as a single stereoisomer or a mixture thereof; or a pharmaceutically acceptable salt thereof; and a pharmaceutically acceptable excipient.

17. A method of treating an inflammatory disorder selected from the group consisting of multiple sclerosis and encephalomyelitis in a human, which method comprises administering to a human in need of such treatment a therapeutically effective amount of a compound of formula (Ia):

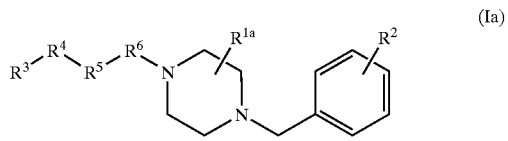

(Ia)

wherein:

$R^{1a}$ is one or more substituents independently selected from the group consisting of oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl, hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl, aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl) aminoalkyl, azidoalkyl, ureidoalkyl, monoalkylureidoalkyl, dialkylureidoalkyl, (alkoxycarbonylalkyl)ureidoalkyl alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;

$R^2$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl) aminoalkyl, alkoxycarbonylamino, (alkoxycarbonyl)

(alkyl)amino, alkoxycarbonylaminoalkyl, (alkoxycarbonyl)(alkyl)aminoalkyl, carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl) aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

$R^4$ is —C($R^8$)$_2$—;

$R^5$ is an alkylene chain or an alkylidene chain;

$R^6$ is —C(O)—; and each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl;

as a single stereoisomer or a mixture thereof; or a pharmaceutically acceptable salt thereof.

18. A method of treating an inflammatory disorder selected from the group consisting of multiple sclerosis and encephalomyelitis in a human, which method comprises administering to a human in need of such treatment a therapeutically effective amount of a compound of formula (Ib):

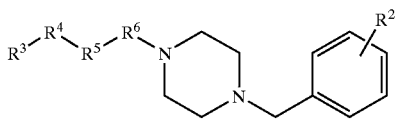
(Ib)

wherein:

R² is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl) (alkyl)aminoalkyl carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

R³ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy) aralkyl, (monoalkylamino)aralkyl, (hydroxyalkyl) hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, heterocyclylamino, (cycloalkylalkyl)amino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl) aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy) carbonyl, carboxyalkyl, alkoxycarbonylalkyl, aralkoxycarbonylalkyl, alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl) aminocarbonyl, (monoalkylaminocarbonylalkyl) aminocarbonyl, (carboxyalkyl)aminocarbonyl, (alkoxycarbonylalkyl)aminocarbonyl, (aminoalkyl) aminocarbonyl, (hydroxyalkyl)aminocarbonyl, aminocarbonylalkyl, monoalkylaminocarbonylalkyl, dialkylaminocarbonylalkyl, monoarylaminocarbonylalkyl monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl) ureidoalkyl, (alkoxycarbonylalkyl)ureidoalkyl, glycinamido, monoalkylglycinamido, aminocarbonylglycinamido, (alkoxyalkylcarbonyl) glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl) glycinamido, (monoaralkylaminocarbonyl) glycinamido, (monoaralkylaminocarbonyl)(alkyl) glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl heterocyclyl and heterocyclylalkyl;

R⁴ is —C(R⁸)₂—;

R⁵ is an alkylene chain or an alkylidene chain;

R⁶ is —C(O)—; and each R⁸ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl;

as a single stereoisomer or a mixture thereof; or a pharmaceutically acceptable salt thereof.

19. A method of treating an inflammatory disorder selected from the group consisting of multiple sclerosis and encephalomyelitis in a human, which method comprises administering to a human in need of such treatment a therapeutically effective amount of a compound of formula (Ic):

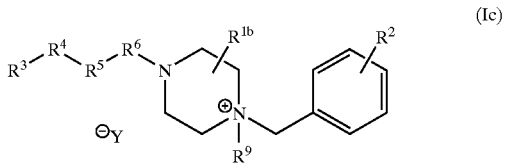

wherein:

Y is a pharmaceutically acceptable counterion:

$R^{1b}$ is one or more substituents independently selected from the group consisting of hydrogen, oxo, halo, alkyl, cycloalkyl, cycloalkylalkyl, cycloalkylaminoalkyl, (cycloalkylalkyl)aminoalkyl, haloalkyl, alkenyl, alkynyl, aryl, aralkyl, aralkenyl, formyl, formylalkyl, hydroxyalkyl hydroxyalkenyl, hydroxyalkynyl, (hydroxy)aralkyl, (hydroxy)cycloalkylalkyl, mercaptoalkyl, cyanoalkyl, haloalkylcarbonylaminoalkyl, (alkoxy)aralkyl, alkoxyalkyl, aryloxyalkyl aralkoxyalkyl, alkylthioalkyl, alkylsulfinylalkyl, alkylsulfonylalkyl, hydroxyalkylthioalkyl, aminoalkyl, monoalkylaminoalkyl, dialkylaminoalkyl, monoarylaminoalkyl, monoaralkylaminoalkyl, alkylcarbonylaminoalkyl, (alkylcarbonyl)(alkyl)aminoalkyl, azidoalkyl, ureidoalkyl, monoalkylureidoalkyl, dialkylureidoalkyl, (alkoxycarbonylalkyl)ureidoalkyl, alkoxycarbonylaminoalkyl, hydroxyalkylaminoalkyl, aryloxyalkylcarbonyloxyalkyl, alkoxyalkylcarbonyloxyalkyl, aralkoxyalkylcarbonyloxyalkyl, alkylcarbonyl, alkylcarbonylalkyl, carboxy, alkoxycarbonyl, aralkoxycarbonyl, aralkylcarbonyl, aminocarbonyl, monoalkylaminocarbonyl, dialkylaminocarbonyl, monoarylaminocarbonyl, monoaralkylaminocarbonyl, carboxyalkyl, alkoxycarbonylalkyl, aralkoxycarbonylalkyl, aminocarbonylalkyl, monoalkylaminocarbonylalkyl, dialkylaminocarbonylalkyl, monoarylaminocarbonylalkyl, monoaralkylaminocarbonylalkyl, arylsulfonyl, heterocyclyl and heterocyclylalkyl;

$R^2$ is one or more substituents independently selected from the group consisting of hydrogen, hydroxy, hydroxysulfonyl, halo, alkyl, mercapto, mercaptoalkyl, alkylthio, alkylsulfinyl, alkylsufonyl, alkylthioalkyl, alkylsulfinylalkyl, alkylsulfonylalkyl, alkoxy, aryloxy, haloalkyl, formyl, formylalkyl, nitro, nitroso, cyano, aralkoxy, haloalkoxy, cycloalkyl, cycloalkylalkyl, (hydroxy)cycloalkylalkyl, cycloalkylamino, cycloalkylaminoalkyl, (cycloalkylalkyl)amino, (cycloalkyalkyl)aminoalkyl, cyanoalkyl, alkenyl, alkynyl, aryl, aralkyl, aralkenyl, hydroxyalkyl, (hydroxy)aralkyl, hydroxyalkylthioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkyl, monoalkylaminoalkyl, dialkylaminoalkyl, hydroxyalkylaminoalkyl, monoarylaminoalkyl, monoaralkylaminoalkyl, alkylcarbonylamino, (alkylcarbonyl)(alkyl)amino, alkylcarbonylaminoalkyl, (alkylcarbonyl)(alkyl)aminoalkyl, alkoxycarbonylamino, (alkoxycarbonyl)(alkyl)amino, alkoxycarbonylaminoalkyl, (alkoxycarbonyl)(alkyl)aminoalkyl carboxy, alkoxycarbonyl, aralkoxycarbonyl, alkylcarbonyl, alkylcarbonylalkyl, arylcarbonyl, arylcarbonylalkyl, aralkylcarbonyl, aralkylcarbonylalkyl, carboxyalkyl, alkoxycarbonylalkyl, aralkoxycarbonylalkyl, alkoxyalkylcarbonyloxyalkyl, aminocarbonyl, monoalkylaminocarbonyl, dialkylaminocarbonyl, monoarylaminocarbonyl, monoaralkylaminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, guanidino, ureido, monoalkylureido, dialkylureido, ureidoalkyl, monoalkylureidoalkyl, dialkylureidoalkyl, heterocyclyl and heterocyclylalkyl;

$R^3$ is a carbocylic ring system substituted by one or more substituents independently selected from the group consisting of hydrogen, hydroxy, hydroxysulfonyl, halo, alkyl, mercapto, mercaptoalkyl, alkylthio, alkylsulfinyl, alkylsufonyl, arylsulfonyl, alkylthioalkyl, alkylsulfinylalkyl, alkylsulfonylalkyl, alkoxy, hydroxyalkoxy, aryloxy, haloalkyl, formyl, formylalkyl, nitro, nitroso, cyano, aralkoxy, haloalkoxy, aminoalkoxy, cycloalkyl, cycloalkylalkyl, (hydroxy)cycloalkylalkyl, cycloalkylamino, cycloalkylaminoalkyl, cyanoalkyl, alkenyl, alkynyl, aryl, aralkyl, aralkenyl, hydroxyalkyl, (hydroxy)aralkyl, (monoalkylamino)aralkyl, (hydroxyalkyl)hioalkyl, hydroxyalkenyl, hydroxyalkynyl, alkoxyalkyl, (alkoxy)aralkyl, aryloxyalkyl, aralkoxyalkyl, amino, monoalkylamino, dialkylamino, monoarylamino, monoaralkylamino, aminoalkylamino, heterocyclylamino, (cycloalkylalkyl)amino, alkylcarbonylamino, alkoxycarbonylamino, alkenylcarbonylamino, cycloalkylcarbonylamino, arylcarbonylamino, heterocyclylcarbonylamino, haloalkylcarbonylamino, alkoxyalkylcarbonylamino, alkoxycarbonylalkylcarbonylamino, (alkylcarbonyl)(alkyl)amino, (alkoxycarbonyl)(alkyl)amino, alkylsulfonylamino, aminoalkyl, monoalkylaminoalkyl, dialkylaminoalkyl, hydroxyalkylaminoalkyl, monoarylaminoalkyl, monoaralkylaminoalkyl, alkylcarbonylaminoalkyl, arylcarbonylaminoalkyl, (alkylcarbonyl)(alkyl)aminoalkyl, (cycloalkyalkyl)aminoalkyl, alkoxycarbonylaminoalkyl, alkoxycarbonylalkylcarbonylaminoalkyl, (alkoxycarbonyl)(alkyl)aminoalkyl, alkylsulfonylaminoalkyl, (alkylsulfonyl)(alkyl)aminoalkyl, arylsulfonylaminoalkyl, (arylsulfonyl)(alkyl)aminoalkyl, heterocyclylaminoalkyl, carboxy, alkoxycarbonyl, aralkoxycarbonyl, alkylcarbonyl, arylcarbonyl, aralkylcarbonyl, (hydroxyalkoxy)carbonyl, carboxyalkyl, alkoxycarbonylalkyl, aralkoxycarbonylalkyl alkoxyalkylcarbonyloxyalkyl, dialkylaminocarbonyloxyalkyl, alkylcarbonylalkyl, arylcarbonylalkyl, aralkylcarbonylalkyl, aminocarbonyl, monoalkylaminocarbonyl, dialkylaminocarbonyl, monoarylaminocarbonyl, monoaralkylaminocarbonyl, (aminocarbonylalkyl)aminocarbonyl, (monoalkylaminocarbonylalkyl)aminocarbonyl, (carboxyalkyl)aminocarbonyl, (alkoxycarbonylalkyl)aminocarbonyl, (aminoalkyl)aminocarbonyl, (hydroxyalkyl)aminocarbonyl, aminocarbonylalkyl, monoalkylaminocarbonylalkyl, dialkylaminocarbonylalkyl, monoarylaminocarbonylalkyl, monoaralkylaminocarbonylalkyl, amidino, hydroxyamidino, guanidino, ureido, monoalkylureido, monoarylureido, monoaralkylureido, monohaloalkylureido, (monoalkyl)(monoaryl)ureido, dialkylureido, diarylureido, (haloalkylcarbonyl)ureido, ureidoalkyl, monoalkylureidoalkyl, dialkylureidoalkyl, monoarylureidoalkyl, monoaralkylureidoalkyl, monohaloalkylureidoalkyl, (haloalkyl)(alkyl)ureidoalkyl, (alkoxycarbonylalkyl)ureidoalkyl, glycinamido, monoalkylglycinamido, aminocarbonylglycinamido, (alkoxyalkylcarbonyl)glycinamido, (aminocarbonyl)(alkyl)glycinamido, (alkoxycarbonylalkylcarbonyl)(alkyl)glycinamido, (alkoxycarbonylaminoalkylcarbonyl)glycinamido, arylcarbonylglycinamido, (arylcarbonyl)(alkyl)glycinamido, (monoaralkylaminocarbonyl)glycinamido, (monoaralkylaminocarbonyl)(alkyl)glycinamido, (monoarylaminocarbonyl)glycinamido, (monoarylaminocarbonyl)(alkyl)glycinamido, glycinamidoalkyl, alaninamido, monoalkylalaninamido, alaninamidoalkyl, heterocyclyl and heterocyclylalkyl;

$R^4$ is —C($R^8$)$_2$—;

$R^5$ is an alkylene chain or an alkylidene chain;

$R^6$ is —C(O)—;

each $R^8$ is independently selected from the group consisting of hydrogen, alkyl, aryl, aralkyl, hydroxy, alkoxy, hydroxyalkyl, alkoxyalkyl, amino, monoalkylamino, dialkylamino, alkylcarbonylamino, cycloalkylcarbonylamino, cycloalkylalkylcarbonylamino, alkoxycarbonylamino, alkylsulfonylamino, arylcarbonylamino, alkoxycarbonylalkylcarbonylamino, (alkylcarbonyl)(alkyl)amino, aralkylcarbonylamino, (aralkylcarbonyl)(alkyl)amino, alkylcarbonylaminoalkyl, cycloalkylcarbonylaminoalkyl, alkoxycarbonylaminoalkyl, (alkylcarbonyl)(alkyl)aminoalkyl, aralkylcarbonylaminoalkyl, heterocyclylcarbonylaminoalkyl, (aralkylcarbonyl)(alkyl)aminoalkyl, arylsulfonylamino, alkylsulfonylaminoalkyl, ureido, monoalkylureido, monohaloalkylureido, dialkylureido, ureidoalkyl, monoalkylureidoalkyl, dialkylureidoalkyl, monohaloalkylureidoalkyl, aminoalkyl, monoalkylaminoalkyl, dialkylaminoalkyl, carboxyalkyl, alkoxycarbonylalkyl, aminocarbonylalkyl, monoalkylaminocarbonylalkyl, and dialkylaminocarbonylalkyl; and $R^9$ is alkyl, aralkyl, haloalkyl, hydroxyalkyl, alkoxyalkyl, carboxyalkyl, alkoxycarbonylalkyl, alkylcarbonylalkyl, alkylcarbonylaminoalkyl, aminocarbonylalkyl, monoalkylaminocarbonylalkyl, dialkylaminocarbonylalkyl, heterocyclylalkyl, or cycloalkylalkyl;

as a single stereoisomer or a mixture thereof; or a pharmaceutically acceptable salt thereof.

\* \* \* \* \*